United States Patent
Sparling et al.

(10) Patent No.: US 12,391,709 B2
(45) Date of Patent: Aug. 19, 2025

(54) INHIBITORS OF KIF18A AND USES THEREOF

(71) Applicant: ACCENT THERAPEUTICS, INC., Lexington, MA (US)

(72) Inventors: Brian Andrew Sparling, Saugus, MA (US); Kenneth W. Duncan, Westwood, MA (US); Mary-Margaret Zablocki, Lexington, MA (US)

(73) Assignee: ACCENT THERAPEUTICS, INC., Lexington, MA (US)

( * ) Notice: Subject to any disclaimer, the term of this patent is extended or adjusted under 35 U.S.C. 154(b) by 0 days.

(21) Appl. No.: 19/020,085

(22) Filed: Jan. 14, 2025

(65) Prior Publication Data
US 2025/0197428 A1  Jun. 19, 2025

Related U.S. Application Data

(63) Continuation of application No. PCT/US2023/030544, filed on Aug. 18, 2023.

(60) Provisional application No. 63/463,617, filed on May 3, 2023, provisional application No. 63/399,003, filed on Aug. 18, 2022.

(51) Int. Cl.
C07F 7/08 (2006.01)
A61K 31/506 (2006.01)
A61K 31/695 (2006.01)
C07D 401/14 (2006.01)

(52) U.S. Cl.
CPC .......... *C07F 7/0816* (2013.01); *A61K 31/506* (2013.01); *A61K 31/695* (2013.01); *C07D 401/14* (2013.01)

(58) Field of Classification Search
CPC ... C07F 7/0816; C07D 401/14; A61K 31/506; A61K 31/695
See application file for complete search history.

(56) References Cited

U.S. PATENT DOCUMENTS

2020/0239441 A1 * 7/2020 Tamayo ............... C07D 405/14

FOREIGN PATENT DOCUMENTS

| CN | 115772159 A | 3/2023 |
|---|---|---|
| CN | 115785068 A | 3/2023 |
| CN | 116199636 A | 6/2023 |
| CN | 116514777 A | 8/2023 |
| CN | 116535400 A | 8/2023 |
| CN | 116554151 A | 8/2023 |
| CN | 116789637 A | 9/2023 |
| CN | 116804005 A | 9/2023 |
| CN | 116925065 A | 10/2023 |
| CN | 117069694 A | 11/2023 |
| CN | 117510463 A | 2/2024 |
| CN | 117683017 A | 3/2024 |
| CN | 117917405 A | 4/2024 |
| WO | 2020132648 A1 | 6/2020 |
| WO | 2020132649 A1 | 6/2020 |
| WO | 2020132651 A1 | 6/2020 |
| WO | 2020132653 A1 | 6/2020 |
| WO | 2021026098 A1 | 2/2021 |
| WO | 2021026099 A1 | 2/2021 |
| WO | 2021026100 A1 | 2/2021 |
| WO | 2021026101 A1 | 2/2021 |
| WO | 2021211549 A1 | 10/2021 |
| WO | 2021231413 A1 | 11/2021 |
| WO | 2022268230 A1 | 12/2022 |
| WO | 2023004075 A1 | 1/2023 |
| WO | 2023028564 A1 | 3/2023 |
| WO | 2023041055 A1 | 3/2023 |
| WO | 2023049209 A1 | 3/2023 |
| WO | 2023088441 A1 | 5/2023 |
| WO | 2023146973 A1 | 8/2023 |
| WO | 2023174175 A1 | 9/2023 |
| WO | 2023198209 A1 | 10/2023 |
| WO | 2023212240 A1 | 11/2023 |
| WO | 2023212714 A1 | 11/2023 |
| WO | 2023217230 A1 | 11/2023 |

(Continued)

OTHER PUBLICATIONS

Phillips et al., Targeting chromosomally unstable tumors with a selective KIF18A inhibitor. Nat Commun. Jan. 2, 2025;16(1): 307, 20 pages.

(Continued)

*Primary Examiner* — Clinton A Brooks
*Assistant Examiner* — Josmalen M. Ramos-Lewis
(74) *Attorney, Agent, or Firm* — McCarter & English, LLP; Jill Mello; Xin Zhang

(57) ABSTRACT

Provided are compounds of the Formula (IIIA):

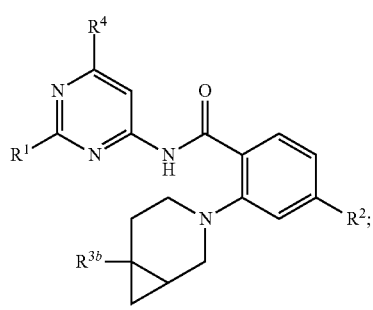

or pharmaceutically acceptable salts thereof, which are useful for the inhibition of KIF18A and in the treatment of a variety of KIF18A mediated conditions or diseases, such as cancer.

20 Claims, 6 Drawing Sheets

(56) References Cited

FOREIGN PATENT DOCUMENTS

| | | | |
|---|---|---|---|
| WO | 2023217232 A1 | 11/2023 |
| WO | 2023217233 A1 | 11/2023 |
| WO | 2024002328 A1 | 1/2024 |
| WO | 2024022508 A1 | 2/2024 |
| WO | 2024032661 A1 | 2/2024 |
| WO | 2024039829 A1 | 2/2024 |
| WO | 2024051755 A1 | 3/2024 |
| WO | 2024051812 A1 | 3/2024 |
| WO | 2024067465 A1 | 4/2024 |
| WO | 2024067675 A1 | 4/2024 |
| WO | 2024078569 A1 | 4/2024 |
| WO | 2024083137 A1 | 4/2024 |
| WO | 2024083208 A1 | 4/2024 |
| WO | 2024108765 A1 | 5/2024 |
| WO | 2024109923 A1 | 5/2024 |
| WO | 2024114730 A1 | 6/2024 |
| WO | 2024114787 A1 | 6/2024 |
| WO | 2024125488 A1 | 6/2024 |
| WO | 2024125626 A1 | 6/2024 |
| WO | 2024137778 A1 | 6/2024 |
| WO | 2024140799 A1 | 7/2024 |
| WO | 2024146593 A1 | 7/2024 |
| WO | 2024149189 A1 | 7/2024 |
| WO | 2024153217 A1 | 7/2024 |
| WO | 2024178255 A1 | 8/2024 |
| WO | 2024217348 A1 | 10/2024 |
| WO | 2024235073 A1 | 11/2024 |
| WO | 2024244972 A1 | 12/2024 |
| WO | 2024259146 A1 | 12/2024 |
| WO | 2025007055 A1 | 1/2025 |

OTHER PUBLICATIONS

Sabnis, Novel KIF18A Inhibitors for Treating Cancer. ACS Medicinal Chemistry Letters. Sep. 4, 2020;11 (11):2079-2080.

Tamayo et al., Targeting the Mitotic Kinesin KIF18A in Chromosomally Unstable Cancers: Hit Optimization Toward an In Vivo Chemical Probe. J Med Chem. Mar. 24, 2022;65(6):4972-4990. Pre-publication edition.

Zhang et al., Design, Biological Characterization, and Discovery of Novel Cyclohexenyl Derivatives as Kinesin KIF18A Inhibitors for the Treatment of Ovarian Cancer. ACS Med Chem Lett. Sep. 17, 2024;15(10):1778-1786. Pre-publication edition.

International Search Report and Written Opinion for Application No. PCT/US2023/030544, dated Dec. 14, 2023, 15 pages.

* cited by examiner

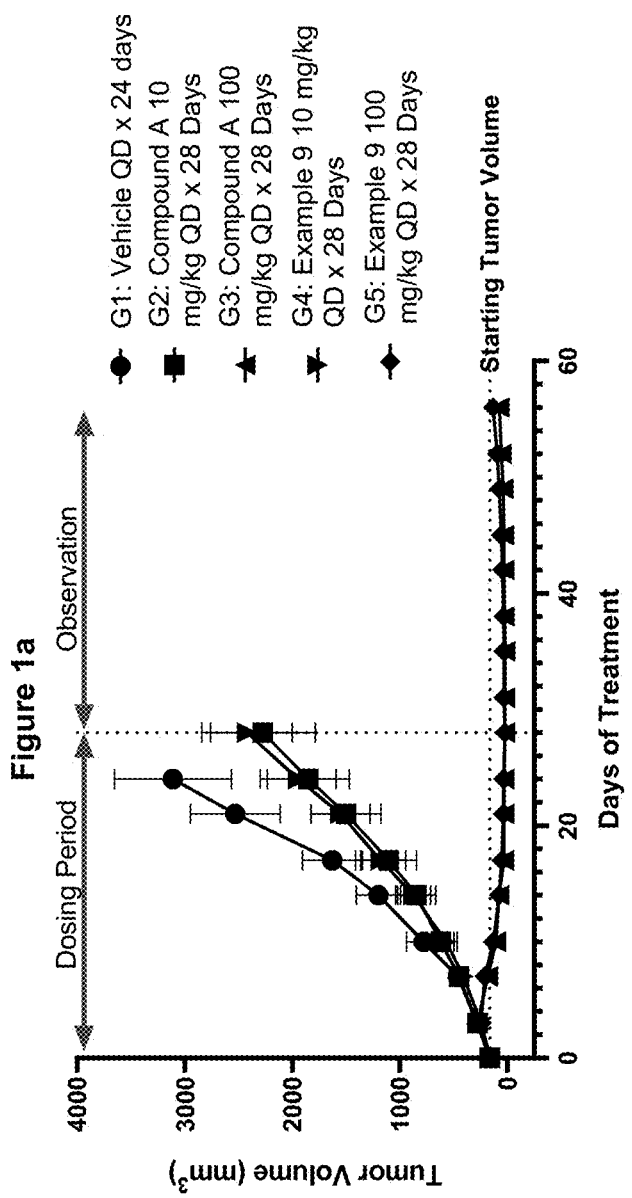

INHIBITORS OF KIF18A AND USES THEREOF

RELATED APPLICATIONS

This application is a continuation of International Application No. PCT/US2023/030544, filed on Aug. 18, 2023, which in turn claims priority to U.S. Provisional Application No. 63/463,617, filed on May 3, 2023 and U.S. Provisional Application No. 63/399,003, filed on Aug. 18, 2022. The entire contents of each of the foregoing applications are expressly incorporated herein by reference.

FIELD OF THE INVENTION

The present disclosure relates to inhibitors of kinesin family member 18A (KIF18A), and pharmaceutically acceptable salts thereof, compositions of these compounds, processes for their preparation, and their use in the treatment of diseases.

BACKGROUND OF THE INVENTION

Chromosomal abnormalities, such as an aneuploidy, are common in a number of different cancer types. For example, whole-genome duplication has been found in more than 30% of tumors, and can act as a biomarker for tumorigenesis. (Prasad et. al., *Cancer Res.* 2022 May 3; 82(9):1736-1752; Bielski et al., *Nat Genet.* 2018 August; 50(8):1189-1195). This genomic instability and duplication is believed to be the result of errors in cell division and propagation which occur and/or support the rapid cell division which characterized cancer cells. (Davoli, *Annu Rev Cell Dev Biol.* 2011; 27:585-610). In order to target this rapid cell division and genetic instability, many traditional cancer drugs, such as Paclitaxel, target tubulin and prevents mitosis of cells. However, these drugs are generally cytotoxic, and often have issues with side effects and off-target toxicity. As such, research has been focused on compounds with more selectivity and fewer side effects.

Kinesin family member 18A (KIF18A) is, as the name suggests, a member of the kinesin protein family, which are a group of motor proteins that use ATP hydrolysis to move along microtubule filaments and support mitosis and meiosis. KIF18A has been found to be a key enzyme in the proliferation of cancers with chromosomal instability (Marquis et al., *Nat Commun.* 2021 Feb. 22; 12(1):1213). Further, KIF18A knockout models show viability in non-cancer cells and mice, indicating that KIF18A is not essential for normal cell division, and as such, may be able to be targeted with less side effects than essential targets. (Tamayo et al., *J Med Chem.* 2022 Mar. 24; 65(6):4972-4990). The clinical utility of previous inhibitors of the kinesin motor protein target class, such as KIF18A, have been limited by several properties of these compounds, such as high cellular efflux, long pharmacokinetic terminal half-life and dose-limiting myelosuppression, specifically neutropenia and thrombocytopenia, as previously seen, for example, with the kinesin motor protein KIF11 (Eg-5) inhibitors, as discussed in P. Navais, et, al. Pharmaceutics 2021, 13, 1011.

Thus, there is a need for KIF18A inhibitors as potential therapeutic agents for treating diseases or disorders that are responsive to KIF18A inhibition, and specifically compounds which demonstrate improvements in the properties described above (i.e., better cellular efflux, different pharmacokinetic terminal half-life, and decreased myelosuppression, specifically neutropenia and thrombocytopenia).

SUMMARY OF THE INVENTION

The present disclosure provides compounds that are KIF18A inhibitors. In a first aspect, the present disclosure relates to compounds having the Formula I:

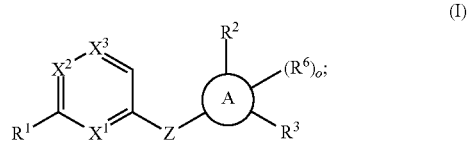

or a pharmaceutically acceptable salt thereof, wherein:
$X^1$ and $X^2$ are each independently $CR^5$ or N, and $X^3$ is $CR^4$ or N;
Ring A is phenyl, 6-membered heteroaryl, 6,5-bicyclic heteroaryl, or 4- to 10-membered monocyclic or bicyclic heterocyclyl;
Z is *—NHC(O)— or *—C(O)NH—, wherein *- represents the attachment to ring A;
o is an integer from 0 to 3;
$R^1$ is $C_{1-6}$alkyl, $C_{3-6}$cycloalkyl, 3- to 6-membered monocyclic heterocyclyl, $OR^{O1a}$, $SO_2R^{1a}$, $NR^{N1a}SO_2R^{1a}$, $NR^{N1a}R^{N1b}$, $—C(O)R^{1a}$, halo, cyano, wherein the $C_{1-6}$alkyl, $C_{3-6}$cycloalkyl and 3- to 6-membered monocyclic heterocyclyl are each optionally substituted with one or more $R^{1b}$;
$R^{1a}$ is $C_{1-6}$alkyl, $NR^{N1a}R^{N1b}$, $OR^{O1a}$, $C_{3-6}$cycloalkyl, or 3- to 6-membered monocyclic heterocyclyl, wherein the $C_{1-6}$alkyl, $C_{3-6}$cycloalkyl, and 3- to 6-membered monocyclic heterocyclyl are each optionally substituted with one or more $R^{1b}$;
each $R^{1b}$ is independently selected from halo, cyano, hydroxy, $C_{1-6}$alkyl, $C_{1-6}$haloalkyl, $C_{1-6}$alkoxy, and $C_{1-6}$haloalkoxy;
or two $R^{1b}$, together with the atom or atoms to which they are attached, form $C_{3-6}$cycloalkyl;
$R^{N1a}$ and $R^{N1b}$ are each independently selected from H and $C_{1-6}$alkyl, wherein the $C_{1-6}$alkyl is optionally substituted with one or more $R^{1b}$;
$R^{O1a}$ is H or $C_{1-6}$alkyl, wherein the $C_{1-6}$alkyl is optionally substituted with one or more $R^{1b}$;
$R^2$ is H, $C_{1-6}$alkyl, $SO_2R^{2a}$, $NR^{N2a}SO_2R^{2a}$, $OR^{O2a}$, $S(O)(NR^{N2c})R^{2a}$, halo, cyano, $—C(O)R^{2a}$, or $NR^{N2a}R^{N2b}$, wherein the $C_{1-6}$alkyl is optionally substituted with 1 or more $R^{2b}$;
$R^{2a}$ is $C_{1-6}$alkyl, $NR^{N2a}R^{N2b}$, $OR^{O2a}$, $C_{3-6}$cycloalkyl, or 3- to 6-membered monocyclic heterocyclyl, wherein the $C_{1-6}$alkyl, $C_{3-6}$cycloalkyl, and heterocyclyl are each optionally substituted with 1 or more $R^{2b}$;
each $R^{2b}$ is independently selected from $C_{1-6}$alkyl, halo, hydroxy, $C_{1-6}$alkoxy, $C_{1-6}$haloalkoxy, $—N(R^{N2c})_2$, and $—C(O)OC_{1-6}$alkyl;
$R^{N2a}$ and $R^{N2b}$ are each independently selected from H and $C_{1-6}$alkyl, wherein the $C_{1-6}$alkyl is optionally substituted with one or more $R^{2b}$;
each $R^{N2c}$ is independently H, $C_{1-3}$alkyl, $—C(O)(C_{1-3}$alkyl);
$R^{O2a}$ is H or $C_{1-6}$alkyl, wherein the $C_{1-6}$alkyl is optionally substituted with 1 or more halo, hydroxy, $C_{1-6}$alkoxy, or $C_{1-6}$haloalkoxy;

$R^3$ is $C_{3-6}$cycloalkyl, phenyl, or 3- to 6-membered monocyclic heterocyclyl, wherein the 3- to 6-membered monocyclic heterocyclyl is optionally substituted with 1 or more $R^{3a}$;

each $R^{3a}$ is independently selected from halo, $C_{1-6}$haloalkyl, or $C_{1-6}$alkyl; or two $R^{3a}$, together with the atom or atoms to which they are attached, form $C_{3-6}$cycloalkyl substituted with 1 or more $R^{3b}$;

each $R^{3b}$ is independently selected from H, halo, $C_{1-6}$alkoxy, and $C_{1-6}$alkyl optionally substituted with one or more halo, OH, or $C_{1-3}$alkoxy;

$R^4$ is H, $C_{1-6}$alkyl, $C_{1-6}$haloalkyl, or halo;

$R^5$ is H, halo, or $C_{1-6}$alkyl;

each $R^6$ is independently $C_{1-6}$alkyl, $C_{1-6}$haloalkyl, or halo;

provided that if ring A is phenyl or 6-membered heteroaryl, then $R^3$ is

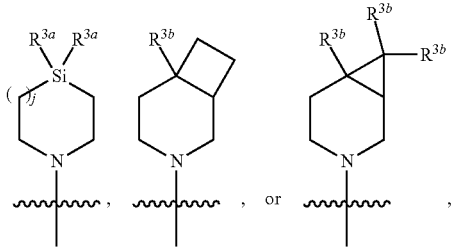

where j is 0 or 1. In some embodiments, $R^2$ is $C_{1-6}$alkyl, $SO_2R^{2a}$, $NR^{N2a}SO_2R^{2a}$, $OR^{O2a}$, halo, cyano, —$C(O)R^{2a}$, or $NR^{N2a}R^{N2b}$, wherein the $C_{1-6}$alkyl is optionally substituted with one or more $R^{2b}$; and the remaining variables are as described above.

Another aspect of the disclosure relates to pharmaceutical compositions comprising compounds of Formula (I) or pharmaceutically acceptable salts thereof, and a pharmaceutical carrier.

In yet another aspect, the present disclosure provides a method of treating a disease or disorder that is responsive to inhibition of KIF18A in a subject comprising administering to said subject an effective amount of at least one compound described herein or a pharmaceutically acceptable salt thereof. In some embodiments, the method is for the treatment of cancer.

Another aspect of the present disclosure relates to the use of at least one compound described herein or a pharmaceutically acceptable salt thereof, for the manufacture of a medicament for the treatment of a disease or disorder responsive to inhibition of KIF18A. Also provided is a compound described herein or a pharmaceutically acceptable salt thereof for use in treating a disease or disorder responsive to inhibition of KIF18A.

In some aspects, the compounds of the present disclosure have low efflux, especially in comparison to similar compounds known in the art. The benefits of compounds with low efflux are well known, such as overcoming resistance of cells with increased efflux pump prevalence, greater disease scope and targeting abilities, and higher cellular concentration.

In some aspects, the compounds of the present disclosure are less cytotoxic against bone marrow cells, especially in comparison to similar compounds known in the art. In some aspects, the compounds have a faster terminal half-life and/or clearance which allows for less systemic exposure and reduced potential for toxicity to bone-marrow cells. The benefits of compounds with low reactivity against bone marrow cells are well known, such as low risk of cytopenia, such as neutropenia or thrombocytopenia, for patients treated with the compounds.

DETAILED DESCRIPTION OF THE INVENTION

The present disclosure provides compounds and pharmaceutical compositions thereof that may be useful in the treatment of diseases or disorders through mediation of KIF18A function/activity. In some embodiments, the compounds of present disclosure are KIF18A inhibitors.

BRIEF DESCRIPTION OF THE FIGURES

FIG. 1a shows 28 day in vivo efficacy for compound of Example 9 and Compound A in OVCAR-3 Xenografts.

COMPOUNDS AND COMPOSITIONS

Figure 1B:
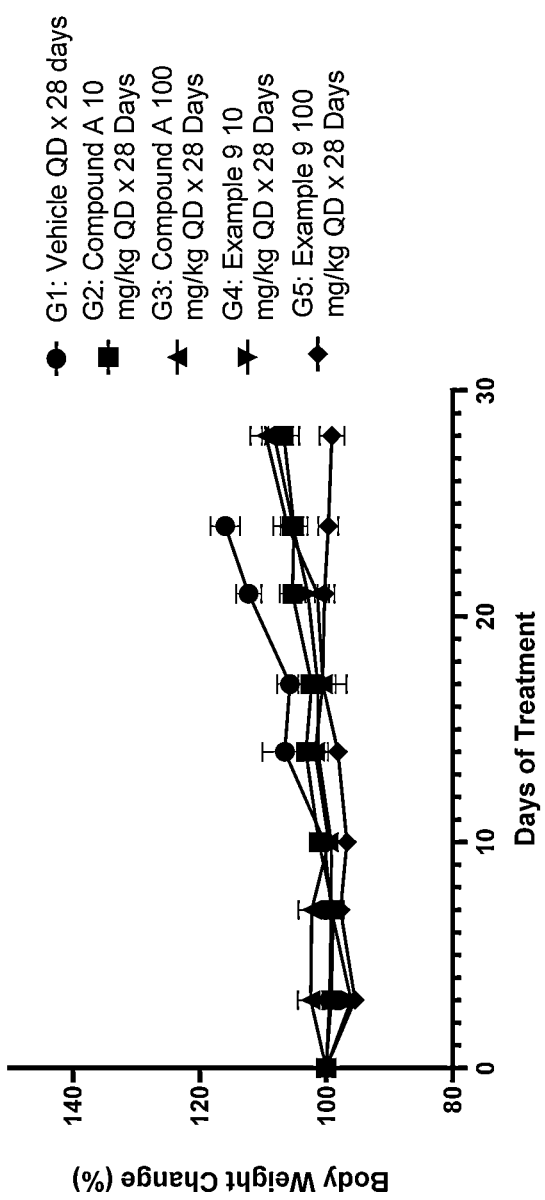
FIG. 1b shows tolerability for compound of Example 9 and Compound A in a 28 day in vivo efficacy study in OVCAR-3 Xenografts.

In a first embodiment, the present disclosure provides a compound of Formula (I):

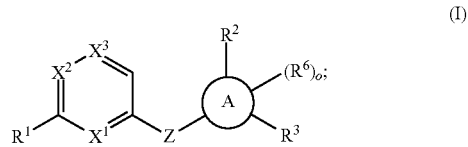

or a pharmaceutically acceptable salt thereof, therein the variables in Formula (I) are as defined as follows:

$X^1$ and $X^2$ are each independently $CR^5$ or N, and $X^3$ is $CR^4$ or N;

Ring A is phenyl, 6-membered heteroaryl, 6,5-bicyclic heteroaryl, or 4- to 10-membered monocyclic or bicyclic heterocyclyl;

Z is *—NHC(O)— or *—C(O)NH—, wherein *- represents the attachment to ring A;

o is an integer from 0 to 3;

$R^1$ is $C_{1-6}$alkyl, $C_{3-6}$cycloalkyl, 3- to 6-membered monocyclic heterocyclyl, $OR^{O1a}$, $SO_2R^{1a}$, $NR^{N1a}SO_2R^{1a}$, $NR^{N1a}R^{N1b}$, —$C(O)R^{1a}$, halo, cyano, wherein the $C_{1-6}$alkyl, $C_{3-6}$cycloalkyl and 3- to 6-membered monocyclic heterocyclyl are each optionally substituted with one or more $R^{1b}$;

$R^{1a}$ is $C_{1-6}$alkyl, $NR^{N1a}R^{N1b}$, $OR^{O1a}$ $C_{3-6}$cycloalkyl, or 3- to 6-membered monocyclic heterocyclyl, wherein the $C_{1-6}$alkyl, $C_{3-6}$cycloalkyl, and 3- to 6-membered monocyclic heterocyclyl are each optionally substituted with one or more $R^{1b}$;

each $R^{1b}$ is independently selected from halo, hydroxy, $C_{1-6}$alkyl, $C_{1-6}$alkoxy, and $C_{1-6}$haloalkoxy;

or two $R^{1b}$, together with the atom to which they are attached, form $C_{3-6}$cycloalkyl;

$R^{N1a}$ and $R^{N1b}$ are each independently selected from H and $C_{1-6}$alkyl, wherein the $C_{1-6}$alkyl is optionally substituted with one or more $R^{1b}$;

$R^{O1a}$ is H or $C_{1-6}$alkyl, wherein the $C_{1-6}$alkyl is optionally substituted with one or more $R^{1b}$;

$R^2$ is H, $C_{1-6}$alkyl, $SO_2R^{2a}$, $NR^{N2a}SO_2R^{2a}$, $OR^{O2a}$, halo, cyano, —C(O)$R^{2a}$, or $NR^{N2a}R^{2b}$, wherein the $C_{1-6}$alkyl is optionally substituted with one or more $R^{2b}$;

$R^{2a}$ is $C_{1-6}$alkyl, $NR^{N2a}R^{N2b}$, $OR^{O2a}$, $C_{3-6}$cycloalkyl, or 3- to 6-membered monocyclic heterocyclyl, wherein the $C_{1-6}$alkyl, $C_{3-6}$cycloalkyl, and heterocyclyl are each optionally substituted with one or more $R^{2b}$;

each $R^{2b}$ is independently selected from $C_{1-6}$alkyl, halo, hydroxy, $C_{1-6}$alkoxy, $C_{1-6}$haloalkoxy, and —C(O)OC$_{1-6}$ alkyl;

$R^{N2a}$ and $R^{N2b}$ are each independently selected from H and $C_{1-6}$alkyl, wherein the $C_{1-6}$alkyl is optionally substituted with one or more $R^{2b}$;

$R^{O2a}$ is H or $C_{1-6}$alkyl, wherein the $C_{1-6}$alkyl is optionally substituted with 1 or more halo, hydroxy, $C_{1-6}$alkoxy, or $C_{1-6}$haloalkoxy;

$R^3$ is $C_{3-6}$cycloalkyl, phenyl, or 3- to 6-membered monocyclic heterocyclyl, wherein the 3- to 6-membered monocyclic heterocyclyl is optionally substituted with one or more $R^{3a}$;

each $R^{3a}$ is independently selected from halo or $C_{1-6}$alkyl; or two $R^{3a}$, together with the atom to which they are attached, form $C_{3-6}$cycloalkyl;

$R^4$ is H, $C_{1-6}$alkyl, $C_{1-6}$haloalkyl, or halo;

$R^5$ is H or $C_{1-6}$alkyl;

each $R^6$ is independently $C_{1-6}$alkyl, $C_{1-6}$haloalkyl, or halo;

provided that if ring A is phenyl or 6-membered heteroaryl, then $R^3$ is

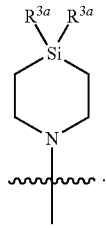

In an alternative first embodiment, the present disclosure provides a compound of Formula (I):

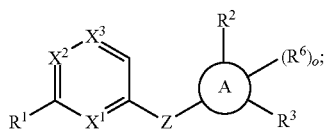

or a pharmaceutically acceptable salt thereof, wherein the variables in Formula (I) are as defined as follows:

$X^1$ and $X^2$ are each independently $CR^5$ or N, and $X^3$ is $CR^4$ or N;

Ring A is phenyl, 6-membered heteroaryl, 6,5-bicyclic heteroaryl, or 4- to 10-membered monocyclic or bicyclic heterocyclyl;

Z is *—NHC(O)— or *—C(O)NH—, wherein *- represents the attachment to ring A;

o is an integer from 0 to 3;

$R^1$ is $C_{1-6}$alkyl, $C_{3-6}$cycloalkyl, 3- to 6-membered monocyclic heterocyclyl, $OR^{O1a}$, $SO_2R^{1a}$, $NR^{N1a}SO_2R^{1a}$, $NR^{N1a}R^{N1b}$, —C(O)$R^{1a}$, halo, cyano, wherein the $C_{1-6}$alkyl, $C_{3-6}$cycloalkyl and 3- to 6-membered monocyclic heterocyclyl are each optionally substituted with one or more $R^{1b}$;

$R^{1a}$ is $C_{1-6}$alkyl, $NR^{N1a}R^{N1b}$, $OR^{O1a}$, $C_{3-6}$cycloalkyl, or 3- to 6-membered monocyclic heterocyclyl, wherein the $C_{1-6}$alkyl, $C_{3-6}$cycloalkyl, and 3- to 6-membered monocyclic heterocyclyl are each optionally substituted with one or more $R^{1b}$;

each $R^{1b}$ is independently selected from halo, hydroxy, $C_{1-6}$alkyl, $C_{1-6}$alkoxy, and $C_{1-6}$haloalkoxy;

or two $R^{1b}$, together with the atom to which they are attached, form $C_{3-6}$cycloalkyl;

$R^{N1a}$ and $R^{N1b}$ are each independently selected from H and $C_{1-6}$alkyl, wherein the $C_{1-6}$alkyl is optionally substituted with one or more $R^{1b}$;

$R^{O1a}$ is H or $C_{1-6}$alkyl, wherein the $C_{1-6}$alkyl is optionally substituted with one or more $R^{1b}$;

$R^2$ is H, $C_{1-6}$alkyl, $SO_2R^{2a}$, $NR^{N2a}SO_2R^{2a}$, $OR^{O2a}$, halo, cyano, —C(O)$R^{2a}$, or $NR^{N2a}R^{N2b}$, wherein the $C_{1-6}$alkyl is optionally substituted with one or more $R^{2b}$;

$R^{2a}$ is $C_{1-6}$alkyl, $NR^{N2a}R^{N2b}$, $OR^{O2a}$, $C_{3-6}$cycloalkyl, or 3- to 6-membered monocyclic heterocyclyl, wherein the $C_{1-6}$alkyl, $C_{3-6}$cycloalkyl, and heterocyclyl are each optionally substituted with one or more $R^{2b}$;

each $R^{2b}$ is independently selected from $C_{1-6}$alkyl, halo, hydroxy, $C_{1-6}$alkoxy, $C_{1-6}$haloalkoxy, and —C(O)OC$_{1-6}$ alkyl;

$R^{N2a}$ and $R^{N2b}$ are each independently selected from H and $C_{1-6}$alkyl, wherein the $C_{1-6}$alkyl is optionally substituted with one or more $R^{2b}$;

$R^{O2a}$ is H or $C_{1-6}$alkyl, wherein the $C_{1-6}$alkyl is optionally substituted with 1 or more halo, hydroxy, $C_{1-6}$alkoxy, or $C_{1-6}$haloalkoxy;

$R^3$ is $C_{3-6}$cycloalkyl, phenyl, or 3- to 6-membered monocyclic heterocyclyl, wherein the 3- to 6-membered monocyclic heterocyclyl is optionally substituted with one or more $R^{3a}$;

each $R^{3a}$ is independently selected from halo or $C_{1-6}$alkyl; or two $R^{3a}$, together with the atom or atoms to which they are attached, form $C_{3-6}$cycloalkyl substituted with 1 or more $R^{3b}$;

each $R^{3b}$ is independently selected from H, halo, $C_{1-6}$alkoxy, and $C_{1-6}$alkyl optionally substituted with one or more halo or OH;

$R^4$ is H, $C_{1-6}$alkyl, $C_{1-6}$haloalkyl, or halo;

$R^5$ is H or $C_{1-6}$alkyl;

each $R^6$ is independently $C_{1-6}$alkyl, $C_{1-6}$haloalkyl, or halo;

provided that if ring A is phenyl or 6-membered heteroaryl, then $R^3$ is

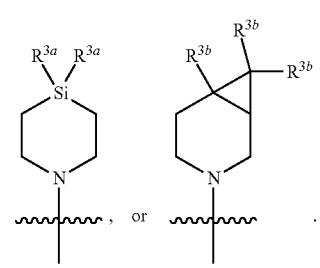

In a second embodiment, for the compounds of Formula (I), or a pharmaceutically acceptable salt thereof, Z is *—C(O)NH—, wherein *- represents the attachment to ring A; and the remaining variables are as described in the first embodiment or first aspect or any alternative embodiment described therein.

In a third embodiment, for the compounds of Formula (I), or a pharmaceutically acceptable salt thereof, Ring A is phenyl, 6-membered heteroaryl or a 6,5-bicyclic heteroaryl, each of which is substituted with $R^2$, $R^3$, and 0 to 1 $R^6$; and the remaining variables are as described in the first or second embodiment or first aspect or any alternative embodiments described therein. In an alternative third embodiment, for the compounds of Formula (I), or a pharmaceutically acceptable salt thereof, Ring A is phenyl, 6-membered heteroaryl or a 6,5-bicyclic heteroaryl, each of which is substituted with $R^2$, $R^3$, and 0 to 2 $R^6$; and the remaining variables are as described in the first or second embodiment or first aspect or any alternative embodiments describe therein.

In a fourth embodiment, for the compounds of Formula (I), or a pharmaceutically acceptable salt thereof, Ring A is phenyl, pyridinyl, or indazolyl, each of which is substituted with $R^2$, $R^3$, and 0 to 1 $R^6$; and the remaining variables are as described in the first, second, or third embodiment or first aspect or any alternative embodiments described therein. In an alternative fourth embodiment, for the compounds of Formula (I), or a pharmaceutically acceptable salt thereof, Ring A is phenyl, pyrazinyl, pyridinyl, or indazolyl, each of which is substituted with $R^2$, $R^3$, and 0 to 2 $R^6$; and the remaining variables are as described in the first, second, or third embodiment or first aspect or any alternative embodiments described therein.

In a fifth embodiment, for the compounds of Formula (I), or a pharmaceutically acceptable salt thereof, Ring A is represented by the following structural formula:

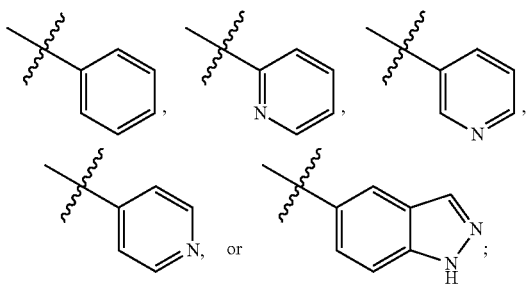

each of which is substituted with $R^2$, $R^3$, and 0 to 1 $R^6$; and the remaining variables are as described in the fourth embodiment or first aspect or any alternative embodiments described therein. In an alternative fifth embodiment, for the compounds of Formula (I), or a pharmaceutically acceptable salt thereof, Ring A is represented by the following structural formula:

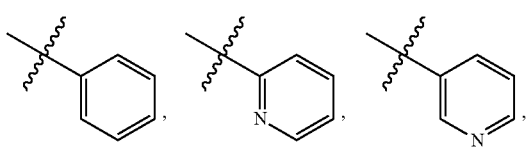

-continued

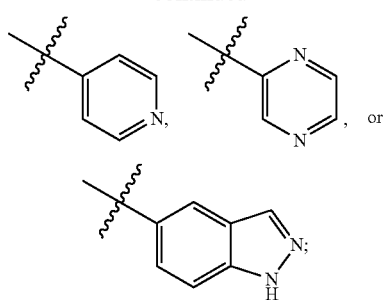

each of which is substituted with $R^2$, $R^3$, and 0 to 2 $R^6$; and the remaining variables are as described in the fourth embodiment or first aspect or any alternative embodiments described therein.

In a sixth embodiment, for the compounds of Formula (I), or a pharmaceutically acceptable salt thereof, Ring A is represented by the following structural formula:

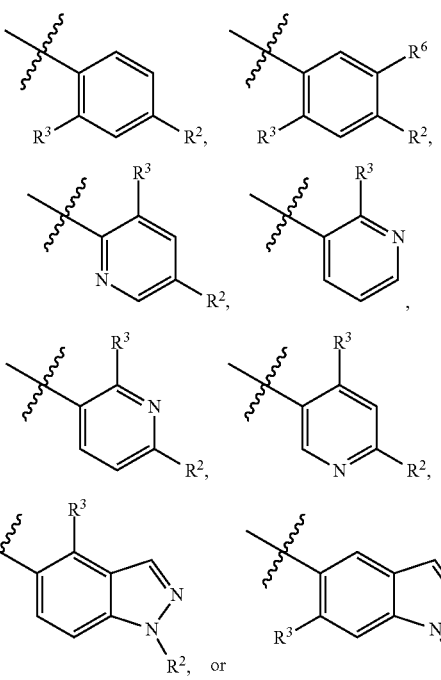

and the remaining variables are as described in the fourth embodiment or first aspect or any alternative embodiments described therein. In an alternative sixth embodiment, for the compounds of Formula (I), or a pharmaceutically acceptable salt thereof, Ring A is represented by the following structural formula:

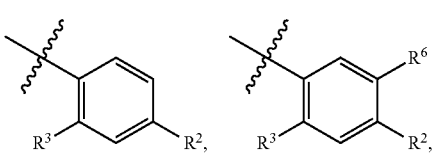

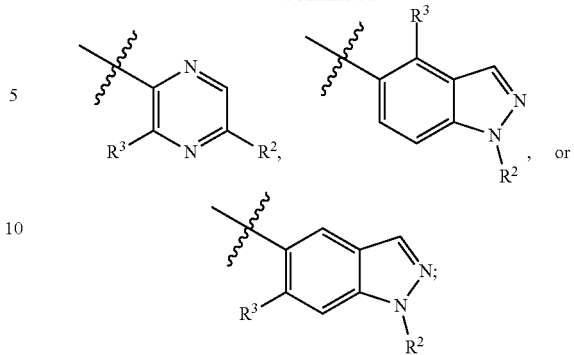

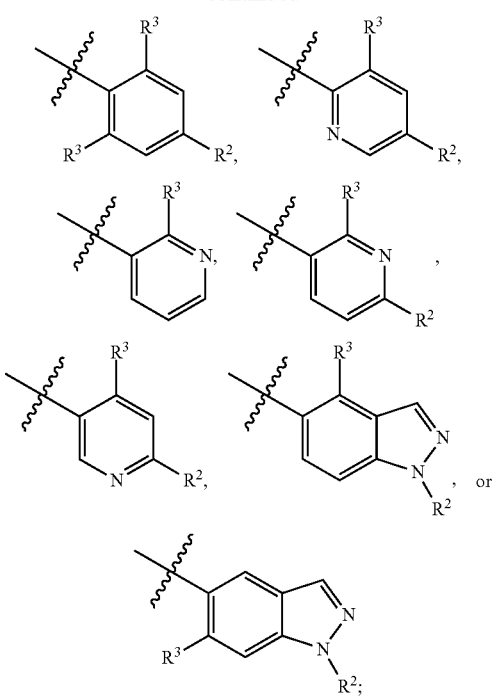

and the remaining variables are as described in the fourth embodiment or first aspect or any alternative embodiments described therein. In another alternative sixth embodiment, for the compounds of Formula (I), or a pharmaceutically acceptable salt thereof, Ring A is represented by the following structural formula:

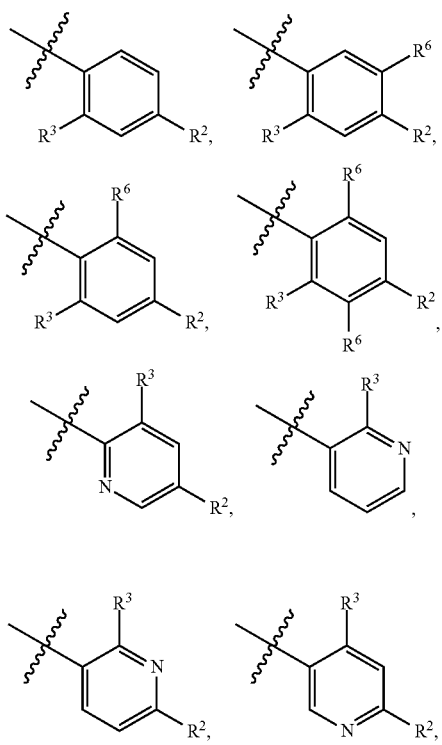

and the remaining variables are as described in the fourth embodiment or first aspect or any alternative embodiments described therein.

In a seventh embodiment, for the compounds of Formula (I), or a pharmaceutically acceptable salt thereof, Ring A is phenyl substituted with $R^2$ and $R^3$; and the remaining variables are as described in the first, second, or third embodiment or first aspect or any alternative embodiments described therein.

In an eighth embodiment, for the compounds of Formula (I), or a pharmaceutically acceptable salt thereof, Ring A is represented by the following structural formula:

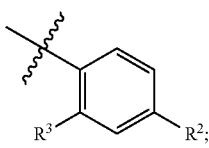

and the remaining variables are as described in the seventh embodiment or first aspect or any alternative embodiments described therein.

In a ninth embodiment, the compound of the present disclosure is represented by Formula (IA):

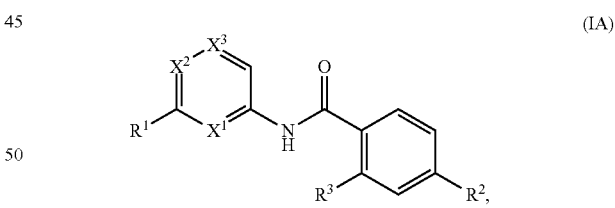

(IA)

or a pharmaceutically acceptable salt thereof; wherein the variables $R^1$, $R^2$, $R^3$, $R^4$, X, $X^2$, and $X^3$ depicted in Formula (IA) are as described in the first, second, third, fourth, fifth, sixth, seventh, or eighth embodiment or first aspect or any alternative embodiments described therein.

In a tenth embodiment, for the compounds of Formula (I) or (IA), or a pharmaceutically acceptable salt thereof, $X^1$ and $X^2$ are both N and $X^3$ is $CR^4$; or $X^1$ and $X^3$ are both N and $X^2$ is $CR^5$; and the remaining variables are as described in the first, second, third, fourth, fifth, sixth, seventh, eighth, or ninth embodiment or first aspect or any alternative embodiments described therein.

In an eleventh embodiment, for the compounds of Formula (I) or (IA), or a pharmaceutically acceptable salt thereof, $X^3$ is $CR^4$, one of $X^1$ or $X^2$ is N, and the other is $CR^5$; and the remaining variables are as described in the first, second, third, fourth, fifth, sixth, seventh, eighth, or ninth embodiment or first aspect or any alternative embodiments described therein.

In a twelfth embodiment, for the compounds of Formula (I) or (IA), or a pharmaceutically acceptable salt thereof, $X^3$ is $CR^4$, and $X^1$ and $X^2$ are both $CR^5$; and the remaining variables are as described in the first, second, third, fourth, fifth, sixth, seventh, eighth, or ninth embodiment or any alternative embodiments described therein.

In a thirteenth embodiment, for the compounds of Formula (I) or (IA), or a pharmaceutically acceptable salt thereof, $R^4$ is H and $R^5$ is H or —$CH_3$; and the remaining variables are as described in the first, second, third, fourth, fifth, sixth, seventh, eighth, ninth, tenth, eleventh, or twelfth embodiment or first aspect or any alternative embodiments described therein. In an alternative thirteenth embodiment, for the compounds of Formula (I) or (IA), or a pharmaceutically acceptable salt thereof, $R^4$ is H or —$CH_3$, and $R^5$ is H or —$CH_3$; and the remaining variables are as described in the first, second, third, fourth, fifth, sixth, seventh, eighth, ninth, tenth, eleventh, or twelfth embodiment or first aspect or any alternative embodiments described therein. In another alternative thirteenth embodiment, for the compounds of Formula (I) or (IA), or a pharmaceutically acceptable salt thereof, $R^4$ is H or —$CH_3$, and $R^5$ is H, F, or —$CH_3$; and the remaining variables are as described in the first, second, third, fourth, fifth, sixth, seventh, eighth, ninth, tenth, eleventh, or twelfth embodiment or first aspect or any alternative embodiments described therein.

In a fourteenth embodiment, for the compounds of Formula (I) or (IA), or a pharmaceutically acceptable salt thereof, $R^3$ is a 6-membered monocyclic heterocyclyl optionally substituted with 1 to 3 $R^{3a}$; and the remaining variables are as described in the first, second, third, fourth, fifth, sixth, seventh, eighth, ninth, tenth, eleventh, twelfth, or thirteenth embodiment or first aspect or any alternative embodiments described therein. In an alternative fourteenth embodiment, for the compounds of Formula (I) or (IA), or a pharmaceutically acceptable salt thereof, $R^3$ is a 5- or 6-membered monocyclic heterocyclyl optionally substituted with 1 to 3 $R^{3a}$; and the remaining variables are as described in the first, second, third, fourth, fifth, sixth, seventh, eighth, ninth, tenth, eleventh, twelfth, or thirteenth embodiment or first aspect or any alternative embodiments described therein.

In a fifteenth embodiment, for the compounds of Formula (I) or (IA), or a pharmaceutically acceptable salt thereof, $R^3$ is piperdinyl or 1,4-azasilinanyl, each of which is optionally substituted with 1 to 3 $R^{3a}$; and the remaining variables are as described in the first, second, third, fourth, fifth, sixth, seventh, eighth, ninth, tenth, eleventh, twelfth, thirteenth, or fourteenth embodiment or first aspect or any alternative embodiments described therein. In an alternative fifteenth embodiment, for the compounds of Formula (I) or (IA), or a pharmaceutically acceptable salt thereof, $R^3$ is piperdinyl, 1,3-azasilolidinyl, or 1,4-azasilinanyl, each of which is optionally substituted with 1 to 3 $R^{3a}$; and the remaining variables are as described in the first, second, third, fourth, fifth, sixth, seventh, eighth, ninth, tenth, eleventh, twelfth, thirteenth, or fourteenth embodiment or first aspect or any alternative embodiments described therein.

In a sixteenth embodiment, for the compounds of Formula (I) or (IA), or a pharmaceutically acceptable salt thereof, $R^3$ is represented by the following structural formula:

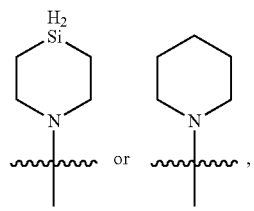

each of which is optionally substituted with 1 to 3 $R^{3a}$; and the remaining variables are as described in the fifteenth embodiment or first aspect or any alternative embodiments described therein. In an alternative sixteenth embodiment, for the compounds of Formula (I) or (IA), or a pharmaceutically acceptable salt thereof, $R^3$ is represented by the following structural formula:

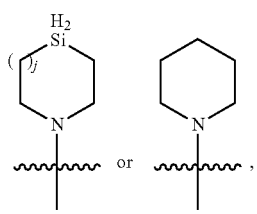

wherein j is 0 or 1, each of which is optionally substituted with 1 to 3 $R^{3a}$; and the remaining variables are as described in the fifteenth embodiment or first aspect or any alternative embodiments described therein.

In a seventeenth embodiment, for the compounds of Formula (I) or (IA), or a pharmaceutically acceptable salt thereof, $R^3$ is represented by the following structural formula:

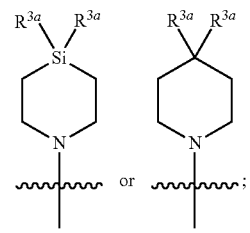

and each $R^{3a}$ is $C_{1-3}$alkyl, or two $R^{3a}$, together with the atom to which they are attached, form $C_{3-6}$cycloalkyl; and the remaining variables are as described in the sixteenth embodiment or first aspect or any alternative embodiments described therein. In an alternative seventeenth embodiment, for the compounds of Formula (I) or (IA), or a pharmaceutically acceptable salt thereof, $R^3$ is represented by the following structural formula:

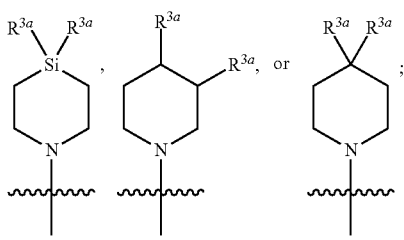

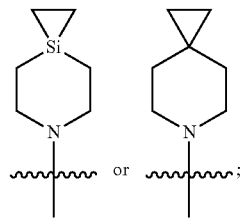

and each $R^{3a}$ is $C_{1-3}$alkyl, or two $R^{3a}$, together with the atom or atoms to which they are attached, form $C_{3-6}$cycloalkyl substituted with 1 to 3 $R^{3b}$; and the remaining variables are as described in the sixteenth embodiment or first aspect or any alternative embodiments described therein. In another alternative seventeenth embodiment, for the compounds of Formula (I) or (IA), or a pharmaceutically acceptable salt thereof, $R^3$ is represented by the following structural formula:

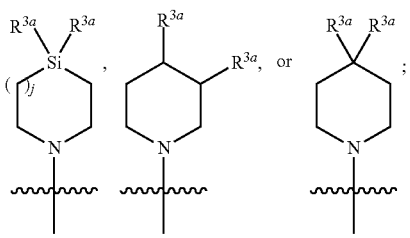

and each $R^{3a}$ is $C_{1-3}$alkyl, or two $R^{3a}$, together with the atom or atoms to which they are attached, form $C_{3-6}$cycloalkyl substituted with 1 to 3 $R^{3b}$; and the remaining variables are as described in the sixteenth embodiment or first aspect or any alternative embodiments described therein.

In an eighteenth embodiment, for the compounds of Formula (I) or (IA), or a pharmaceutically acceptable salt thereof, each $R^{3a}$ is —$CH_3$, or two $R^{3a}$, together with the atom to which they are attached, form cyclopropyl; and the remaining variables are as described in the seventeenth embodiment or first aspect. In an alternative eighteenth embodiment, for the compounds of Formula (I) or (IA), or a pharmaceutically acceptable salt thereof, each $R^{3a}$ is —$CH_3$, or two $R^{3a}$, together with the atom or atoms to which they are attached, form cyclopropyl substituted with 1 to 3 $R^{3b}$, and each $R^{3b}$ is independently H, halo, —$CH_3$, —$CHF_2$, or —$CH_2OH$; and the remaining variables are as described in the seventeenth embodiment or first aspect or any alternative embodiments described therein. In another alternative eighteenth embodiment, for the compounds of Formula (I) or (IA), or a pharmaceutically acceptable salt thereof, each $R^{3a}$ is —$CH_3$ or —$CH_2CH_3$, or two $R^{3a}$, together with the atom or atoms to which they are attached, form cyclopropyl or cyclobutyl substituted with 1 to 3 $R^{3b}$, and each $R^{3b}$ is independently H, halo, —$CH_3$, —$OCH_3$, —$CH_2F$, —$CHF_2$, —$CF_3$, —$CF_2CH_3$, —$CH_2OCH_3$, or —$CH_2OH$; and the remaining variables are as described in the seventeenth embodiment or first aspect or any alternative embodiments described therein.

In a nineteenth embodiment, for the compounds of Formula (I) or (IA), or a pharmaceutically acceptable salt thereof, $R^3$ is represented by the following structural formula:

and the remaining variables are as described in the eighteenth embodiment or first aspect or any alternative embodiments described therein. In an alternative nineteenth embodiment, for the compounds of Formula (I) or (IA), or a pharmaceutically acceptable salt thereof, $R^3$ is represented by the following structural formula:

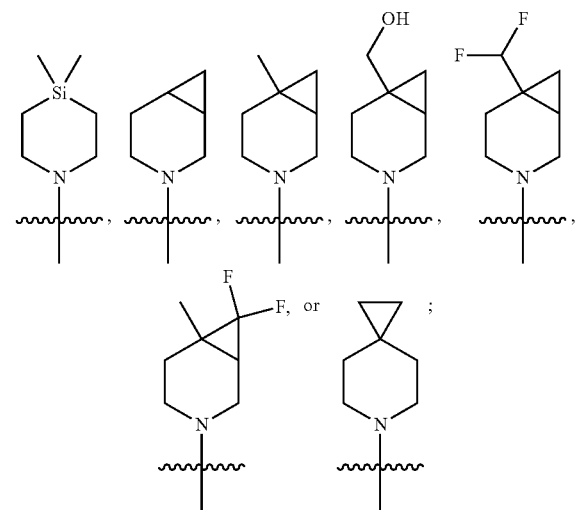

and the remaining variables are as described in the eighteenth embodiment or first aspect or any alternative embodiments described therein. In another alternative nineteenth embodiment, for the compounds of Formula (I) or (IA), or a pharmaceutically acceptable salt thereof, $R^3$ is represented by the following structural formula:

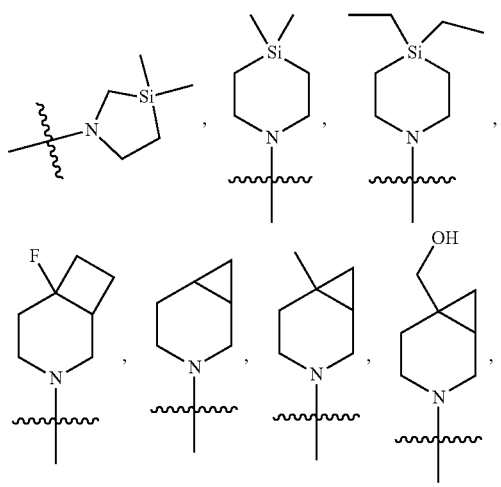

-continued

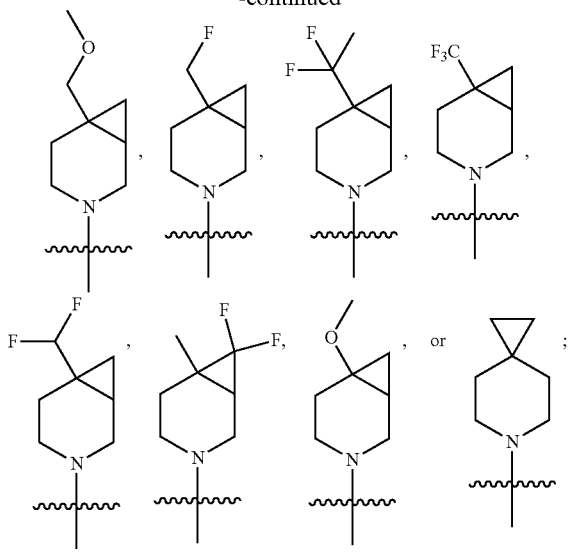

and the remaining variables are as described in the eighteenth embodiment or first aspect or any alternative embodiments described therein.

In a twentieth embodiment, for the compounds of Formula (I) or (IA), or a pharmaceutically acceptable salt thereof, each $R^{3a}$ is —$CH_3$; and the remaining variables are as described in the eighteenth embodiment or first aspect or any alternative embodiments described therein.

In a twenty-first embodiment, for the compounds of Formula (I) or (IA), or a pharmaceutically acceptable salt thereof, $R^1$ is $C_{3-6}$cycloalkyl, 3- to 6-membered monocyclic heterocyclyl, $OR^{O1a}$, or $SO_2R^{1a}$, wherein the $C_{3-6}$cycloalkyl and 3- to 6-membered monocyclic heterocyclyl are each optionally substituted with 1 to 3 $R^{1b}$; $R^{1a}$ is —$NHR^{N1b}$ or $C_{3-6}$Cycloalkyl; $R^{N1b}$ is $C_{1-4}$alkyl optionally substituted with 1 or 2 $R^{1b}$; $R^{O1a}$ is $C_{1-3}$alkyl optionally substituted with 1 to 3 $R^{1b}$; each $R^{1b}$ is independently selected from halo and $C_{1-3}$alkyl; or two $R^{1b}$, together with the atom to which they are attached, form $C_{3-6}$cycloalkyl; and the remaining variables are as described in the first, second, third, fourth, fifth, sixth, seventh, eighth, ninth, tenth, eleventh, twelfth, thirteenth, fourteenth, fifteenth, sixteenth, seventeenth, eighteenth, nineteenth, or twentieth embodiment or first aspect or any alternative embodiments described therein. In an alternative twenty-first embodiment, for the compounds of Formula (I) or (IA), or a pharmaceutically acceptable salt thereof, $R^1$ is $C_{3-6}$cycloalkyl, 3- to 6-membered monocyclic heterocyclyl, $OR^{O1a}$, or $SO_2R^{1a}$, wherein the $C_{3-6}$cycloalkyl and 3- to 6-membered monocyclic heterocyclyl are each optionally substituted with 1 to 3 $R^{1b}$; $R^{1a}$ is —$NHR^{N}1b$, $C_{3-6}$cycloalkyl, or 3- to 6-membered monocyclic heterocyclyl, wherein the 3- to 6-membered monocyclic heterocyclyl is optionally substituted with 1 to 3 halo; $R^{N}1b$ is $C_{1-4}$alkyl optionally substituted with 1 or 2 $R^{1b}$; $R^{O1a}$ is $C_{1-3}$alkyl optionally substituted with 1 to 3 $R^{1b}$; each $R^{1b}$ is independently selected from halo and $C_{1-3}$alkyl; or two $R^{1b}$, together with the atom to which they are attached, form $C_{3-6}$cycloalkyl; and the remaining variables are as described in the first, second, third, fourth, fifth, sixth, seventh, eighth, ninth, tenth, eleventh, twelfth, thirteenth, fourteenth, fifteenth, sixteenth, seventeenth, eighteenth, nineteenth, or twentieth embodiment or first aspect or any alternative embodiments described therein. In another alternative twenty-first embodiment, for the compounds of Formula (I) or (IA), or a pharmaceutically acceptable salt thereof, $R^1$ is $C_{3-6}$cycloalkyl, 3- to 6-membered monocyclic heterocyclyl, $OR^{O1a}$, or $SO_2R^{1a}$, wherein the $C_{3-6}$cycloalkyl and 3- to 6-membered monocyclic heterocyclyl are each optionally substituted with 1 to 3 $R^{1b}$; $R^{1a}$ is —$NHR^{N1b}$ $C_{3-6}$cycloalkyl, or 3- to 6-membered monocyclic heterocyclyl, wherein the 3- to 6-membered monocyclic heterocyclyl is optionally substituted with 1 to 3 halo; $R^{N}1b$ is $C_{1-4}$alkyl optionally substituted with 1 or 2 $R^{1b}$; $R^{O1a}$ is $C_{1-3}$alkyl optionally substituted with 1 to 3 $R^{1b}$; each $R^{1b}$ is independently selected from halo, cyano, $C_{1-3}$haloalkyl, and $C_{1-3}$alkyl; or two $R^{1b}$, together with the atom or atoms to which they are attached, form $C_{3-6}$cycloalkyl; and the remaining variables are as described in the first, second, third, fourth, fifth, sixth, seventh, eighth, ninth, tenth, eleventh, twelfth, thirteenth, fourteenth, fifteenth, sixteenth, seventeenth, eighteenth, nineteenth, or twentieth embodiment or first aspect or any alternative embodiments described therein.

In a twenty-second embodiment, for the compounds of Formula (I) or (IA), or a pharmaceutically acceptable salt thereof, $R^1$ is —$S(O)_2NHC(CH_3)_3$, —$SO_2$-cyclopentyl, —$OCH_2CH_2CF_3$, cyclopropyl, cyclohexyl, morpholinyl, piperdinyl, azetidinyl, or pyrrolidinyl, wherein the cyclopropyl, cyclohexyl, morpholinyl, piperdinyl, azetidinyl, and pyrrolidinyl are each optionally substituted with 1 to 3 $R^{1b}$; and each $R^{1b}$ is —F or —$CH_3$; or two $R^{1b}$, together with the atom to which they are attached, form cyclopropyl; and the remaining variables are as described in the twenty-first embodiment or first aspect or any alternative embodiments described therein. In an alternative twenty-second embodiment, for the compounds of Formula (I) or (IA), or a pharmaceutically acceptable salt thereof, $R^1$ is —$S(O)_2NHC(CH_3)_3$, —$SO_2$-cyclopentyl, —$SO_2$-piperdinyl, —$OCH_2CH_2CF_3$, cyclopropyl, cyclohexyl, morpholinyl, piperdinyl, azetidinyl, or pyrrolidinyl, wherein the cyclopropyl, cyclohexyl, morpholinyl, piperdinyl, piperdinyl of the —$SO_2$-piperdinyl, azetidinyl, and pyrrolidinyl are each optionally substituted with 1 to 3 $R^{1b}$; and each $R^{1b}$ is —F or —$CH_3$; or two $R^{1b}$, together with the atom to which they are attached, form cyclopropyl; and the remaining variables are as described in the twenty-first embodiment or first aspect or any alternative embodiments described therein. In another alternative twenty-second embodiment, for the compounds of Formula (I) or (IA), or a pharmaceutically acceptable salt thereof, $R^1$ is —$S(O)_2NHC(CH_3)_3$, —$SO_2$-cyclopentyl, —$SO_2$-piperdinyl, —$OCH_2CH_2CF_3$, —$OCH_2CH(OH)CF_3$, cyclopropyl, cyclohexyl, morpholinyl, piperdinyl, azetidinyl, 3H-diazirinyl, or pyrrolidinyl, wherein the cyclopropyl, cyclohexyl, morpholinyl, piperdinyl, piperdinyl of the —$SO_2$-piperdinyl, azetidinyl, 3H-diazirinyl, and pyrrolidinyl are each optionally substituted with 1 to 3 $R^{1b}$; and each $R^{1b}$ is —F, —CN, —$CF_3$, or —$CH_3$; or two $R^{1b}$, together with the atom to which they are attached, form cyclopropyl; and the remaining variables are as described in the twenty-first embodiment or first aspect or any alternative embodiments described therein.

In a twenty-third embodiment, for the compounds of Formula (I) or (IA), or a pharmaceutically acceptable salt thereof, $R^1$ is $C_{3-6}$cycloalkyl, 3- to 6-membered monocyclic heterocyclyl, or $SO_2R^{1a}$, wherein the $C_{3-6}$cycloalkyl and 3- to 6-membered monocyclic heterocyclyl are each optionally substituted with 1 to 3 $R^{1b}$; $R^{1a}$ is —$NHR^{N1b}$; $R^{N1b}$ is $C_{1-4}$alkyl; each $R^{1b}$ is independently halo; and the remaining variables are as described in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, or twenty-second embodiment or first aspect or any alternative embodiments described therein.

In a twenty-fourth embodiment, for the compounds of Formula (I) or (IA), or a pharmaceutically acceptable salt thereof, $R^1$ is —S(O)$_2$NHC(CH$_3$)$_3$, cyclohexyl, morpholinyl, or piperdinyl, wherein the cyclohexyl, morpholinyl, and piperdinyl are each optionally substituted with 1 to 3 $R^{1b}$; and each $R^{1b}$ is —F; and the remaining variables are as described in the twenty-third embodiment or first aspect or any alternative embodiments described therein.

In a twenty-fifth embodiment, for the compounds of Formula (I) or (IA), or a pharmaceutically acceptable salt thereof, $R^1$ is
—S(O)$_2$NHC(CH$_3$)$_3$, or $R^1$ is represented by the following structural formula:

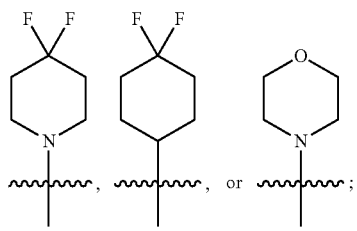

and the remaining variables are as described in the twenty-third embodiment or first aspect or any alternative embodiments described therein.

In a twenty-sixth embodiment, for the compounds of Formula (I) or (IA), or a pharmaceutically acceptable salt thereof, $R^2$ is H, C$_{1-3}$alkyl, SO$_2$R$^{2a}$, or NHSO$_2$R$^{2a}$, wherein the C$_{1-3}$alkyl is optionally substituted with 1 to 3 $R^{2b}$; $R^{2a}$ is C$_{1-4}$alkyl, —NHR$^{N2b}$, or 3- to 6-membered monocyclic heterocyclyl, wherein the C$_{1-3}$ alkyl and 3- to 6-membered monocyclic heterocyclyl are each optionally substituted with 1 to 3 $R^{2b}$; $R^{N2b}$ is C$_{1-3}$alkyl optionally substituted with 1 to 3 $R^{2b}$; each $R^{2b}$ is independently selected from hydroxy and C$_{1-3}$alkyl; and the remaining variables are as described in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, or twenty-fifth embodiment or first aspect or any alternative embodiments described therein. In an alternative twenty-sixth embodiment, for the compounds of Formula (I) or (IA), or a pharmaceutically acceptable salt thereof, $R^2$ is H, C$_{1-3}$alkyl, NR$^{N2a}$R$^{N2b}$, SO$_2$R$^{2a}$, S(O)(NH)R$^{2a}$, or NHSO$_2$R$^{2a}$, wherein the C$_{1-3}$alkyl is optionally substituted with 1 to 3 $R^{2b}$; $R^{2a}$ is C$_{1-4}$alkyl, —NHR$^{N2b}$, C$_{3-4}$cycloalkyl, or 3- to 6-membered monocyclic heterocyclyl, wherein the C$_{1-3}$ alkyl and 3- to 6-membered monocyclic heterocyclyl are each optionally substituted with 1 to 3 $R^{2b}$; $R^{N2a}$ and $R^{N2b}$ are each independently H or C$_{1-3}$alkyl optionally substituted with 1 to 3 $R^{2b}$; each $R^{2b}$ is independently selected from hydroxy, —N(R$^{N2c}$)$_2$ and C$_{1-3}$alkyl; each R$^{N2c}$ is independently H, C$_{1-3}$alkyl, —C(O)(C$_{1-3}$alkyl); and the remaining variables are as described in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, or twenty-fifth embodiment or first aspect or any alternative embodiments described therein.

In a twenty-seventh embodiment, for the compounds of Formula (I) or (IA), or a pharmaceutically acceptable salt thereof, $R^2$ is H, —NHS(O)$_2$CH$_3$, —NHS(O)$_2$CH$_2$CH$_2$OH, —NHS(O)$_2$C(CH$_3$)$_3$, —S(O)$_2$NHCH$_2$CH$_2$OH, —CH$_2$CH$_2$OH, or $R^2$ is represented by the following formula:

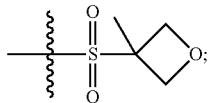 [SMILES: *S(=O)(=O)C1(C)COC1]

and the remaining variables are as described in the twenty-sixth embodiment or first aspect or any alternative embodiments described therein. In an alternative twenty-seventh embodiment, for the compounds of Formula (I) or (IA), or a pharmaceutically acceptable salt thereof, $R^2$ is H, —NHS(O)$_2$CH$_3$, —NHS(O)$_2$CH$_2$CH$_2$OH, —NHS(O)$_2$C(CH$_3$)$_3$, —NHS(O)$_2$NHCH$_2$CH$_2$OH, —S(O)$_2$NHCH$_2$CH$_2$OH, —CH$_2$CH$_2$OH, or $R^2$ is represented by the following formula:

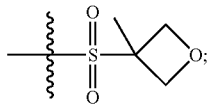 [SMILES: *S(=O)(=O)C1(C)COC1]

and the remaining variables are as described in the twenty-sixth embodiment or first aspect or any alternative embodiments described therein. In another alternative twenty-seventh embodiment, for the compounds of Formula (I) or (IA), or a pharmaceutically acceptable salt thereof, $R^2$ is H, —NHS(O)$_2$CH$_3$, —NHS(O)$_2$CH$_2$CH$_2$OH, —NHS(O)$_2$CH$_2$CH$_2$NH$_2$, —NHS(O)$_2$CH$_2$CH$_2$NHCH$_3$, —NHS(O)$_2$CH$_2$CH$_2$NHC(O)CH$_3$, —NHS(O)$_2$C(CH$_3$)$_3$, —NHS(O)$_2$NHCH$_3$, —NHS(O)$_2$NHCH$_2$CH$_2$OH, —NHS(O)$_2$N(CH$_3$)CH$_2$CH$_2$OH, —S(O)$_2$NHCH$_2$CH$_2$OH, —NHC(CH$_3$)$_2$CH$_2$OH, —S(O)(NH)-cyclopropyl, —S(O)$_2$CH$_2$CH$_2$OH, —CH$_2$CH$_2$OH, —N(CH$_3$)CH$_2$CH$_2$OH, or $R^2$ is represented by the following formula:

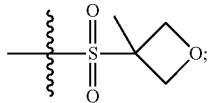 [SMILES: *S(=O)(=O)C1(C)COC1]

and
the remaining variables are as described in the twenty-sixth embodiment or first aspect or any alternative embodiments described therein.

In a twenty-eighth embodiment, for the compounds of Formula (I) or (IA), or a pharmaceutically acceptable salt thereof, $R^2$ is NHSO$_2$R$^{2a}$; $R^{2a}$ is C$_{1-4}$alkyl optionally substituted with 1 to 3 $R^{2b}$; each $R^{2b}$ is hydroxy; and the remaining variables are as described in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, or twenty-fifth embodiment or first aspect or any alternative embodiments described therein.

In a twenty-ninth embodiment, for the compounds of Formula (I) or (IA), or a pharmaceutically acceptable salt thereof, $R^2$ is —NHS(O)$_2$CH$_2$CH$_2$OH or —NHS(O)$_2$C(CH$_3$)$_3$; and the remaining variables are as described in the twenty-eighth embodiment or first aspect or any alternative embodiments described therein.

In a thirtieth embodiment, for the compounds of Formula (I) or (IA), or a pharmaceutically acceptable salt thereof, $R_4$ is H or $C_{1-3}$alkyl; and the remaining variables are as described in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, or twenty-ninth embodiment or first aspect or any alternative embodiments described therein.

In a thirty-first embodiment, for the compounds of Formula (I) or (IA), or a pharmaceutically acceptable salt thereof, $R^4$ is H or —CH$_3$; and the remaining variables are as described in the thirtieth embodiment or first aspect or any alternative embodiments described therein.

In a thirty-second embodiment, for the compounds of Formula (I) or (IA), or a pharmaceutically acceptable salt thereof, each $R^6$ is independently halo; and the remaining variables are as described in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, or thirty-first embodiment or first aspect or any alternative embodiments described therein.

In a thirty-third embodiment, for the compounds of Formula (I) or (IA), or a pharmaceutically acceptable salt thereof, each $R^6$ is —F; and the remaining variables are as described in the thirty-first embodiment or first aspect or any alternative embodiments described therein.

In a thirty-fourth embodiment, for the compounds of Formula (I) or (IA), or a pharmaceutically acceptable salt thereof, o is 0; and the remaining variables are as described in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, or thirty-first embodiment or first aspect or any alternative embodiments described therein.

In a thirty-fifth embodiment, the compound of the present disclosure is represented by Formula (II):

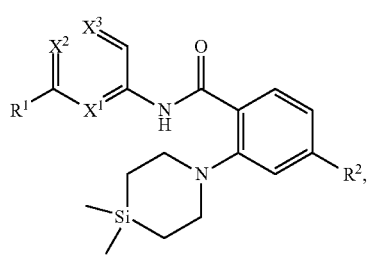

(II)

or a pharmaceutically acceptable salt thereof; wherein:
$X^1$ and $X^2$ are each independently CR$^5$ or N, and $X^3$ is CR$^4$ or N;
$R^1$ is $C_{3-6}$cycloalkyl, 3- to 6-membered monocyclic heterocyclyl, or SO$_2$R$^{1a}$, wherein the $C_{3-6}$cycloalkyl and 3- to 6-membered monocyclic heterocyclyl are each optionally substituted with 1 to 3 R$^{1b}$;
$R^{1a}$ is —NHR$^{N1b}$;
$R^{N1b}$ is $C_{1-4}$alkyl;
each $R^{1b}$ is independently halo;
$R^2$ is NHSO$_2$R$^{2a}$;
$R^{2a}$ is $C_{1-4}$alkyl optionally substituted with 1 or 2 R$^{2b}$;
each $R^{2b}$ is hydroxy;
$R^4$ is H or $C_{1-3}$alkyl;
$R^5$ is H or $C_{1-3}$alkyl; and the remaining variables are as described in the first embodiment or first aspect. In some embodiments, $X^3$ is CR$^4$. In an alternative thirty-fifth embodiment, the compound of the present disclosure is represented by Formula (II) or (III):

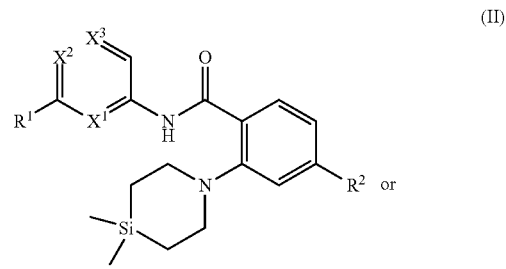

(II)

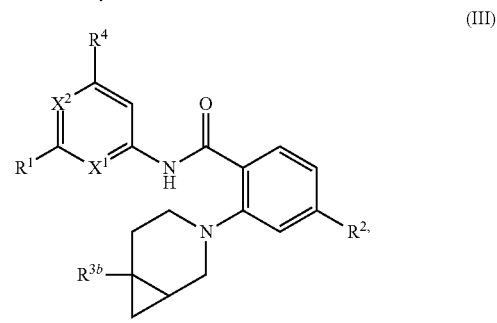

(III)

or a pharmaceutically acceptable salt thereof; wherein:
$X^1$ and $X^2$ are each independently CR$^5$ or N, and $X^3$ is CR$^4$ or N;
$R^1$ is $C_{3-6}$cycloalkyl, 3- to 6-membered monocyclic heterocyclyl, or SO$_2$R$^{1a}$; wherein the $C_{3-6}$cycloalkyl and 3- to 6-membered monocyclic heterocyclyl are each optionally substituted with 1 to 3 R$^{1b}$;
$R^{1a}$ is —NHR$^{N1b}$;
$R^{N1b}$ is $C_{1-4}$alkyl;
each $R^{1b}$ is independently halo;
$R^2$ is NHSO$_2$R$^{2a}$;
$R^{2a}$ is $C_{1-4}$alkyl optionally substituted with 1 or 2 R$^{2b}$;
each $R^{2b}$ is hydroxy;
$R^{3b}$ is H, $C_{1-3}$alkyl, or $C_{1-3}$haloalkyl;
$R^4$ is H or $C_{1-3}$alkyl;
$R^5$ is H or $C_{1-3}$alkyl; and the remaining variables are as described in the first embodiment or first aspect. In some embodiments, $X^3$ is CR$^4$.

In another alternative thirty-fifth embodiment, the compound of the present disclosure is represented by Formula (II), (III), or (IV):

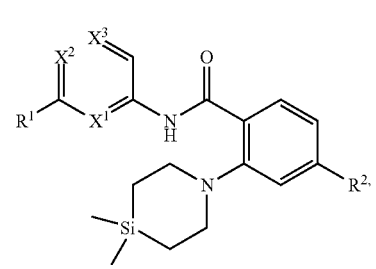
(II)

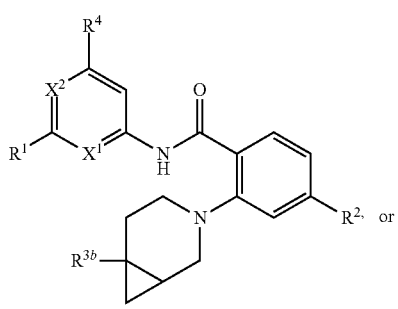
(III)

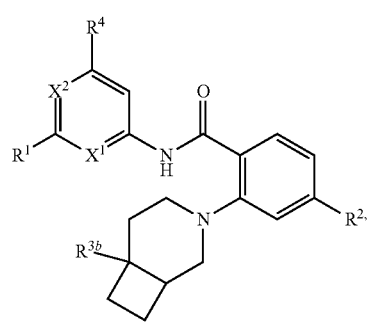
(IV)

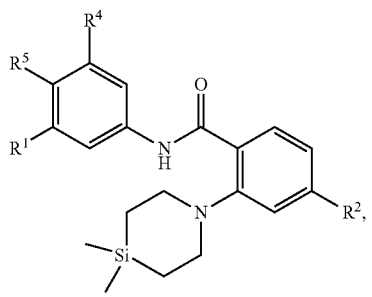
(IIA)

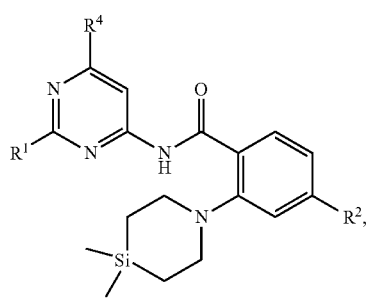
(IIB)

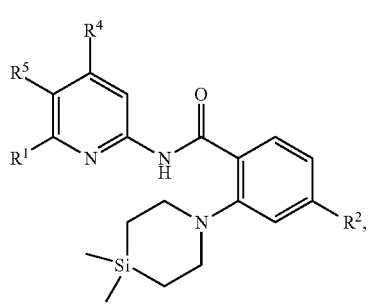
(IIC)

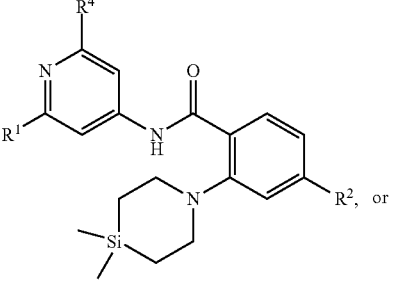
(IID)

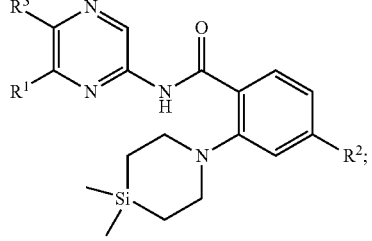
(IIE)

or a pharmaceutically acceptable salt thereof; wherein:
$X^1$ and $X^2$ are each independently $CR^5$ or N, and $X^3$ is $CR^4$ or N;
$R^1$ is $C_{3-6}$cycloalkyl, 3- to 6-membered monocyclic heterocyclyl, or $SO_2R^{1a}$, wherein the $C_{3-6}$cycloalkyl and 3- to 6-membered monocyclic heterocyclyl are each optionally substituted with 1 to 3 $R^{1b}$;
$R^{1a}$ is —$NHR^{N1b}$;
$R^{N1b}$ is $C_{1-4}$alkyl;
each $R^{1b}$ is independently halo;
$R^2$ is $NHSO_2R^{2a}$;
$R^{2a}$ is $C_{1-4}$alkyl optionally substituted with 1 or 2 $R^{2b}$;
each $R^{2b}$ is hydroxy;
$R^{3b}$ is H, halo, $C_{1-3}$alkyl, or $C_{1-3}$haloalkyl;
$R^4$ is H or $C_{1-3}$alkyl;
$R^5$ is H or $C_{1-3}$alkyl; and the remaining variables are as described in the first embodiment or first aspect. In some embodiments, $X^3$ is $CR^4$.

In a thirty-sixth embodiment, the compound of the present disclosure is represented by Formula (IIA), (IIB), (IIC), (IID) or (IIE):

or a pharmaceutically acceptable salt thereof; wherein the variables $R^1$, $R^2$, $R^4$, and $R^5$ depicted in Formula (IIA), (IIB), (IIC), (IID) or (IIE) are as described in the thirty-fifth embodiment or first aspect or any alternative embodiments described therein. In some embodiments, $R^5$ is H. In an alternative thirty-sixth embodiment, the compound of the present disclosure is represented by Formula (IIA), (IIB), (IIC), (IID), (IIE), or (IIIA):

(IIA)
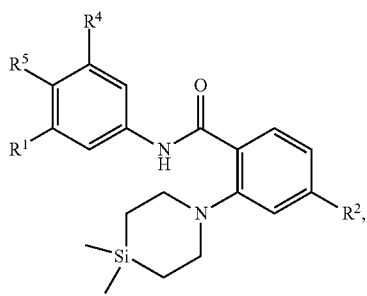

(IIB)
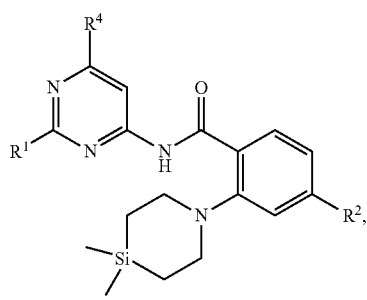

(IIC)
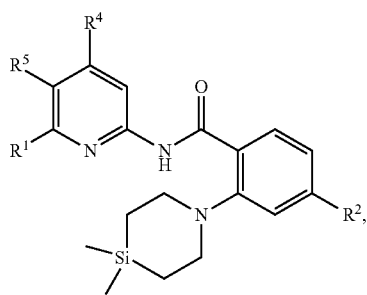

(IID)
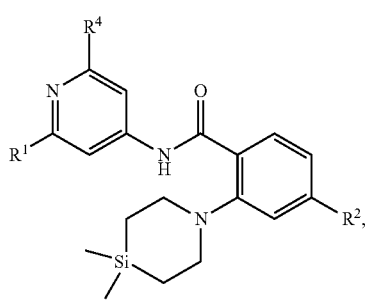

(IIE)
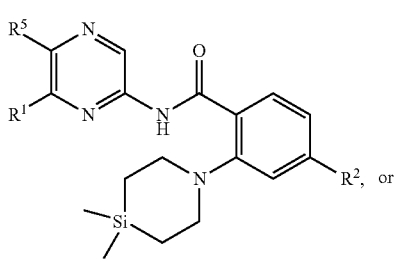

(IIIA)
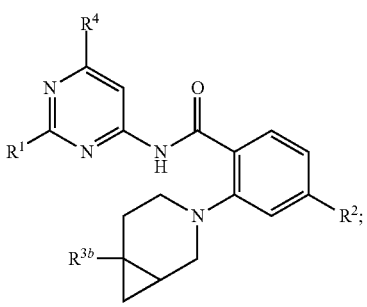

or a pharmaceutically acceptable salt thereof; wherein the variables $R^1$, $R^2$, $R^{3b}$, $R^4$, and $R^5$ depicted in Formula (IIA), (IIB), (IIC), (IID), (IIE), or (IIIA) are as described in the thirty-fifth embodiment or first aspect or any alternative embodiments described therein. In some embodiments, $R^5$ is H. In another alternative thirty-sixth embodiment, the compound of the present disclosure is represented by Formula (IIA), (IIB), (IIC), (IID) (IIE), (IIIA), or (IVA):

(IIA)
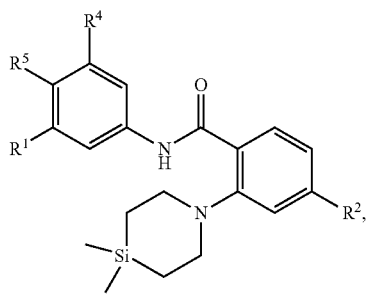

(IIB)
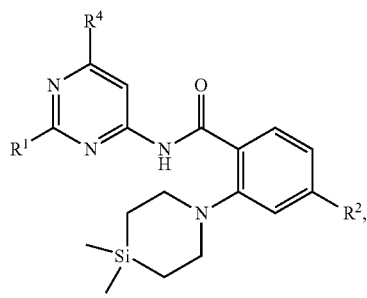

(IIC)
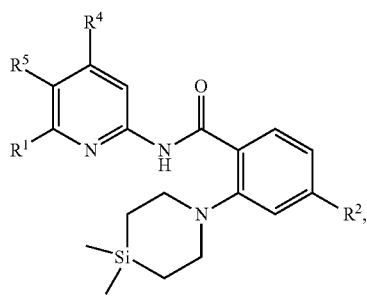

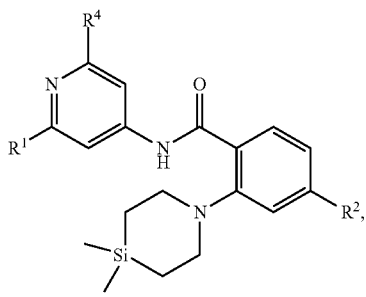

(IID)

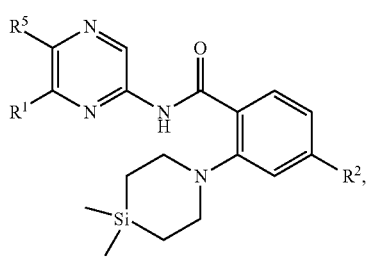

(IIE)

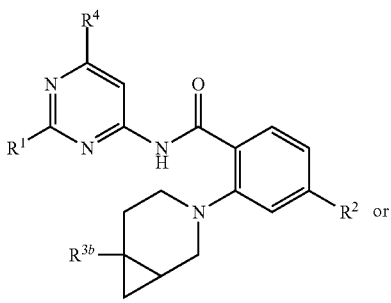

(IIIA)

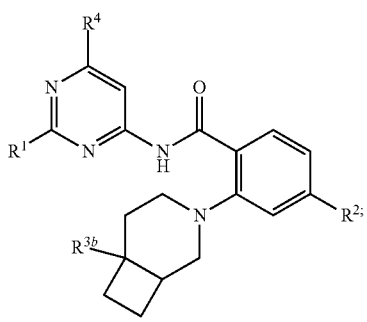

(IVA)

or a pharmaceutically acceptable salt thereof; wherein the variables $R^1$, $R^2$, $R^{3b}$, $R^4$, and $R^5$ depicted in Formula (IIA), (IIB), (IIC), (IID), (IIE), (IIIA), or (IVA) are as described in the thirty-fifth embodiment or first aspect or any alternative embodiments described therein. In yet another alternative thirty-sixth embodiment, the compound of the present disclosure is represented by Formula (IIIA):

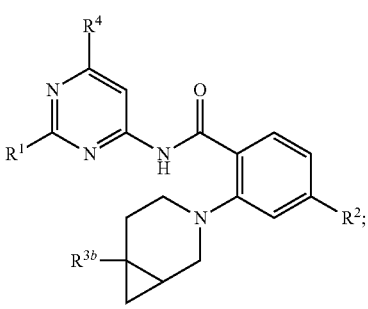

(IIIA)

or a pharmaceutically acceptable salt thereof; wherein the variables $R^1$, $R^2$, $R^{3b}$, and $R^4$ depicted in Formula (IIIA) are as described in the thirty-fifth embodiment or first aspect or any alternative embodiments described therein. In yet another alternative thirty-sixth embodiment, the compound of the present disclosure is represented by Formula (IVA):

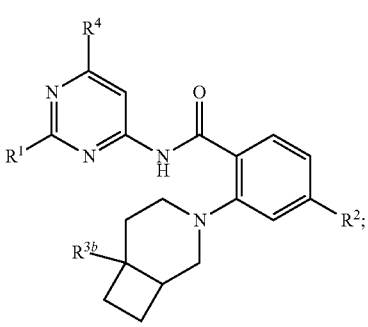

(IVA)

or a pharmaceutically acceptable salt thereof; wherein the variables $R^1$, $R^2$, $R^{3b}$, and $R^4$ depicted in Formula (IVA) are as described in the thirty-fifth embodiment or first aspect or any alternative embodiments described therein.

In a thirty-seventh embodiment, for the compounds of Formula (II), (IIA), (IIB), (IIC), (IID) or (IIE), or a pharmaceutically acceptable salt thereof, $R^1$ is —S(O)$_2$NHC(CH$_3$)$_3$, cyclohexyl, morpholinyl, or piperdinyl, wherein the cyclohexyl, morpholinyl, and piperdinyl are each optionally substituted with 1 to 2 $R^{1b}$; and each $R^{1b}$ is —F; and the remaining variables are as described in the thirty-fifth or thirty-sixth embodiment or first aspect or any alternative embodiments described therein. In an alternative thirty-seventh embodiment, for the compounds of Formula (II), (IIA), (IIB), (IIC), (IID), (IIE), (IIIA) or (IVA) or a pharmaceutically acceptable salt thereof, $R^1$ is —S(O)$_2$NHC(CH$_3$)$_3$, cyclohexyl, morpholinyl, or piperdinyl, wherein the cyclohexyl, morpholinyl, and piperdinyl are each optionally substituted with 1 to 2 $R^{1b}$; and each $R^{1b}$ is —F; and the remaining variables are as described in the thirty-fifth or thirty-sixth embodiment or first aspect or any alternative embodiments described therein.

In a thirty-eighth embodiment, for the compounds of Formula (II), (IIA), (IIB), (IIC), (IID) or (IIE), or a pharmaceutically acceptable salt thereof, $R^1$ is —S(O)$_2$NHC(CH$_3$)$_3$, or $R^1$ is represented by the following structural formula:

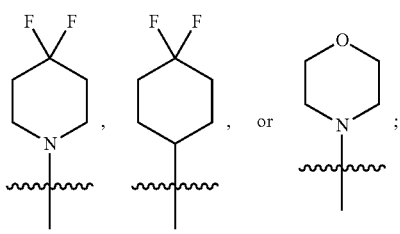

and the remaining variables are as described in the thirty-seventh embodiment or first aspect or any alternative embodiments described therein. In an alternative thirty-eighth embodiment, for the compounds of Formula (II), (IIA), (JIB), (IIC), (IID), (IIE), (IIIA) or (IVA), or a pharmaceutically acceptable salt thereof, $R^1$ is —S(O)$_2$NHC (CH$_3$)$_3$, or $R^1$ is represented by the following structural formula:

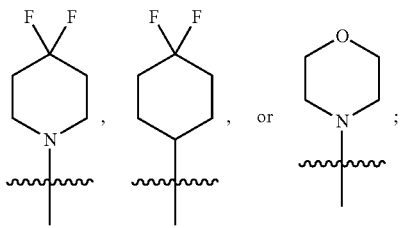

and the remaining variables are as described in the thirty-seventh embodiment or first aspect or any alternative embodiments described therein.

In a thirty-ninth embodiment, for the compounds of Formula (II), (IIA), (IIB), (IIC), (IID) or (IIE), or a pharmaceutically acceptable salt thereof, $R^2$ is —NHS(O)$_2$CH$_2$CH$_2$OH or —NHS(O)$_2$C(CH$_3$)$_3$; and the remaining variables are as described in the thirty-fifth, thirty-sixth, thirty-seventh, or thirty-eighth embodiment or first aspect. In an alternative thirty-ninth embodiment, for the compounds of Formula (II), (IIA), (IIB), (IIC), (IID), (IIE), (IIIA) or (IVA), or a pharmaceutically acceptable salt thereof, $R^2$ is —NHS(O)$_2$CH$_2$CH$_2$OH or —NHS(O)$_2$C(CH$_3$)$_3$; and the remaining variables are as described in the thirty-fifth, thirty-sixth, thirty-seventh, or thirty-eighth embodiment or first aspect or any alternative embodiments described therein.

In a fortieth embodiment, for the compounds of Formula (TI), (IIA), (IIB), (IIC), (IID) or (IIE), or a pharmaceutically acceptable salt thereof, $R^4$ and $R^5$ are each H or —CH$_3$; and the remaining variables are as described in the thirty-fifth, thirty-sixth, thirty-seventh, thirty-eighth, or thirty-ninth embodiment or first aspect or any alternative embodiments described therein. In some embodiments, $R^4$ is H or —CH$_3$ and $R^5$ is H. In other embodiments, $R^4$ and $R^5$ are both H. In an alternative fortieth embodiment, for the compounds of Formula (II), (IIA), (IIB), (IIC), (IID), (IIE), (IIIA) or (IVA), or a pharmaceutically acceptable salt thereof, $R^4$ and $R^5$ are each H or —CH$_3$; and the remaining variables are as described in the thirty-fifth, thirty-sixth, thirty-seventh, thirty-eighth, or thirty-ninth embodiment or first aspect or any alternative embodiments described therein. In some embodiments, $R^4$ is H or —CH$_3$ and $R^5$ is H. In other embodiments, $R^4$ and $R^5$ are both H.

In a forty-first embodiment, for the compounds of Formula (IIIA) or (IVA), or a pharmaceutically acceptable salt thereof, $R^{3b}$ is H, —CH$_3$, or —CHF$_2$; and the remaining variables are as described in the thirty-fifth, thirty-sixth, thirty-seventh, thirty-eighth, thirty-ninth, or fortieth embodiment or first aspect. In an alternative forty-first embodiment, for the compounds of Formula (IIIA) or (IVA), or a pharmaceutically acceptable salt thereof, $R^{3b}$ is H, —F, —CH$_3$, —CH$_2$F, or —CHF$_2$; and the remaining variables are as described in the thirty-fifth, thirty-sixth, thirty-seventh, thirty-eighth, thirty-ninth, or fortieth embodiment or first aspect.

In a forty-second embodiment, the present disclosure provides a compound described herein (e.g., a compound of any one of Examples 1-134), or a pharmaceutically acceptable salt thereof.

In an alternative forty-second embodiment, the present disclosure provides a compound selected from the group consisting of:

N-(2-(4,4-difluorocyclohexyl)-6-methylpyrimidin-4-yl)-2-(4,4-dimethyl-1,4-azasilinan-1-yl)-4-((2-hydroxyethyl)sulfonamido)benzamide;

2-(4,4-dimethyl-1,4-azasilinan-1-yl)-4-((2-hydroxyethyl)sulfonamido)-N-(5-methyl-6-morpholinopyridin-2-yl)benzamide;

N-(6-(4,4-difluoropiperidin-1-yl)pyridin-2-yl)-2-(4,4-dimethyl-1,4-azasilinan-1-yl)-4-((2-hydroxyethyl)sulfonamido)benzamide;

N-(3-(N-(tert-butyl)sulfamoyl)phenyl)-2-(4,4-dimethyl-1,4-azasilinan-1-yl)-4-((1,1-dimethylethyl)sulfonamido)benzamide;

2-(4,4-dimethyl-1,4-azasilinan-1-yl)-4-((2-hydroxyethyl)sulfonamido)-N-(4-methyl-6-morpholinopyridin-2-yl)benzamide;

N-(3-(4,4-difluoropiperidin-1-yl)phenyl)-2-(4,4-dimethyl-1,4-azasilinan-1-yl)-4-((2-hydroxyethyl)sulfonamido)benzamide;

N-(2-(4,4-difluoropiperidin-1-yl)pyridin-4-yl)-2-(4,4-dimethyl-1,4-azasilinan-1-yl)-4-((2-hydroxyethyl)sulfonamido)benzamide;

N-(6-(4,4-difluoropiperidin-1-yl)-4-methylpyridin-2-yl)-2-(4,4-dimethyl-1,4-azasilinan-1-yl)-4-((2-hydroxyethyl)sulfonamido)benzamide;

N-(2-(4,4-difluoropiperidin-1-yl)-6-methylpyrimidin-4-yl)-2-(4,4-dimethyl-1,4-azasilinan-1-yl)-4-((2-hydroxyethyl)sulfonamido)benzamide;

2-(4,4-dimethyl-1,4-azasilinan-1-yl)-4-((2-hydroxyethyl)sulfonamido)-N-(2-(3,3,3-trifluoropropoxy)pyrimidin-4-yl)benzamide;

2-(4,4-dimethyl-1,4-azasilinan-1-yl)-4-((2-hydroxyethyl)sulfonamido)-N-(2-(2-methylmorpholino)pyrimidin-4-yl)benzamide;

N-(2-(4,4-difluoropiperidin-1-yl)pyrimidin-4-yl)-1-(2-hydroxyethyl)-6-(6-azaspiro[2.5]octan-6-yl)-1,3-dihydro-2l2-indazole-5-carboxamide;

N-(2-(4,4-difluoropiperidin-1-yl)pyrimidin-4-yl)-2-(4,4-dimethyl-1,4-azasilinan-1-yl)-5-fluoro-4-((2-hydroxyethyl)sulfonamido)benzamide;

N-(6-(4,4-difluoropiperidin-1-yl)pyridin-2-yl)-2-(4,4-dimethyl-1,4-azasilinan-1-yl)-5-fluoro-4-((2-hydroxyethyl)sulfonamido)benzamide;

N-(2-cyclopropylpyrimidin-4-yl)-2-(4,4-dimethyl-1,4-azasilinan-1-yl)-4-((2-hydroxyethyl)sulfonamido)benzamide;

2-(4,4-dimethyl-1,4-azasilinan-1-yl)-4-((2-hydroxyethyl)sulfonamido)-N-(6-(3,3,3-trifluoropropoxy)pyridin-2-yl)benzamide;

(S)-2-(4,4-dimethyl-1,4-azasilinan-1-yl)-4-((2-hydroxyethyl)sulfonamido)-N-(6-(2-methylmorpholino)pyridin-2-yl)benzamide;

2-(4,4-dimethyl-1,4-azasilinan-1-yl)-4-(N-(2-hydroxyethyl)sulfamoyl)-N-(6-(2-methylmorpholino)pyridin-2-yl)benzamide;

(R)-2-(4,4-dimethyl-1,4-azasilinan-1-yl)-4-((2-hydroxyethyl)sulfonamido)-N-(6-(2-methylmorpholino)pyridin-2-yl)benzamide;

N-(6-(3,3-difluoroazetidin-1-yl)-4-methylpyridin-2-yl)-2-(4,4-dimethyl-1,4-azasilinan-1-yl)-4-(methylsulfonamido)benzamide;

2-(4,4-dimethyl-1,4-azasilinan-1-yl)-4-((2-hydroxyethyl)sulfonamido)-N-(6-methyl-2-(5-azaspiro[2.4]heptan-5-yl)pyrimidin-4-yl)benzamide;

N-(6-(cyclopentylsulfonyl)pyridin-2-yl)-2-(4,4-dimethyl-1,4-azasilinan-1-yl)-4-((2-hydroxyethyl)sulfonamido)benzamide;

2-(4,4-difluoropiperidin-1-yl)-N-(2-(4,4-dimethyl-1,4-azasilinan-1-yl)-4-((2-hydroxyethyl)sulfonamido)phenyl)pyrimidine-4-carboxamide;

N-(3-(N-(tert-butyl)sulfamoyl)phenyl)-2-(4,4-dimethyl-1,4-azasilinan-1-yl)-4-((3-methyloxetan-3-yl)sulfonyl)benzamide;

N-(2-(4,4-difluoropiperidin-1-yl)pyrimidin-4-yl)-1-(2-hydroxyethyl)-4-(6-azaspiro[2.5]octan-6-yl)-1H-indazole-5-carboxamide;

N-(2-(4,4-difluoropiperidin-1-yl)-6-methylpyrimidin-4-yl)-3-(4,4-dimethyl-1,4-azasilinan-1-yl)-5-((2-hydroxyethyl)sulfonamido)picolinamide;

N-(3-((4,4-difluoropiperidin-1-yl)sulfonyl)phenyl)-2-(4,4-dimethyl-1,4-azasilinan-1-yl)nicotinamide;

2-(7,7-difluoro-6-methyl-3-azabicyclo[4.1.0]heptan-3-yl)-N-(2-(4,4-difluoropiperidin-1-yl)-6-methylpyrimidin-4-yl)-4-((2-hydroxyethyl)sulfonamido)benzamide;

2-((1S,6R)-6-(difluoromethyl)-3-azabicyclo[4.1.0]heptan-3-yl)-N-(2-(4,4-difluoropiperidin-1-yl)-6-methylpyrimidin-4-yl)-4-((2-hydroxyethyl)sulfonamido)benzamide;

2-((1R,6S)-6-(difluoromethyl)-3-azabicyclo[4.1.0]heptan-3-yl)-N-(2-(4,4-difluoropiperidin-1-yl)-6-methylpyrimidin-4-yl)-4-((2-hydroxyethyl)sulfonamido)benzamide;

N-(2-(4,4-difluoropiperidin-1-yl)-6-methylpyrimidin-4-yl)-4-((2-hydroxyethyl)sulfonamido)-2-(6-(hydroxymethyl)-3-azabicyclo[4.1.0]heptan-3-yl)benzamide;

N-(2-(4,4-difluoropiperidin-1-yl)-6-methylpyrimidin-4-yl)-2-fluoro-4-((2-hydroxyethyl)sulfonamido)-6-((1R,6R)-6-methyl-3-azabicyclo[4.1.0]heptan-3-yl)benzamide;

N-(2-(4,4-difluoropiperidin-1-yl)-6-methylpyrimidin-4-yl)-2-fluoro-4-((2-hydroxyethyl)sulfonamido)-6-((1S,6S)-6-methyl-3-azabicyclo[4.1.0]heptan-3-yl)benzamide;

N-(2-(4,4-difluoropiperidin-1-yl)-6-methylpyrimidin-4-yl)-2-((1R,6R)-6-methyl-3-azabicyclo[4.1.0]heptan-3-yl)-4-(methylsulfonamido)benzamide;

N-(2-(4,4-difluoropiperidin-1-yl)-6-methylpyrimidin-4-yl)-2-((1S,6S)-6-methyl-3-azabicyclo[4.1.0]heptan-3-yl)-4-(methylsulfonamido)benzamide;

2-(3-azabicyclo[4.1.0]heptan-3-yl)-N-(2-(4,4-difluoropiperidin-1-yl)-6-methylpyrimidin-4-yl)-4-((2-hydroxyethyl)sulfonamido)benzamide;

N-(2-(4,4-difluoropiperidin-1-yl)-6-methylpyrimidin-4-yl)-4-((2-hydroxyethyl)sulfonamido)-2-((1S,6S)-6-methyl-3-azabicyclo[4.1.0]heptan-3-yl)benzamide;

N-(2-(4,4-difluoropiperidin-1-yl)-6-methylpyrimidin-4-yl)-4-((2-hydroxyethyl)sulfonamido)-2-((1R,6R)-6-methyl-3-azabicyclo[4.1.0]heptan-3-yl)benzamide;

N-(2-(4,4-difluoropiperidin-1-yl)-6-methylpyrimidin-4-yl)-4-((2-hydroxyethyl)sulfonamido)-2-(6-methyl-3-azabicyclo[4.1.0]heptan-3-yl)benzamide;

N-(2-(4,4-difluoropiperidin-1-yl)-6-methylpyrimidin-4-yl)-4-((2-hydroxyethyl)sulfonamido)-2-((1R,6S)-6-(hydroxymethyl)-3-azabicyclo[4.1.0]heptan-3-yl)benzamide;

N-(2-(4,4-difluoropiperidin-1-yl)-6-methylpyrimidin-4-yl)-4-((2-hydroxyethyl)sulfonamido)-2-((1S,6R)-6-(hydroxymethyl)-3-azabicyclo[4.1.0]heptan-3-yl)benzamide;

N-(2-(4,4-difluoropiperidin-1-yl)-6-methylpyrimidin-4-yl)-4-((N-(2-hydroxyethyl)sulfamoyl)amino)-2-((1R,6R)-6-methyl-3-azabicyclo[4.1.0]heptan-3-yl)benzamide;

N-(2-(4,4-difluoropiperidin-1-yl)-6-methylpyrimidin-4-yl)-4-((N-(2-hydroxyethyl)sulfamoyl)amino)-2-((1S,6S)-6-methyl-3-azabicyclo[4.1.0]heptan-3-yl)benzamide;

2-(3-azabicyclo[4.1.0]heptan-3-yl)-N-(3-((4,4-difluoropiperidin-1-yl)sulfonyl)phenyl)nicotinamide;

N-(3-((4,4-difluoropiperidin-1-yl)sulfonyl)phenyl)-2-(6-methyl-3-azabicyclo[4.1.0]heptan-3-yl)nicotinamide;

N-(3-((4,4-difluoropiperidin-1-yl)sulfonyl)phenyl)-2-((1S,6S)-6-methyl-3-azabicyclo[4.1.0]heptan-3-yl)nicotinamide;

N-(3-((4,4-difluoropiperidin-1-yl)sulfonyl)phenyl)-2-((1R,6R)-6-methyl-3-azabicyclo[4.1.0]heptan-3-yl)nicotinamide;

2-((1R,6S)-6-(difluoromethyl)-3-azabicyclo[4.1.0]heptan-3-yl)-N-(6-(4,4-difluoropiperidin-1-yl)-4-methylpyridin-2-yl)-4-((2-hydroxyethyl)sulfonamido)benzamide;

N-(2-(4,4-difluoropiperidin-1-yl)-6-methylpyrimidin-4-yl)-4-(N-(2-hydroxyethyl)sulfamoyl)-2-((1S,6S)-6-methyl-3-azabicyclo[4.1.0]heptan-3-yl)benzamide;

N-(2-(4,4-difluoropiperidin-1-yl)-6-methylpyrimidin-4-yl)-4-(N-(2-hydroxyethyl)sulfamoyl)-2-((1R,6R)-6-methyl-3-azabicyclo[4.1.0]heptan-3-yl)benzamide;

2-((1S,6R)-6-(difluoromethyl)-3-azabicyclo[4.1.0]heptan-3-yl)-N-(2-(4,4-difluoropiperidin-1-yl)-6-methylpyrimidin-4-yl)-4-(methylsulfonamido)benzamide;

2-((1R,6S)-6-(difluoromethyl)-3-azabicyclo[4.1.0]heptan-3-yl)-N-(2-(4,4-difluoropiperidin-1-yl)-6-methylpyrimidin-4-yl)-4-(methylsulfonamido)benzamide;

2-((1S,6R)-6-(difluoromethyl)-3-azabicyclo[4.1.0]heptan-3-yl)-N-(2-(4,4-difluoropiperidin-1-yl)-6-methylpyrimidin-4-yl)-4-((N-(2-hydroxyethyl)sulfamoyl)amino)benzamide;

2-((1R,6S)-6-(difluoromethyl)-3-azabicyclo[4.1.0]heptan-3-yl)-N-(2-(4,4-difluoropiperidin-1-yl)-6-methylpyrimidin-4-yl)-4-((N-(2-hydroxyethyl)sulfamoyl)amino)benzamide;

N-(2-(4,4-difluorocyclohexyl)-6-methylpyrimidin-4-yl)-2-((1S,6R)-6-(difluoromethyl)-3-azabicyclo[4.1.0]heptan-3-yl)-4-((2-hydroxyethyl)sulfonamido)benzamide;

N-(2-(4,4-difluorocyclohexyl)-6-methylpyrimidin-4-yl)-2-((1R,6S)-6-(difluoromethyl)-3-azabicyclo[4.1.0]heptan-3-yl)-4-((2-hydroxyethyl)sulfonamido)benzamide;

2-((1S,6R)-6-(difluoromethyl)-3-azabicyclo[4.1.0]heptan-3-yl)-N-(2-(4,4-difluoropiperidin-1-yl)pyrimidin-4-yl)-4-((2-hydroxyethyl)sulfonamido)benzamide;

2-((1R,6S)-6-(difluoromethyl)-3-azabicyclo[4.1.0]heptan-3-yl)-N-(2-(4,4-difluoropiperidin-1-yl)pyrimidin-4-yl)-4-((2-hydroxyethyl)sulfonamido)benzamide;

N-(2-(4,4-difluorocyclohexyl)-6-methylpyrimidin-4-yl)-4-((2-hydroxyethyl)sulfonamido)-2-((1S,6S)-6-methyl-3-azabicyclo[4.1.0]heptan-3-yl)benzamide;

N-(2-(4,4-difluorocyclohexyl)-6-methylpyrimidin-4-yl)-4-((2-hydroxyethyl)sulfonamido)-2-((1R,6R)-6-methyl-3-azabicyclo[4.1.0]heptan-3-yl)benzamide;

2-((1S,6R)-6-(difluoromethyl)-3-azabicyclo[4.1.0]heptan-3-yl)-N-(6-(4,4-difluoropiperidin-1-yl)pyridin-2-yl)-4-((2-hydroxyethyl)sulfonamido)benzamide;

2-((1S,6R)-6-(difluoromethyl)-3-azabicyclo[4.1.0]heptan-3-yl)-N-(6-(4,4-difluoropiperidin-1-yl)-4-methylpyridin-2-yl)-4-((2-hydroxyethyl)sulfonamido)benzamide;

2-((1R,6S)-6-(difluoromethyl)-3-azabicyclo[4.1.0]heptan-3-yl)-N-(6-(4,4-difluoropiperidin-1-yl)pyridin-2-yl)-4-((2-hydroxyethyl)sulfonamido)benzamide;

2-((1S,6R)-6-(difluoromethyl)-3-azabicyclo[4.1.0]heptan-3-yl)-4-((2-hydroxyethyl)sulfonamido)-N-(6-methyl-2-((S)-3,3,3-trifluoro-2-hydroxypropoxy)pyrimidin-4-yl)benzamide;

2-((1R,6S)-6-(difluoromethyl)-3-azabicyclo[4.1.0]heptan-3-yl)-4-((2-hydroxyethyl)sulfonamido)-N-(6-methyl-2-((S)-3,3,3-trifluoro-2-hydroxypropoxy)pyrimidin-4-yl)benzamide;

2-((1S,6R)-6-(difluoromethyl)-3-azabicyclo[4.1.0]heptan-3-yl)-N-(2-(4,4-difluoropiperidin-1-yl)pyrimidin-4-yl)-6-fluoro-4-((2-hydroxyethyl)sulfonamido)benzamide;

2-((1R,6S)-6-(difluoromethyl)-3-azabicyclo[4.1.0]heptan-3-yl)-N-(2-(4,4-difluoropiperidin-1-yl)pyrimidin-4-yl)-6-fluoro-4-((2-hydroxyethyl)sulfonamido)benzamide;

2-((1S,6R)-6-(difluoromethyl)-3-azabicyclo[4.1.0]heptan-3-yl)-N-(2-(4,4-difluoropiperidin-1-yl)-6-methylpyrimidin-4-yl)-6-fluoro-4-((2-hydroxyethyl)sulfonamido)benzamide;

2-((1R,6S)-6-(difluoromethyl)-3-azabicyclo[4.1.0]heptan-3-yl)-N-(2-(4,4-difluoropiperidin-1-yl)-6-methylpyrimidin-4-yl)-6-fluoro-4-((2-hydroxyethyl)sulfonamido)benzamide;

2-((1S,6R)-6-(difluoromethyl)-3-azabicyclo[4.1.0]heptan-3-yl)-4-((2-hydroxyethyl)sulfonamido)-N-(6-methyl-2-((R)-3,3,3-trifluoro-2-hydroxypropoxy)pyrimidin-4-yl)benzamide;

2-((1R,6S)-6-(difluoromethyl)-3-azabicyclo[4.1.0]heptan-3-yl)-4-((2-hydroxyethyl)sulfonamido)-N-(6-methyl-2-((R)-3,3,3-trifluoro-2-hydroxypropoxy)pyrimidin-4-yl)benzamide;

N-(2-(4,4-difluorocyclohexyl)pyrimidin-4-yl)-2-((1S,6R)-6-(difluoromethyl)-3-azabicyclo[4.1.0]heptan-3-yl)-4-((2-hydroxyethyl)sulfonamido)benzamide;

N-(2-(4,4-difluorocyclohexyl)pyrimidin-4-yl)-2-((1R,6S)-6-(difluoromethyl)-3-azabicyclo[4.1.0]heptan-3-yl)-4-((2-hydroxyethyl)sulfonamido)benzamide;

2-((1S,6R)-6-(difluoromethyl)-3-azabicyclo[4.1.0]heptan-3-yl)-N-(2-(4,4-difluoropiperidin-1-yl)-6-methylpyrimidin-4-yl)-4-(N-(2-hydroxyethyl)sulfamoyl)benzamide;

2-((1R,6S)-6-(difluoromethyl)-3-azabicyclo[4.1.0]heptan-3-yl)-N-(2-(4,4-difluoropiperidin-1-yl)-6-methylpyrimidin-4-yl)-4-(N-(2-hydroxyethyl)sulfamoyl)benzamide;

2-((1S,6R)-6-(1,1-difluoroethyl)-3-azabicyclo[4.1.0]heptan-3-yl)-N-(2-(4,4-difluoropiperidin-1-yl)-6-methylpyrimidin-4-yl)-4-((2-hydroxyethyl)sulfonamido)benzamide;

2-((1R,6S)-6-(1,1-difluoroethyl)-3-azabicyclo[4.1.0]heptan-3-yl)-N-(2-(4,4-difluoropiperidin-1-yl)-6-methylpyrimidin-4-yl)-4-((2-hydroxyethyl)sulfonamido)benzamide;

N-(2-(4,4-difluoropiperidin-1-yl)-6-methylpyrimidin-4-yl)-4-((2-hydroxyethyl)sulfonamido)-2-((1R,6R)-6-methoxy-3-azabicyclo[4.1.0]heptan-3-yl)benzamide;

N-(2-(4,4-difluoropiperidin-1-yl)-6-methylpyrimidin-4-yl)-4-((2-hydroxyethyl)sulfonamido)-2-((1S,6S)-6-methoxy-3-azabicyclo[4.1.0]heptan-3-yl)benzamide;

2-((1S,6R)-6-(difluoromethyl)-3-azabicyclo[4.1.0]heptan-3-yl)-N-(6-(4,4-difluoropiperidin-1-yl)pyridin-2-yl)-6-fluoro-4-((2-hydroxyethyl)sulfonamido)benzamide;

2-((1R,6S)-6-(difluoromethyl)-3-azabicyclo[4.1.0]heptan-3-yl)-N-(6-(4,4-difluoropiperidin-1-yl)pyridin-2-yl)-6-fluoro-4-((2-hydroxyethyl)sulfonamido)benzamide;

N-(2-(4,4-difluoropiperidin-1-yl)-6-methylpyrimidin-4-yl)-4-((2-hydroxyethyl)sulfonamido)-2-((1R,6S)-6-(trifluoromethyl)-3-azabicyclo[4.1.0]heptan-3-yl)benzamide;

N-(2-(4,4-difluoropiperidin-1-yl)-6-methylpyrimidin-4-yl)-4-((2-hydroxyethyl)sulfonamido)-2-((1S,6R)-6-(trifluoromethyl)-3-azabicyclo[4.1.0]heptan-3-yl)benzamide;

2-(4,4-dimethyl-1,4-azasilinan-1-yl)-4-((2-hydroxyethyl)sulfonamido)-N-(3-(3-(trifluoromethyl)-3H-diazirin-3-yl)phenyl)benzamide;

N-(2-(4,4-dimethyl-1,4-azasilinan-1-yl)-4-((2-hydroxyethyl)sulfonamido)phenyl)-2-(3,3,3-trifluoropropoxy)pyrimidine-4-carboxamide;

N-(2-(cyclopentylsulfonyl)pyrimidin-4-yl)-2-(4,4-dimethyl-1,4-azasilinan-1-yl)-4-((2-hydroxyethyl)sulfonamido)benzamide;

2-(4,4-difluoropiperidin-1-yl)-N-(2-(4,4-dimethyl-1,4-azasilinan-1-yl)-5-fluoro-4-((2-hydroxyethyl)sulfonamido)phenyl)pyrimidine-4-carboxamide;

(S)—N-(2-(4,4-dimethyl-1,4-azasilinan-1-yl)-4-((2-hydroxyethyl)sulfonamido)phenyl)-2-(2-methylmorpholino)pyrimidine-4-carboxamide;

2-(4,4-diethyl-1,4-azasilinan-1-yl)-N-(3-((4,4-difluoropiperidin-1-yl)sulfonyl)phenyl)nicotinamide;

N-(3-((4,4-difluoropiperidin-1-yl)sulfonyl)phenyl)-2-(3,3-dimethyl-1,3-azasilolidin-1-yl)nicotinamide;

N-(2-(3-cyanopiperidin-1-yl)pyrimidin-4-yl)-2-(4,4-dimethyl-1,4-azasilinan-1-yl)-4-((2-hydroxyethyl)sulfonamido)benzamide;

6-(4,4-difluoropiperidin-1-yl)-N-(2-(4,4-dimethyl-1,4-azasilinan-1-yl)-5-fluoro-4-((2-hydroxyethyl)sulfonamido)phenyl)picolinamide;

6-(4,4-difluoropiperidin-1-yl)-N-(2-(4,4-dimethyl-1,4-azasilinan-1-yl)-4-((2-hydroxyethyl)sulfonamido)phenyl)picolinamide;

N-(3-(cyclopentylsulfonyl)phenyl)-2-(4,4-dimethyl-1,4-azasilinan-1-yl)-6-((1-hydroxy-2-methylpropan-2-yl)amino)nicotinamide;

N-(6-(N-(tert-butyl)sulfamoyl)pyridin-2-yl)-2-(4,4-dimethyl-1,4-azasilinan-1-yl)-4-((2-hydroxyethyl)sulfonamido)benzamide;

2-(4,4-dimethyl-1,4-azasilinan-1-yl)-4-(N-(2-hydroxyethyl)sulfamoyl)-N-(6-(3,3,3-trifluoropropoxy)pyridin-2-yl)benzamide;

4-((2-aminoethyl)sulfonamido)-N-(6-(4,4-difluoropiperidin-1-yl)pyridin-2-yl)-2-(4,4-dimethyl-1,4-azasilinan-1-yl)benzamide;

N-(6-(4,4-difluoropiperidin-1-yl)pyridin-2-yl)-2-(4,4-dimethyl-1,4-azasilinan-1-yl)-4-((2-(methylamino)ethyl)sulfonamido)benzamide;

2-(4,4-dimethyl-1,4-azasilinan-1-yl)-4-((2-hydroxyethyl)sulfonamido)-N-(6-methyl-2-(4-oxa-7-azaspiro[2.5]octan-7-yl)pyrimidin-4-yl)benzamide;

N-(2-(4,4-difluoropiperidin-1-yl)-6-methylpyrimidin-4-yl)-2-(4,4-dimethyl-1,4-azasilinan-1-yl)-5-fluoro-4-((2-hydroxyethyl)sulfonamido)benzamide;

4-((2-acetamidoethyl)sulfonamido)-N-(6-(4,4-difluoropiperidin-1-yl)pyridin-2-yl)-2-(4,4-dimethyl-1,4-azasilinan-1-yl)benzamide;

N-(2-(4,4-difluoropiperidin-1-yl)-6-methylpyrimidin-4-yl)-3-(4,4-dimethyl-1,4-azasilinan-1-yl)-5-((2-hydroxyethyl)sulfonamido)pyrazine-2-carboxamide;
N-(2-(4,4-difluoropiperidin-1-yl)-6-methylpyrimidin-4-yl)-4-(4,4-dimethyl-1,4-azasilinan-1-yl)-6-((2-hydroxyethyl)sulfonamido)nicotinamide;
N-(6-(4,4-difluoropiperidin-1-yl)-4-methylpyridin-2-yl)-2-(4,4-dimethyl-1,4-azasilinan-1-yl)-5-fluoro-4-((2-hydroxyethyl)sulfonamido)benzamide;
N-(6-(4,4-difluoropiperidin-1-yl)pyrazin-2-yl)-2-(4,4-dimethyl-1,4-azasilinan-1-yl)-4-((2-hydroxyethyl)sulfonamido)benzamide;
N-(2-(4,4-difluoropiperidin-1-yl)-6-methylpyrimidin-4-yl)-2-(4,4-dimethyl-1,4-azasilinan-1-yl)-6-((2-hydroxyethyl)sulfonamido)nicotinamide;
N-(2-(4,4-difluoropiperidin-1-yl)-6-methylpyrimidin-4-yl)-2-(4,4-dimethyl-1,4-azasilinan-1-yl)-6-fluoro-4-((2-hydroxyethyl)sulfonamido)benzamide;
(R)—N-(2-(4,4-difluoropiperidin-1-yl)-6-methylpyrimidin-4-yl)-2-(4,4-dimethyl-1,4-azasilinan-1-yl)-4-((2-hydroxy-1-methylethyl)sulfonamido)benzamide;
(S)—N-(2-(4,4-difluoropiperidin-1-yl)-6-methylpyrimidin-4-yl)-2-(4,4-dimethyl-1,4-azasilinan-1-yl)-4-((2-hydroxy-1-methylethyl)sulfonamido)benzamide;
2-(4,4-dimethyl-1,4-azasilinan-1-yl)-4-((2-hydroxy-1-methylethyl)sulfonamido)-N-(6-(3,3,3-trifluoropropoxy)pyridin-2-yl)benzamide;
N-(6-(3,3-difluoroazetidin-1-yl)-4-methylpyridin-2-yl)-2-(4,4-dimethyl-1,4-azasilinan-1-yl)-4-((2-hydroxy-1-methylethyl)sulfonamido)benzamide;
N-(2-(2,2-difluoromorpholino)-6-methylpyrimidin-4-yl)-2-(4,4-dimethyl-1,4-azasilinan-1-yl)-4-((2-hydroxyethyl)sulfonamido)benzamide;
N-(2-(4,4-difluoropiperidin-1-yl)-6-methylpyrimidin-4-yl)-2-(4,4-dimethyl-1,4-azasilinan-1-yl)-3,6-difluoro-4-((2-hydroxyethyl)sulfonamido)benzamide;
N-(2-(4,4-difluorocyclohexyl)-6-methylpyrimidin-4-yl)-2-(4,4-dimethyl-1,4-azasilinan-1-yl)-4-((N-(2-hydroxyethyl)sulfamoyl)amino)benzamide;
N-(2-(4,4-difluorocyclohexyl)-6-methylpyrimidin-4-yl)-2-(4,4-dimethyl-1,4-azasilinan-1-yl)-4-((N-methylsulfamoyl)amino)benzamide;
2-(4,4-dimethyl-1,4-azasilinan-1-yl)-4-((2-hydroxyethyl)sulfonamido)-N-(6-(3,3,3-trifluoro-2-hydroxypropoxy)pyridin-2-yl)benzamide;
4-(cyclopropanesulfonimidoyl)-N-(6-(4,4-difluoropiperidin-1-yl)pyridin-2-yl)-2-(4,4-dimethyl-1,4-azasilinan-1-yl)benzamide;
(R)-2-(4,4-dimethyl-1,4-azasilinan-1-yl)-4-((2-hydroxyethyl)sulfonamido)-N-(6-(3,3,3-trifluoro-2-hydroxypropoxy)pyridin-2-yl)benzamide;
(S)-2-(4,4-dimethyl-1,4-azasilinan-1-yl)-4-((2-hydroxyethyl)sulfonamido)-N-(6-(3,3,3-trifluoro-2-hydroxypropoxy)pyridin-2-yl)benzamide;
(R)-2-(4,4-dimethyl-1,4-azasilinan-1-yl)-6-fluoro-4-((2-hydroxyethyl)sulfonamido)-N-(6-(3,3,3-trifluoro-2-hydroxypropoxy)pyridin-2-yl)benzamide;
(S)-2-(4,4-dimethyl-1,4-azasilinan-1-yl)-6-fluoro-4-((2-hydroxyethyl)sulfonamido)-N-(6-(3,3,3-trifluoro-2-hydroxypropoxy)pyridin-2-yl)benzamide;
(R)-2-(4,4-dimethyl-1,4-azasilinan-1-yl)-4-((N-(2-hydroxyethyl)sulfamoyl)amino)-N-(6-(3,3,3-trifluoro-2-hydroxypropoxy)pyridin-2-yl)benzamide;
(S)-2-(4,4-dimethyl-1,4-azasilinan-1-yl)-4-((N-(2-hydroxyethyl)sulfamoyl)amino)-N-(6-(3,3,3-trifluoro-2-hydroxypropoxy)pyridin-2-yl)benzamide;
(R)-2-(4,4-dimethyl-1,4-azasilinan-1-yl)-4-(methylsulfonamido)-N-(6-(3,3,3-trifluoro-2-hydroxypropoxy)pyridin-2-yl)benzamide;
(S)-2-(4,4-dimethyl-1,4-azasilinan-1-yl)-4-(methylsulfonamido)-N-(6-(3,3,3-trifluoro-2-hydroxypropoxy)pyridin-2-yl)benzamide;
(R)-2-(4,4-dimethyl-1,4-azasilinan-1-yl)-4-((2-hydroxyethyl)sulfonyl)-N-(6-(3,3,3-trifluoro-2-hydroxypropoxy)pyridin-2-yl)benzamide;
(S)-2-(4,4-dimethyl-1,4-azasilinan-1-yl)-4-((2-hydroxyethyl)sulfonyl)-N-(6-(3,3,3-trifluoro-2-hydroxypropoxy)pyridin-2-yl)benzamide;
(R)-2-(4,4-dimethyl-1,4-azasilinan-1-yl)-4-(N-(2-hydroxyethyl)sulfamoyl)-N-(6-(3,3,3-trifluoro-2-hydroxypropoxy)pyridin-2-yl)benzamide;
(S)-2-(4,4-dimethyl-1,4-azasilinan-1-yl)-4-(N-(2-hydroxyethyl)sulfamoyl)-N-(6-(3,3,3-trifluoro-2-hydroxypropoxy)pyridin-2-yl)benzamide;
N-(6-(4,4-difluoropiperidin-1-yl)-5-fluoro-4-methylpyridin-2-yl)-2-(4,4-dimethyl-1,4-azasilinan-1-yl)-4-((2-hydroxyethyl)sulfonamido)benzamide;
N-(2-(4,4-difluorocyclohexyl)-6-methylpyrimidin-4-yl)-2-(4,4-dimethyl-1,4-azasilinan-1-yl)-4-((N-(2-hydroxyethyl)-N-methylsulfamoyl)amino)benzamide;
N-(2-(4,4-difluoropiperidin-1-yl)-6-methylpyrimidin-4-yl)-4-((2-hydroxyethyl)sulfonamido)-2-((1S,6R)-6-(methoxymethyl)-3-azabicyclo[4.1.0]heptan-3-yl)benzamide;
N-(2-(4,4-difluoropiperidin-1-yl)-6-methylpyrimidin-4-yl)-4-((2-hydroxyethyl)sulfonamido)-2-((1R,6S)-6-(methoxymethyl)-3-azabicyclo[4.1.0]heptan-3-yl)benzamide;
N-(2-(4,4-difluoropiperidin-1-yl)-6-methylpyrimidin-4-yl)-2-((1R,6R)-6-fluoro-3-azabicyclo[4.2.0]octan-3-yl)-4-((2-hydroxyethyl)sulfonamido)benzamide;
N-(2-(4,4-difluoropiperidin-1-yl)-6-methylpyrimidin-4-yl)-2-((1S,6S)-6-fluoro-3-azabicyclo[4.2.0]octan-3-yl)-4-((2-hydroxyethyl)sulfonamido)benzamide;
N-(2-(4,4-difluoropiperidin-1-yl)-6-methylpyrimidin-4-yl)-2-((1S,6R)-6-(fluoromethyl)-3-azabicyclo[4.1.0]heptan-3-yl)-4-((2-hydroxyethyl)sulfonamido)benzamide; and
N-(2-(4,4-difluoropiperidin-1-yl)-6-methylpyrimidin-4-yl)-2-((1R,6S)-6-(fluoromethyl)-3-azabicyclo[4.1.0]heptan-3-yl)-4-((2-hydroxyethyl)sulfonamido)benzamide;
or a pharmaceutically acceptable salt thereof.

The compounds and intermediates described herein may be isolated and used as the compound per se. Alternatively, when a moiety is present that is capable of forming a salt, the compound or intermediate may be isolated and used as its corresponding salt. As used herein, the terms "salt" or "salts" refers to an acid addition or base addition salt of a compound described herein. "Salts" include in particular "pharmaceutical acceptable salts".

The term "pharmaceutically acceptable salts" refers to salts that retain the biological effectiveness and properties of the compounds described herein and, which typically are not biologically or otherwise undesirable. In many cases, the compounds of the present disclosure are capable of forming acid and/or base salts by virtue of the presence of amino and/or carboxyl groups or groups similar thereto.

Pharmaceutically acceptable acid addition salts can be formed with inorganic acids or organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The salts can be synthesized by conventional chemical methods from a compound containing a basic or acidic moiety. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two.

Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Isotopically-labeled compounds of Formula (I) can generally be prepared by conventional techniques known to those skilled in the art or by processes analogous to those described in the accompanying Examples and Preparations using appropriate isotopically-labeled reagents in place of the non-labeled reagent previously employed. In one embodiment, the present disclosure provides deuterated compounds described herein or a pharmaceutically acceptable salt thereof.

Pharmaceutically acceptable solvates in accordance with the disclosure include those wherein the solvent of crystallization may be isotopically substituted, e.g. $D_2O$, $d_6$-acetone, $d_6$-DMSO.

It will be recognized by those skilled in the art that the compounds of the present disclosure may contain chiral centers and as such may exist in different stereoisomeric forms. As used herein, the term "an optical isomer" or "a stereoisomer" refers to any of the various stereo isomeric configurations which may exist for a given compound of the present disclosure. It is understood that a substituent may be attached at a chiral center of a carbon atom. Therefore, the disclosure includes enantiomers, diastereomers or racemates of the compound.

"Enantiomers" are a pair of stereoisomers that are non-superimposable mirror images of each other. A 1:1 mixture of a pair of enantiomers is a "racemic" mixture. The term "racemic" or "rac" is used to designate a racemic mixture where appropriate. When designating the stereochemistry for the compounds of the present disclosure, a single stereoisomer with known relative and absolute configuration of the two chiral centers is designated using the conventional RS system (e.g., (1S,2S)). "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Alternatively, the resolved compounds can be defined by the respective retention times for the corresponding enantiomers/diastereomers via chiral HPLC.

Certain of the compounds described herein contain one or more asymmetric centers or axes and may thus give rise to enantiomers, diastereomers, and other stereoisomeric forms that may be defined, in terms of absolute stereochemistry, as (R)- or (S)-.

Unless specified otherwise, the compounds of the present disclosure are meant to include all such possible stereoisomers, including racemic mixtures, optically pure forms and intermediate mixtures. Optically active (R)- and (S)-stereoisomers may be prepared using chiral synthons or chiral reagents, or resolved using conventional techniques (e.g., separated on chiral SFC or HPLC chromatography columns, such as CHIRALPAK® and CHIRALCEL® available from DAICEL Corp. using the appropriate solvent or mixture of solvents to achieve good separation). If the compound contains a double bond, the substituent may be E or Z configuration. If the compound contains a disubstituted cycloalkyl, the cycloalkyl substituent may have a cis- or trans-configuration. All tautomeric forms are also intended to be included.

The present disclosure also provides a pharmaceutical composition comprising a compound described herein (e.g., a compound according to any one of the preceding embodiments), or a pharmaceutically acceptable salt thereof, and one or more pharmaceutically acceptable carriers.

Methods of Use

The compounds described herein have KIF18A inhibitory activity. As used herein, "KIF18A inhibitory activity" refers to the ability of a compound or composition to induce a detectable decrease in KIF18A activity in vivo or in vitro (e.g., at least 10% decrease in KIF18A activity as measured by a given assay such as the bioassay described in the examples and known in the art).

In certain embodiments, the present disclosure provides a method of treating a disease or disorder responsive to inhibition of KIF18A activity (referred herein as "KIF18A mediated disease or disorder") in a subject in need of the treatment. The method comprises administering to the subject a compound described herein (e.g., a compound described in any one of the first to forty-second embodiments) or a pharmaceutically acceptable salt thereof or a pharmaceutical composition thereof.

In certain embodiments, the present disclosure provides the use of a compound described herein (e.g., a compound described in any one of the first to forty-second embodiments) or a pharmaceutically acceptable salt thereof or a pharmaceutical composition comprising a compound described herein or a pharmaceutically acceptable salt thereof for the manufacture of a medicament for the treatment of a KIF18A mediated disorder or disease in a subject in need of the treatment.

In certain embodiments, the present disclosure provides a compound described herein (e.g., a compound described in any one of the first to forty-second embodiments) or a pharmaceutically acceptable salt thereof or a pharmaceutical composition comprising a compound described herein or a pharmaceutically acceptable salt thereof for use in the treatment of a KIF18A mediated disorder or disease in a subject in need of the treatment.

In certain embodiments, the KIF18A mediated disease or disorder is a cancer.

In some embodiments, the cancer is a cancer with chromosomal instability. In other embodiments, the cancer displays whole-genome doubling. In other embodiment, the cancer has a mutation in the TP53, BRCA1, BRCA2, RB1, genes and/or an amplification in the CCNE1 gene.

In some embodiments, the cancer is small-cell lung cancer, non-small cell lung cancer, pancreatic cancer, triple-negative breast cancer, colorectal cancer, hepatobiliary cancer, esophagogastric cancer, endometrial cancer, head and neck squamous cell carcinoma, ovarian cancer, platinum resistant ovarian cancer, bladder cancer, soft-tissue sarcoma, renal cell cancer, uterine cancer, cervical cancer, or bone cancer.

In other embodiments, the KIF18A mediated disease or disorder is (a) a solid or hematologically derived tumor selected from the cancer of the bladder, endometrial, lung squamous cell, breast, colon, kidney, liver, lung, small cell lung cancer, esophagus, gall-bladder, brain, head and neck, ovary, pancreas, stomach, cervix, thyroid, prostate and skin, (b) a hematopoietic tumor of lymphoid lineage selected from leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma, (c) a hematopoietic tumor of myeloid lineage selected from acute and chronic myelogenous leukemias, myelodysplastic syndrome and promyelocytic leukemia (d) a tumor of mesenchymal origin selected from fibrosarcoma and rhabdomyosarcoma, (e) a tumor of the central and peripheral nervous system selected from astrocytoma, neuroblastoma, glioma and schwannoma, or (f) a melanoma, seminoma, teratocarcinoma, osteosarcoma, xenoderoma pigmentosum, keratoctanthoma, thyroid follicular cancer or Kaposi's sarcoma.

The compounds, or pharmaceutically acceptable salts thereof described herein may be used to decrease the expression or activity of KIF18A, or to otherwise affect the properties and/or behavior of KIF18A in a cell.

One embodiment of the present disclosure includes a method of decreasing the expression or activity of KIF18A, or to otherwise affect the properties and/or behavior of KIF18A in a subject comprising administering to said subject an effective amount of at least one compound described herein, or a pharmaceutically acceptable salt thereof.

In certain embodiments, the present disclosure relates to the aforementioned methods, wherein said subject is a mammal.

In certain embodiments, the present disclosure relates to the aforementioned methods, wherein said subject is a primate.

In certain embodiments, the present disclosure relates to the aforementioned methods, wherein said subject is a human.

As used herein, an "effective amount" and a "therapeutically effective amount" can used interchangeably. It means an amount effective for treating or lessening the severity of one or more of the diseases, disorders or conditions as recited herein. In some embodiments, the effective dose can be between 10 μg and 500 mg.

The compounds and compositions, according to the methods of the present disclosure, may be administered using any amount and any route of administration effective for treating or lessening the severity of one or more of the diseases, disorders or conditions recited above.

In certain embodiments, the present disclosure relates to the aforementioned methods, wherein said compound is administered parenterally.

In certain embodiments, the present disclosure relates to the aforementioned methods, wherein said compound is administered intramuscularly, intravenously, subcutaneously, orally, pulmonary, rectally, intrathecally, topically or intranasally.

In certain embodiments, the present disclosure relates to the aforementioned methods, wherein said compound is administered systemically.

The compounds of the present disclosure are typically used as a pharmaceutical composition (e.g., a compound of the present disclosure and at least one pharmaceutically acceptable carrier). As used herein, the term "pharmaceutically acceptable carrier" includes generally recognized as safe (GRAS) solvents, dispersion media, surfactants, antioxidants, preservatives (e.g., antibacterial agents, antifungal agents), isotonic agents, salts, preservatives, drug stabilizers, buffering agents (e.g., maleic acid, tartaric acid, lactic acid, citric acid, acetic acid, sodium bicarbonate, sodium phosphate, and the like), and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated. For purposes of this disclosure, solvates and hydrates are considered pharmaceutical compositions comprising a compound of the present disclosure and a solvent (i.e., solvate) or water (i.e., hydrate).

The formulations may be prepared using conventional dissolution and mixing procedures. For example, the bulk drug substance (i.e., compound of the present disclosure or stabilized form of the compound (e.g., complex with a cyclodextrin derivative or other known complexation agent)) is dissolved in a suitable solvent in the presence of one or more of the excipients described above. The compound of the present disclosure is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The pharmaceutical composition comprising a compound of the present disclosure is generally formulated for use as a parenteral or oral administration or alternatively suppositories.

For example, the pharmaceutical oral compositions of the present disclosure can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethylene glycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include a compound of the disclosure in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

The parenteral compositions (e.g., intravenous (IV) formulation) are aqueous isotonic solutions or suspensions. The parenteral compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are generally prepared according to conventional mixing, granulating or coating methods, respectively, and contain about 0.1-75%, or contain about 1-50%, of the active ingredient.

The compound of the present disclosure or pharmaceutical composition thereof for use in a subject (e.g., human) is typically administered orally or parenterally at a therapeutic dose. When administered intravenously via infusion, the dosage may depend upon the infusion rate at which an IV formulation is administered. In general, the therapeutically effective dosage of a compound, the pharmaceutical composition, or the combinations thereof, is dependent on the species of the subject, the body weight, age and individual condition, the disorder or disease or the severity thereof being treated. A physician, pharmacist, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present disclosure can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations.

Definitions

As used herein, a "patient," "subject" or "individual" are used interchangeably and refer to either a human or non-human animal. The term includes mammals such as humans. Typically, the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In some embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease, condition or disorder, refers to the management and care of a patient for the purpose of combating the disease, condition, or disorder and includes the administration of a compound of the present disclosure to obtaining desired pharmacological and/or physiological effect. The effect can be therapeutic, which includes achieving, partially or substantially, one or more of the following results: partially or totally reducing the extent of the disease, condition or disorder; ameliorating or improving a clinical symptom, complications or indicator associated with the disease, condition or disorder; or delaying, inhibiting or decreasing the likelihood of the progression of the disease, condition or disorder; or eliminating the disease, condition or disorder. In certain embodiments, the effect can be to prevent the onset of the symptoms or complications of the disease, condition or disorder.

As used herein the term "cancer" has the meaning normally accepted in the art. The term can broadly refer to abnormal cell growth.

As used herein, a subject is "in need of" a treatment if such subject would benefit biologically, medically or in quality of life from such treatment (in some embodiments, a human).

As used herein, the phrase "optionally substituted" is used interchangeably with the phrase "substituted or unsubstituted." In general the term "optionally substituted" refers to the replacement of hydrogen radicals in a given structure with the radical of a specified substituent. Specific substituents are described in the definitions and in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. In some embodiments, the "one or more" substituents can be 1, 2, 3, 4, 5, 6, etc. substituents, each of which can the same or different. In some embodiment, the "one or more" substituents can be 1 to 6, 1 to 4, 1 to 3 or 1 to 2 substituents, each of which can the same or different.

As used herein, the term "alkyl" refers to a fully saturated branched or unbranched hydrocarbon moiety. The term "$C_{1-4}$alkyl" refers to an alkyl having 1 to 4 carbon atoms. The terms "$C_{1-3}$alkyl" and "$C_{1-2}$alkyl" are to be construed accordingly. Representative examples of "$C_{1-4}$alkyl" include, but are not limited to, methyl, ethyl, n-propyl, iso-propyl, n-butyl, sec-butyl, iso-butyl, and tert-butyl. Similarly, the alkyl portion (i.e., alkyl moiety) of an alkoxy have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls).

As used herein, the term "alkoxy" refers to a fully saturated branched or unbranched alkyl moiety attached through an oxygen bridge (i.e., a —O—$C_{1-4}$ alkyl group wherein $C_{1-4}$ alkyl is as defined herein). Representative examples of alkoxy include, but are not limited to, methoxy, ethoxy, propoxy, 2-propoxy, butoxy, tert-butoxy and the like. In some embodiments, alkoxy groups have 1-6 carbons, 1-4 carbons, or 1-3 carbons, and in some embodiments about 1-2 carbons. The term "$C_{1-2}$ alkoxy" is to be construed accordingly.

The number of carbon atoms in a group is specified herein by the prefix "$C_{x-xx}$" wherein x and xx are integers. For example, "$C_{1-3}$alkyl" is an alkyl group which has from 1 to 3 carbon atoms.

"Halogen" or "halo" may be fluorine, chlorine, bromine or iodine.

As used herein, the term "haloalkyl" refers to an alkyl group as defined herein, wherein at least one of the hydrogen atoms is replaced by a halo atom. The term "$C_{1-6}$haloalkyl" refers to a haloalkyl group having 1 to 6 carbon atoms. The terms "$C_{1-4}$haloalkyl" and "$C_{1-3}$haloalkyl" are to be construed accordingly. The haloalkyl group can be monohalo alkyl, dihaloalkyl or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Typically the polyhaloalkyl group contains up to 13, or 12, or 11, or 10, or 9, or 8, or 7, or 6, or 5, or 4, or 3, or 2 halo groups. Non-limiting examples of $C_{1-6}$haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl group refers to an alkyl group having all hydrogen atoms replaced with halo atoms.

As used herein, the term "haloalkoxy" refers to an alkoxy group as defined herein, wherein at least one of the hydrogen atoms on the alkyl moiety is replaced by a halo atom. The term "$C_{1-6}$haloalkoxy" refers to a haloalkoxy group having 1 to 6 carbon atoms. The terms "$C_{1-4}$haloalkoxy" and "$C_{1-3}$haloalkoxy" are to be construed accordingly. The haloalkoxy group can be monohaloalkoxy, dihaloalkoxy or polyhaloalkoxy including perhaloalkyl. A monohaloalkyoxy can have one iodo, bromo, chloro or fluoro within the alkyl moiety of the alkoxy group. Dihaloalkoxy and polyhaloalkoxy groups can have two or more of the same halo atoms or a combination of different halo groups within the alkyl moiety of the alkoxy group. Typically the polyhaloalkoxy group contains up to 13, or 12, or 11, or 10, or 9, or 8, or 7, or 6, or 5, or 4, or 3, or 2 halo groups. Non-limiting examples of $C_{1-6}$haloalkoxy include fluoromethoxy, difluoromethoxy, trifluoromethoxy, chloromethoxy, dichloromethoxy, trichloromethoxy, pentafluoroethoxy, heptafluoropropoxy, difluorochloromethoxy, dichlorofluoromethoxy, difluoroethoxy, difluoropropoxy, dichloroethoxy and dichloropropoxy.

The term "aryl" refers to an aromatic carbocyclic single ring or two fused ring system containing 6 to 10 carbon atoms. Examples include phenyl and naphthyl.

The term "heteroaryl" refers to a 5- to 12-membered aromatic radical containing 1-4 heteroatoms selected from N, O, and S. In some instances, nitrogen atoms in a heteroaryl may be quaternized. The term "heteroaryl" may be used interchangeably with the terms "heteroaryl ring", "heteroaryl group", or "heteroaromatic". A heteroaryl group may be mono- or bi-cyclic. Monocyclic heteroaryl includes, for example, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, and the like. Bi-cyclic heteroaryls include groups in which a monocyclic heteroaryl ring is fused to one aryl or heteroaryl ring. Non-limiting examples include indolyl, indazoyl, benzofuranyl, benzimidazolyl, and imidazo[1,2-a]pyridine. The term "6,5-bicyclic heteroaryl" refers to a bicycle heteroaryl in which one of ring is 5-membered ring and the other ring is 6-membered ring. For example, "6,5-bicyclic heteroaryl" is a phenyl ring fused to a 5-membered heteroaryl or a 6-membered heteroaryl fused to a 5-membered heteroaryl. In some embodiments, the "6,5-bicyclic heteroaryl" is attached to group Z through the 6-membered heteroaryl or phenyl ring. In other embodiments, the "6,5-bicyclic heteroaryl" is attached to group Z through the 5-membered heteroaryl.

The term "carbocyclic ring" or "carbocyclyl" refers to a 4- to 12-membered saturated or partially unsaturated hydrocarbon ring and may exist as a single ring, bicyclic ring (including fused, spiro or bridged carbocyclic rings) or a spiro ring. Bi-cyclic carbocyclyl groups include, e.g., unsaturated carbocyclic radicals fused to another unsaturated carbocyclic radical, cycloalkyl, or aryl, such as, for example, cyclohexyl, cyclohexenyl, 2,3-dihydroindenyl, indanyl, decahydronaphthalenyl, and 1,2,3,4-tetrahydronaphthalenyl. Unless specified otherwise, the carbocyclic ring generally contains 4- to 10-ring members.

The term "$C_{3-6}$ cycloalkyl" refers to a carbocyclic ring which is fully saturated (e.g., cyclopropyl, cyclobutyl, cyclopentyl, and cyclohexyl).

The term "heterocycle" or "heterocyclyl" refers to a 4- to 12-membered saturated or partially unsaturated heterocyclic ring containing 1 to 4 heteroatoms independently selected from N, O, and S. A heterocyclyl group may be mono- or bicyclic (e.g., a bridged, fused, or spiro bicyclic ring). Examples of monocyclic saturated or partially unsaturated heterocyclic radicals include, without limitation, piperidinyl, piperazinyl, tetrahydropyranyl, morpholinyl, and pyrrolidinyl. Bi-cyclic heterocyclyl groups include, e.g., unsaturated heterocyclic radicals fused to another unsaturated heterocyclic radical, cycloalkyl, aryl, or heteroaryl ring, such as, for example, indolinyl, 2,3-dihydro-1H-pyrrolopyridinyl, 6,7-dihydro-5H-pyrrolopyrazinyl, 2-oxo-2,3-dihydro-1H-benzo[d]imidazolyl, 1,4,5,6-tetrahydrocyclopenta[c]pyrazolyl, 4,5,6,7-tetrahydrothieno[2,3-c]pyridinyl, 5,6-dihydro-4H-cyclopenta[b]thiophenyl, and 4,7-dihydro-5H-thieno[2,3-c]pyranyl. In some embodiments, the heterocyclyl group is a 4 to 6 membered monocyclic heterocyclyl group. In some embodiments, the heterocyclyl group is a 8 to 10 membered bicyclic heterocyclyl group.

As used herein the term "spiro" ring means a two-ring system wherein both rings share one common atom. Examples of spiro rings include 5-oxaspiro[2.3]hexane, oxaspiro[2.4]heptanyl, 5-oxaspiro[2.4]heptanyl, 4-oxaspiro[2.4]heptane, 4-oxaspiro[2.5]octanyl, 6-oxaspiro[2.5]octanyl, oxaspiro[2.5]octanyl, oxaspiro[3.4]octanyl, oxaspiro[bicyclo[2.1.1]hexane-2,3'-oxetan]-1-yl, oxaspiro[bicyclo[3.2.0]heptane-6,1'-cyclobutan]-7-yl, 2,6-diazaspiro[3.3]heptanyl, -oxa-6-azaspiro[3.3]heptane, 2,2,6-diazaspiro[3.3]heptane, 3-azaspiro[5.5]undecanyl, 3,9-diazaspiro[5.5]undecanyl, 7-azaspiro[3.5]nonane, 2,6-diazaspiro[3.4]octane, 8-azaspiro[4.5]decane, 1,6-diazaspiro[3.3]heptane, 5-azaspiro[2.5]octane, 4,7-diazaspiro[2.5]octane, 5-oxa-2-azaspiro[3.4]octane, 6-oxa-1-azaspiro[3.3]heptane, 3-azaspiro[5.5]undecanyl, 3,9-diazaspiro[5.5]undecanyl, and the like.

The term "fused" ring refers to two ring systems share two adjacent ring atoms. Fused heterocycles have at least one of the ring systems contain a ring atom that is a heteroatom selected from O, N and S (e.g., 3-oxabicyclo[3.1.0]hexane).

As used herein the term "bridged" refers to a 5 to 10 membered cyclic moiety connected at two non-adjacent ring atoms (e.g. bicyclo[1.1.1]pentane, bicyclo[2.2.1]heptane and bicyclo[3.2.1]octane).

The phrase "pharmaceutically acceptable" indicates that the substance, composition or dosage form must be compatible chemically and/or toxicologically, with the other ingredients comprising a formulation, and/or the mammal being treated therewith.

Unless specified otherwise, the term "compounds of the present disclosure" refers to compounds of Formula (I), as well as all stereoisomers (including diastereoisomers and enantiomers), rotamers, tautomers, isotopically labeled compounds (including deuterium substitutions). When a moiety is present that is capable of forming a salt, then salts are included as well, in particular pharmaceutically acceptable salts.

As used herein, the term "a," "an," "the" and similar terms used in the context of the present disclosure (especially in the context of the claims) are to be construed to cover both the singular and plural unless otherwise indicated herein or clearly contradicted by the context. The use of any and all examples, or exemplary language (e.g. "such as") provided herein is intended merely to better illuminate the disclosure and does not pose a limitation on the scope of the disclosure otherwise claimed.

It is also possible that the intermediates and compounds of the present disclosure may exist in different tautomeric forms, and all such forms are embraced within the scope of the disclosure. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

In one embodiment, the present disclosure relates to a compound of the Formula (I) as defined herein, in free form. In another embodiment, the present disclosure relates to a compound of the Formula (I) as defined herein, in salt form. In another embodiment, the present disclosure relates to a compound of the Formula (I) as defined herein, in acid addition salt form. In a further embodiment, the present disclosure relates to a compound of the Formula (I) as defined herein, in pharmaceutically acceptable salt form. In yet a further embodiment, the present disclosure relates to a compound of the Formula (I) as defined herein, in pharmaceutically acceptable acid addition salt form. In yet a further embodiment, the present disclosure relates to any one of the compounds of the Examples in free form. In yet a further embodiment, the present disclosure relates to any one of the compounds of the Examples in salt form. In yet a further embodiment, the present disclosure relates to any one of the compounds of the Examples in acid addition salt form. In yet a further embodiment, the present disclosure relates to any one of the compounds of the Examples in pharmaceutically acceptable salt form. In still another embodiment, the present disclosure relates to any one of the compounds of the Examples in pharmaceutically acceptable acid addition salt form.

Compounds of the present disclosure may be synthesized by synthetic routes that include processes analogous to those well-known in the chemical arts, particularly in light of the description contained herein. The starting materials are generally available from commercial sources such as Sigma-Aldrich or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present disclosure as well as key intermediates. For a more detailed description of the individual reaction steps, see the Examples section below. Although specific starting materials and reagents are depicted in the schemes and discussed below, other starting materials and reagents can be easily substituted to provide a variety of derivatives and/or reaction conditions.

EXEMPLIFICATION

Abbreviations

BAST=bis(2-methoxyethyl)aminosulfur trifluoride
BID=twice daily
BINAP=(2,2'-bis(diphenylphosphino)-1,1'-binaphthyl)
Bn=benzyl
BnBr=benzyl bromide
Boc=tert-butoxycarbonyl
Boc$_2$O=di-tert-butyl decarbonate
BSA=bovine serum albumin
CFU-MK=clonogenic progenitors of human megakaryocyte
CH$_2$I$_2$=diiodomethane
Cs$_2$CO$_3$=cesium carbonate
DCM=dichloromethane
DMF=dimethylformamide
DIPEA=DIEA=diisopropylethyl amine
DMEM=Dulbecco's Modified Eagle Medium
DMP=Dess-Martin periodinane
DMSO=dimetylsulfoxide
EDTA=ethylenediaminetetraacetic acid
ESI=electrospray ionization
Et=ethyl
Et$_2$Zn=diethylzinc
Et$_3$N=triethylamine
EtOAc=EA=ethyl acetate
EtOH=ethanol
FA=formic acid
FBS=fetal bovine serum
H$_2$=hydrogen
H$_2$O=water
HBSS=Hanks' Balanced Salt Solution
HEPES=(4-(2-hydroxyethyl)-1-piperazineethanesulfonic acid)
HPLC=high pressure liquid chromatography
IMDM=Iscove's Modified Dulbecco's Medium
K$_2$CO$_3$=potassium carbonate
K$_3$PO$_4$=potassium phosphate
LCMS=liquid chromatography mass spectrometry
LiBH$_4$=lithium borohydride
LiHMDS=lithium bis(trimethylsilyl)amide
MeOH=methanol
MeCN=ACN=acetonitrile
N$_2$=nitrogen
Na$_2$SO$_3$=sodium sulfite
Na$_2$SO$_4$=sodium sulfate
NaI=sodium iodide
NaOH=sodium hydroxide
NH$_4$Cl=ammonium chloride
NH$_4$OH=ammonium hydroxide
NMP=N-methylpyrrolidone
NMI=1-methylimidazole
Pd/C=palladium on carbon
Pd(OH)$_2$=palladium(II) hydroxide
Pd$_2$(dba)$_3$=tris(dibenzylideneacetone)dipalladium(0)
PE=petroleum ether
QD=once daily
QOD=every other day
SFC=supercritical fluid chromatography
SOCl$_2$=thionyl chloride
t-BuXPhos Pd G3=[(2-di-tert-butylphosphino-2',4',6'-triisopropyl-1,1'-biphenyl)-2-(2'-amino-1,1'-biphenyl)]palladium(II) methanesulfonate
TBAI=tetra-n-butylammonium iodide
TCFH=N'-tetramethylformamidinium hexafluorophosphate
TFA=trifluoroacetic acid
THF=tetrahydrofuran
TMS=trimethylsilyl
TMS-CHN$_2$=trimethylsilyldiazomethane
TMSCF$_3$=trimethyl(trifluoromethyl)silane
Xantphos=4,5-bis(diphenylphosphino)-9,9-dimethylxanthene General Methods 1. $^1$H NMR spectra were recorded on:
   NMR10 Bruker AVANCE III HD 300 MHz
   NMR16 Bruker AVANCE III HD 300 MHz
   NMR19 Bruker AVANCE III HD 400 MHz
   NMR24 Bruker AVANCE NEO 400 MHz
   NMR30 Bruker AVANCE NEO 400 MHz
2. LCMS measurement was run on SHIMADZU LCMS-2020 using the follow conditions:
   Method A: Mobile Phase: A: Water (0.05% TFA) B: Acetonitrile (0.05% TFA); Gradient Phase: 5% B to 100% B within 2.0 min, 100% B with 0.7 min (total runtime: 2.8 min); Flow Rate: 1.5 mL/min; Column: HALO C18, 3.0*30 mm, 2.0 µm; Column Temperature: 40° C. Detectors: AD2 ELSD, PDA (220 nm and 254 nm), ESI.
   Method B: Mobile Phase: A: Water (0.1% FA) B: Acetonitrile (0.1% FA); Gradient Phase: 5% B to 100% B within 2.0 min, 100% B with 0.7 min (total runtime: 2.8 min); Flow Rate: 1.5 mL/min; Column: HALO C18, 3.0*30 mm, 2.0 µm; Column Temperature: 40° C. Detectors: AD2 ELSD, PDA (220 nm and 254 nm), ESI.
   Method C: Mobile Phase: A: Water (5 mM NH$_4$HCO$_3$) B: Acetonitrile; Gradient Phase: 10% B to 95% B within 2.0 min, 100% B with 0.6 min (total runtime: 2.8 min); Flow Rate: 1.5 mL/min; Column: Poroshell HPH-C18, 3.0*50 mm, 4.0 µm; Column Temperature: 40° C. Detectors: AD2 ELSD, PDA (220 nm and 254 nm), ESI.
   The observed molecular ion for all compounds listed below is for [M+H]$^+$, unless otherwise indicated.

Common Intermediate I: Synthesis of methyl 2-(4,4-dimethyl-1,4-azasilinan-1-yl)-4-nitrobenzoate

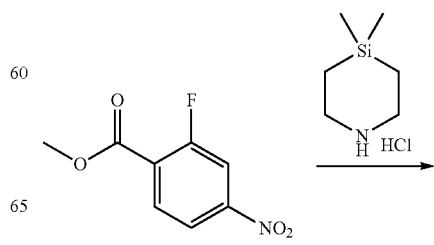

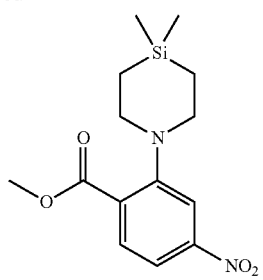

To a solution of methyl 2-fluoro-4-nitrobenzoate (20 g, 100 mmol) and 4,4-dimethyl-1,4-azasilinane hydrochloride (15 g, 90.5 mmol) in DMSO (150 mL) was added DIEA (30 mL, 171 mmol). The reaction mixture was stirred at 100° C. for 60 h. The reaction mixture was diluted with water (200 mL), acidified with HCl (2 N in H$_2$O) to pH 4, and then extracted with EA (200 mL×3). The combined organic extracts were washed with brine, dried over Na$_2$SO$_4$, and concentrated to give methyl 2-(4,4-dimethyl-1,4-azasilinan-1-yl)-4-nitrobenzoate (30 g) as a brown oil. LCMS: MS ESI (M+1)$^+$=309.2. $^1$H NMR (400 MHz, CHLOROFORM-d) δ=7.86 (d, J=1.5 Hz, 1H), 7.72-7.62 (m, 2H), 3.94 (s, 3H), 3.53-3.31 (m, 4H), 1.03-0.81 (m, 4H), 0.22-0.04 (m, 6H).

Preparation of Common Intermediate II: N-(2-(4,4-difluoropiperidin-1-yl)-6-methylpyrimidin-4-yl)-2-fluoro-6-((1S,6S)-6-methyl-3-azabicyclo[4.1.0]heptan-3-yl)-4-nitrobenzamide and Common Intermediate III N-(2-(4,4-difluoropiperidin-1-yl)-6-methylpyrimidin-4-yl)-2-fluoro-6-((1R,6R)-6-methyl-3-azabicyclo[4.1.0]heptan-3-yl)-4-nitrobenzamide

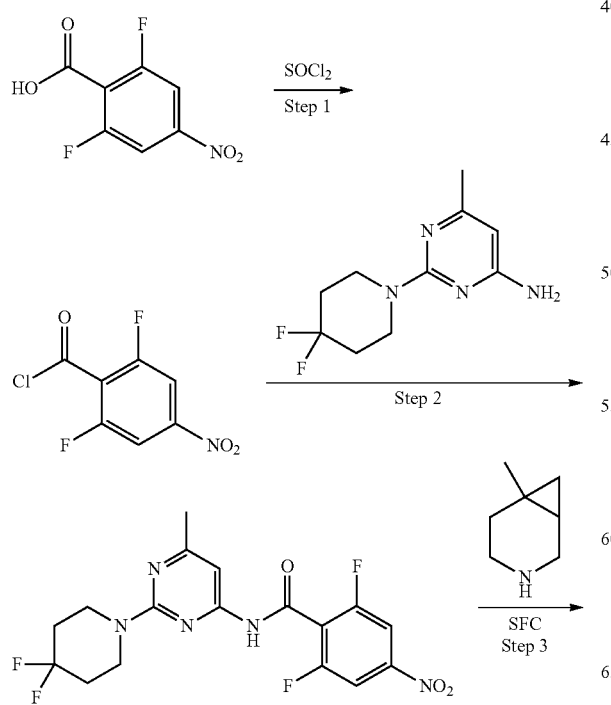

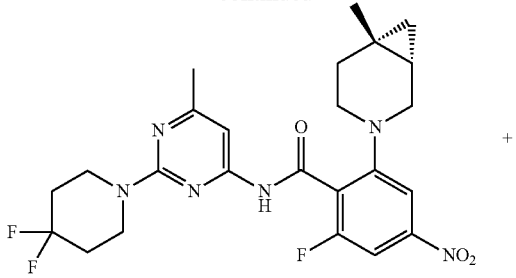

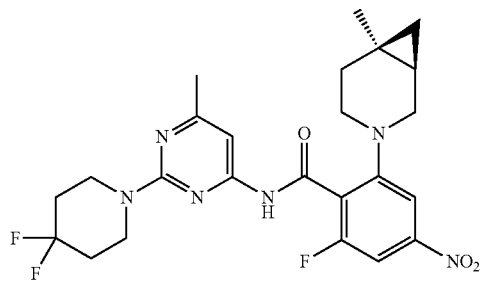

Step 1: Preparation of 2,6-difluoro-4-nitrobenzoyl chloride

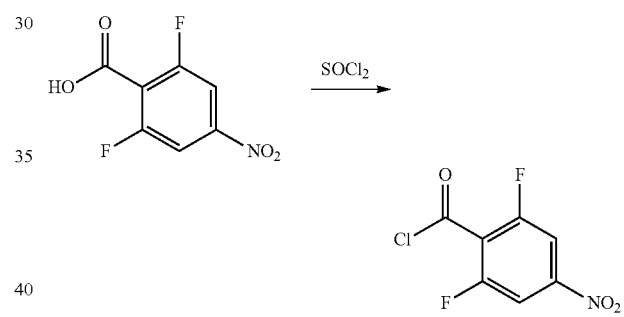

To a solution of 2,6-difluoro-4-nitrobenzoic acid (500 mg, 2.46 mmol) in DCM (10 mL) was added SOCl$_2$ (1.56 g, 12.3 mmol) at 0° C. Then the reaction mixture was stirred at room temperature for 2 h. The mixture was then concentrated in vacuo to afford 2,6-difluoro-4-nitrobenzoyl chloride (500 mg, 2.25 mmol) as a colorless solid.

Step 2: Preparation of N-(2-(4,4-difluoropiperidin-1-yl)-6-methylpyrimidin-4-yl)-2,6-difluoro-4-nitrobenzamide

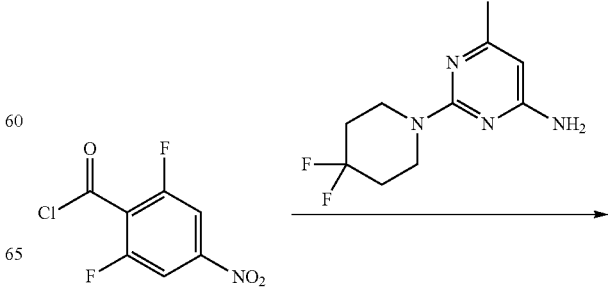

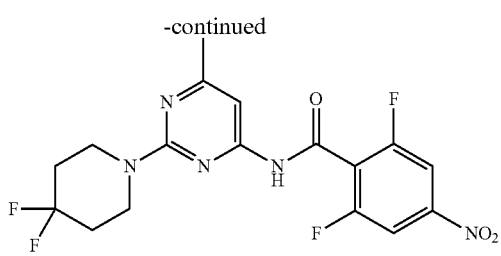

To a solution of 2,6-difluoro-4-nitrobenzoyl chloride (500 mg, 2.19 mmol) and Et₃N (912 μL, 6.57 mmol) in THF (1 mL) was added 2-(4,4-difluoropiperidin-1-yl)-6-methylpyrimidin-4-amine (507 mg, 2.29 mmol), and the mixture was stirred at room temperature for 2 h. The mixture was then diluted with H₂O (10 mL) and extracted with EtOAc (2×20 mL). The combined organic extracts were concentrated in vacuo. The residue was dissolved in MeOH (10 mL), and K₂CO₃ (500 mg) was added. The mixture was stirred at room temperature for 2 h. The mixture was then filtered and concentrated in vacuo to afford N-(2-(4,4-difluoropiperidin-1-yl)-6-methylpyrimidin-4-yl)-2,6-difluoro-4-nitrobenzamide (500 mg, 0.84 mmol) as a brown solid.

Step 3: Preparation of N-(2-(4,4-difluoropiperidin-1-yl)-6-methylpyrimidin-4-yl)-2-fluoro-6-((1S,6S)-6-methyl-3-azabicyclo[4.1.0]heptan-3-yl)-4-nitrobenzamide and N-(2-(4,4-difluoropiperidin-1-yl)-6-methylpyrimidin-4-yl)-2-fluoro-6-((1R,6R)-6-methyl-3-azabicyclo[4.1.0]heptan-3-yl)-4-nitrobenzamide To a solution of N-(2-(4,4-difluoropiperidin-1-yl)-6-methylpyrimidin-4-yl)-2,6-difluoro-4-nitrobenzamide (460 mg, 1.11 mmol) in DMSO (5 mL) was added 6-methyl-3-azabicyclo[4.1.0]heptane (184 mg, 1.66 mmol) and DIEA (430 mg, 3.33 mmol), and the mixture was stirred at 40° C. overnight. The mixture was then diluted with H₂O (10 mL) and extracted with EtOAc (2×20 mL). The combined organic extracts were washed with brine (3×30 mL) and concentrated in vacuo. The residue was purified by silica gel column chromatography (PE:EA gradient) to afford racemic N-(2-(4,4-difluoropiperidin-1-yl)-6-methylpyrimidin-4-yl)-2-fluoro-6-(6-methyl-3-azabicyclo[4.1.0]heptan-3-yl)-4-nitrobenzamide (300 mg, 0.59 mmol) as a yellow solid. Chiral SFC separation (CO₂-EtOH (0.1% NH₃H₂O) of this racemate afforded first eluting peak, arbitrarily assigned as N-(2-(4,4-difluoropiperidin-1-yl)-6-methylpyrimidin-4-yl)-2-fluoro-6-((1S,6S)-6-methyl-3-azabicyclo[4.1.0]heptan-3-yl)-4-nitrobenzamide (120 mg, 0.24 mmol) as a yellow solid LCMS: MS ESI (M+1)⁺ 505.4, and second eluting peak, arbitrarily assigned as N-(2-(4,4-difluoropiperidin-1-yl)-6-methylpyrimidin-4-yl)-2-fluoro-6-((1R,6R)-6-methyl-3-azabicyclo[4.1.0]heptan-3-yl)-4-nitrobenzamide (110 mg, 0.22 mmol) as a yellow solid. First eluting peak LCMS: MS ESI (M+1)⁺ 505.4. Second eluting peak LCMS: MS ESI (M+1)⁺ 505.4.

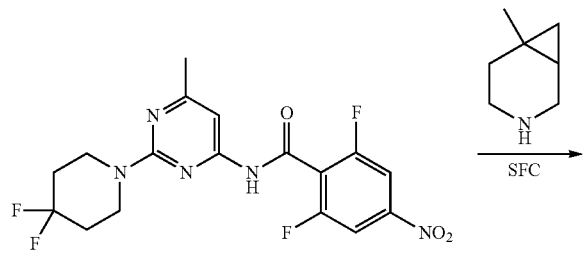

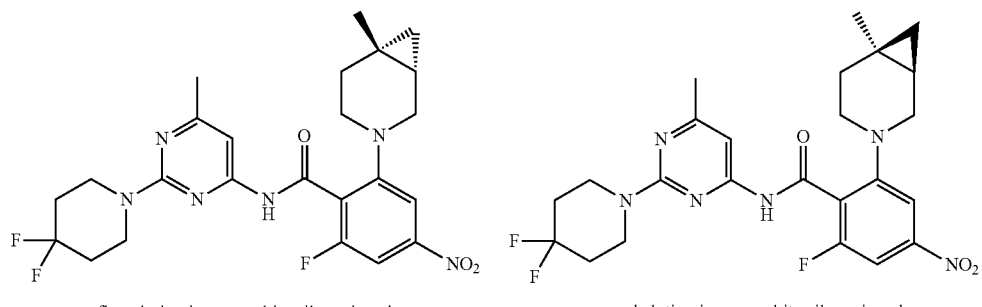

first eluting isomer, arbitrarily assigned     second eluting isomer, arbitrarily assigned Common Intermediates IV and V: Synthesis of methyl 2-((1R,6S)-6-(difluoromethyl)-3-azabicyclo[4.1.0]heptan-3-yl)-4-nitrobenzoate and methyl 2-((1S,6R)-6-(difluoromethyl)-3-azabicyclo[4.1.0]heptan-3-yl)-4-nitrobenzoate

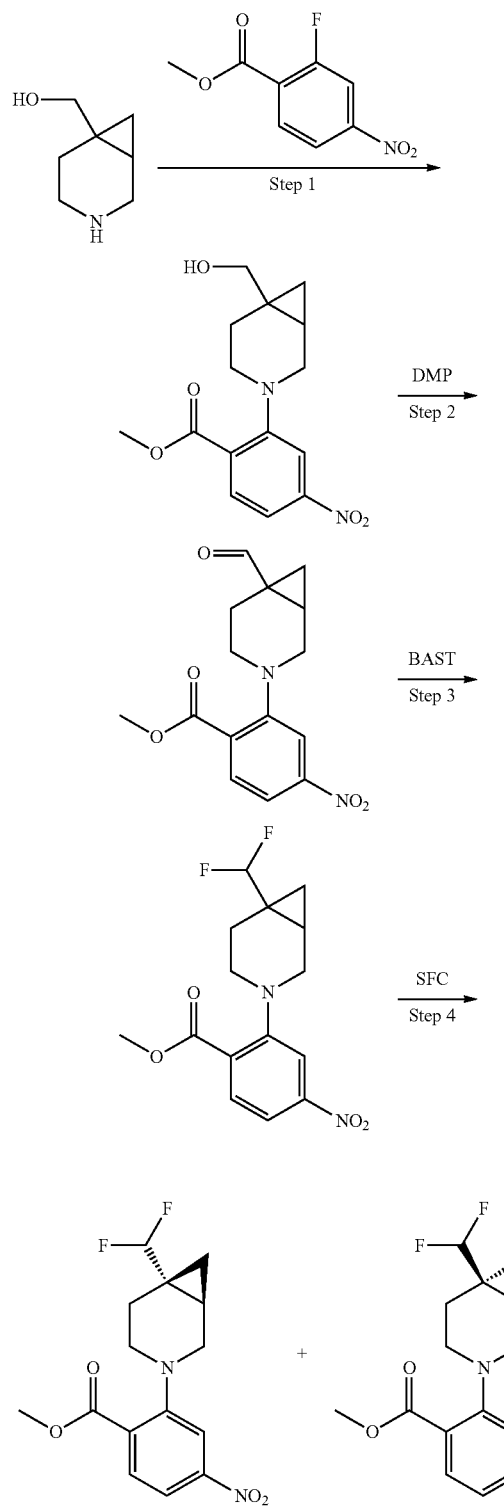

Step 1: Preparation of methyl 2-(6-(hydroxymethyl)-3-azabicyclo[4.1.0]heptan-3-yl)-4-nitrobenzoate

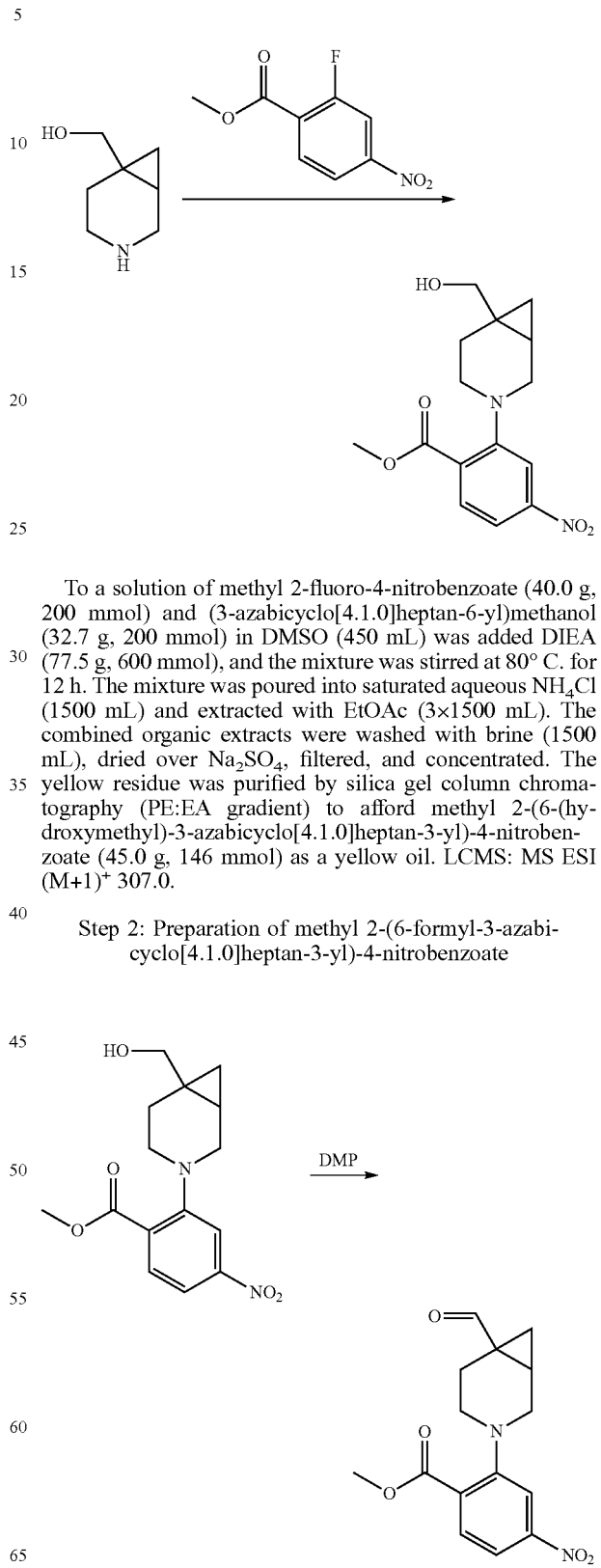

To a solution of methyl 2-fluoro-4-nitrobenzoate (40.0 g, 200 mmol) and (3-azabicyclo[4.1.0]heptan-6-yl)methanol (32.7 g, 200 mmol) in DMSO (450 mL) was added DIEA (77.5 g, 600 mmol), and the mixture was stirred at 80° C. for 12 h. The mixture was poured into saturated aqueous NH$_4$Cl (1500 mL) and extracted with EtOAc (3×1500 mL). The combined organic extracts were washed with brine (1500 mL), dried over Na$_2$SO$_4$, filtered, and concentrated. The yellow residue was purified by silica gel column chromatography (PE:EA gradient) to afford methyl 2-(6-(hydroxymethyl)-3-azabicyclo[4.1.0]heptan-3-yl)-4-nitrobenzoate (45.0 g, 146 mmol) as a yellow oil. LCMS: MS ESI (M+1)$^+$ 307.0.

Step 2: Preparation of methyl 2-(6-formyl-3-azabicyclo[4.1.0]heptan-3-yl)-4-nitrobenzoate To a solution of methyl 2-(6-(hydroxymethyl)-3-azabicyclo[4.1.0]heptan-3-yl)-4-nitrobenzoate (45.0 g, 146 mmol) in DCM (450 mL) was added Dess-Martin periodinane (123 g, 292 mmol) at 0° C., and the mixture was stirred at room temperature for 2 h. The mixture was poured into saturated aqueous Na$_2$SO$_3$ (1500 mL) and extracted with EtOAc (3×800 mL). The combined organic extracts were washed with brine (1000 mL), dried over Na$_2$SO$_4$, filtered, and concentrated. The yellow residue was purified by silica gel column chromatography (PE:EA gradient) to afford methyl 2-(6-formyl-3-azabicyclo[4.1.0]heptan-3-yl)-4-nitrobenzoate (35.0 g, 115 mmol) as a yellow solid. LCMS: MS ESI (M+1)$^+$ 305.2.

Step 3: Preparation of methyl 2-(6-(difluoromethyl)-3-azabicyclo[4.1.0]heptan-3-yl)-4-nitrobenzoate

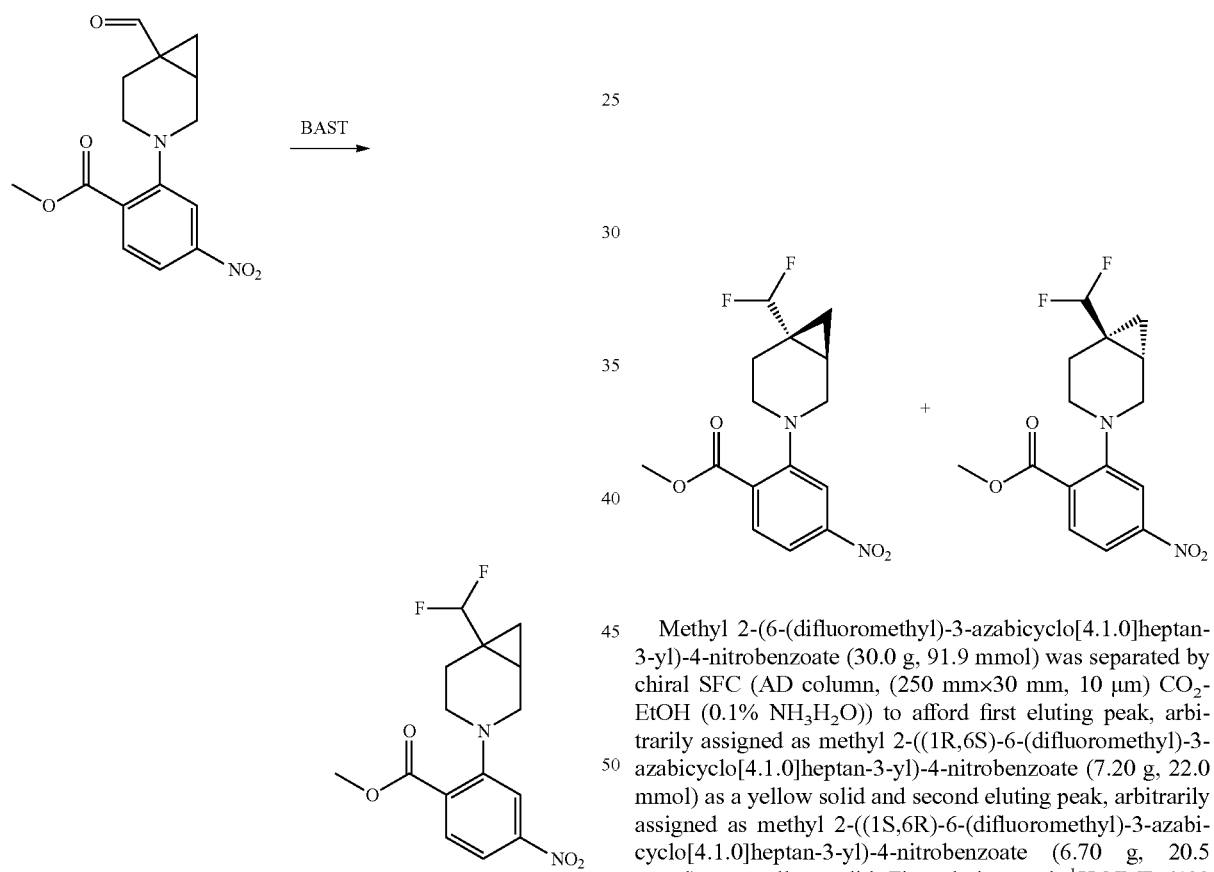

To a solution of methyl 2-(6-formyl-3-azabicyclo[4.1.0]heptan-3-yl)-4-nitrobenzoate (35.0 g, 115 mmol) in DCM (350 mL) was dropwise added bis(2-methoxyethyl)aminosulfur trifluoride (50.8 g, 230 mmol) at 0° C. The mixture was warmed to room temperature and stirred for 12 h. To the mixture was added silica gel (70 g) at 0° C., and the mixture was concentrated. The yellow residue was purified by silica gel column chromatography (PE:EA gradient) to afford methyl 2-(6-(difluoromethyl)-3-azabicyclo[4.1.0]heptan-3-yl)-4-nitrobenzoate (30.0 g, 91.9 mmol) as a yellow solid. LCMS: MS ESI (M+1)$^+$ 327.1.

Step 4: Preparation of methyl 2-((1R,6S)-6-(difluoromethyl)-3-azabicyclo[4.1.0]heptan-3-yl)-4-nitrobenzoate and methyl 2-((1S,6R)-6-(difluoromethyl)-3-azabicyclo[4.1.0]heptan-3-yl)-4-nitrobenzoate

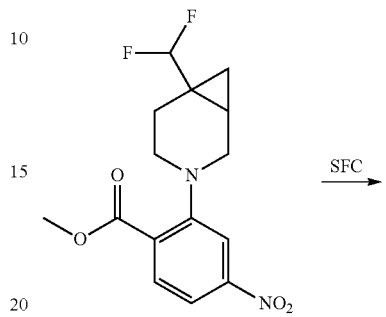

Methyl 2-(6-(difluoromethyl)-3-azabicyclo[4.1.0]heptan-3-yl)-4-nitrobenzoate (30.0 g, 91.9 mmol) was separated by chiral SFC (AD column, (250 mm×30 mm, 10 μm) CO$_2$-EtOH (0.1% NH$_3$H$_2$O)) to afford first eluting peak, arbitrarily assigned as methyl 2-((1R,6S)-6-(difluoromethyl)-3-azabicyclo[4.1.0]heptan-3-yl)-4-nitrobenzoate (7.20 g, 22.0 mmol) as a yellow solid and second eluting peak, arbitrarily assigned as methyl 2-((1S,6R)-6-(difluoromethyl)-3-azabicyclo[4.1.0]heptan-3-yl)-4-nitrobenzoate (6.70 g, 20.5 mmol) as a yellow solid. First eluting peak $^1$H NMR (400 MHz, CHLOROFORM-d) δ=7.80 (s, 1H), 7.75 (s, 2H), 5.65-5.14 (m, 1H), 3.94 (s, 3H), 3.47 (br d, J=11.6 Hz, 1H), 3.34 (dd, J=4.2, 11.6 Hz, 1H), 3.10 (dtd, J=2.0, 3.9, 10.8 Hz, 1H), 2.83 (ddd, J=5.1, 10.9, 12.7 Hz, 1H), 2.24-2.13 (m, 1H), 2.12-2.00 (m, 1H), 1.46-1.35 (m, 1H), 0.99 (dd, J=5.0, 9.2 Hz, 1H), 0.90 (q, J=4.8 Hz, 1H). Second eluting peak $^1$H NMR (400 MHz, CHLOROFORM-d) δ=7.81 (s, 1H), 7.75 (s, 2H), 5.63-5.20 (m, 1H), 3.94 (s, 3H), 3.48 (br d, J=11.8 Hz, 1H), 3.34 (dd, J=4.2, 11.6 Hz, 1H), 3.10 (td, J=4.2, 8.0 Hz, 1H), 2.83 (ddd, J=5.0, 11.0, 12.6 Hz, 1H), 2.23-2.13 (m, 1H), 2.12-2.00 (m, 1H), 1.46-1.36 (m, 1H), 1.00 (dd, J=5.0, 9.2 Hz, 1H), 0.90 (q, J=4.8 Hz, 1H).

Example 1: Synthesis of N-(2-(4,4-difluorocyclo-hexyl)-6-methylpyrimidin-4-yl)-2-(4,4-dimethyl-1,4-azasilinan-1-yl)-4-((2-hydroxyethyl)sulfonamido)benzamide

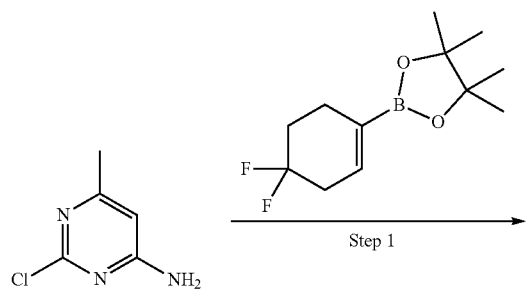

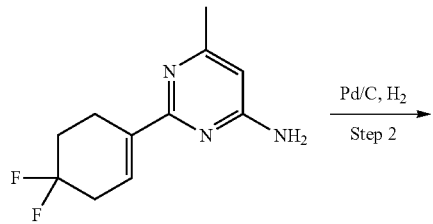

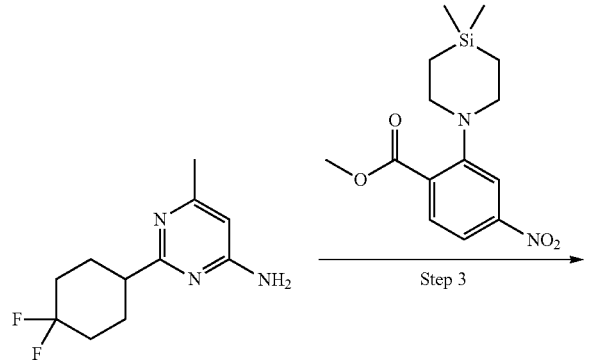

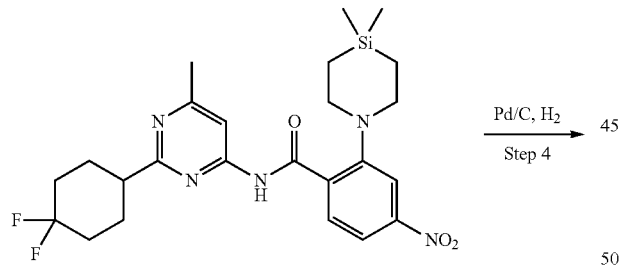

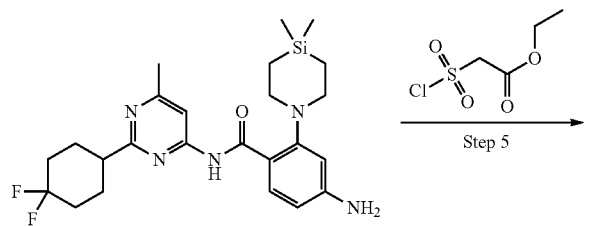

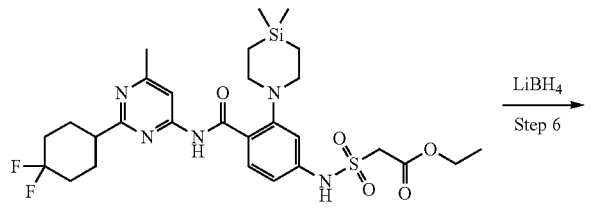

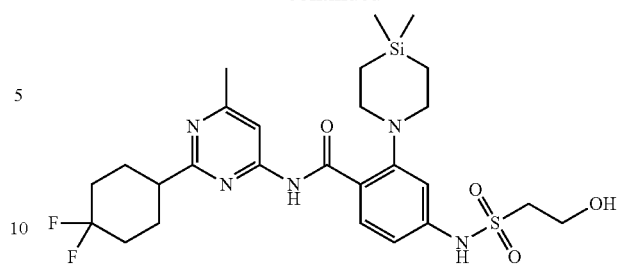

Step 1: Preparation of 2-(4,4-difluorocyclohex-1-en-1-yl)-6-methylpyrimidin-4-amine

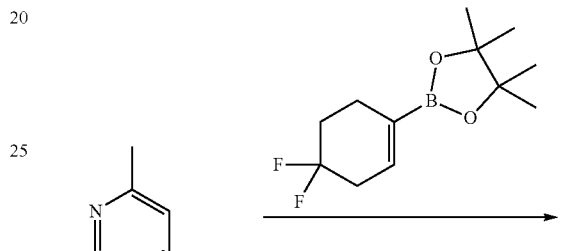

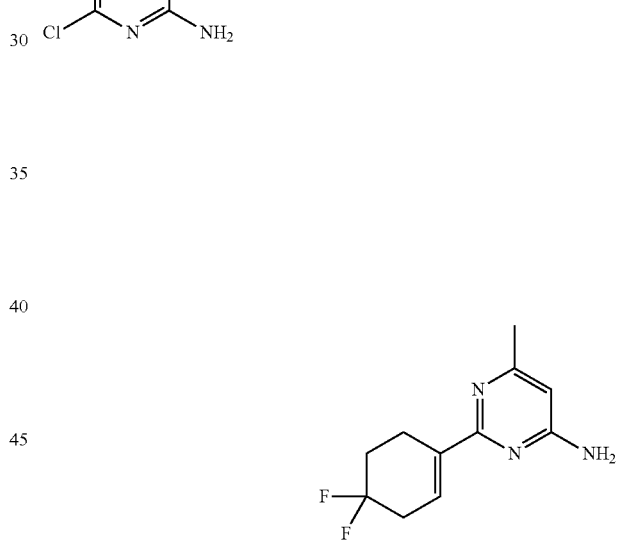

To a solution of 2-chloro-6-methylpyrimidin-4-amine (300 mg, 2.08 mmol) and 2-(4,4-difluorocyclohex-1-en-1-yl)-4,4,5,5-tetramethyl-1,3,2-dioxaborolane (507 mg, 2.08 mmol) in dioxane (6 mL) and $H_2O$ (2 mL) was added potassium dihydrogen phosphate (1.32 g, 6.24 mmol) and [1,1′-Bis(diphenylphosphino)ferrocene]dichloropalladium (II) (169 mg, 208 μmol) at 20° C. The mixture was stirred at 100° C. for 16 h. The mixture was then poured into $H_2O$ (50 mL) and extracted with EA (2×30 mL). The combined organic extracts were washed with brine (30 mL), dried over $Na_2SO_4$, filtered, and concentrated under reduced pressure to give a residue. The residue was purified by silica gel column chromatography (PE:EA 10:1) to afford 2-(4,4-difluorocyclohex-1-en-1-yl)-6-methylpyrimidin-4-amine (380 mg, 1.68 mmol) as a white solid. LCMS: MS ESI $(M+1)^+$ 226.1.

Step 2: Preparation of 2-(4,4-difluorocyclohexyl)-6-methylpyrimidin-4-amine

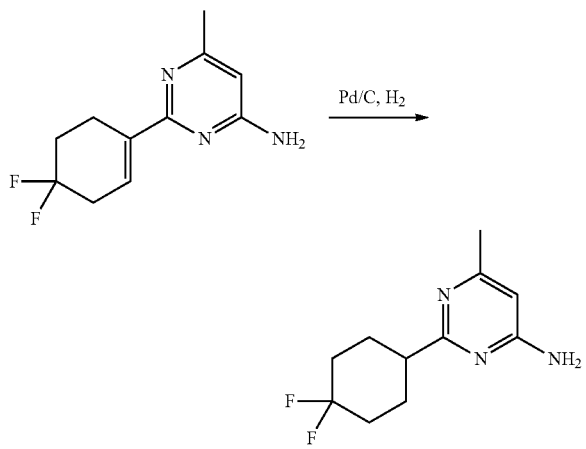

To a solution of 2-(4,4-difluorocyclohex-1-en-1-yl)-6-methylpyrimidin-4-amine (130 mg, 577 µmol) in EtOH (3 mL) was added Pd/C (60 mg, 10% w/w) at 25° C. The mixture was stirred at 25° C. for 16 h under H$_2$ atmosphere (15 psi). The mixture was filtered, and the filter cake was washed with DCM (40 mL). The filtrate was concentrated in vacuo to afford 2-(4,4-difluorocyclohexyl)-6-methylpyrimidin-4-amine (100 mg, 440 µmol) as a gray solid. LCMS: MS ESI (M+1)$^+$ 228.2.

Step 3: Preparation of N-(2-(4,4-difluorocyclohexyl)-6-methylpyrimidin-4-yl)-2-(4,4-dimethyl-1,4-azasilinan-1-yl)-4-nitrobenzamide

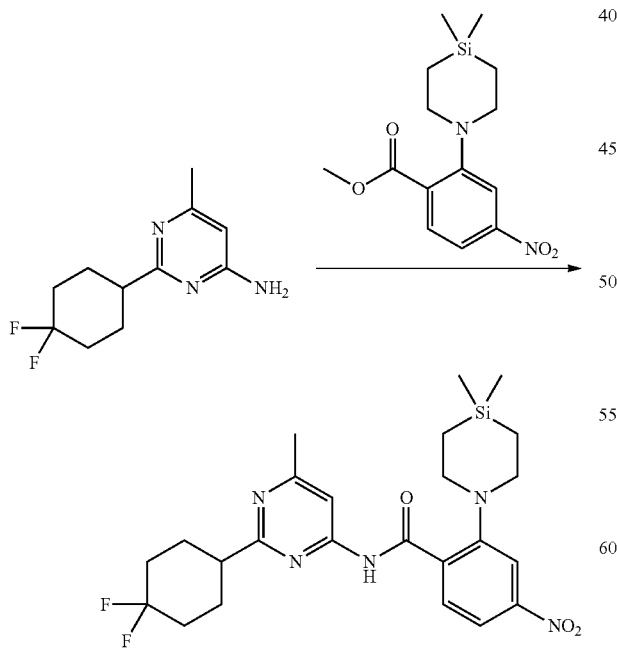

To a solution of 2-(4,4-difluorocyclohexyl)-6-methylpyrimidin-4-amine (100 mg, 440 µmol) and methyl 2-(4,4-dimethyl-1,4-azasilinan-1-yl)-4-nitrobenzoate (135 mg, 440 µmol) in THF (4 mL) was added lithium bis(trimethylsilyl)amide (1.32 mL, 1.32 mmol, 1 M in THF) at 25° C. The mixture was stirred at 25° C. for 1 h. The mixture was poured into H$_2$O (20 mL) which was then extracted with ethyl acetate (2×30 mL). The combined organic extracts were washed with brine (30 mL), dried over Na$_2$SO$_4$, filtered, and concentrated under reduced pressure to give a residue. The residue was purified by silica gel column chromatography (PE:EA 10:1) to afford N-(2-(4,4-difluorocyclohexyl)-6-methylpyrimidin-4-yl)-2-(4,4-dimethyl-1,4-azasilinan-1-yl)-4-nitrobenzamide (130 mg, 258 µmol) as a yellow solid. LCMS: MS ESI (M+1)$^+$ 504.2.

Step 4: Preparation of 4-amino-N-(2-(4,4-difluorocyclohexyl)-6-methylpyrimidin-4-yl)-2-(4,4-dimethyl-1,4-azasilinan-1-yl)benzamide

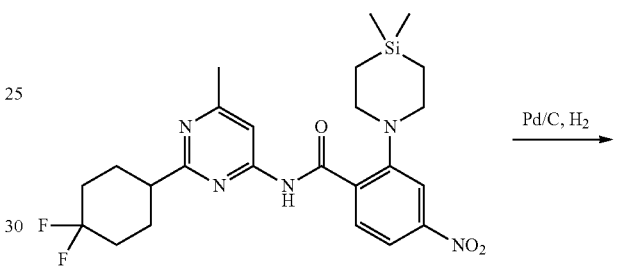

To a solution of N-(2-(4,4-difluorocyclohexyl)-6-methylpyrimidin-4-yl)-2-(4,4-dimethyl-1,4-azasilinan-1-yl)-4-nitrobenzamide (130 mg, 258 µmol) in THF (4 mL) was added Pd/C (100 mg, 10% w/w) at 25° C. The mixture was stirred at 25° C. for 4 h under H$_2$ atmosphere (15 psi). The mixture was filtered, and the filter cake was washed with MeOH (20 mL) and DCM (20 mL). The filtrate was concentrated in vacuo to afford 4-amino-N-(2-(4,4-difluorocyclohexyl)-6-methylpyrimidin-4-yl)-2-(4,4-dimethyl-1,4-azasilinan-1-yl)benzamide (110 mg, 232 µmol) as a white solid. LCMS: MS ESI (M+1)$^+$ 474.4.

Step 5: Preparation of ethyl 2-(N-(4-((2-(4,4-difluorocyclohexyl)-6-methylpyrimidin-4-yl)carbamoyl)-3-(4,4-dimethyl-1,4-azasilinan-1-yl)phenyl)sulfamoyl)acetate

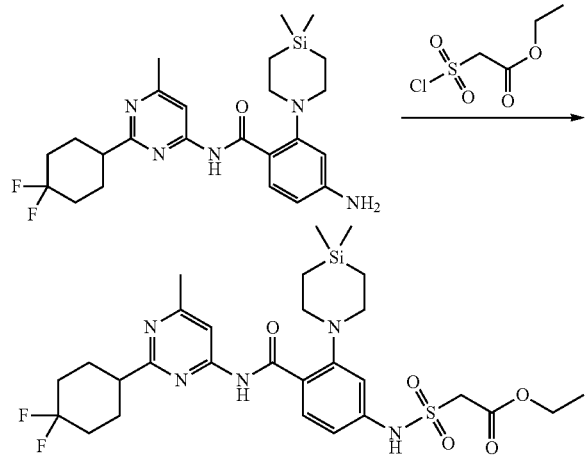

To a solution of 4-amino-N-(2-(4,4-difluorocyclohexyl)-6-methylpyrimidin-4-yl)-2-(4,4-dimethyl-1,4-azasilinan-1-yl)benzamide (110 mg, 232 µmol) and pyridine (91.7 mg, 1.16 mmol) in DCM (3 mL) was added ethyl 2-(chlorosulfonyl)acetate (129 mg, 696 µmol) at 0° C. The mixture was stirred at 25° C. for 4 h. The mixture was poured into H₂O (50 mL) and was extracted with EA (2×30 mL). The combined organic extracts were washed with brine (30 mL), dried over Na₂SO₄, filtered, and concentrated under reduced pressure to give a residue. The residue was purified by silica gel column chromatography (PE:EA 10:1) to afford ethyl 2-(N-(4-((2-(4,4-difluorocyclohexyl)-6-methylpyrimidin-4-yl)carbamoyl)-3-(4,4-dimethyl-1,4-azasilinan-1-yl)phenyl) sulfamoyl)acetate (140 mg, 224 µmol) as a colorless oil. LCMS: MS ESI (M+1)⁺ 624.6.

Step 6: Preparation of N-(2-(4,4-difluorocyclohexyl)-6-methylpyrimidin-4-yl)-2-(4,4-dimethyl-1,4-azasilinan-1-yl)-4-((2-hydroxyethyl)sulfonamido) benzamide

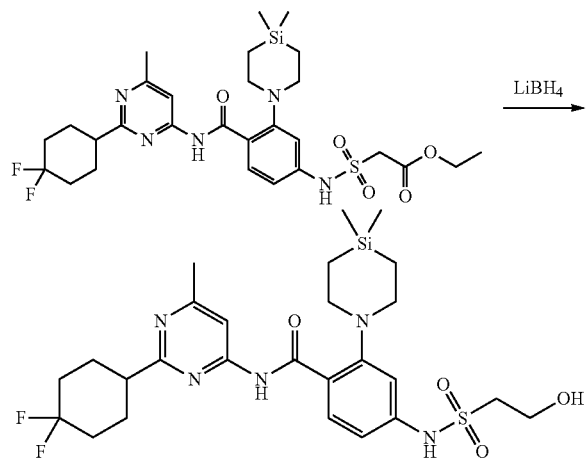

To a solution of ethyl 2-(N-(4-((2-(4,4-difluorocyclohexyl)-6-methylpyrimidin-4-yl)carbamoyl)-3-(4,4-dimethyl-1,4-azasilinan-1-yl)phenyl)sulfamoyl)acetate (140 mg, 224 µmol) in THF (4 mL) was added lithium borohydride (0.168 mL, 336 µmol, 2 M in THF) at 0° C. The mixture was stirred at 0° C. for 0.5 h. The reaction was poured into saturated aqueous NH₄Cl (20 mL). The mixture was extracted with EA (2×30 mL). The combined organic extracts were washed with brine (30 mL), dried over Na₂SO₄, filtered, and concentrated under reduced pressure. The residue was purified by prep-HPLC (TFA) to afford N-(2-(4,4-difluorocyclohexyl)-6-methylpyrimidin-4-yl)-2-(4,4-dimethyl-1,4-azasilinan-1-yl)-4-((2-hydroxyethyl) sulfonamido)benzamide (57.25 mg, 98.4 µmol) as a white solid. LCMS: MS ESI (M+1)⁺ 582.3. ¹H NMR (400 MHz, DMSO-d₆) δ=13.17 (s, 1H), 10.06 (s, 1H), 7.99-7.75 (m, 2H), 7.10 (d, J=2.0 Hz, 1H), 6.96 (dd, J=2.0, 8.7 Hz, 1H), 3.56 (br s, 2H), 3.18 (t, J=6.4 Hz, 2H), 3.06-2.94 (m, 4H), 2.78-2.63 (m, 1H), 2.29 (s, 3H), 1.95-1.56 (m, 8H), 0.92-0.79 (m, 4H), 0.00 (s, 6H).

Example 2: Synthesis of 2-(4,4-dimethyl-1,4-azasilinan-1-yl)-4-((2-hydroxyethyl)sulfonamido)-N-(5-methyl-6-morpholinopyridin-2-yl)benzamide

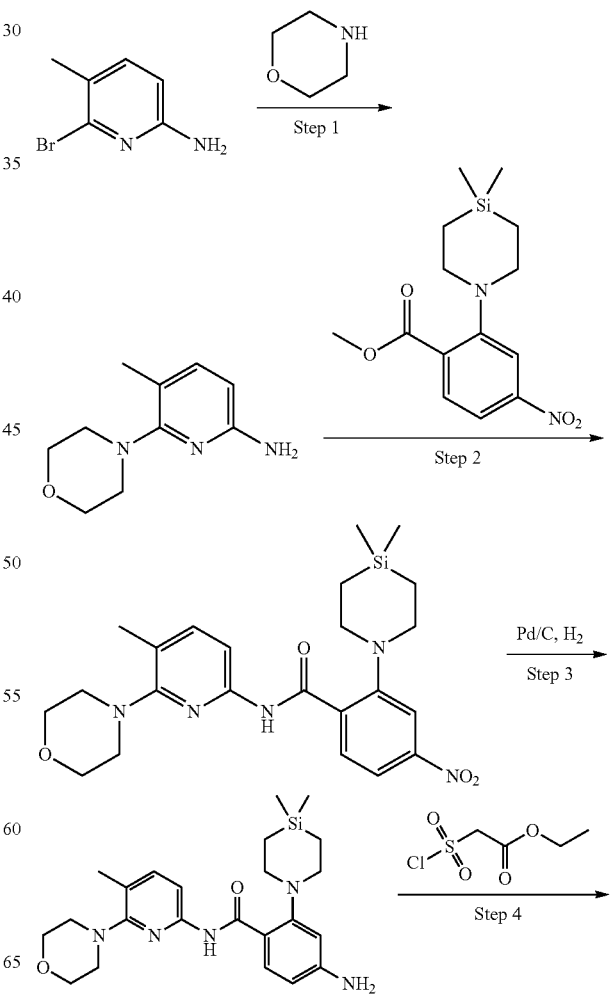

-continued

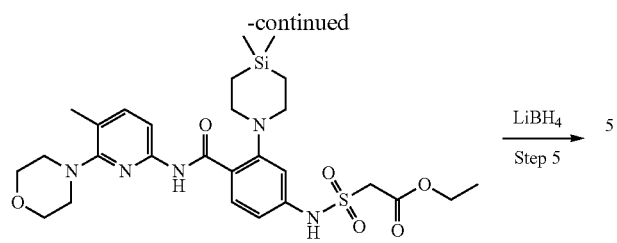

Step 1: Preparation of
5-methyl-6-morpholinopyridin-2-amine

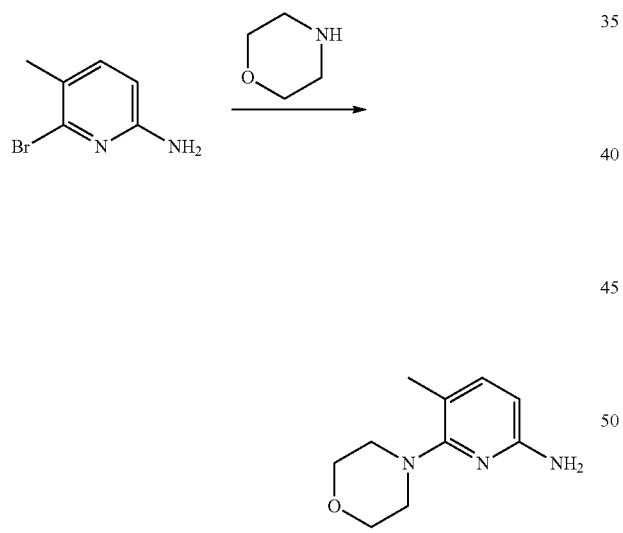

A solution of 6-bromo-5-methylpyridin-2-amine (2.00 g, 10.6 mmol) in morpholine (20 mL, 10.6 mmol) was stirred at 130° C. under $N_2$ atmosphere for 16 h. The reaction mixture was concentrated under reduced pressure to give a residue. The residue was purified by silica gel; column chromatography (PE:EA 10:1). 5-Methyl-6-morpholinopyridin-2-amine (850 mg, 4.39 mmol) was obtained as a white solid. LCMS: MS ESI (M+1)$^+$ 194.2. $^1$H NMR (400 MHz, Chloroform-d) δ=7.19 (d, J=8.0 Hz, 1H), 6.12 (d, J=8.0 Hz, 1H), 4.23-4.06 (m, 2H), 3.87-3.77 (m, 4H), 3.18-3.06 (m, 4H), 2.15 (s, 3H).

Step 2: Preparation of 2-(4,4-dimethyl-1,4-azasilinan-1-yl)-N-(5-methyl-6-morpholinopyridin-2-yl)-4-nitrobenzamide

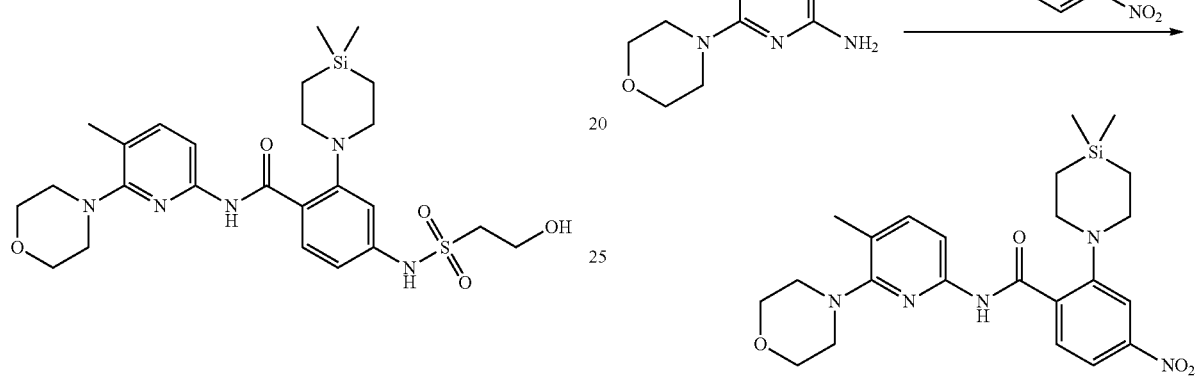

To a solution of 5-methyl-6-morpholinopyridin-2-amine (400 mg, 2.06 mmol), methyl 2-(4,4-dimethyl-1,4-azasilinan-1-yl)-4-nitrobenzoate (635 mg, 2.06 mmol) in THF (5 mL) was added LiHMDS (6.18 mL, 6.18 mmol, 1 M in THF) at 0° C., and the mixture was stirred at 25° C. for 0.5 h. The reaction mixture was quenched with sat. aq. $NH_4Cl$ (30 mL) and then extracted with ethyl acetate (3×20 mL). The combined organic extracts were dried over $Na_2SO_4$, filtered, and concentrated under reduced pressure. The residue was purified by silica gel column chromatography (PE:EA 50:1) to obtain 2-(4,4-dimethyl-1,4-azasilinan-1-yl)-N-(5-methyl-6-morpholinopyridin-2-yl)-4-nitrobenzamide (950 mg, 2.02 mmol) as a yellow solid. LCMS: MS ESI (M+1)$^+$ 470.2. $^1$H NMR (400 MHz, Chloroform-d) δ=12.16 (s, 1H), 8.40 (d, J=8.8 Hz, 1H), 8.15 (d, J=2.4 Hz, 1H), 8.06 (dd, J=2.0, 8.6 Hz, 1H), 8.00 (d, J=8.0 Hz, 1H), 7.50 (d, J=8.0 Hz, 1H), 3.92-3.81 (m, 4H), 3.41-3.28 (m, 4H), 3.21-3.07 (m, 4H), 2.28 (s, 3H), 1.18-1.05 (m, 4H), 0.20 (s, 6H).

Step 3: Preparation of 4-amino-2-(4,4-dimethyl-1,4-azasilinan-1-yl)-N-(5-methyl-6-morpholinopyridin-2-yl)benzamide

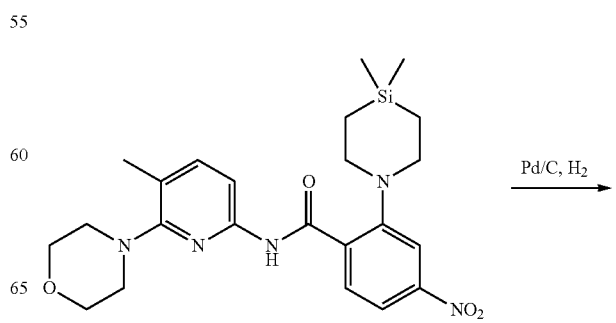

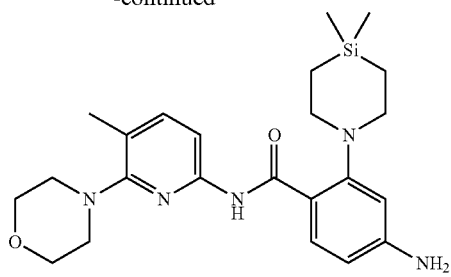

To a solution of 2-(4,4-dimethyl-1,4-azasilinan-1-yl)-N-(5-methyl-6-morpholinopyridin-2-yl)-4-nitrobenzamide (100 mg, 212 μmol) in MeOH (3 mL) was added Pd/C (40 mg, 10% w/w), and then the mixture was stirred at 25° C. for 2 h under H₂ atmosphere (15 psi). The reaction mixture was filtered and concentrated under reduced pressure to afford 4-amino-2-(4,4-dimethyl-1,4-azasilinan-1-yl)-N-(5-methyl-6-morpholinopyridin-2-yl)benzamide (75 mg, 0.1705 mmol) as a white solid. LCMS: MS ESI (M+1)⁺ 440.2.

Step 4: Preparation of ethyl 2-(N-(3-(4,4-dimethyl-1,4-azasilinan-1-yl)-4-((5-methyl-6-morpholinopyridin-2-yl)carbamoyl)phenyl)sulfamoyl)acetate

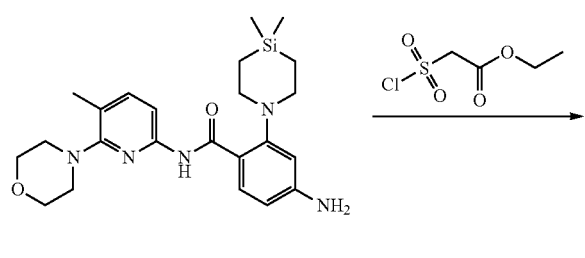

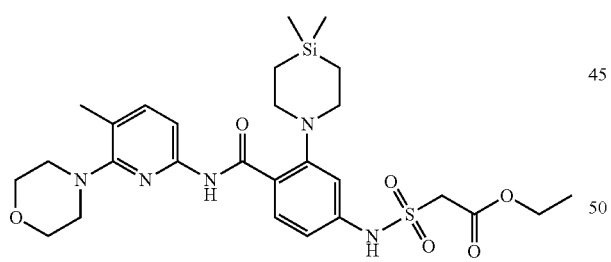

To a solution of 4-amino-2-(4,4-dimethyl-1,4-azasilinan-1-yl)-N-(5-methyl-6-morpholinopyridin-2-yl)benzamide (75 mg, 0.1705 mmol) and pyridine (40.4 mg, 0.5115 mmol) in DCM (1 mL) was added ethyl 2-(chlorosulfonyl)acetate (63.6 mg, 0.341 mmol) at 0° C., and the mixture was stirred at 25° C. for 1 h. The reaction mixture was extracted with DCM (3×20 mL) and H₂O (3×10 mL). The combined organic extracts were dried over Na₂SO₄, filtered, and concentrated under reduced pressure to give a residue. Ethyl 2-(N-(3-(4,4-dimethyl-1,4-azasilinan-1-yl)-4-((5-methyl-6-morpholinopyridin-2-yl)carbamoyl)phenyl)sulfamoyl)acetate (90 mg, 0.1525 mmol) was obtained as a yellow oil. LCMS: MS ESI (M+1)⁺ 590.3.

Step 5: Preparation of 2-(4,4-dimethyl-1,4-azasilinan-1-yl)-4-((2-hydroxyethyl)sulfonamido)-N-(5-methyl-6-morpholinopyridin-2-yl)benzamide

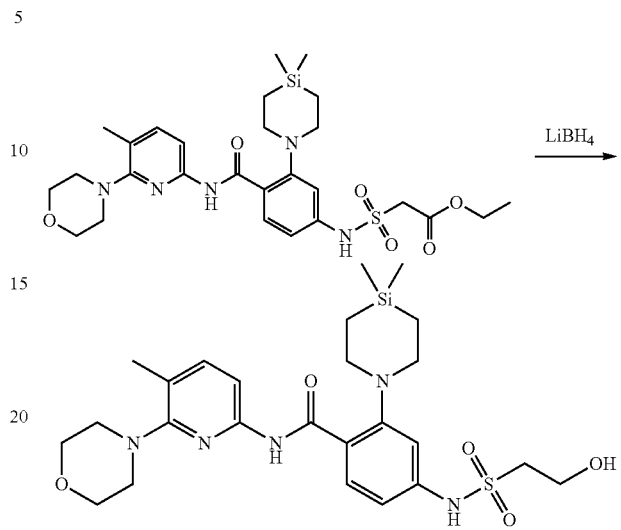

To a solution of ethyl 2-(N-(3-(4,4-dimethyl-1,4-azasilinan-1-yl)-4-((5-methyl-6-morpholinopyridin-2-yl)carbamoyl)phenyl)sulfamoyl)acetate (90 mg, 0.1525 mmol) in THF (1 mL) was added LiBH₄ (228 μL, 0.4575 mmol, 2 M in THF) at 0° C., and then the mixture was stirred at 25° C. for 0.5 h. The reaction mixture was quenched with sat. aq. NH₄Cl (30 mL), and then extracted with ethyl acetate (2×20 mL). The combined organic extracts were dried over Na₂SO₄, filtered, and concentrated under reduced pressure to give a residue. The residue was purified by prep-HPLC (TFA condition). 2-(4,4-Dimethyl-1,4-azasilinan-1-yl)-4-((2-hydroxyethyl)sulfonamido)-N-(5-methyl-6-morpholinopyridin-2-yl)benzamide (TFA salt, 38.52 mg, 0.07032 mmol) was obtained as a white solid. LCMS: MS ESI (M+1)⁺ 548.3. ¹H NMR (400 MHz, DMSO-d₆) δ 12.45 (s, 1H), 10.13 (s, 1H), 8.05-7.99 (m, 1H), 7.87 (d, J=8.0 Hz, 1H), 7.55 (d, J=8.4 Hz, 1H), 7.25 (d, J=2.0 Hz, 1H), 7.09 (dd, J=2.0, 8.6 Hz, 1H), 3.75-3.71 (m, 6H), 3.34 (s, 2H), 3.19-3.15 (m, 4H), 3.06-3.03 (m, 4H), 2.22 (s, 3H), 1.06-1.01 (m, 4H), 0.18-0.16 (m, 6H).

Example 3: Synthesis of N-(6-(4,4-difluoropiperidin-1-yl)pyridin-2-yl)-2-(4,4-dimethyl-1,4-azasilinan-1-yl)-4-((2-hydroxyethyl)sulfonamido)benzamide

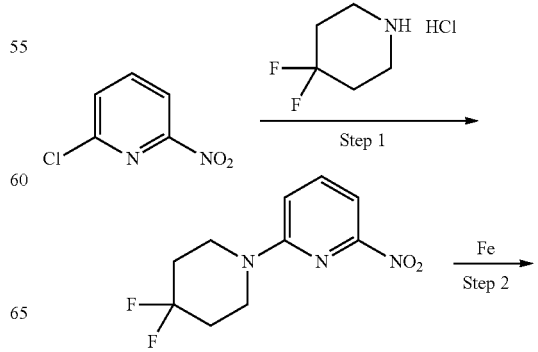

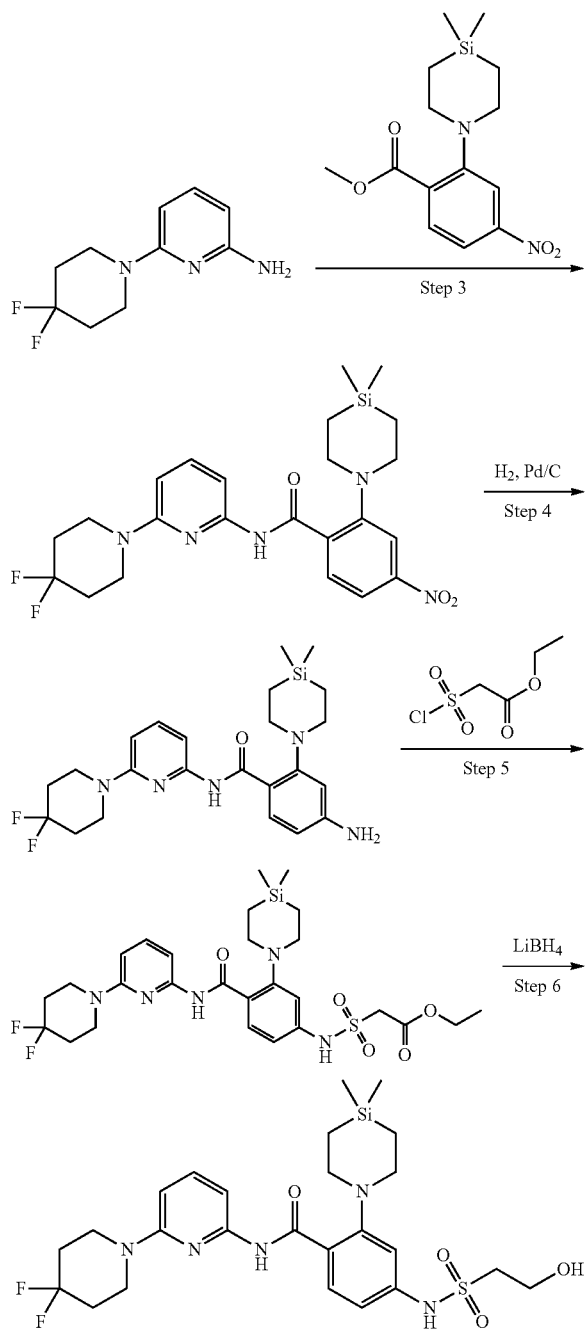

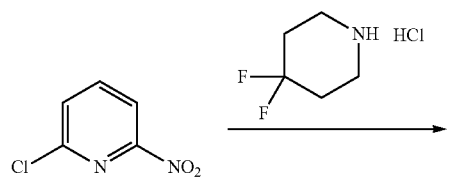

Step 1: Preparation of
2-(4,4-difluoropiperidin-1-yl)-6-nitropyridine

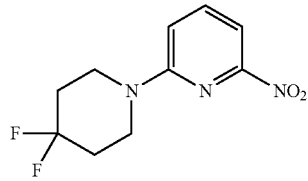

To a solution of 2-chloro-6-nitropyridine (500 mg, 3.15 mmol) and 4,4-difluoropiperidine hydrochloride (595 mg, 3.78 mmol) in DMSO (5 mL) was added DIPEA (1.22 g, 9.45 mmoL) at 25° C. The mixture was stirred at 100° C. for 16 h. The mixture was poured into H$_2$O (50 mL) and extracted with ethyl acetate (2×30 mL). The combined organic extracts were washed with brine (30 mL), dried over Na$_2$SO$_4$, filtered, and concentrated under reduced pressure. The residue was purified by silica gel column chromatography (PE:EA 10:1) to afford 2-(4,4-difluoropiperidin-1-yl)-6-nitropyridine (600 mg, 2.46 mmol) as a yellow oil. LCMS: MS ESI (M+1)$^+$ 244.0.

Step 2: Preparation of
6-(4,4-difluoropiperidin-1-yl)pyridin-2-amine

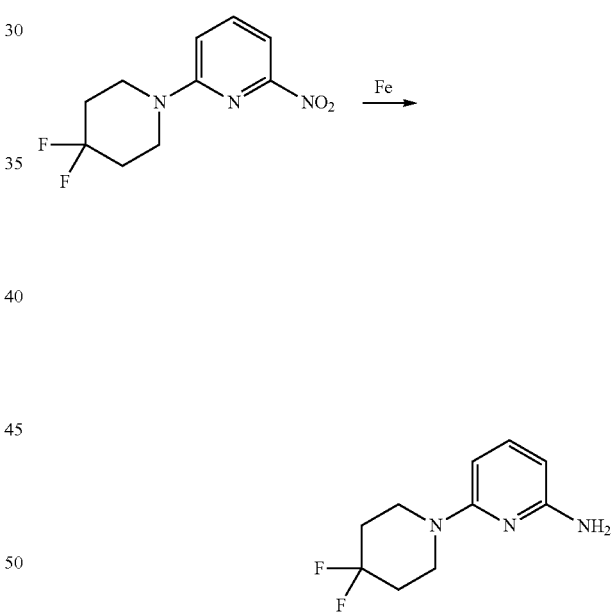

To a solution of 2-(4,4-difluoropiperidin-1-yl)-6-nitropyridine (300 mg, 1.23 mmol) in EtOH (5 mL) and H$_2$O (1 mL) was added ammonium chloride (328 mg, 6.15 mmol) and iron powder (686 mg, 12.3 mmol) at 25° C. The mixture was stirred at 80° C. for 16 h. The mixture was filtered, and the filter cake was washed with ethyl acetate (50 mL). The filtrate was poured into H$_2$O (50 mL). The mixture was extracted with ethyl acetate (2×30 mL). The combined organic extracts were washed with brine (30 mL), dried over Na$_2$SO$_4$, filtered, and concentrated under reduced pressure to give 6-(4,4-difluoropiperidin-1-yl) pyridin-2-amine (250 mg, 1.17 mmol) as a yellow oil. LCMS: MS ESI (M+1)$^+$= 214.1.

Step 3: Preparation of N-(6-(4,4-difluoropiperidin-1-yl)pyridin-2-yl)-2-(4,4-dimethyl-1,4-azasilinan-1-yl)-4-nitrobenzamide

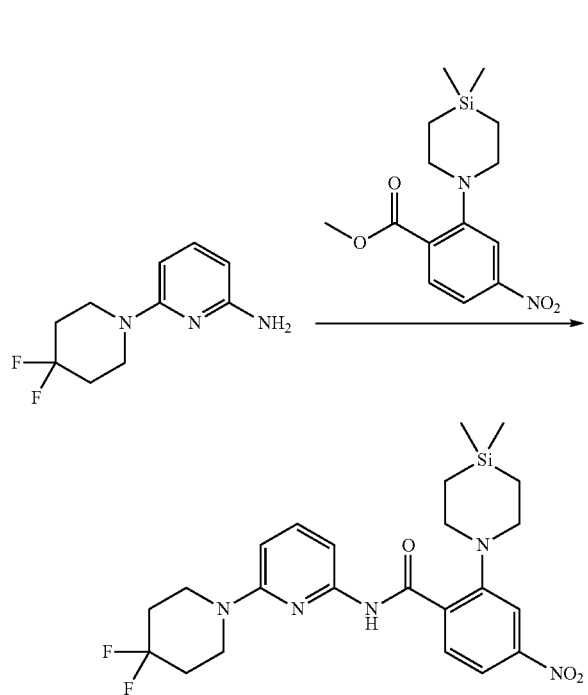

To a solution of 6-(4,4-difluoropiperidin-1-yl)pyridin-2-amine (230 mg, 1.07 mmol) and methyl 2-(4,4-dimethyl-1,4-azasilinan-1-yl)-4-nitrobenzoate (329 mg, 1.07 mmol) in THF (4 mL) was added LiHMDS (3.2 mL, 3.21 mmol, 1 M in THF) at 25° C. The mixture was stirred at 25° C. for 1 h. The mixture was poured into H$_2$O (20 mL). The mixture was extracted with ethyl acetate (2×20 mL). The combined organic extracts were washed with brine (30 mL), dried over Na$_2$SO$_4$, filtered, and concentrated under reduced pressure. The residue was purified by silica gel column chromatography (PE:EA 10:1) to afford N-(6-(4,4-difluoropiperidin-1-yl)pyridin-2-yl)-2-(4,4-dimethyl-1,4-azasilinan-1-yl)-4-nitrobenzamide (260 mg, 531 μmol) as a yellow solid. MS ESI (M+1)$^+$ 490.3.

Step 4: Preparation of 4-amino-N-(6-(4,4-difluoropiperidin-1-yl)pyridin-2-yl)-2-(4,4-dimethyl-1,4-azasilinan-1-yl)benzamide

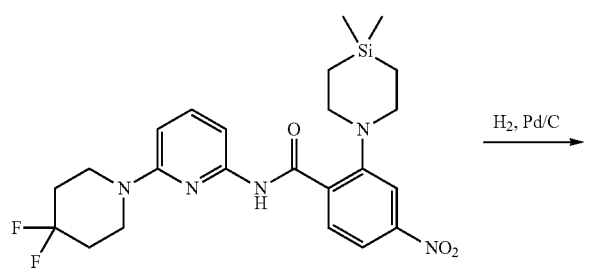

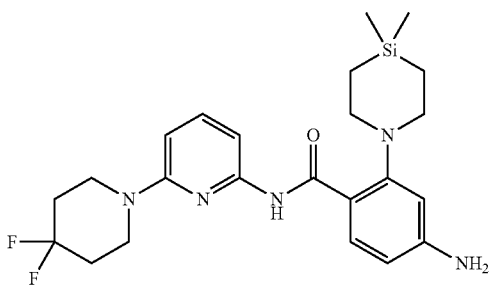

To a solution of N-(6-(4,4-difluoropiperidin-1-yl)pyridin-2-yl)-2-(4,4-dimethyl-1,4-azasilinan-1-yl)-4-nitrobenzamide (260 mg, 531 μmol) in THF (5 mL) was added Pd/C (130 mg, 531 μmol) at 25° C. The mixture was stirred at 25° C. for 16 h under H$_2$ atmosphere (15 psi). The mixture was filtered, and filter cake was washed with DCM (20 mL). The filtrate was concentrated in vacuo to afford 4-amino-N-(6-(4,4-difluoropiperidin-1-yl)pyridin-2-yl)-2-(4,4-dimethyl-1,4-azasilinan-1-yl)benzamide (220 mg, 478 μmol) as a white solid. LCMS: MS ESI (M+1)$^+$=460.3.

Step 5: Preparation of ethyl 2-(N-(4-((6-(4,4-difluoropiperidin-1-yl)pyridin-2-yl)carbamoyl)-3-(4,4-dimethyl-1,4-azasilinan-1-yl)phenyl)sulfamoyl)acetate

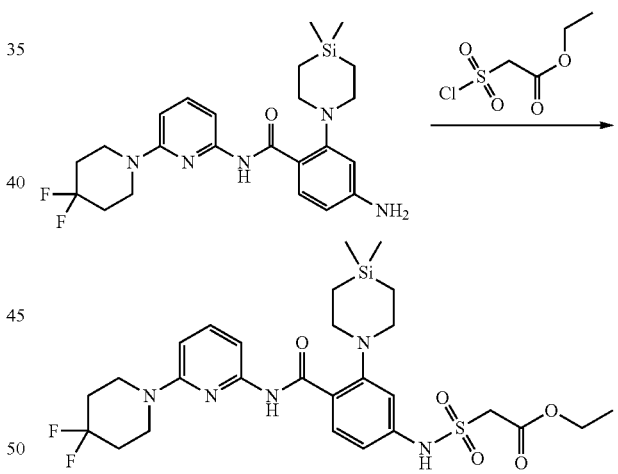

To a solution of 4-amino-N-(6-(4,4-difluoropiperidin-1-yl)pyridin-2-yl)-2-(4,4-dimethyl-1,4-azasilinan-1-yl)benzamide (100 mg, 217 μmol) and pyridine (51.4 mg, 651 μmol) in DCM (3 mL) was added ethyl 2-(chlorosulfonyl)acetate (60.6 mg, 325 μmol) at 0° C. The mixture was stirred at 25° C. for 3 h. The mixture was poured into H$_2$O (50 mL) and was extracted with ethyl acetate (2×30 mL). The combined organic extracts were washed with brine (30 mL), dried over Na$_2$SO$_4$, filtered, and concentrated under reduced pressure. The residue was purified by silica gel column chromatography (PE:EA 10:1) to afford ethyl 2-(N-(4-((6-(4,4-difluoropiperidin-1-yl)pyridin-2-yl)carbamoyl)-3-(4,4-dimethyl-1,4-azasilinan-1-yl)phenyl)sulfamoyl)acetate (110 mg, 180 μmol) as a white solid. LCMS: MS ESI (M+1)$^+$ 610.4.

Step 6: Preparation of N-(6-(4,4-difluoropiperidin-1-yl)pyridin-2-yl)-2-(4,4-dimethyl-1,4-azasilinan-1-yl)-4-((2-hydroxyethyl)sulfonamido)benzamide

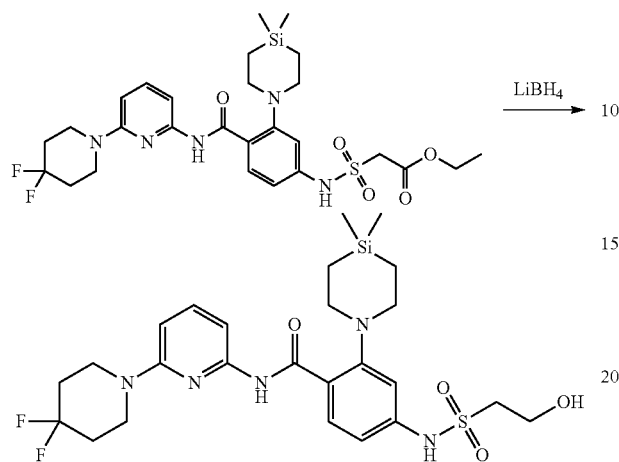

To a solution of ethyl 2-(N-(4-((6-(4,4-difluoropiperidin-1-yl)pyridin-2-yl)carbamoyl)-3-(4,4-dimethyl-1,4-azasilinan-1-yl)phenyl)sulfamoyl)acetate (110 mg, 180 µmol) in THF (4 mL) was added lithium borohydride (180 µL, 360 µmol, 2 M in THF) at 0° C. The solution was then stirred at 25° C. for 1 h. The mixture was poured into sat. aq. NH$_4$Cl (50 mL) and was extracted with ethyl acetate (2×30 mL). The combined organic extracts were washed with brine (30 mL), dried over Na$_2$SO$_4$, filtered, and concentrated under reduced pressure. The residue was purified by prep-HPLC (TFA condition) to afford N-(6-(4,4-difluoropiperidin-1-yl)pyridin-2-yl)-2-(4,4-dimethyl-1,4-azasilinan-1-yl)-4-((2-hydroxyethyl)sulfonamido)benzamide (35.66 mg, 62.8 µmol) as an off-white solid. LCMS: MS ESI (M+1)$^+$ 568.4. $^1$H NMR (400 MHz, DMSO-d$_6$) δ=12.13 (s, 1H), 9.99 (s, 1H), 7.86 (br d, J=8.6 Hz, 1H), 7.58-7.40 (m, 2H), 7.10 (s, 1H), 6.95 (br d, J=8.5 Hz, 1H), 6.56 (d, J=7.9 Hz, 1H), 3.61 (br t, J=6.4 Hz, 2H), 3.54 (br d, J=4.8 Hz, 4H), 3.29-3.16 (m, 2H), 3.09-2.93 (m, 4H), 1.91-1.77 (m, 4H), 0.87 (br d, J=4.9 Hz, 4H), 0.00 (s, 6H).

Example 4: Synthesis of N-(3-(N-(tert-butyl)sulfamoyl)phenyl)-2-(4,4-dimethyl-1,4-azasilinan-1-yl)-4-((1,1-dimethylethyl)sulfonamido)benzamide

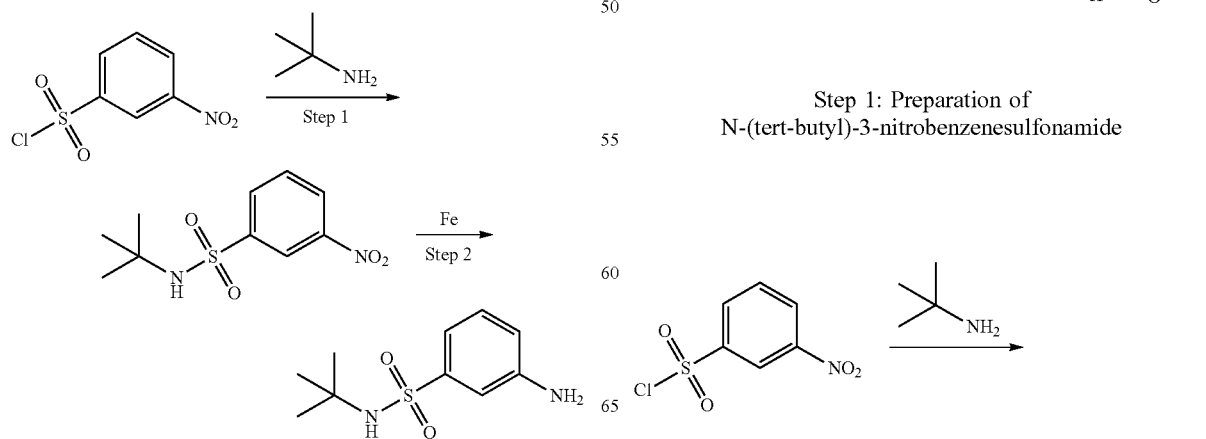

Step 1: Preparation of N-(tert-butyl)-3-nitrobenzenesulfonamide

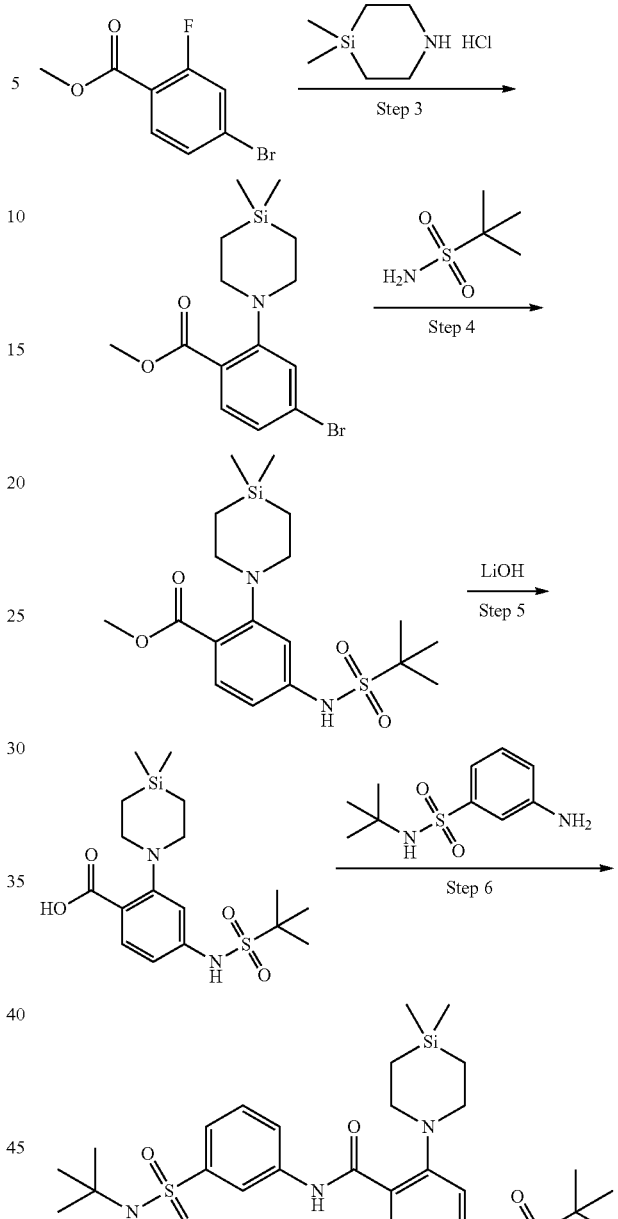

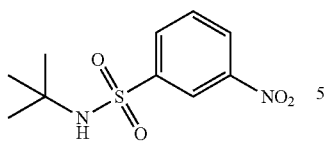

A solution of 3-nitrobenzenesulfonyl chloride (2.21 g, 0.01 mol) in DCM (15 mL) was treated with 2-methylpropan-2-amine (2.18 g, 0.030 mol) followed by DIPEA (3.86 g, 0.03 mol) at 0° C. The resulting reaction mixture was stirred at 25° C. for 4 h. The reaction mixture was diluted with DCM (50 mL). The mixture was washed with saturated aqueous citric acid solution (2×20 mL) and brine (20 mL). The separated organic extract was dried over Na₂SO₄ and concentrated under reduced pressure. N-(tert-Butyl)-3-nitrobenzenesulfonamide (1.8 g, 6.96 mmol) was obtained as a light-yellow solid. $^1$H NMR (400 MHz, DMSO-d$_6$) δ=8.59 (t, J=2.0 Hz, 1H), 8.44 (dd, J=1.6, 8.0 Hz, 1H), 8.25 (d, J=8.0 Hz, 1H), 7.97-7.82 (m, 2H), 1.11 (s, 9H).

Step 2: Preparation of 3-amino-N-(tert-butyl)benzenesulfonamide

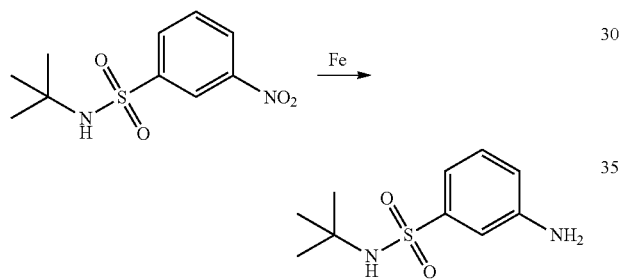

To a solution of N-(tert-butyl)-3-nitrobenzenesulfonamide (1.8 g, 6.96 mmol) in EtOH (20 mL) and water (5 mL) was added Fe powder (3.1 g, 55.6 mmol) and NH₄Cl (2.97 g, 55.6 mol). The mixture was stirred at 80° C. for 1.5 h. The suspension was filtered through a pad of Celite, and the filter cake was washed with MeOH (20 mL). The combined filtrates were concentrated. The residue was partitioned between ethyl acetate (60 mL) and water (20 mL). The separated organic extract was washed with brine (2×20 mL), dried over Na₂SO₄, and concentrated to dryness. 3-Amino-N-(tert-butyl)benzenesulfonamide (1.35 g, 5.91 mmol) was obtained as a colorless oil. LCMS: MS ESI (M+1)⁺ 229.2.

Step 3: Preparation of methyl 4-bromo-2-(4,4-dimethyl-1,4-azasilinan-1-yl)benzoate

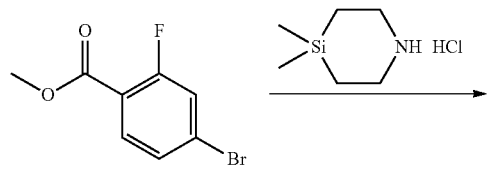

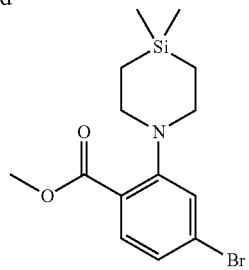

To a solution of methyl 4-bromo-2-fluorobenzoate (354 mg, 1.51 mmol) and 4,4-dimethyl-1,4-azasilinane hydrochloride (311 mg, 1.88 mmol) in DMSO (5 mL) was added K₂CO₃ (420 mg, 3.02 mmol) at 25° C. The mixture was stirred at 100° C. for 15 h. The mixture was cooled to 25° C., poured into water (25 mL) and extracted with ethyl acetate (3×35 mL). The combined organic extracts were washed with brine (3×25 mL), dried over Na₂SO₄, filtered, and concentrated under reduced pressure. The residue was purified by silica gel column chromatography (PE:EA 50:1). Methyl 4-bromo-2-(4,4-dimethyl-1,4-azasilinan-1-yl)benzoate (460 mg, 1.34 mmol) was obtained as a colorless oil. $^1$H NMR (400 MHz, CHLOROFORM-d) δ=7.50 (d, J=8.4 Hz, 1H), 7.20 (d, J=1.6 Hz, 1H), 7.02 (dd, J=1.6, 8.4 Hz, 1H), 3.90 (s, 3H), 3.45-3.21 (m, 4H), 0.93-0.88 (m, 4H), 0.13 (s, 6H).

Step 4: Preparation of methyl 2-(4,4-dimethyl-1,4-azasilinan-1-yl)-4-((1,1-dimethylethyl)sulfonamido)benzoate

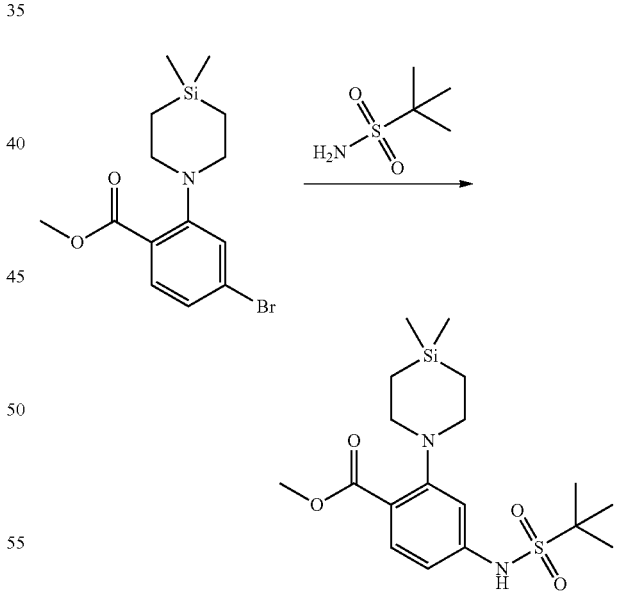

To a solution of methyl 4-bromo-2-(4,4-dimethyl-1,4-azasilinan-1-yl)benzoate (450 mg, 1.31 mmol) in dioxane (5 mL) was added 2-methylpropane-2-sulfonamide (268 mg, 1.96 mmol), cesium carbonate (426 mg 1.31 mmol), and t-BuXPhos Pd G3 (0.104 g, 1.31 mmol) under N₂ atmosphere. The mixture was stirred at 90° C. for 15 h. The mixture was poured into water (20 mL) and extracted with ethyl acetate (3×25 mL). The combined organic extracts were washed with brine (2×15 mL), dried over Na₂SO₄, filtered, and concentrated. The residue was purified by silica gel column chromatography (PE:EA 20:1) to obtain methyl 2-(4,4-dimethyl-1,4-azasilinan-1-yl)-4-((1,1-dimethylethyl)sulfonamido)benzoate (320 mg, 802 µmol) as a yellow solid.

Step 5: Preparation of 2-(4,4-dimethyl-1,4-azasilinan-1-yl)-4-((1,1-dimethylethyl)sulfonamido)benzoic acid

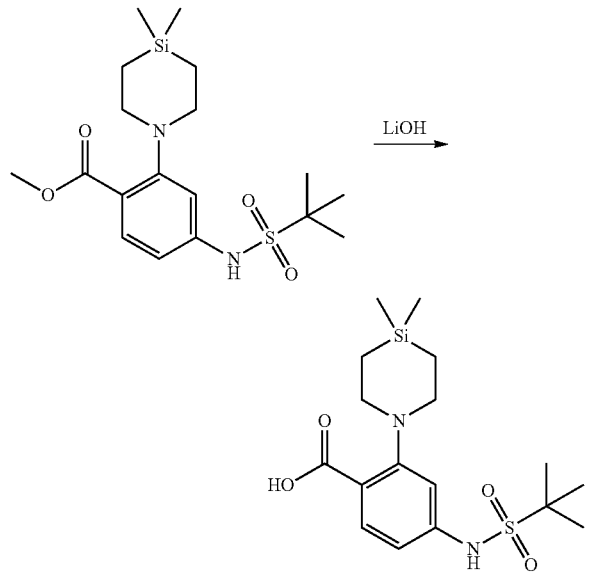

To a solution of methyl 2-(4,4-dimethyl-1,4-azasilinan-1-yl)-4-((1,1-dimethylethyl)sulfonamido)benzoate (0.31 g, 0.777 mmol) in MeOH (5 mL), H₂O (5 mL), and THF (5 mL) was added LiOH·H₂O (97.7 mg, 2.33 mmol). The mixture was stirred at 55° C. for 15 h. The mixture was cooled to 25° C., adjusted to pH 3-4 with 1 N HCl, and extracted with ethyl acetate (2×30 mL). The combined organic extracts were washed with brine (2×15 mL), dried over Na₂SO₄, filtered, and concentrated to give a 2-(4,4-dimethyl-1,4-azasilinan-1-yl)-4-((1,1-dimethylethyl)sulfonamido)benzoic acid (265 mg, 689 µmol) as a white solid. LCMS: MS ESI (M+1)⁺ 385.1.

Step 6: Preparation of N-(3-(N-(tert-butyl)sulfamoyl)phenyl)-2-(4,4-dimethyl-1,4-azasilinan-1-yl)-4-((1,1-dimethylethyl)sulfonamido)benzamide

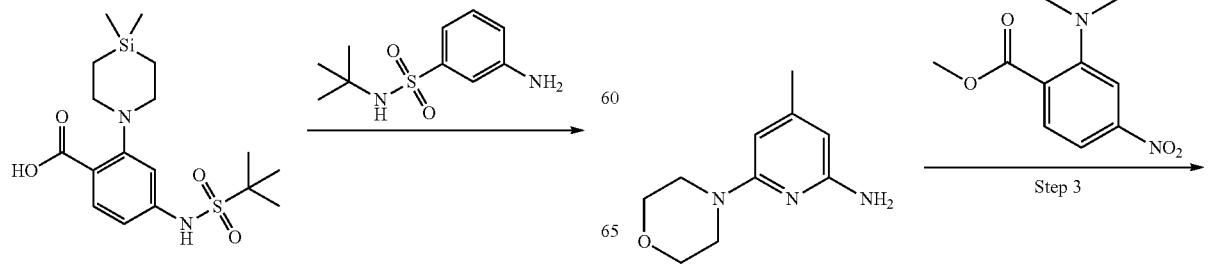

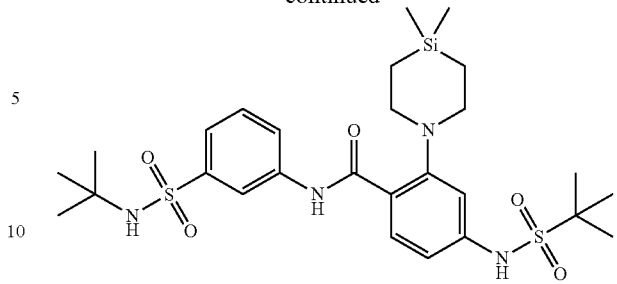

To a solution of 2-(4,4-dimethyl-1,4-azasilinan-1-yl)-4-((1,1-dimethylethyl)sulfonamido)benzoic acid (150 mg, 390 µmol) and 3-amino-N-(tert-butyl)benzenesulfonamide (115 mg, 507 µmol) in MeCN (3 mL) was added NMI (160 mg, 1.95 mmol) and TCFH (218 mg, 780 µmol). The mixture was stirred at 20° C. for 15 h. The mixture was poured into water (20 mL) and extracted with ethyl acetate (3×25 mL). The combined organic extracts were washed with brine (3×15 mL), dried over Na₂SO₄, filtered, and concentrated. The residue was purified by prep-HPLC (TFA condition). N-(3-(N-(tert-Butyl)sulfamoyl)phenyl)-2-(4,4-dimethyl-1,4-azasilinan-1-yl)-4-((1,1-dimethylethyl)sulfonamido)benzamide (95.45 mg, 157 µmol) was obtained as a white solid. LCMS: MS ESI (M+1)⁺ 595.4. ¹H NMR (400 MHz, DMSO-d₆) δ=11.95 (s, 1H), 9.93 (s, 1H), 8.33 (s, 1H), 7.91-7.71 (m, 2H), 7.62-7.47 (m, 3H), 7.29 (d, J=1.6 Hz, 1H), 7.08 (dd, J=1.6, 8.8 Hz, 1H), 3.17 (br t, J=5.6 Hz, 4H), 1.31 (s, 9H), 1.11 (s, 9H), 0.89 (br t, J=5.6 Hz, 4H), 0.10 (s, 6H).

Example 5: Synthesis of 2-(4,4-dimethyl-1,4-azasilinan-1-yl)-4-((2-hydroxyethyl)sulfonamido)-N-(4-methyl-6-morpholinopyridin-2-yl)benzamide

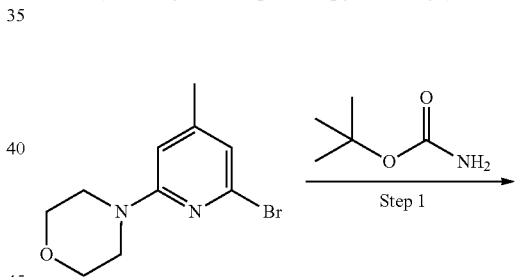

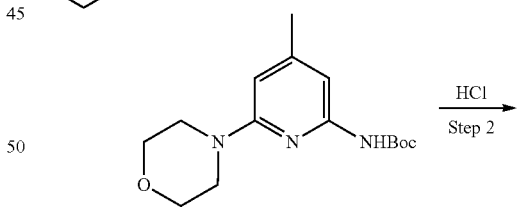

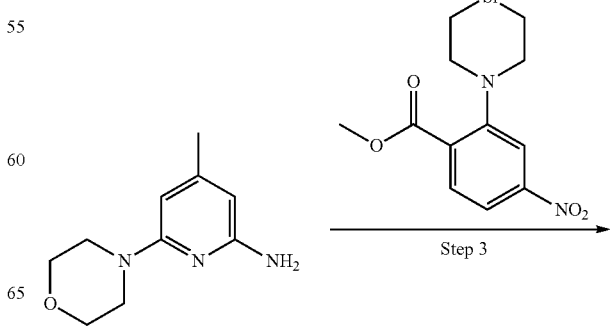

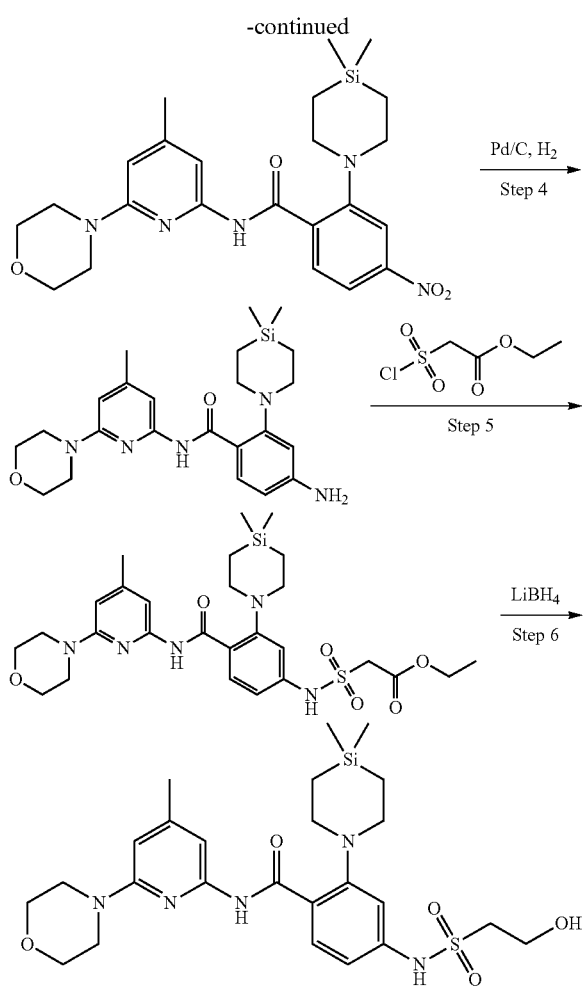

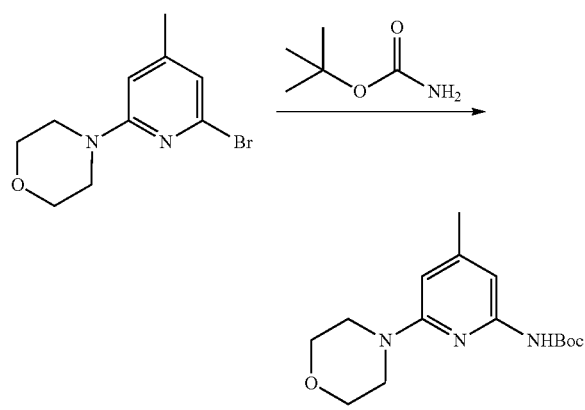

Step 1: Preparation of tert-butyl (4-methyl-6-morpholinopyridin-2-yl)carbamate

A solution of 4-(6-bromo-4-methylpyridin-2-yl)morpholine (300 mg, 1.16 mmol), tert-butyl carbamate (407 mg, 3.48 mmol), Pd$_2$(dba)$_3$ (106 mg, 116 μmol), Xantphos (134 mg, 232 μmol), and Cs$_2$CO$_3$ (1.13 g, 3.48 mmol) in 2-methyl-2-butanol (6 mL) was stirred at 100° C. for 16 h. The mixture was poured into H$_2$O (50 mL) and extracted with ethyl acetate (2×30 mL). The combined organic extracts were washed with brine (30 mL), dried over Na$_2$SO$_4$, filtered, and concentrated under reduced pressure. The residue was purified by silica gel column chromatography (PE:EA 3:1). tert-Butyl (4-methyl-6-morpholinopyridin-2-yl)carbamate (300 mg, 1.02 mmol) was obtained as a yellow oil.

Step 2: Preparation of 4-methyl-6-morpholinopyridin-2-amine

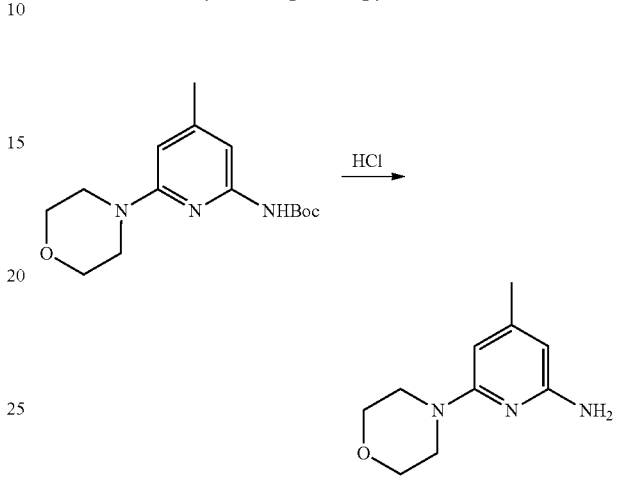

To a solution of tert-butyl (4-methyl-6-morpholinopyridin-2-yl)carbamate (250 mg, 852 μmol) in dioxane (2 mL) was added HCl (2 mL, 4 M in dioxane). The solution was stirred at 25° C. for 1 h. The solution was concentrated to afford 4-methyl-6-morpholinopyridin-2-amine (150 mg, 776 μmol) as a yellow oil. LCMS: MS ESI (M+1)$^+$ 194.1.

Step 3: Preparation of 2-(4,4-dimethyl-1,4-azasilinan-1-yl)-N-(4-methyl-6-morpholinopyridin-2-yl)-4-nitrobenzamide

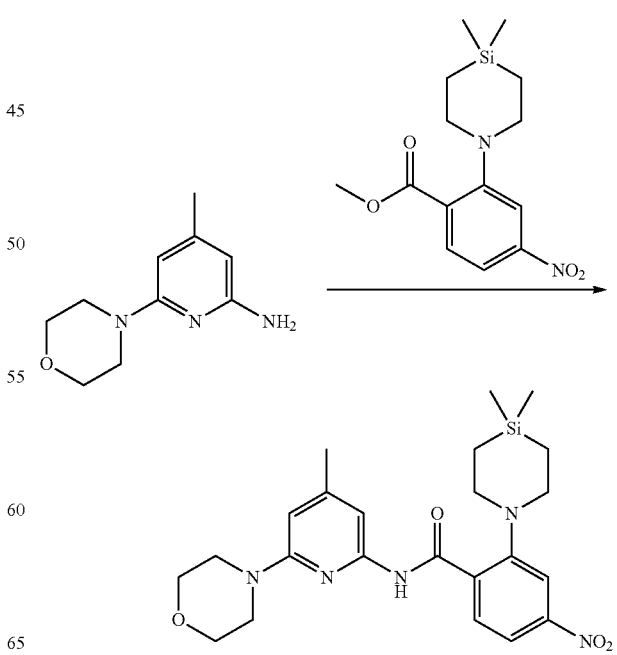

To a solution of 4-methyl-6-morpholinopyridin-2-amine (150 mg, 776 µmol) and methyl 2-(4,4-dimethyl-1,4-azasilinan-1-yl)-4-nitrobenzoate (215 mg, 698 µmol) in THF (4 mL) was added LiHMDS (3.10 mL, 3.10 mmol, 1 M in THF). The solution was stirred at 25° C. for 1 h. The mixture was poured into sat. aq. NH₄Cl (50 mL) and was extracted with ethyl acetate (2×30 mL). The combined organic extracts were washed with brine (30 mL), dried over Na₂SO₄, filtered, and concentrated under reduced pressure. The residue was purified by silica gel column chromatography (PE:EA 1:1). 2-(4,4-Dimethyl-1,4-azasilinan-1-yl)-N-(4-methyl-6-morpholinopyridin-2-yl)-4-nitrobenzamide (200 mg, 425 µmol) was obtained as a yellow oil. LCMS: MS ESI (M+1)⁺ 470.3.

Step 4: Preparation of 4-amino-2-(4,4-dimethyl-1,4-azasilinan-1-yl)-N-(4-methyl-6-morpholinopyridin-2-yl)benzamide

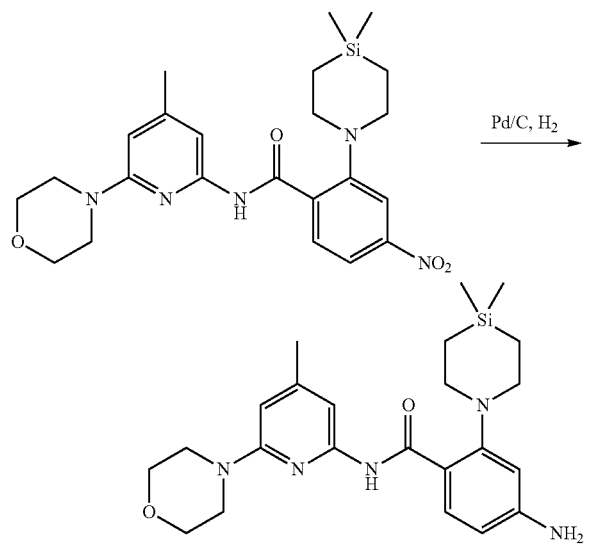

To a solution of 2-(4,4-dimethyl-1,4-azasilinan-1-yl)-N-(4-methyl-6-morpholinopyridin-2-yl)-4-nitrobenzamide (150 mg, 354 µmol) in THF (5 mL) was added Pd/C (50 mg, 10% w/w). The reaction was stirred at 25° C. for 3 h under H₂ atmosphere (15 psi). The solution was filtered and concentrated. 4-Amino-2-(4,4-dimethyl-1,4-azasilinan-1-yl)-N-(4-methyl-6-morpholinopyridin-2-yl)benzamide (180 mg, 409 µmol) was obtained as a yellow oil. LCMS: MS ESI (M+1)⁺ 440.4.

Step 5: Preparation of ethyl 2-(N-(3-(4,4-dimethyl-1,4-azasilinan-1-yl)-4-((4-methyl-6-morpholinopyridin-2-yl)carbamoyl)phenyl)sulfamoyl)acetate

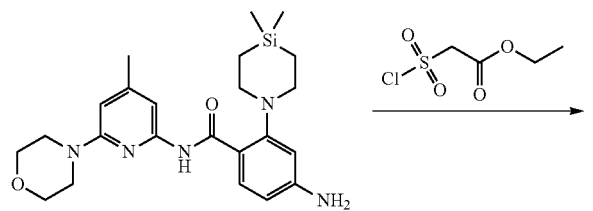

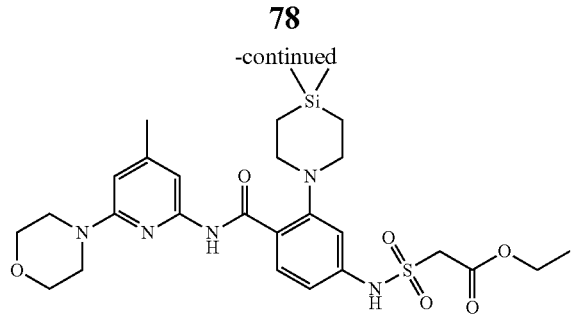

To a solution of 4-amino-2-(4,4-dimethyl-1,4-azasilinan-1-yl)-N-(4-methyl-6-morpholinopyridin-2-yl)benzamide (180 mg, 409 µmol) and pyridine (161 mg, 2.04 mmol) in DCM (4 mL) was added ethyl 2-(chlorosulfonyl)acetate (227 mg, 1.22 mmol) at 0° C. The reaction was stirred at 25° C. for 1 h. The mixture was poured into water (50 mL) and was extracted with ethyl acetate (2×30 mL). The combined organic extracts were washed with brine (30 mL), dried over Na₂SO₄, filtered, and concentrated under reduced pressure. Ethyl 2-(N-(3-(4,4-dimethyl-1,4-azasilinan-1-yl)-4-((4-methyl-6-morpholinopyridin-2-yl)carbamoyl)phenyl)sulfamoyl)acetate (200 mg, 339 µmol) was obtained as a yellow oil. LCMS: MS ESI (M+1)⁺ 590.2.

Step 6: Preparation of 2-(4,4-dimethyl-1,4-azasilinan-1-yl)-4-((2-hydroxyethyl)sulfonamido)-N-(4-methyl-6-morpholinopyridin-2-yl)benzamide

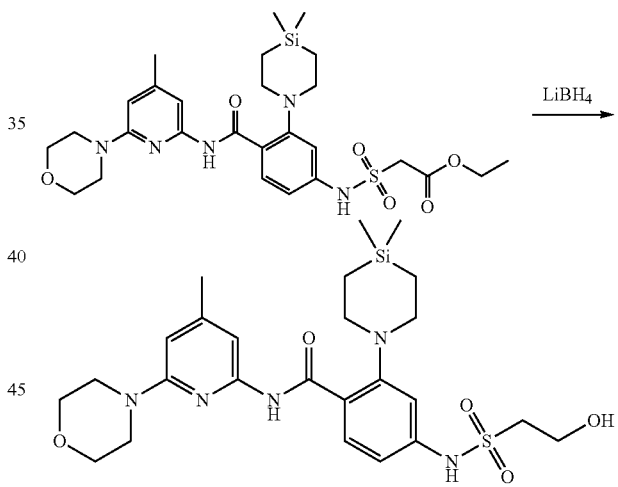

To a solution of ethyl 2-(N-(3-(4,4-dimethyl-1,4-azasilinan-1-yl)-4-((4-methyl-6-morpholinopyridin-2-yl)carbamoyl)phenyl)sulfamoyl)acetate (180 mg, 186 µmol) in THF (4 mL) was added LiBH₄ (457 µL, 915 µmol, 2 M in THF) at 0° C. The reaction was stirred at 25° C. for 1 h. The mixture was poured into sat. aq. NH₄Cl (50 mL) and was extracted with ethyl acetate (2×30 mL). The combined organic extracts were washed with brine (30 mL), dried over Na₂SO₄, filtered, and concentrated under reduced pressure. The residue was purified by prep-HPLC (TFA condition). 2-(4,4-Dimethyl-1,4-azasilinan-1-yl)-4-((2-hydroxyethyl)sulfonamido)-N-(4-methyl-6-morpholinopyridin-2-yl)benzamide (53.57 mg, 97.8 µmol) was obtained as a yellow gum. LCMS: MS ESI (M+1)⁺ 548.3. ¹H NMR (400 MHz, DMSO-d₆) δ=12.19 (s, 1H), 10.13 (s, 1H), 7.99 (d, J=8.6 Hz, 1H), 7.53 (s, 1H), 7.22 (d, J=1.6 Hz, 1H), 7.08 (dd, J=1.9, 8.6 Hz, 1H), 6.43 (s, 1H), 3.80-3.61 (m, 6H), 3.47-3.28 (m, 6H), 3.25-3.10 (m, 4H), 2.26 (s, 3H), 1.07-0.86 (m, 4H), 0.12 (s, 6H).

Example 6: Synthesis of N-(3-(4,4-difluoropiperidin-1-yl)phenyl)-2-(4,4-dimethyl-1,4-azasilinan-1-yl)-4-((2-hydroxyethyl)sulfonamido)benzamide
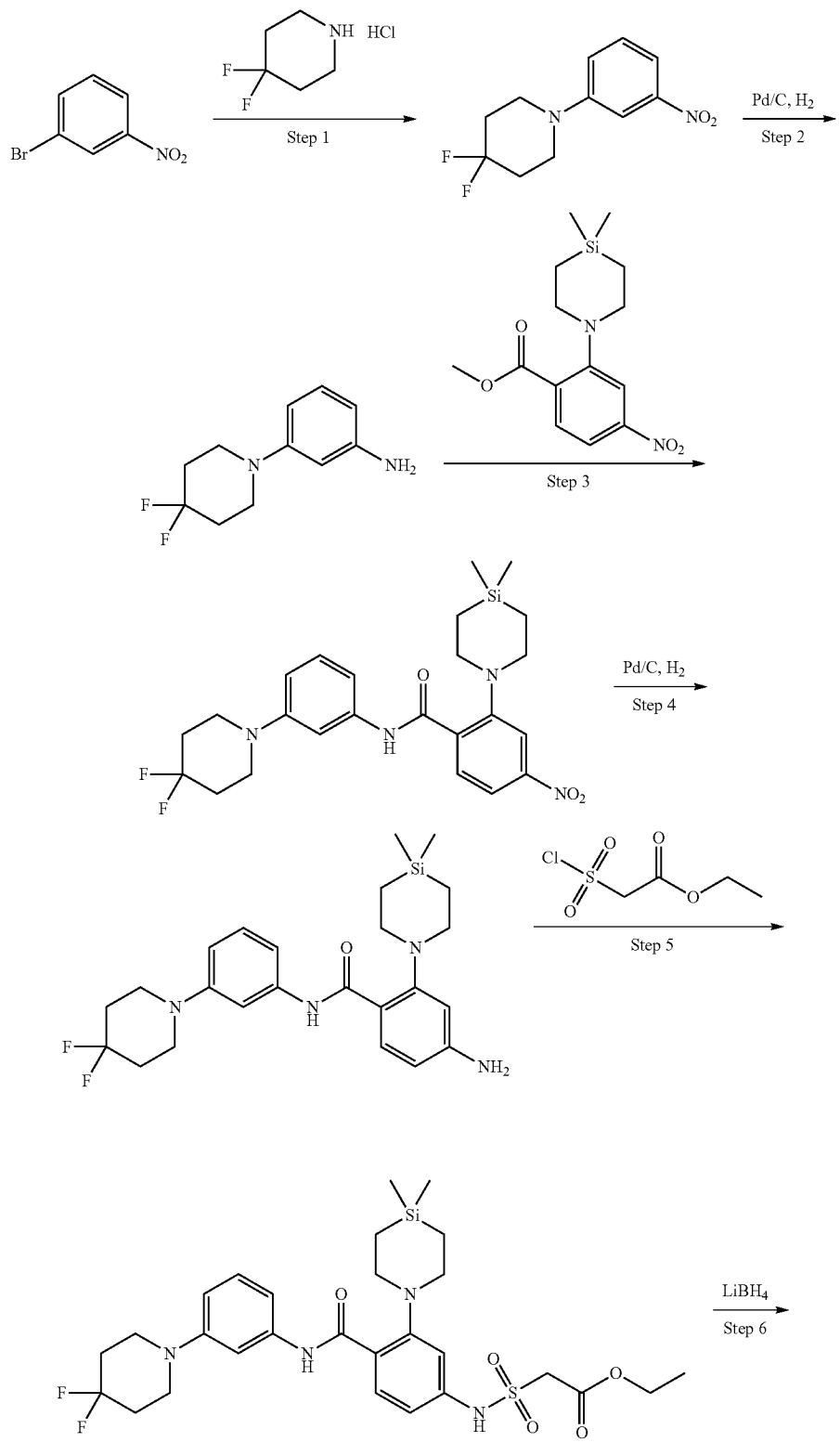

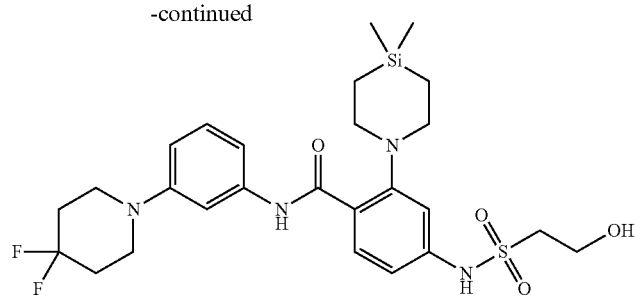

Step 1: Preparation of 4,4-difluoro-1-(3-nitrophenyl)piperidine

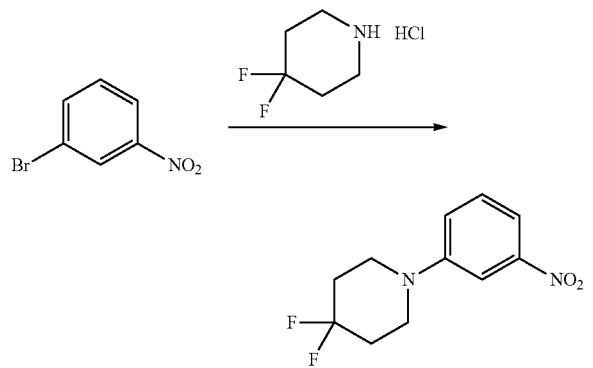

To a solution of 1-bromo-3-nitrobenzene (500 mg, 2.47 mmol) and 4,4-difluoropiperidine hydrochloride (358 mg, 2.96 mmol) in toluene (5 mL) was added BINAP (153 mg, 247 μmol), sodium tert-butoxide (712 mg, 7.41 mmol) and Pd$_2$(dba)$_3$ (112 mg, 123 μmol). The mixture was stirred at 100° C. for 12 h. The reaction mixture was poured into saturated aqueous NH$_4$Cl (40 mL) and extracted with ethyl acetate (3×35 mL). The combined organic extracts were washed with brine (100 mL), dried over Na$_2$SO$_4$, filtered, and concentrated. The yellow residue was purified by silica gel column chromatography (PE:EA 50:1). 4,4-Difluoro-1-(3-nitrophenyl)piperidine (300 mg, 1.23 mmol) was obtained as a yellow solid. LCMS: MS ESI (M+1)$^+$ 243.1. $^1$H NMR (400 MHz, DMSO-d$_6$) δ=7.75-7.71 (m, 1H), 7.60 (td, J=2.3, 6.5 Hz, 1H), 7.52-7.45 (m, 2H), 3.52-3.44 (m, 4H), 2.11-2.01 (m, 4H).

Step 2: Preparation of 3-(4,4-difluoropiperidin-1-yl)aniline

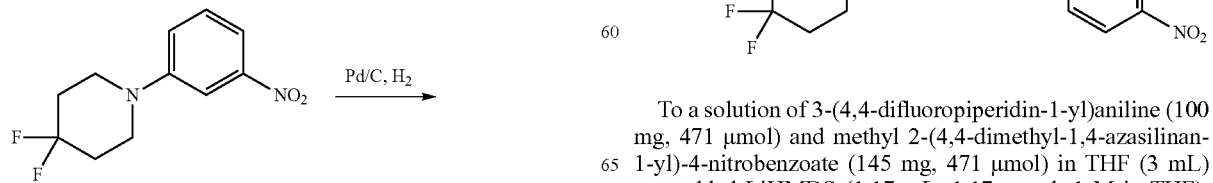

To a solution of 4,4-difluoro-1-(3-nitrophenyl)piperidine (300 mg, 1.23 mmol) in MeOH (10 mL) was added Pd/C (130 mg, 10% w/w). The mixture was stirred at 25° C. for 2 h under H$_2$ atmosphere (15 psi). The reaction mixture was filtered and concentrated under vacuum. 3-(4,4-Difluoropiperidin-1-yl)aniline (250 mg, 1.17 mmol) was obtained as a yellow solid. LCMS: MS ESI (M+1)$^+$ 213.1.

Step 3: Preparation of N-(3-(4,4-difluoropiperidin-1-yl)phenyl)-2-(4,4-dimethyl-1,4-azasilinan-1-yl)-4-nitrobenzamide To a solution of 3-(4,4-difluoropiperidin-1-yl)aniline (100 mg, 471 μmol) and methyl 2-(4,4-dimethyl-1,4-azasilinan-1-yl)-4-nitrobenzoate (145 mg, 471 μmol) in THF (3 mL) was added LiHMDS (1.17 mL, 1.17 mmol, 1 M in THF). The mixture was stirred at 25° C. for 1 h. The reaction mixture was poured into saturated aqueous NH₄Cl (40 mL) and extracted with ethyl acetate (3×35 mL). The combined organic extracts were washed with brine (100 mL), dried over Na₂SO₄, filtered, and concentrated. The yellow residue was purified by silica gel column chromatography (PE:EA 50:1). N-(3-(4,4-Difluoropiperidin-1-yl)phenyl)-2-(4,4-dimethyl-1,4-azasilinan-1-yl)-4-nitrobenzamide (80 mg, 163 mol) was obtained as a yellow solid. LCMS: MS ESI (M+1)⁺ 489.3. ¹H NMR (400 MHz, DMSO-d₆) δ=10.90 (s, 1H), 7.93 (d, J=2.3 Hz, 1H), 7.90-7.85 (m, 1H), 7.83-7.78 (m, 1H), 7.45 (d, J=1.9 Hz, 1H), 7.26-7.16 (m, 2H), 6.84-6.74 (m, 1H), 3.38-3.32 (m, 8H), 2.14-2.00 (m, 4H), 0.87-0.82 (m, 4H), 0.05 (s, 6H).

Step 4: Preparation of 4-amino-N-(3-(4,4-difluoropiperidin-1-yl)phenyl)-2-(4,4-dimethyl-1,4-azasilinan-1-yl)benzamide

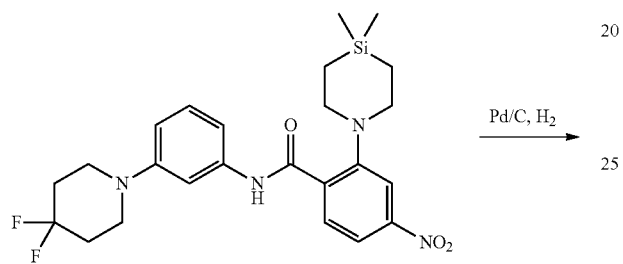

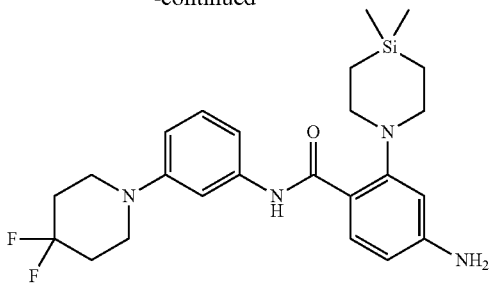

To a solution of N-(3-(4,4-difluoropiperidin-1-yl)phenyl)-2-(4,4-dimethyl-1,4-azasilinan-1-yl)-4-nitrobenzamide (80 mg, 163 mol) in MeOH (10 mL) was added Pd/C (17.3 mg, 10% w/w), and the mixture was stirred at 25° C. for 2 h under H₂ atmosphere (15 psi). The reaction mixture was filtered and concentrated under reduced pressure. 4-Amino-N-(3-(4,4-difluoropiperidin-1-yl)phenyl)-2-(4,4-dimethyl-1,4-azasilinan-1-yl)benzamide (60 mg, 130 μmol) was obtained as a yellow solid.

Step 5: Preparation of ethyl 2-(N-(4-((3-(4,4-difluoropiperidin-1-yl)phenyl)carbamoyl)-3-(4,4-dimethyl-1,4-azasilinan-1-yl)phenyl)sulfamoyl)acetate

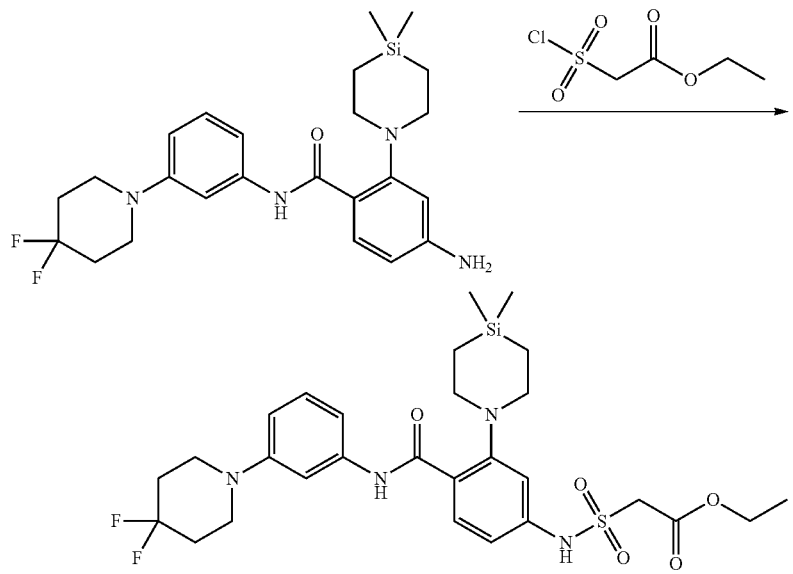

To a solution of 4-amino-N-(3-(4,4-difluoropiperidin-1-yl)phenyl)-2-(4,4-dimethyl-1,4-azasilinan-1-yl)benzamide (60 mg, 130 μmol) and pyridine (31.2 μL, 389 μmol) in DCM (2 mL) was added ethyl 2-(chlorosulfonyl)acetate (28.9 mg, 155 μmol) at 0° C. The mixture was stirred at 25° C. for 2 h. The reaction mixture was poured into saturated aqueous NH₄Cl (40 mL) and extracted with ethyl acetate (3×35 mL). The combined organic extracts were washed with brine (100 mL), dried over Na₂SO₄, filtered, and concentrated. Ethyl 2-(N-(4-((3-(4,4-difluoropiperidin-1-yl)phenyl)carbamoyl)-3-(4,4-dimethyl-1,4-azasilinan-1-yl)phenyl)sulfamoyl)acetate (72 mg, 120 μmol) was obtained as a yellow oil. LCMS: MS ESI (M+1)⁺ 609.2.

Step 6: Preparation of N-(3-(4,4-difluoropiperidin-1-yl)phenyl)-2-(4,4-dimethyl-1,4-azasilinan-1-yl)-4-((2-hydroxyethyl)sulfonamido)benzamide

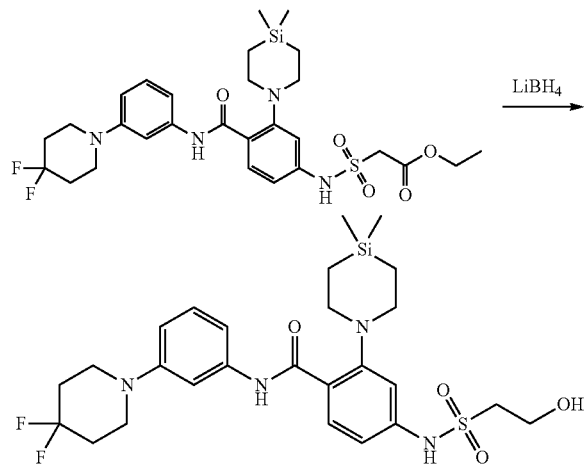

To a solution of ethyl 2-(N-(4-((3-(4,4-difluoropiperidin-1-yl)phenyl)carbamoyl)-3-(4,4-dimethyl-1,4-azasilinan-1-yl)phenyl)sulfamoyl)acetate (75 mg, 123 μmol) in THF (2 mL) was added LiBH$_4$ (122 μL, 245 μmol, 2 M in THF) at 0° C. The mixture was stirred at 25° C. for 0.5 h. The reaction mixture was poured into saturated aqueous NH$_4$Cl solution (40 mL) and extracted with ethyl acetate (3×35 mL). The combined organic extracts were washed with brine (100 mL), dried over Na$_2$SO$_4$, filtered, and concentrated. The yellow residue was purified by Prep-HPLC (FA condition). N-(3-(4,4-Difluoropiperidin-1-yl)phenyl)-2-(4,4-dimethyl-1,4-azasilinan-1-yl)-4-((2-hydroxyethyl)sulfonamido)benzamide (33.94 mg, 59.8 μmol) was obtained as an off-white solid. LCMS: MS ESI (M+1)$^+$ 567.2. $^1$H NMR (400 MHz, DMSO-d$_6$) δ=11.75 (s, 1H), 7.81 (d, J=8.6 Hz, 1H), 7.50 (s, 1H), 7.25-7.17 (m, 1H), 7.14-7.08 (m, 2H), 7.00 (dd, J=2.0, 8.6 Hz, 1H), 6.74 (dd, J=2.0, 8.2 Hz, 1H), 3.74 (t, J=6.6 Hz, 2H), 3.32 (br d, J=1.8 Hz, 6H), 3.17 (br t, J=6.1 Hz, 4H), 2.15-1.97 (m, 4H), 0.92 (br t, J=6.1 Hz, 4H), 0.10 (s, 6H).

Example 7: Synthesis of N-(2-(4,4-difluoropiperidin-1-yl)pyridin-4-yl)-2-(4,4-dimethyl-1,4-azasilinan-1-yl)-4-((2-hydroxyethyl)sulfonamido)benzamide

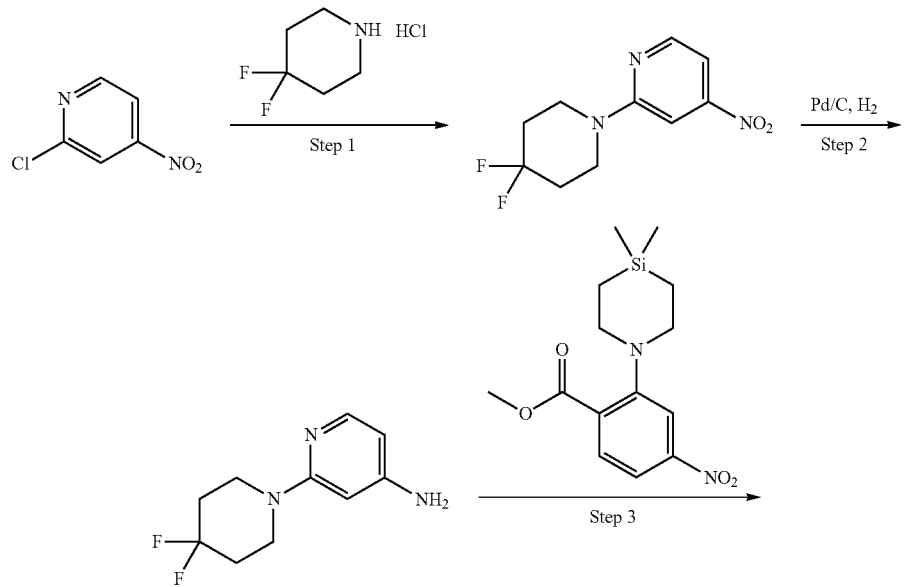

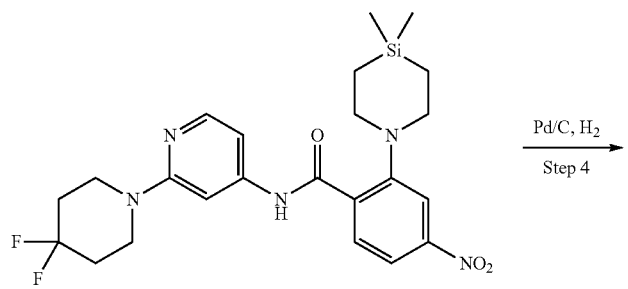

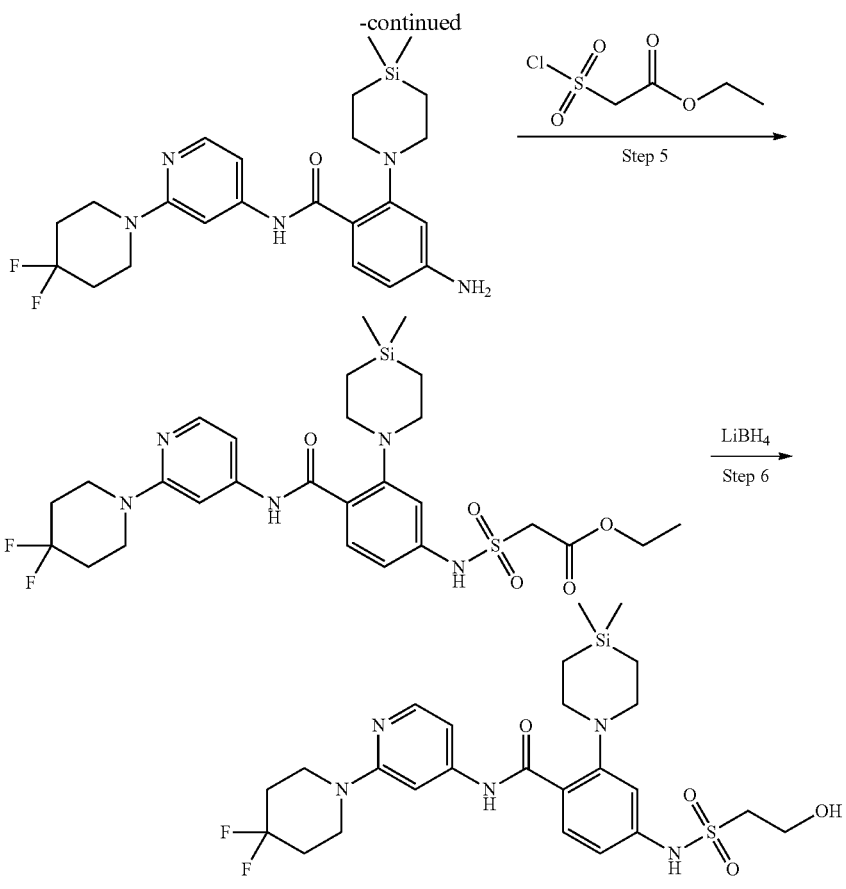

Step 1: Preparation of 2-(4,4-difluoropiperidin-1-yl)-4-nitropyridine

To a solution of 2-chloro-4-nitropyridine (1.0 g, 6.30 mmol) and 4,4-difluoropiperidine hydrochloride (1.48 g, 9.45 mmol) in DMSO (10 mL) was added DIPEA (3.28 mL, 18.9 mmol), and the mixture was stirred at 100° C. for 2 h. The reaction mixture was poured into saturated aqueous $NH_4Cl$ (40 mL) and extracted with ethyl acetate (3×35 mL). The combined organic extracts were washed with brine (100 mL), dried over $Na_2SO_4$, filtered, and concentrated. The yellow residue was purified by silica gel column chromatography (PE:EA 50:1). 2-(4,4-Difluoropiperidin-1-yl)-4-nitropyridine (300 mg, 1.23 mmol) was obtained as a yellow solid. LCMS: MS ESI (M+1)$^+$ 244.1. $^1$H NMR (400 MHz, DMSO-$d_6$) δ=7.96 (d, J=6.0 Hz, 1H), 6.96 (d, J=2.4 Hz, 1H), 6.92 (dd, J=2.4, 6.1 Hz, 1H), 3.61-3.50 (m, 4H), 2.09-1.89 (m, 4H).

Step 2: Preparation of 2-(4,4-difluoropiperidin-1-yl)pyridin-4-amine

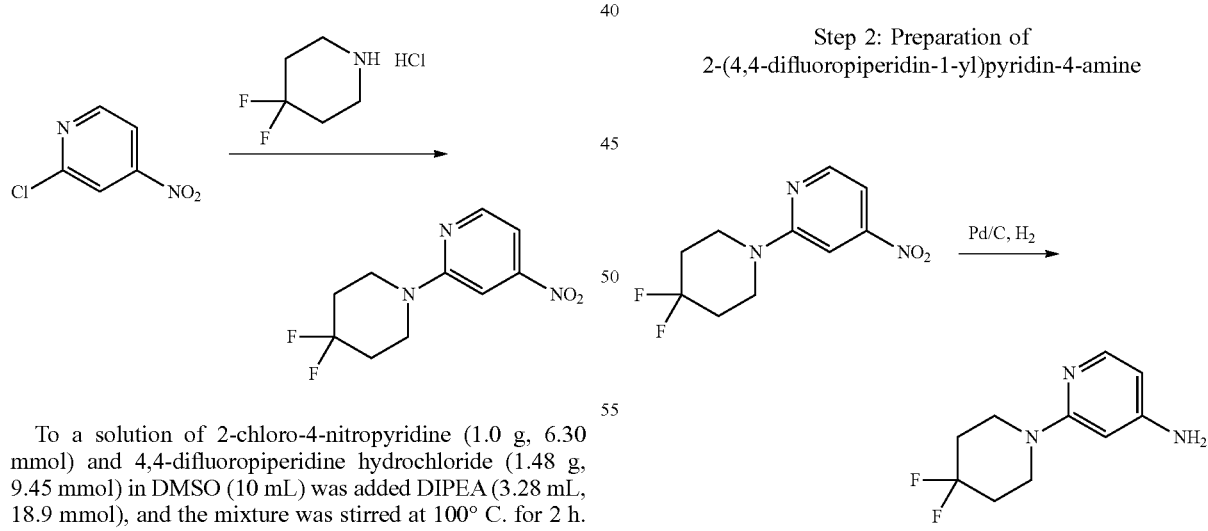

To a solution of 2-(4,4-difluoropiperidin-1-yl)-4-nitropyridine (500 mg, 1.05 mmol) in MeOH (10 mL) was added Pd/C (111 mg, 105 μmol). The mixture was stirred at 25° C. for 2 h under $H_2$ (15 psi). The reaction mixture was filtered and concentrated to afford 2-(4,4-difluoropiperidin-1-yl)pyridin-4-amine (250 mg, 1.17 mmol) as a yellow solid.

Step 3: Preparation of N-(2-(4,4-difluoropiperidin-1-yl)pyridin-4-yl)-2-(4,4-dimethyl-1,4-azasilinan-1-yl)-4-nitrobenzamide

Step 4: Preparation of 4-amino-N-(2-(4,4-difluoropiperidin-1-yl)pyridin-4-yl)-2-(4,4-dimethyl-1,4-azasilinan-1-yl)benzamide

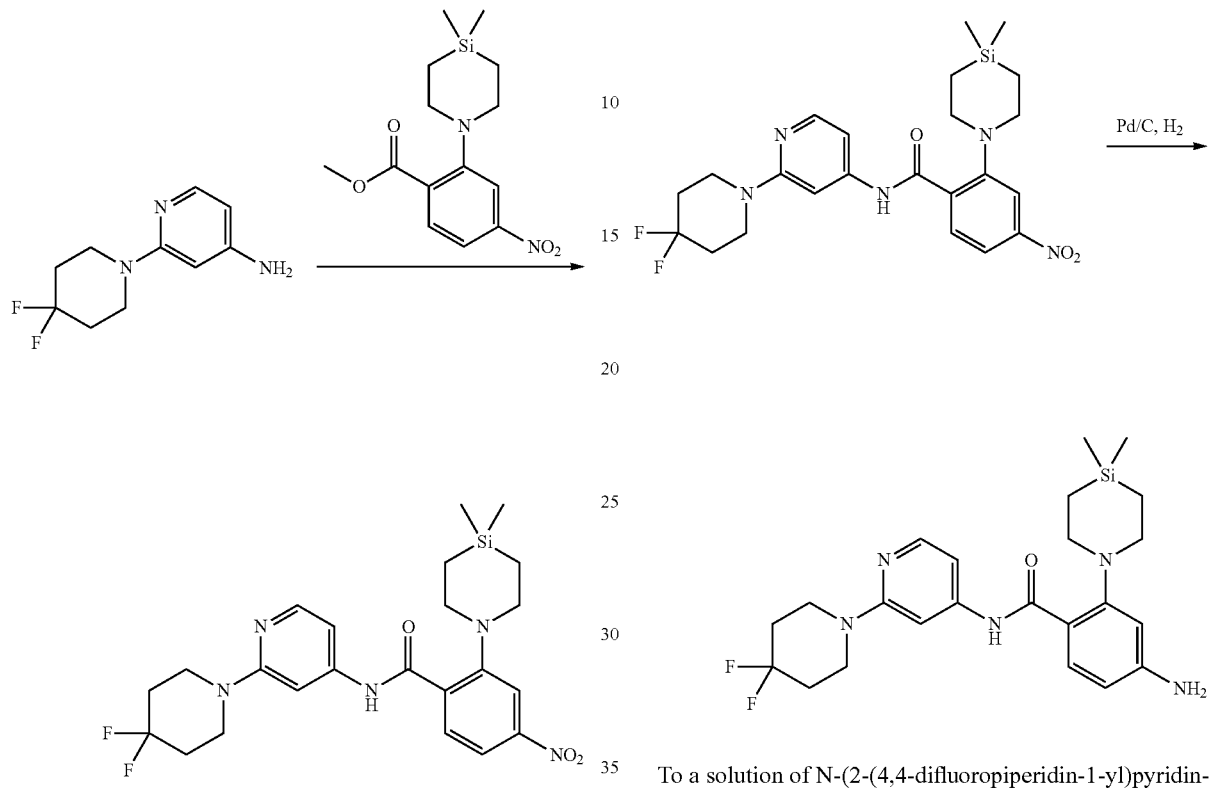

To a solution of methyl 2-(4,4-dimethyl-1,4-azasilinan-1-yl)-4-nitrobenzoate (150 mg, 703 μmol) and 2-(4,4-difluoropiperidin-1-yl)pyridin-4-amine (238 mg, 773 μmol) in THF (5 mL) was added LiHMDS (2.10 mL, 2.10 mmol, 1 M in THF). The mixture was stirred at 25° C. for 2 h. The reaction mixture was poured into saturated aqueous NH₄Cl (40 mL) and extracted with ethyl acetate (3×35 mL). The combined organic extracts were washed with brine (100 mL), dried over Na₂SO₄, filtered, and concentrated. The yellow residue was purified by silica gel column chromatography (PE:EA 50:1) to afford N-(2-(4,4-difluoropiperidin-1-yl)pyridin-4-yl)-2-(4,4-dimethyl-1,4-azasilinan-1-yl)-4-nitrobenzamide (220 mg, 449 μmol) as a yellow solid. LCMS: MS ESI (M+1)$^+$ 490.3.

To a solution of N-(2-(4,4-difluoropiperidin-1-yl)pyridin-4-yl)-2-(4,4-dimethyl-1,4-azasilinan-1-yl)-4-nitrobenzamide (100 mg, 204 μmol) in MeOH (5 mL) was added Pd/C (21.7 mg, 10% w/w). The mixture was stirred at 25° C. for 2 h under H₂ atmosphere (15 psi). The reaction mixture was filtered and concentrated. 4-Amino-N-(2-(4,4-difluoropiperidin-1-yl)pyridine-4-yl)-2-(4,4-dimethyl-1,4-azasilinan-1-yl)benzamide (93 mg, 202 μmol) was obtained as a yellow solid. LCMS: MS ESI (M+1)$^+$ 460.4.

Step 5: Preparation of ethyl 2-(N-(4-((2-(4,4-difluoropiperidin-1-yl)pyridin-4-yl)carbamoyl)-3-(4,4-dimethyl-1,4-azasilinan-1-yl)phenyl)sulfamoyl)acetate

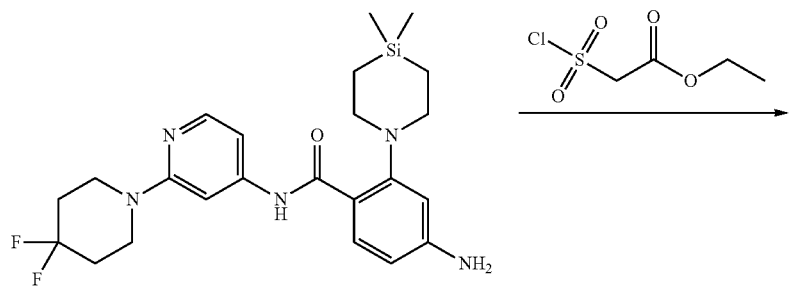

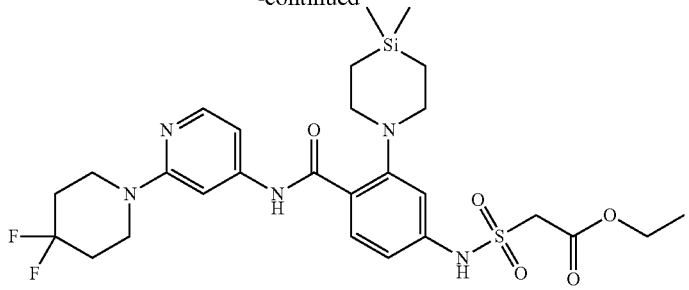

To a solution of N-(2-(4,4-difluoropiperidin-1-yl)pyridin-4-yl)-2-(4,4-dimethyl-1,4-azasilinan-1-yl)-4-nitrobenzamide (93 mg, 202 mol) and pyridine (48.7 μL, 606 μmol) in DCM (5 mL) was added ethyl 2-(chlorosulfonyl)acetate (48.8 mg, 262 μmol) at 0° C. The mixture was stirred at 25° C. for 1 h. The reaction mixture was poured into saturated aqueous NH$_4$Cl solution (10 mL) and extracted with ethyl acetate (3×15 mL). The combined organic extracts were washed with brine (30 mL), dried over Na$_2$SO$_4$, filtered, and concentrated to afford ethyl 2-(N-(4-((2-(4,4-difluoropiperidin-1-yl)pyridin-4-yl)carbamoyl)-3-(4,4-dimethyl-1,4-azasilinan-1-yl)phenyl)sulfamoyl)acetate (120 mg, 196 μmol) as a yellow oil. LCMS: MS ESI (M+1)$^+$ 610.3.

Step 6: Preparation of N-(2-(4,4-difluoropiperidin-1-yl)pyridin-4-yl)-2-(4,4-dimethyl-1,4-azasilinan-1-yl)-4-((2-hydroxyethyl)sulfonamido)benzamide

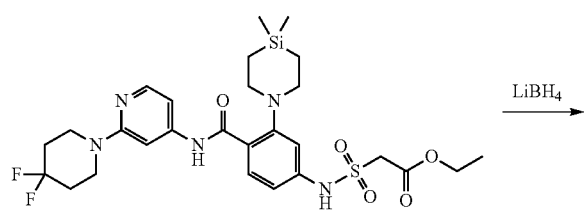

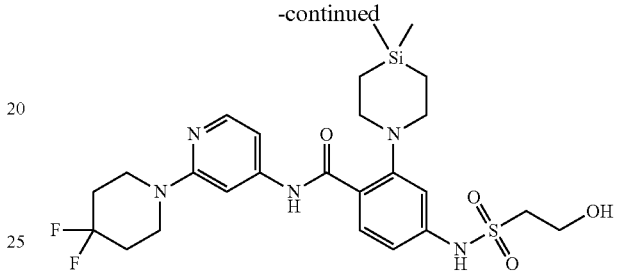

To a solution of ethyl 2-(N-(4-((2-(4,4-difluoropiperidin-1-yl)pyridin-4-yl)carbamoyl)-3-(4,4-dimethyl-1,4-azasilinan-1-yl)phenyl)sulfamoyl)acetate (100 mg, 163 μmol) in THF (3 mL) was added lithium borohydride (163 μL, 326 μmol, 2 M in THF) at 0° C. The mixture was stirred at 25° C. for 0.5 h. The reaction mixture was poured into saturated aqueous NH$_4$Cl (10 mL) and extracted with ethyl acetate (3×15 mL). The combined organic extracts were washed with brine (30 mL), dried over Na$_2$SO$_4$, filtered, and concentrated. The yellow residue was purified by Prep-HPLC (TFA condition) to afford N-(2-(4,4-difluoropiperidin-1-yl)pyridin-4-yl)-2-(4,4-dimethyl-1,4-azasilinan-1-yl)-4-((2-hydroxyethyl)sulfonamido)benzamide (32.93 mg, 58.0 μmol) as a white solid. LCMS: MS ESI (M+1)$^+$ 568.4. $^1$H NMR (400 MHz, DMSO-d$_6$) δ=11.92 (s, 1H), 10.15 (s, 1H), 8.08 (d, J=6.5 Hz, 1H), 7.79-7.68 (m, 2H), 7.12 (d, J=1.6 Hz, 1H), 7.03-6.95 (m, 2H), 3.75 (br t, J=6.5 Hz, 6H), 3.36-3.32 (m, 2H), 3.19 (br t, J=5.9 Hz, 4H), 2.21-2.08 (m, 4H), 0.88 (br t, J=5.8 Hz, 4H), 0.09 (s, 6H).

Example 8: Synthesis of N-(6-(4,4-difluoropiperidin-1-yl)-4-methylpyridin-2-yl)-2-(4,4-dimethyl-1,4-azasilinan-1-yl)-4-((2-hydroxyethyl)sulfonamido)benzamide

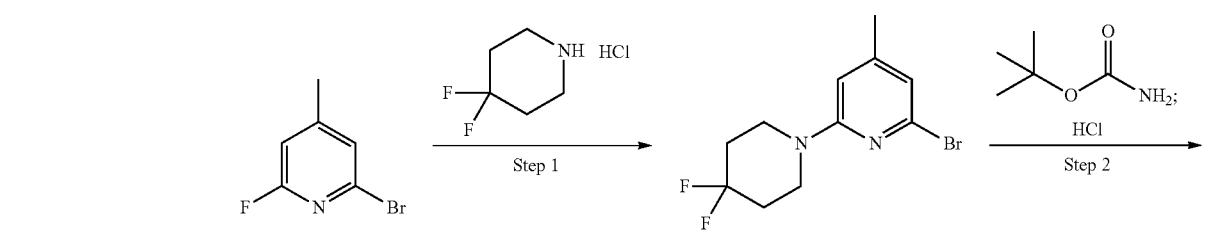

-continued
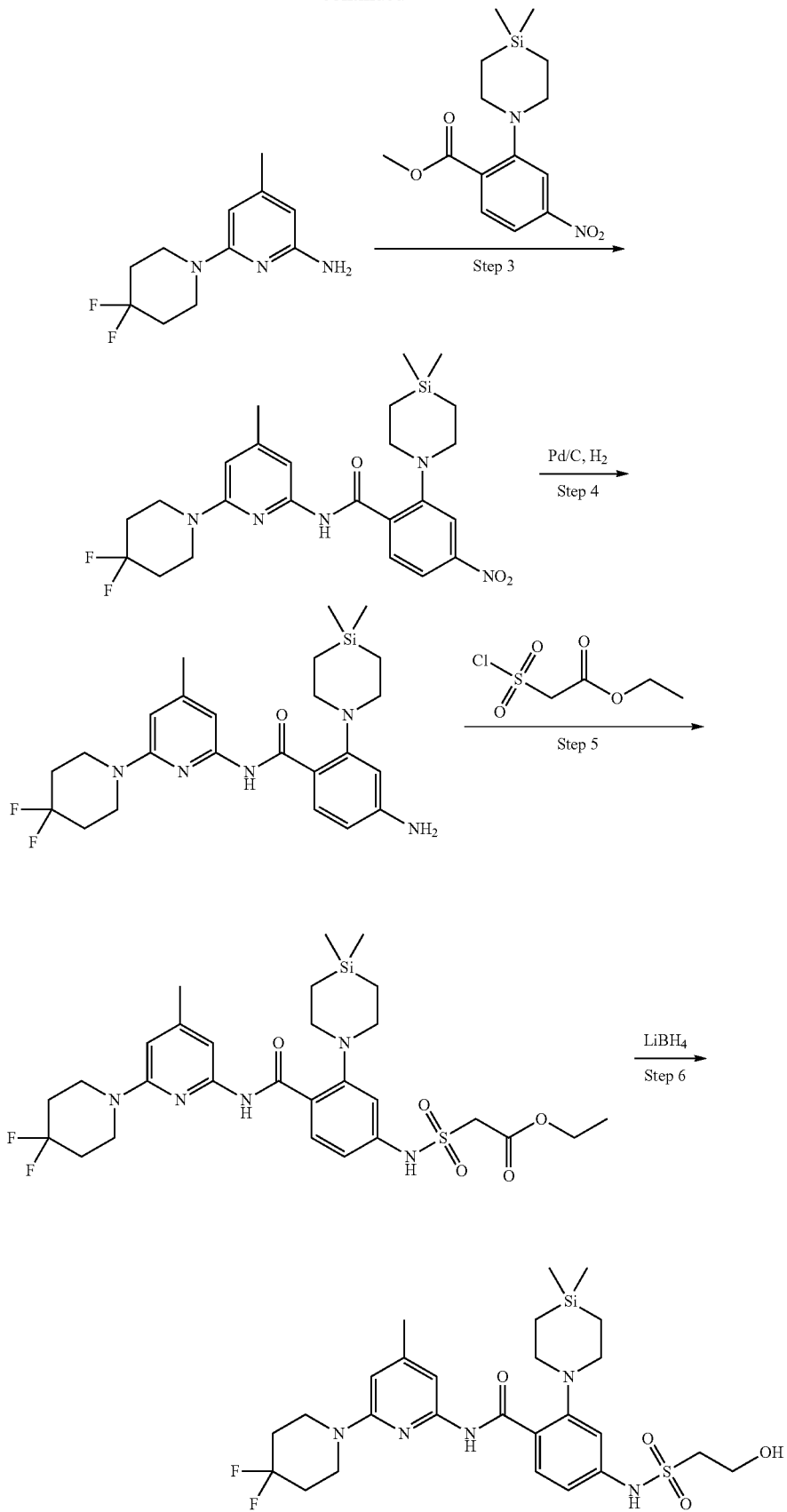

Step 1: Preparation of 2-bromo-6-(4,4-difluoropiperidin-1-yl)-4-methylpyridine

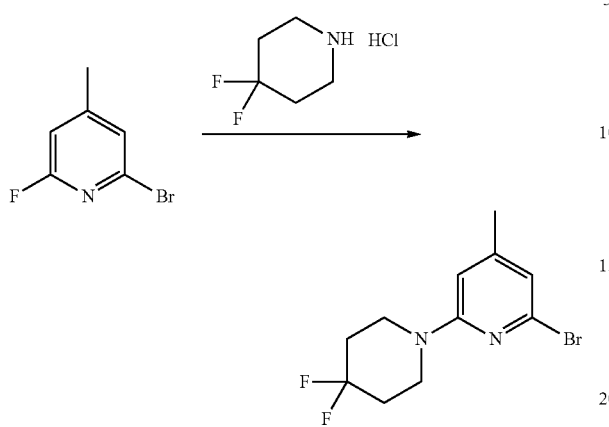

To a solution of 2-bromo-6-fluoro-4-methylpyridine (500 mg, 2.63 mmol) and 4,4-difluoropiperidine hydrochloride (620 mg, 3.94 mmol) in DMSO (5 mL) was added DIPEA (1.36 mL, 7.89 mmol). The mixture was stirred at 100° C. for 12 h. The reaction mixture was poured into saturated aqueous NH$_4$Cl (40 mL) and extracted with ethyl acetate (3×35 mL). The combined organic extracts were washed with brine (100 mL), dried over Na$_2$SO$_4$, filtered, and concentrated. 2-Bromo-6-(4,4-difluoropiperidin-1-yl)-4-methylpyridine (600 mg, 2.06 mmol) was obtained as a yellow oil. LCMS: MS ESI (M+1)$^+$ 290.9.

Step 2: Preparation of 6-(4,4-difluoropiperidin-1-yl)-4-methylpyridin-2-amine

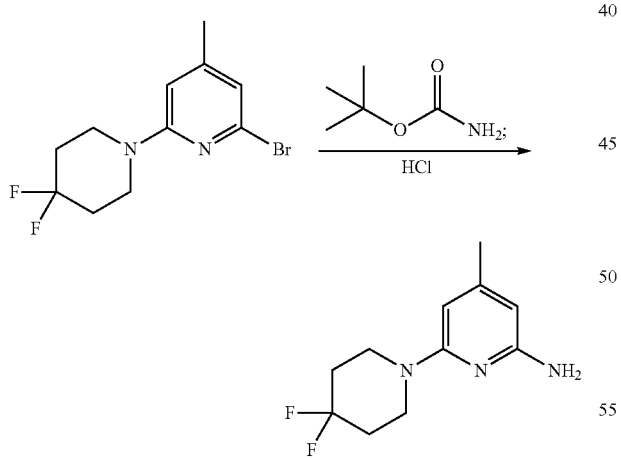

To a solution of 2-bromo-6-(4,4-difluoropiperidin-1-yl)-4-methylpyridine (350 mg, 1.20 mmol) and tert-butyl carbamate (420 mg, 3.59 mmol) in 2-Methyl-2-butanol (5 mL) was added Pd$_2$(dba)$_3$ (109 mg, 120 μmol), Xantphos (138 mg, 240 μmol), and cesium carbonate (1.16 g, 3.59 mmol). The mixture was stirred at 100° C. for 12 h. The reaction mixture was filtered and concentrated under reduced pressure. The yellow residue was purified by silica gel column chromatography (PE:EA 50:1) to give a yellow solid. The solid was dissolved in DCM (1 mL), and HCl (3 mL, 4 M in dioxane) was added to the mixture. The mixture was stirred at 25° C. for 2 h. The reaction mixture was filtered and concentrated under reduced pressure to afford 6-(4,4-difluoropiperidin-1-yl)-4-methylpyridin-2-amine (175 mg, 663 μmol) as a yellow solid.

Step 3: Preparation of N-(6-(4,4-difluoropiperidin-1-yl)-4-methylpyridin-2-yl)-2-(4,4-dimethyl-1,4-azasilinan-1-yl)-4-nitrobenzamide

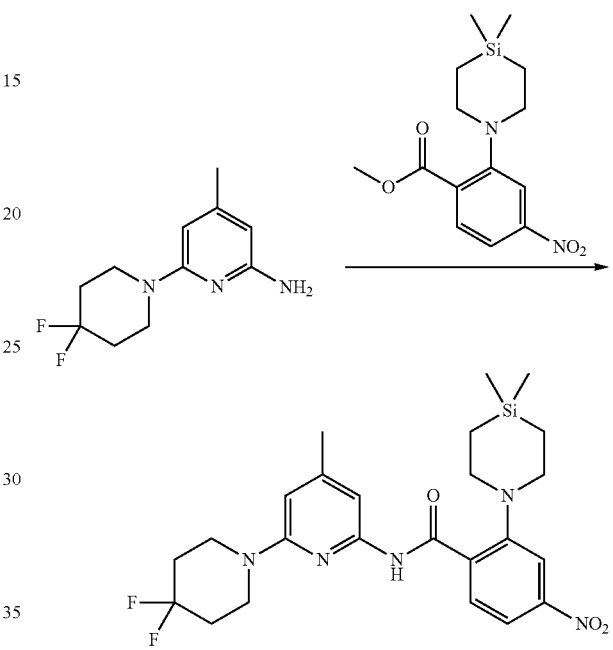

To a solution of 6-(4,4-difluoropiperidin-1-yl)-4-methylpyridin-2-amine (192 mg, 624 μmol) in THF (3 mL) was added LiHMDS (2.27 mL, 2.27 mmol, 1 M in THF). The mixture was stirred at 25° C. for 2 h. The reaction mixture was poured into saturated aqueous NH$_4$Cl (10 mL) and extracted with ethyl acetate (3×15 mL). The combined organic extracts were washed with brine (30 mL), dried over Na$_2$SO$_4$, filtered, and concentrated. The residue was purified by silica gel column chromatography (PE:EA 50:1) to afford N-(6-(4,4-difluoropiperidin-1-yl)-4-methylpyridin-2-yl)-2-(4,4-dimethyl-1,4-azasilinan-1-yl)-4-nitrobenzamide (200 mg, 397 mol) as a yellow solid. LCMS: MS ESI (M+1)$^+$ 504.2.

Step 4: Preparation of 4-amino-N-(6-(4,4-difluoropiperidin-1-yl)-4-methylpyridin-2-yl)-2-(4,4-dimethyl-1,4-azasilinan-1-yl)benzamide

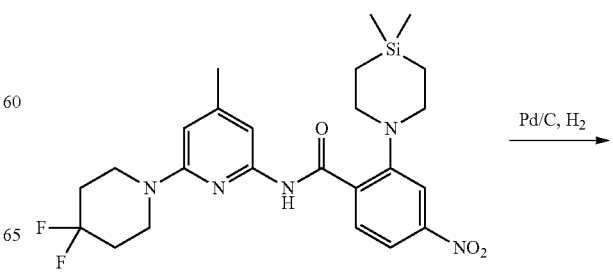

-continued

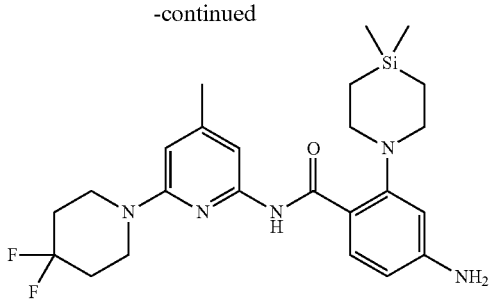

To a solution of N-(6-(4,4-difluoropiperidin-1-yl)-4-methylpyridin-2-yl)-2-(4,4-dimethyl-1,4-azasilinan-1-yl)-4-nitrobenzamide (140 mg, 277 mol) in MeOH (10 mL) was added Pd/C (111 mg, 10% w/w). The mixture was stirred at 25° C. for 2 h under H$_2$ atmosphere (15 psi). The reaction mixture was filtered and concentrated to afford 4-amino-N-(6-(4,4-difluoropiperidin-1-yl)-4-methylpyridin-2-yl)-2-(4,4-dimethyl-1,4-azasilinan-1-yl)benzamide (130 mg, 274 μmol) as a yellow solid. LCMS: MS ESI (M+1)$^+$ 474.3.

Step 5: Preparation of ethyl 2-(N-(4-((6-(4,4-difluoropiperidin-1-yl)-4-methylpyridin-2-yl)carbamoyl)-3-(4,4-dimethyl-1,4-azasilinan-1-yl)phenyl)sulfamoyl)acetate

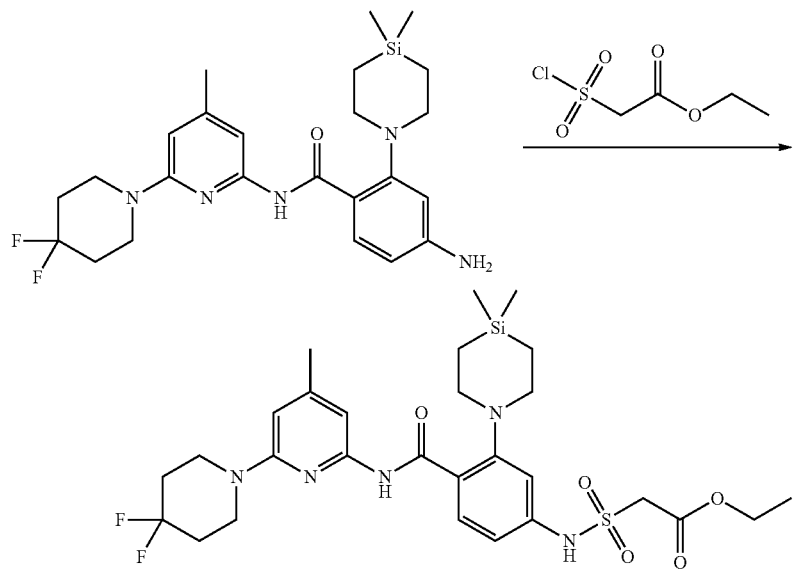

Step 6: Preparation of N-(6-(4,4-difluoropiperidin-1-yl)-4-methylpyridin-2-yl)-2-(4,4-dimethyl-1,4-azasilinan-1-yl)-4-((2-hydroxyethyl)sulfonamido)benzamide

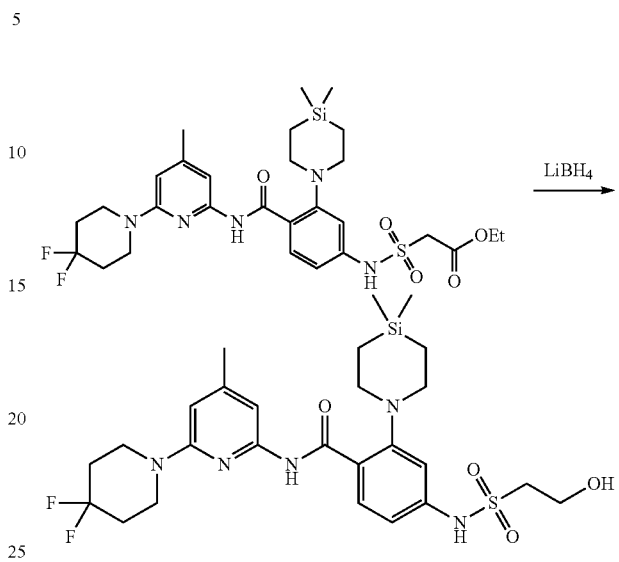

To a solution of ethyl 2-(N-(4-(((6-(4,4-difluoropiperidin-1-yl)-4-methylpyridin-2-yl)carbamoyl)-3-(4,4-dimethyl-1, To a solution of 4-amino-N-(6-(4,4-difluoropiperidin-1-yl)-4-methylpyridin-2-yl)-2-(4,4-dimethyl-1,4-azasilinan-1-yl)benzamide (130 mg, 274 μmol) and pyridine (66.1 μL, 822 μmol) in DCM (3 mL) was added ethyl 2-(chlorosulfonyl)acetate (61.2 mg, 328 μmol) at 0° C. The mixture was stirred at 25° C. for 1 h. The reaction mixture was poured into saturated aqueous NH$_4$Cl solution (10 mL) and extracted with ethyl acetate (3×15 mL). The combined organic extracts were washed with brine (30 mL), dried over Na$_2$SO$_4$, filtered, and concentrated. Ethyl 2-(N-(4-((6-(4,4-difluoropiperidin-1-yl)-4-methylpyridin-2-yl)carbamoyl)-3-(4,4-dimethyl-1,4-azasilinan-1-yl)phenyl)sulfamoyl)acetate (150 mg, 240 μmol) was obtained as a yellow oil. LCMS: MS ESI (M+1)$^+$ 624.2.

4-azasilinan-1-yl)phenyl)sulfamoyl)acetate (100 mg, 160 μmol) in THF (3 mL) was added lithium borohydride (0.160 mL, 320 μmol, 2 M in THF) at 0° C. The reaction was stirred at 25° C. for 0.5 h. The reaction mixture was poured into saturated aqueous NH$_4$Cl solution (10 mL) and extracted with ethyl acetate (3×15 mL). The combined organic extracts were washed with brine (30 mL), dried over Na$_2$SO$_4$, filtered, and concentrated. The residue was purified by Prep-HPLC (TFA condition) to afford N-(6-(4,4-difluoropiperidin-1-yl)-4-methylpyridin-2-yl)-2-(4,4-dimethyl-1,4-azasilinan-1-yl)-4-((2-hydroxyethyl)sulfonamido)benzamide (73.74 mg, 126 μmol) as an off-white solid. LCMS: MS ESI (M+1)$^+$ 582.3. $^1$H NMR (400 MHz, DMSO-d$_6$) δ=12.18 (s, 1H), 10.13 (s, 1H), 7.98 (d, J=8.6 Hz, 1H), 7.53

(s, 1H), 7.22 (s, 1H), 7.08 (br d, J=8.6 Hz, 1H), 6.56 (s, 1H), 3.74 (t, J=6.5 Hz, 2H), 3.66 (br d, J=5.0 Hz, 4H), 3.34 (t, J=6.5 Hz, 2H), 3.17 (br t, J=5.7 Hz, 4H), 2.26 (s, 3H), 2.06-1.86 (m, 4H), 0.99 (br d, J=5.3 Hz, 4H), 0.13 (s, 6H).

Example 9: Synthesis of N-[2-(4,4-difluoropiperidin-1-yl)-6-methylpyrimidin-4-yl]-2-(4,4-dimethyl-1,4-azasilinan-1-yl)-4-(2-hydroxyethanesulfonamido)benzamide

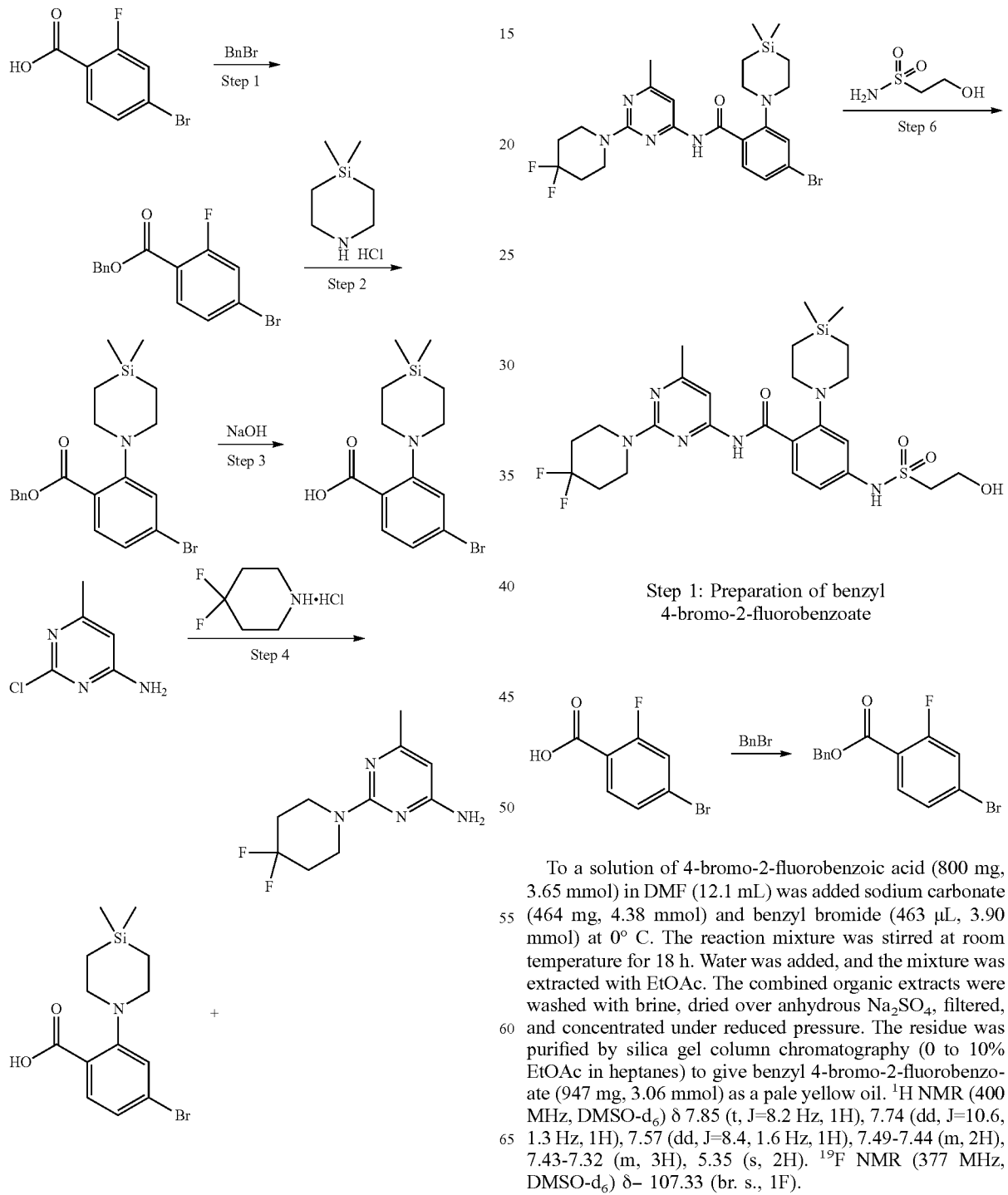

Step 1: Preparation of benzyl 4-bromo-2-fluorobenzoate

To a solution of 4-bromo-2-fluorobenzoic acid (800 mg, 3.65 mmol) in DMF (12.1 mL) was added sodium carbonate (464 mg, 4.38 mmol) and benzyl bromide (463 μL, 3.90 mmol) at 0° C. The reaction mixture was stirred at room temperature for 18 h. Water was added, and the mixture was extracted with EtOAc. The combined organic extracts were washed with brine, dried over anhydrous $Na_2SO_4$, filtered, and concentrated under reduced pressure. The residue was purified by silica gel column chromatography (0 to 10% EtOAc in heptanes) to give benzyl 4-bromo-2-fluorobenzoate (947 mg, 3.06 mmol) as a pale yellow oil. $^1$H NMR (400 MHz, DMSO-$d_6$) δ 7.85 (t, J=8.2 Hz, 1H), 7.74 (dd, J=10.6, 1.3 Hz, 1H), 7.57 (dd, J=8.4, 1.6 Hz, 1H), 7.49-7.44 (m, 2H), 7.43-7.32 (m, 3H), 5.35 (s, 2H). $^{19}$F NMR (377 MHz, DMSO-$d_6$) δ− 107.33 (br. s., 1F).

Step 2: Preparation of benzyl 4-bromo-2-(4,4-dimethyl-1,4-azasilinan-1-yl)benzoate

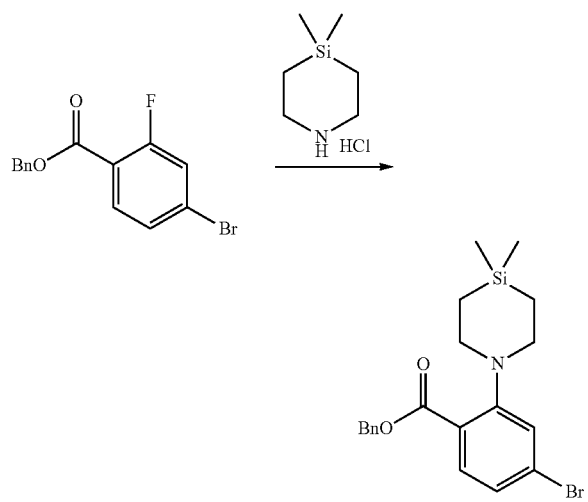

To a solution of benzyl 4-bromo-2-fluorobenzoate (330 mg, 1.06 mmol) in NMP (2.12 mL) was added 4,4-dimethyl-1,4-azasilinane hydrochloride (250 mg, 1.50 mmol) at room temperature. Then, potassium carbonate (439 mg, 3.18 mmol) was added, and the reaction solution was stirred at 100° C. for 18 h under nitrogen. Water was added and the product was extracted three times with EtOAc. Organic extracts were combined, dried with Na$_2$SO$_4$, filtered, and concentrated under vacuum. The residue was purified by silica gel column chromatography (0 to 10% EtOAc in heptanes) to afford benzyl 4-bromo-2-(4,4-dimethyl-1,4-azasilinan-1-yl)benzoate (328 mg, 0.784 mmol). LCMS: MS ESI (M+1)$^+$ 418.0. $^1$H NMR (400 MHz, DMSO-d$_6$) δ 7.49-7.31 (m, 6H), 7.21 (d, J=1.5 Hz, 1H), 7.08 (dd, J=8.1, 1.5 Hz, 1H), 5.30 (s, 2H), 3.26-3.16 (m, 4H), 0.79-0.67 (m, 4H), 0.04 (s, 6H).

Step 3: Preparation of 4-bromo-2-(4,4-dimethyl-1,4-azasilinan-1-yl)benzoic acid

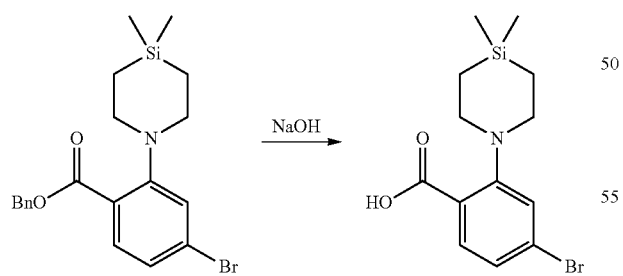

To a solution of benzyl 4-bromo-2-(4,4-dimethyl-1,4-azasilinan-1-yl)benzoate (328 mg, 783 μmol) in 1,4-dioxane (522 μL) was added sodium hydroxide (1 mL, 2.00 mmol, 2 M in water) and the reaction mixture was stirred for 20 h at 100° C. Volatiles were removed under vacuum. Water was added, and the mixture was acidified with aqueous HCl (1 M) until the mixture reached pH 1. The resulting precipitate was recovered by filtration. The solid was dried by co-evaporation with MeCN to give 4-bromo-2-(4,4-dimethyl-1,4-azasilinan-1-yl)benzoic acid (220 mg, 0.67 mmol) as a white solid. LCMS: MS ESI (M+1)$^+$ 328.0. $^1$H NMR (400 MHz, DMSO-d$_6$) δ 8.05 (d, J=1.2 Hz, 1H), 7.89 (d, J=8.6 Hz, 1H), 7.58 (dd, J=8.4, 1.3 Hz, 1H), 3.32 (t, J=5.9 Hz, 4H), 0.95 (t, J=6.1 Hz, 4H), 0.19 (s, 6H).

Step 4: Preparation of 2-(4,4-difluoropiperidin-1-yl)-6-methylpyrimidin-4-amine

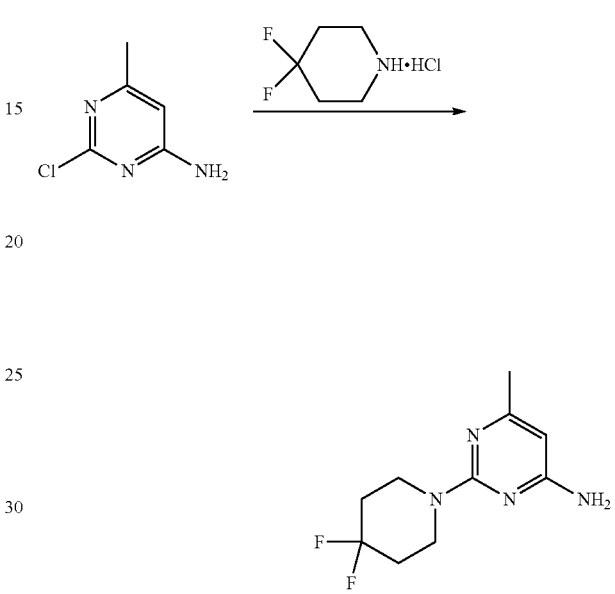

A mixture of 2-chloro-6-methylpyrimidin-4-amine (500 mg, 3.48 mmol), 4,4-difluoropiperidine hydrochloride (822 mg, 5.22 mmol), and N,N-diisopropylethylamine (1.80 mL, 10.4 mmol) in NMP (5.04 mL) was stirred at 180° C. for 24 h in a sealed tube. The reaction mixture was cooled to room temperature, quenched with water, and extracted thrice with ethyl acetate. The organic extracts were combined, washed with brine, dried with Na$_2$SO$_4$, filtered, and concentrated under reduced pressure. The residue was purified by C18 column chromatography (H$_2$O:MeCN gradient) to afford 2-(4,4-difluoropiperidin-1-yl)-6-methylpyrimidin-4-amine (745 mg, 3.26 mmol) as a pale yellow solid. LCMS: MS ESI (M+1)$^+$ 229.2. $^1$H NMR (400 MHz, DMSO-d$_6$) δ 6.33 (br. s., 2H), 5.63 (s, 1H), 3.84-3.72 (m, 4H), 2.06 (s, 3H), 1.97-1.79 (m, 4H).

Step 5: Preparation of 4-bromo-N-[2-(4,4-difluoropiperidin-1-yl)-6-methylpyrimidin-4-yl]-2-(4,4-dimethyl-1,4-azasilinan-1-yl)benzamide

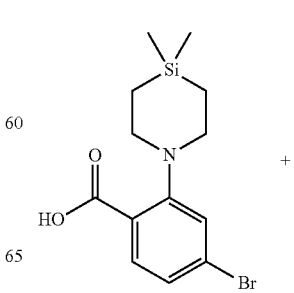

+

103

-continued

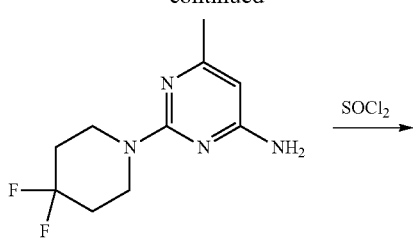

SOCl₂ →

104

Step 6: Preparation of N-[2-(4,4-difluoropiperidin-1-yl)-6-methylpyrimidin-4-yl]-2-(4,4-dimethyl-1,4-azasilinan-1-yl)-4-(2-hydroxyethanesulfonamido)benzamide

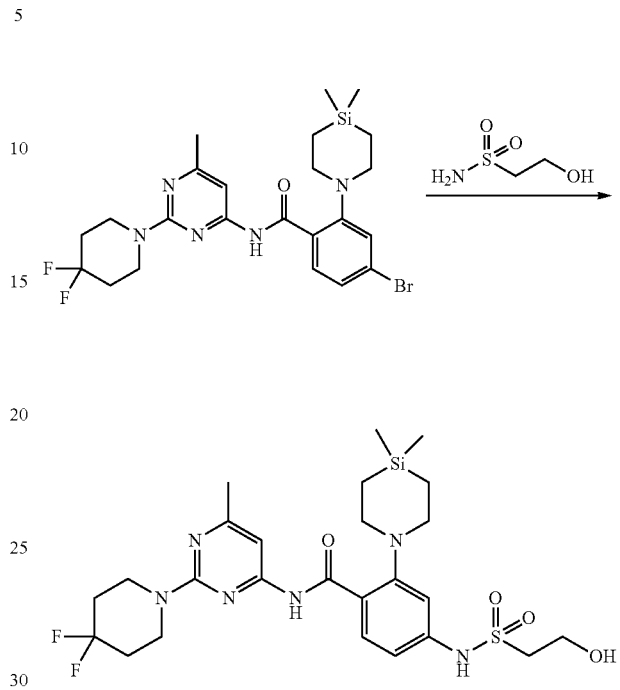

4-Bromo-2-(4,4-dimethyl-1,4-azasilinan-1-yl)benzoic acid (150 mg, 456 μmol) was suspended in DCM (2 mL) under nitrogen. DMF (approx. 1 μL) was added followed by dropwise addition of thionyl chloride (69.2 μL, 957 μmol). After stirring at ambient temperature for 3 h, the mixture was evaporated to dryness under reduced pressure. After suspending the residue in toluene and concentration under reduced pressure twice, the residue was suspended in DCM (2 mL) under nitrogen. Potassium phosphate tribasic (288 mg, 1.36 mmol) was added followed by a solution of 2-(4,4-difluoropiperidin-1-yl)-6-methylpyrimidin-4-amine (108 mg, 474 μmol) and N,N-diisopropylethylamine (158 mg, 1.23 mmol) in DCM (1 mL). The yellow mixture was stirred at room temperature for 21 h. The mixture was evaporated to dryness under reduced pressure. The residue was suspended in dichloromethane and stirred for 10 min. The mixture was filtered, and the resulting filter cake was washed with additional dichloromethane. The filtrate was evaporated to dryness under reduced pressure. The residue was triturated in MeCN to give 4-bromo-N-[2-(4,4-difluoropiperidin-1-yl)-6-methylpyrimidin-4-yl]-2-(4,4-dimethyl-1,4-azasilinan-1-yl)benzamide (156 mg, 0.290 mmol) as a white solid. LCMS: MS ESI (M+1)⁺ 538.0. ¹H NMR (400 MHz, DMSO-d₆) δ 12.64 (br. s., 1H), 7.92 (d, J=8.1 Hz, 1H), 7.72 (br. s., 1H), 7.61-7.35 (m, 2H), 3.97-3.78 (m, 4H), 3.28-3.15 (m, 4H), 2.32 (s, 3H), 2.06-1.88 (m, 4H), 1.04-0.89 (m, 4H), 0.14 (s, 6H). ¹⁹F NMR (377 MHz, DMSO-d₆) δ− 95.21 (br. s., 2F).

A mixture of 2-hydroxyethanesulfonamide (46.3 mg, 370 μmol), copper iodide (17.6 mg, 92.5 μmol), potassium phosphate tribasic (196 mg, 925 μmol), and sarcosine (16.4 mg, 185 μmol) in DMF (1.84 mL) was warmed to 50° C. for 5 min. 4-Bromo-N-[2-(4,4-difluoropiperidin-1-yl)-6-methylpyrimidin-4-yl]-2-(4,4-dimethyl-1,4-azasilinan-1-yl)benzamide (100 mg, 185 μmol) was added, and the mixture was heated to 120° C. for 20 h. The mixture was cooled to room temperature. EtOAc and water were added, and the resulting biphasic mixture was separated. The aqueous extract was washed with EtOAc twice. The combined organic extracts were washed with brine, an aqueous solution of NH₄Cl/NH₄OH (9:1), brine, dried with Na₂SO₄, filtered, and concentrated under vacuum. The residue was purified by silica gel column chromatography (0 to 100% EtOAc in heptanes) to give N-[2-(4,4-difluoropiperidin-1-yl)-6-methylpyrimidin-4-yl]-2-(4,4-dimethyl-1,4-azasilinan-1-yl)-4-(2-hydroxyethanesulfonamido)benzamide (46.7 mg, 80.1 μmol) as a white solid. LCMS: MS ESI (M+1)⁺ 583.2. ¹H NMR (400 MHz, DMSO-d₆) δ 12.63 (s, 1H), 10.18 (br. s., 1H), 7.98 (d, J=8.6 Hz, 1H), 7.46 (s, 1H), 7.24 (s, 1H), 7.10 (d, J=8.6 Hz, 1H), 5.01-4.85 (m, 1H), 3.92-3.80 (m, 4H), 3.79-3.69 (m, 2H), 3.34 (t, J=6.6 Hz, 2H), 3.21-3.12 (m, 4H), 2.31 (s, 3H), 2.04-1.89 (m, 4H), 1.06-0.95 (m, 4H), 0.14 (s, 6H). ¹⁹F NMR (377 MHz, DMSO-d₆) δ −95.19 (br. s., 2F).

Examples 10-27

The following compounds were made using similar procedures to examples 1 to 9 above:

| Example Number | Structure | NMR |
|---|---|---|
| 10 | 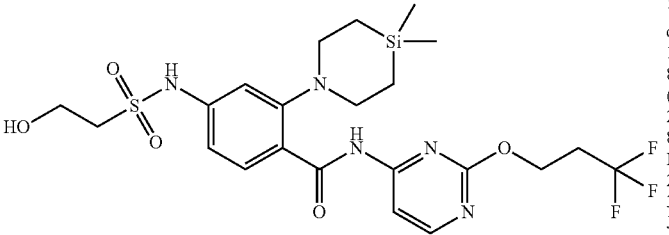 | $^1$H NMR (400 MHz, DMSO-$d_6$) δ = 13.56 (s, 1H), 10.24 (s, 1H), 8.52 (d, J = 5.6 Hz, 1H), 8.03 (d, J = 8.7 Hz, 1H), 7.91 (d, J = 5.6 Hz, 1H), 7.24 (d, J = 2.0 Hz, 1H), 7.13 (dd, J = 2.0, 8.7 Hz, 1H), 4.50 (t, J = 5.9 Hz, 2H), 3.76 (t, J = 6.5 Hz, 2H), 3.36 (t, J = 6.4 Hz, 2H), 3.25-3.13 (m, 4H), 2.78 (tq, J = 5.9, 11.4 Hz, 2H), 1.10-0.99 (m, 4H), 0.18 (s, 6H) |
| 11 | 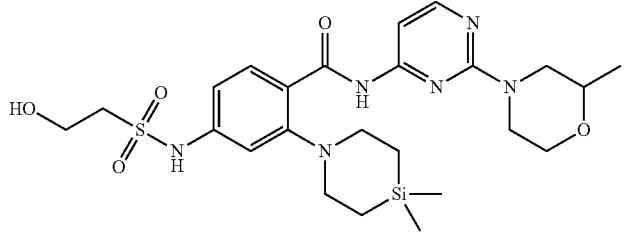 [SMILES: CC1CN(c2nccc(NC(=O)c3ccc(NS(=O)(=O)CCO)cc3N3CC[Si](C)(C)CC3)n2)CCO1] | $^1$H NMR (400 MHz, DMSO-$d_6$) δ = 12.75 (br s, 1H), 10.21 (s, 1H), 8.32 (d, J = 5.6 Hz, 1H), 7.98 (d, J = 8.6 Hz, 1H), 7.53 (d, J = 5.3 Hz, 1H), 7.38-6.98 (m, 2H), 4.48-4.26 (m, 2H), 3.88 (br dd, J = 2.4, 11.7 Hz, 1H), 3.75 (t, J = 6.4 Hz, 2H), 3.59-3.32 (m, 4H), 3.29-3.04 (m, 4H), 3.01-2.87 (m, 1H), 2.70-2.59 (m, 1H), 1.23-0.84 (m, 7H), 0.14 (s, 6H) |
| 12 | 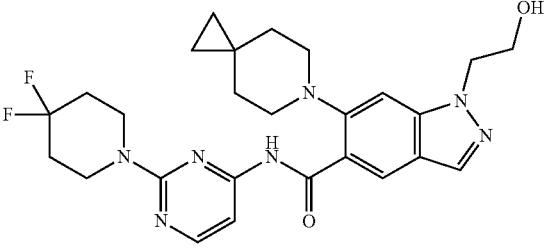 [SMILES: O=C(Nc1ccnc(N2CCC(F)(F)CC2)n1)c1cc2cnn(CCO)c2cc1N1CCC2(CC1)CC2] | $^1$H NMR (400 MHz, DMSO-$d_6$) δ = 14.06 (s, 1H), 8.69 (s, 1H), 8.42 (d, J = 5.4 Hz, 1H), 8.29 (s, 1H), 7.85 (s, 1H), 7.62 (d, J = 5.4 Hz, 1H), 4.55 (t, J = 5.4 Hz, 1H), 3.99 (br d, J = 5.6 Hz, 6H), 3.88 (br t, J = 5.6 Hz, 4H), 3.18 (br t, J = 5.0 Hz, 4H), 2.18-2.04 (m, 4H), 0.48 (s, 4H) |
| 13 | 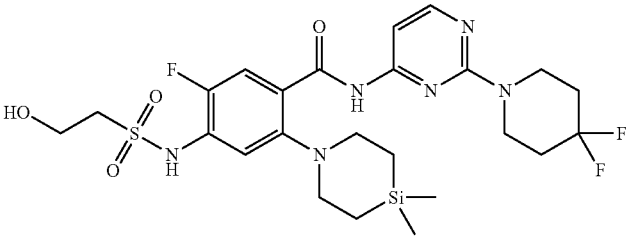 [SMILES: C[Si]1(C)CCN(c2cc(NS(=O)(=O)CCO)c(F)cc2C(=O)Nc2ccnc(N3CCC(F)(F)CC3)n2)CC1] | $^1$H NMR (400 MHz, DMSO-$d_6$) δ = 13.25 (br s, 1H), 8.31 (d, J = 5.5 Hz, 1H), 7.61 (br d, J = 12.3 Hz, 1H), 7.54 (d, J = 5.5 Hz, 1H), 7.39 (br d, J = 7.7 Hz, 1H), 3.86 (br t, J = 5.3 Hz, 4H), 3.73 (t, J = 6.4 Hz, 2H), 3.10 (br d, J = 4.0 Hz, 6H), 2.06-1.89 (m, 4H), 1.08-0.95 (m, 4H), 0.15 (s, 6H) |
| 14 | 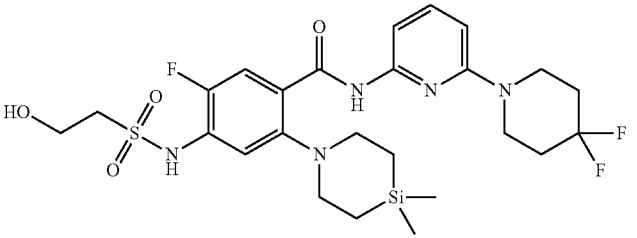 [SMILES: C[Si]1(C)CCN(c2cc(NS(=O)(=O)CCO)c(F)cc2C(=O)Nc2cccc(N3CCC(F)(F)CC3)n2)CC1] | $^1$H NMR (400 MHz, DMSO-$d_6$) δ = 12.58 (s, 1H), 10.47-9.33 (m, 1H), 7.81 (br d, J = 11.6 Hz, 1H), 7.68-7.60 (m, 2H), 7.52 (br d, J = 7.2 Hz, 1H), 6.72 (br dd, J = 1.8, 6.2 Hz, 1H), 5.37-4.68 (m, 1H), 3.79 (br t, J = 6.4 Hz, 2H), 3.67 (br s, 4H), 3.41-3.36 (m, 2H), 3.16 (br s, 4H), 2.09-1.83 (m, 4H), 1.00 (br s, 4H), 0.14 (s, 6H) |
| 15 | 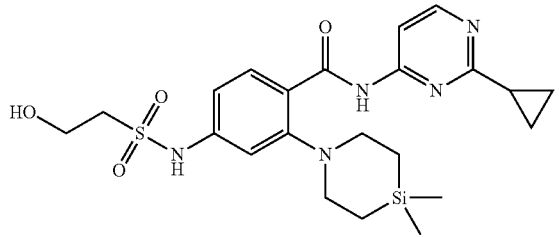 [SMILES: C[Si]1(C)CCN(c2cc(NS(=O)(=O)CCO)ccc2C(=O)Nc2ccnc(C3CC3)n2)CC1] | $^1$H NMR (400 MHz, DMSO-$d_6$) δ = 13.38 (s, 1H), 8.52 (d, J = 5.6 Hz, 1H), 8.08-7.97 (m, 2H), 7.24 (d, J = 1.8 Hz, 1H), 7.10 (dd, J = 1.8, 8.6 Hz, 1H), 6.54 (s, 1H), 3.79 (s, 1H), 3.75 (t, J = 6.6 Hz, 2H), 3.34 (br s, 2H), 3.23-3.11 (m, 4H), 2.15-2.03 (m, 1H), 1.10-0.96 (m, 8H), 0.20 (s, 6H) |

| Example Number | Structure | NMR |
|---|---|---|
| 16 | 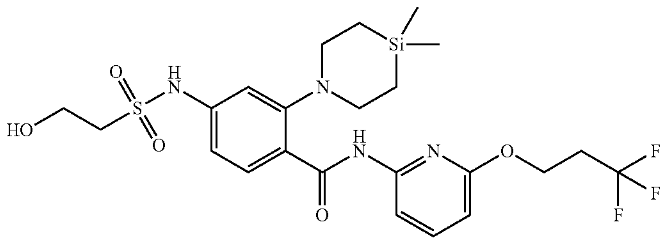 [SMILES: C[Si]1(C)CCN(c2cc(NS(=O)(=O)CCO)ccc2C(=O)Nc2cccc(OCCC(F)(F)F)n2)CC1] | ¹H NMR (400 MHz, DMSO-d₆) δ = 12.40 (s, 1H), 10.02 (s, 1H), 7.86 (d, J = 8.6 Hz, 1H), 7.78 (d, J = 7.8 Hz, 1H), 7.63 (t, J = 8.0 Hz, 1H), 7.11 (d, J = 1.8 Hz, 1H), 6.96 (dd, J = 1.8, 8.6 Hz, 1H), 6.44 (d, J = 8.2 Hz, 1H), 4.31 (t, J = 6.2 Hz, 2H), 3.62 (s, 2H), 3.21 (t, J = 6.4 Hz, 2H), 3.10-2.99 (m, 4H), 2.75-2.56 (m, 2H), 0.92-0.75 (m, 4H), 0.00 (s, 6H) |
| 17 | 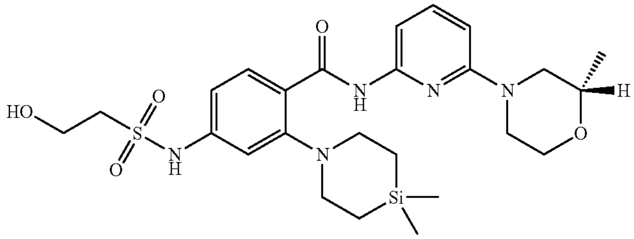 [SMILES: C[C@H]1CN(c2cccc(NC(=O)c3ccc(NS(=O)(=O)CCO)cc3N3CC[Si](C)(C)CC3)n2)CCO1] | ¹H NMR (400 MHz, DMSO-d₆) δ = 12.08 (s, 1H), 10.01 (s, 1H), 7.86 (d, J = 8.6 Hz, 1H), 7.55-7.37 (m, 2H), 7.09 (d, J = 1.6 Hz, 1H), 6.95 (dd, J = 1.8, 8.6 Hz, 1H), 6.45 (d, J = 7.8 Hz, 1H), 3.99-3.73 (m, 3H), 3.63 (t, J = 6.4 Hz, 2H), 3.51-3.35 (m, 2H), 3.21 (t, J = 6.4 Hz, 2H), 3.05 (br t, J = 5.6 Hz, 4H), 2.64 (dt, J = 3.2, 12.34 Hz, 1H), 2.34-2.23 (m, 1H), 1.01 (d, J = 6.2 Hz, 3H), 0.92-0.78 (m, 4H), 0.00 (s, 6H) |
| 18 | 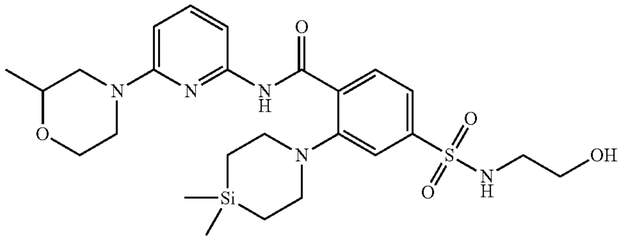 [SMILES: CC1CN(c2cccc(NC(=O)c3ccc(S(=O)(=O)NCCO)cc3N3CC[Si](C)(C)CC3)n2)CCO1] | ¹H NMR (400 MHz, CHLOROFORM-d) δ = 12.08 (br s, 1H), 8.33 (br d, J = 7.7 Hz, 1H), 7.86-7.76 (m, 2H), 7.69 (br d, J = 7.8 Hz, 1H), 7.61 (br t, J = 7.8 Hz, 1H), 6.45 (br d, J = 8.1 Hz, 1H), 5.12 (br d, J = 2.3 Hz, 1H), 4.16-3.94 (m, 3H), 3.80-3.64 (m, 4H), 3.33 (br s, 4H), 3.18 (br s, 2H), 3.03-2.81 (m, 1H), 2.59 (br t, J = 11.2 Hz, 1H), 2.10-1.87 (m, 1H), 1.27 (d, J = 6.0 Hz, 3H), 1.08 (br s, 4H), 0.17 (s, 6H) |
| 19 | 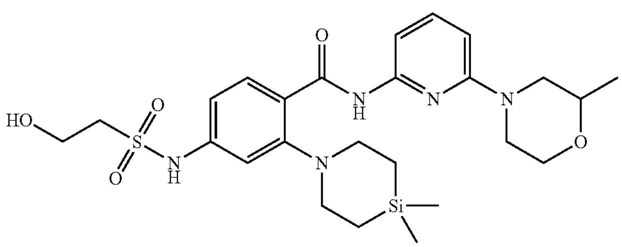 [SMILES: CC1CN(c2cccc(NC(=O)c3ccc(NS(=O)(=O)CCO)cc3N3CC[Si](C)(C)CC3)n2)CCO1] | ¹H NMR (400 MHz, DMSO-d₆) δ = 12.26 (s, 1H), 7.95 (d, J = 8.6 Hz, 1H), 7.68-7.50 (m, 2H), 7.18 (s, 1H), 7.11-6.95 (m, 1H), 6.57 (d, J = 8.2 Hz, 1H), 4.10 (br d, J = 12.2 Hz, 1H), 3.98 (br d, J = 12.6 Hz, 1H), 3.92-3.84 (m, 1H), 3.74 (t, J = 6.4 Hz, 2H), 3.58-3.50 (m, 2H), 3.30 (br t, J = 6.4 Hz, 2H), 3.21-3.11 (m, 4H), 2.76 (br d, J = 2.8 Hz, 1H), 2.42 (br d, J = 10.8 Hz, 1H), 1.14 (d, J = 6.2 Hz, 3H), 0.98 (br s, 4H), 0.12 (s, 6H) |
| 20 | 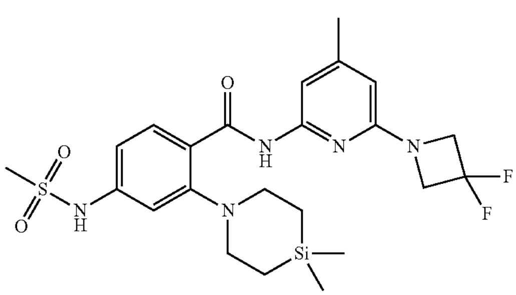 [SMILES: Cc1cc(NC(=O)c2ccc(NS(C)(=O)=O)cc2N2CC[Si](C)(C)CC2)nc(N2CC(F)(F)C2)c1] | ¹H NMR (400 MHz, DMSO-d₆) δ = 12.46 (s, 1H), 10.17 (s, 1H), 7.99 (d, J = 8.6 Hz, 1H), 7.60 (s, 1H), 7.20 (d, J = 1.6 Hz, 1H), 7.09 (dd, J = 2.0, 8.6 Hz, 1H), 6.18 (s, 1H), 4.37-4.31 (m, 4H), 3.21-3.12 (m, 4H), 3.10 (s, 3H), 2.27 (s, 3H), 1.06-0.93 (m, 4H), 0.14 (s, 6H) |

-continued

| Example Number | Structure | NMR |
|---|---|---|
| 21 | 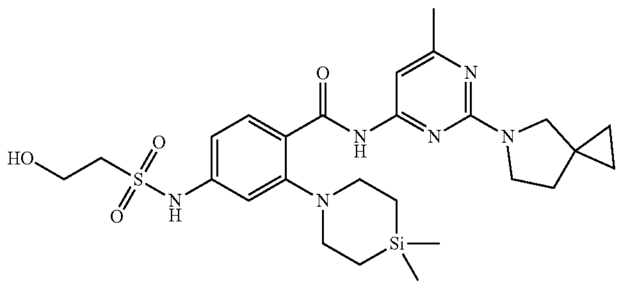 [SMILES: Cc1cc(NC(=O)c2ccc(NS(=O)(=O)CCO)cc2N2CC[Si](C)(C)CC2)nc(N2CCC3(CC3)C2)n1] | ¹H NMR (400 MHz, DMSO-d₆) δ = 13.15-12.75 (m, 1H), 10.10 (s, 1H), 7.88 (d, J = 8.6 Hz, 1H), 7.38 (s, 1H), 7.14 (d, J = 2.0 Hz, 1H), 7.00 (dd, J = 2.2, 8.8 Hz, 1H), 3.62 (t, J = 6.4 Hz, 2H), 3.55 (br t, J = 6.6 Hz, 2H), 3.30 (s, 2H), 3.22 (t, J = 6.4 Hz, 2H), 3.07-2.97 (m, 4H), 2.24 (s, 3H), 1.75 (br s, 2H), 0.88 (br s, 4H), 0.50 (br s, 4H), 0.00 (s, 6H) |
| 22 | 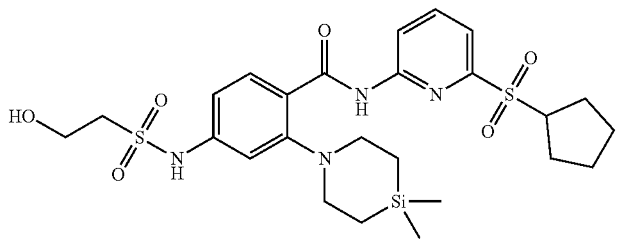 [SMILES: C[Si]1(C)CCN(c2cc(NS(=O)(=O)CCO)ccc2C(=O)Nc2cccc(S(=O)(=O)C3CCCC3)n2)CC1] | ¹H NMR (400 MHz, DMSO-d₆) δ = 13.51 (br s, 1H), 10.21 (s, 1H), 8.60 (d, J = 8.4 Hz, 1H), 8.17 (t, J = 8.0 Hz, 1H), 8.08 (d, J = 8.6 Hz, 1H), 7.77 (d, J = 7.4 Hz, 1H), 7.30 (d, J = 1.9 Hz, 1H), 7.14 (dd, J = 2.0, 8.6 Hz, 1H), 3.89 (br d, J = 2.1 Hz, 1H), 3.75 (t, J = 6.4 Hz, 2H), 3.36 (t, J = 6.4 Hz, 2H), 3.24-3.12 (m, 4H), 1.95-1.77 (m, 4H), 1.72-1.53 (m, 4H), 1.10-0.96 (m, 4H), 0.20 (s, 6H) |
| 23 | 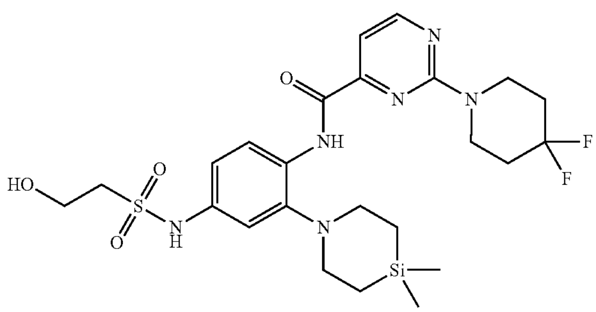 | ¹H NMR (400 MHz, DMSO-d₆) δ = 10.39 (s, 1H), 9.63 (s, 1H), 8.72 (d, J = 4.8 Hz, 1H), 8.25 (d, J = 8.7 Hz, 1H), 7.35 (d, J = 4.8 Hz, 1H), 7.16 (d, J = 2.3 Hz, 1H), 7.00 (dd, J = 2.3, 8.7 Hz, 1H), 4.03 (br t, J = 5.4 Hz, 4H), 3.74-3.72 (m, 2H), 3.21 (t, J = 6.7 Hz, 2H), 3.07-2.97 (m, 4H), 2.22-1.97 (m, 4H), 0.91-0.83 (m, 4H), 0.14 (s, 6H) |
| 24 | 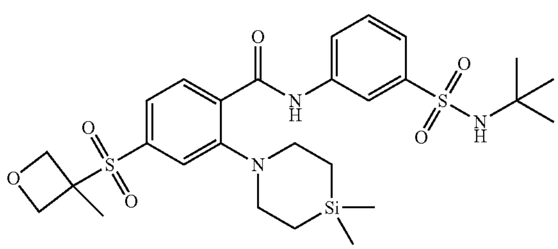 [SMILES: CC(C)(C)NS(=O)(=O)c1cccc(NC(=O)c2ccc(S(=O)(=O)C3(C)COC3)cc2N2CC[Si](C)(C)CC2)c1] | ¹H NMR (400 MHz, DMSO-d₆) δ = 11.07 (s, 1H), 8.38 (s, 1H), 7.93-7.72 (m, 2H), 7.65-7.38 (m, 5H), 4.98 (d, J = 7.2 Hz, 2H), 4.47 (d, J = 7.2 Hz, 2H), 3.32 (br t, J = 6.2 Hz, 4H), 1.57 (s, 3H), 1.09 (s, 9H), 0.90-0.70 (m, 4H), 0.00 (s, 6H) |
| 25 | 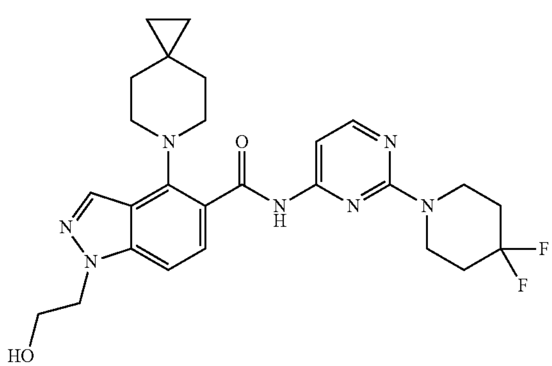 [SMILES: O=C(Nc1ccnc(N2CCC(F)(F)CC2)n1)c1ccc2c(cnn2CCO)c1N1CCC2(CC1)CC2] | ¹H NMR (400 MHz, DMSO-d₆) δ = 14.35 (s, 1H), 8.51 (s, 1H), 8.35 (d, J = 5.6 Hz, 1H), 8.17 (d, J = 8.8 Hz, 1H), 7.64 (d, J = 9.0 Hz, 1H), 7.57 (d, J = 5.6 Hz, 1H), 4.46 (t, J = 5.4 Hz, 2H), 3.94-3.91 (m, 4H), 3.84-3.83 (m, 2H), 3.36 (br s, 4H), 2.13-1.55 (m, 8H), 0.46 (s, 4H) |

| Example Number | Structure | NMR |
|---|---|---|
| 26 | 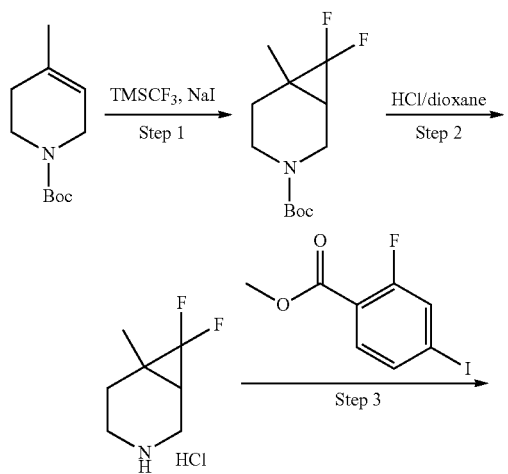 | $^1$H NMR (400 MHz, DMSO-$d_6$) δ = 8.34-7.81 (m, 1H), 7.56-7.22 (m, 2H), 3.84 (br s, 4H), 3.77 (t, J = 6.2 Hz, 2H), 3.36 (td, J = 6.2, 18.4 Hz, 6H), 2.34 (s, 3H), 2.04-1.92 (m, 4H), 0.95-0.80 (m, 4H), 0.08 (s, 6H) |
| 27 | 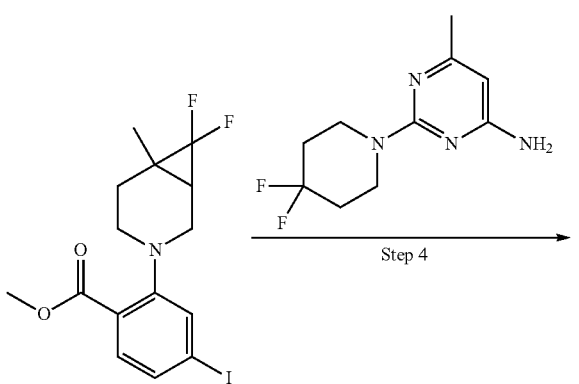 | $^1$H NMR (400 MHz, DMSO-$d_6$) δ 10.81 (s, 1H), 8.33-8.21 (m, 2H), 8.00-7.90 (m, 1H), 7.75 (dd, J = 7.3, 2.0 Hz, 1H), 7.64 (t, J = 7.9 Hz, 1H), 7.49 (d, J = 8.3 Hz, 1H), 6.85 (dd, J = 7.5, 4.8 Hz, 1H), 3.66-3.53 (m, 4H), 3.10 (t, J = 5.6 Hz, 4H), 2.13-1.99 (m, 4H), 0.83-0.68 (m, 4H), 0.06-0.05 (m, 6H) |

Example 28: Synthesis of 2-(7,7-difluoro-6-methyl-3-azabicyclo[4.1.0]heptan-3-yl)-N-(2-(4,4-difluoropiperidin-1-yl)-6-methylpyrimidin-4-yl)-4-((2-hydroxyethyl)sulfonamido)benzamide

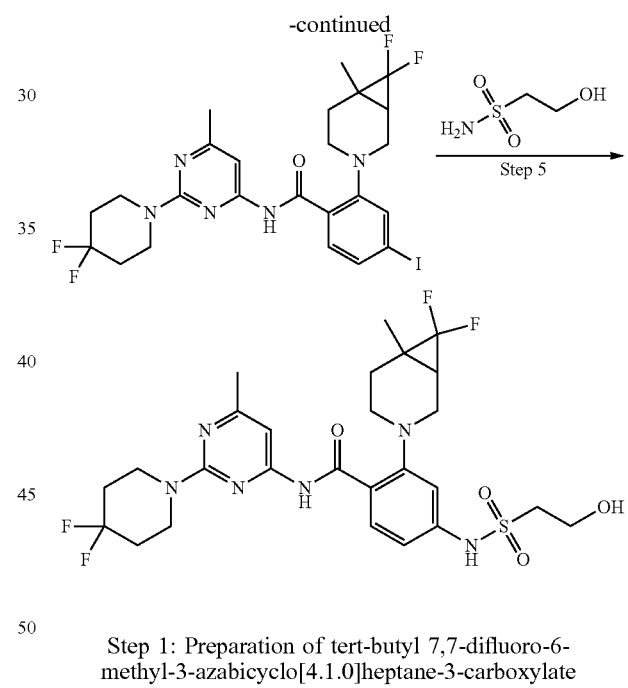

Step 1: Preparation of tert-butyl 7,7-difluoro-6-methyl-3-azabicyclo[4.1.0]heptane-3-carboxylate To a solution of tert-butyl 4-methyl-3,6-dihydropyridine-1(2H)-carboxylate (800 mg, 4.00 mmol), NaI (302 mg, 2.02 mmol) in THF (16 mL) was added TMSCF$_3$ (1.43 g, 10.1 mmol). The mixture was stirred at 60° C. overnight under N₂ atmosphere. The reaction was diluted with water (5 mL) and extracted with EA (10 mL). The organic extract was concentrated and then purified by silica gel column chromatography (PE:EA 4:1) to afford tert-butyl 7,7-difluoro-6-methyl-3-azabicyclo[4.1.0]heptane-3-carboxylate (400 mg, 1.61 mmol) as a yellow oil. ¹H NMR (400 MHz, CHLOROFORM-d) δ=4.17-3.07 (m, 4H), 2.06-1.86 (m, 1H), 1.61 (br s, 1H), 1.51-1.37 (m, 9H), 1.29-1.16 (m, 4H).

Step 2: Preparation of 7,7-difluoro-6-methyl-3-azabicyclo[4.1.0]heptane hydrochloride

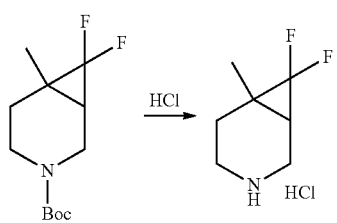

A mixture of tert-butyl 7,7-difluoro-6-methyl-3-azabicyclo[4.1.0]heptane-3-carboxylate (1.0 g, 4.04 mmol) and HCl (20 mL, 80 mmol, 4 M in dioxane) was stirred at room temperature overnight. The mixture was concentrated in vacuo to afford 7,7-difluoro-6-methyl-3-azabicyclo[4.1.0] heptane hydrochloride (500 mg, 2.72 mmol) as a yellow solid.

Step 3: Preparation of methyl 2-(7,7-difluoro-6-methyl-3-azabicyclo[4.1.0]heptan-3-yl)-4-iodobenzoate

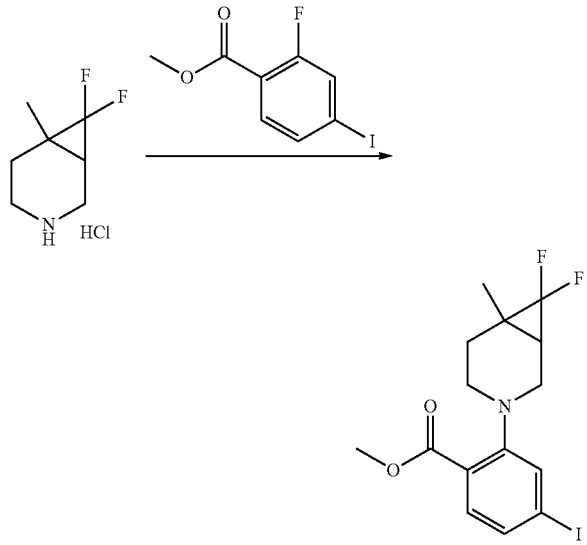

To a solution of 7,7-difluoro-6-methyl-3-azabicyclo[4.1.0]heptane hydrochloride (300 mg, 1.63 mmol) and methyl 2-fluoro-4-iodobenzoate (456 mg, 1.63 mmol) in DMSO (2 mL) was added DIEA (632 mg, 4.89 mmol). The mixture was stirred at 100° C. overnight. The mixture was then diluted with water (10 mL) and extracted with EtOAc (10 mL). The organic extract was concentrated and purified by silica gel column chromatography (PE:EA 3:1) to afford methyl 2-(7,7-difluoro-6-methyl-3-azabicyclo[4.1.0]heptan-3-yl)-4-iodobenzoate (400 mg, 982 μmol) as a yellow solid. LCMS: MS ESI (M+1)⁺ 408.0.

Step 4: Preparation of 2-(7,7-difluoro-6-methyl-3-azabicyclo[4.1.0]heptan-3-yl)-N-(2-(4,4-difluoropiperidin-1-yl)-6-methylpyrimidin-4-yl)-4-iodobenzamide

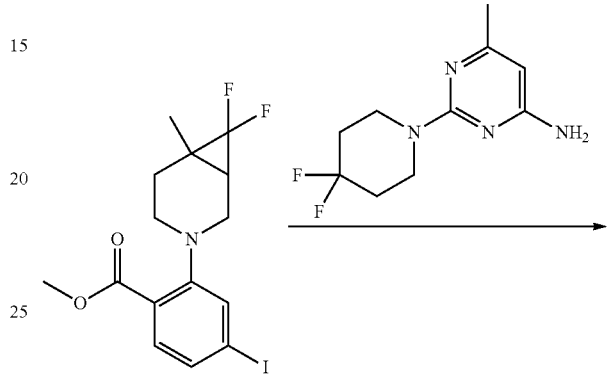

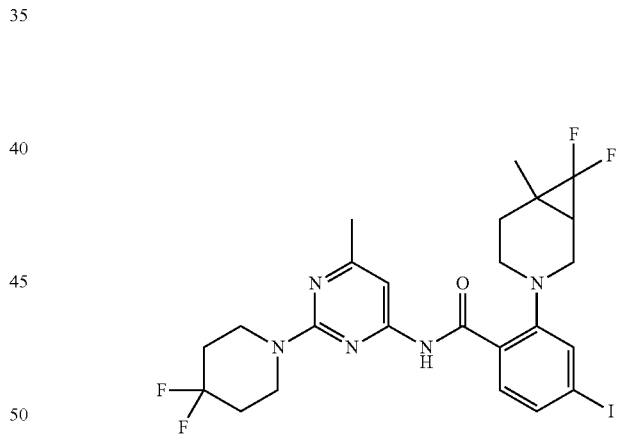

To a solution of methyl 2-(7,7-difluoro-6-methyl-3-azabicyclo[4.1.0]heptan-3-yl)-4-iodobenzoate (400 mg, 982 mol) and 2-(4,4-difluoropiperidin-1-yl)-6-methylpyrimidin-4-amine (335 mg, 1.47 mmol) in THF (8 mL) was added LiHMDS (2.9 mL, 2.9 mmol, 1 M in THF) at room temperature. The mixture was stirred at room temperature for 1 h. The reaction was then quenched with water (10 mL) and extracted with EtOAc (10 mL). The organic extract was concentrated and purified by silica gel column chromatography (PE:EA 3:1) to afford 2-(7,7-difluoro-6-methyl-3-azabicyclo[4.1.0]heptan-3-yl)-N-(2-(4,4-difluoropiperidin-1-yl)-6-methylpyrimidin-4-yl)-4-iodobenzamide (500 mg, 828 μmol) as a yellow solid. LCMS: MS ESI (M+1)⁺ 604.2.

Step 5: Preparation of 2-(7,7-difluoro-6-methyl-3-azabicyclo[4.1.0]heptan-3-yl)-N-(2-(4,4-difluoropiperidin-1-yl)-6-methylpyrimidin-4-yl)-4-((2-hydroxyethyl)sulfonamido)benzamide Examples 29a and 29b: Synthesis of 2-((1S,6R)-6-(difluoromethyl)-3-azabicyclo[4.1.0]heptan-3-yl)-N-(2-(4,4-difluoropiperidin-1-yl)-6-methylpyrimidin-4-yl)-4-((2-hydroxyethyl)sulfonamido)benzamide (Example 29a) and 2-((1R,6S)-6-(difluoromethyl)-3-azabicyclo[4.1.0]heptan-3-yl)-N-(2-(4,4-difluoropiperidin-1-yl)-6-methylpyrimidin-4-yl)-4-((2-hydroxyethyl)sulfonamido)benzamide (Example 29b)

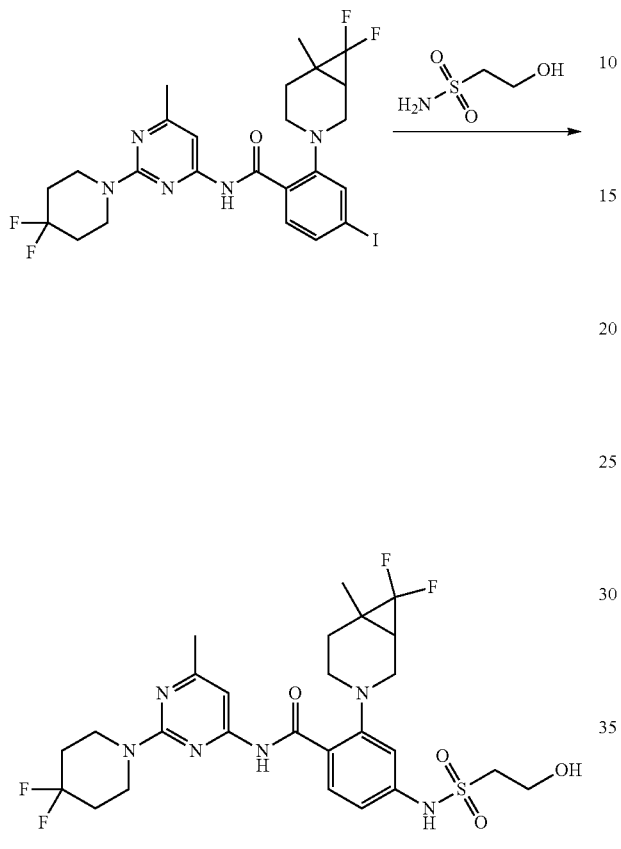

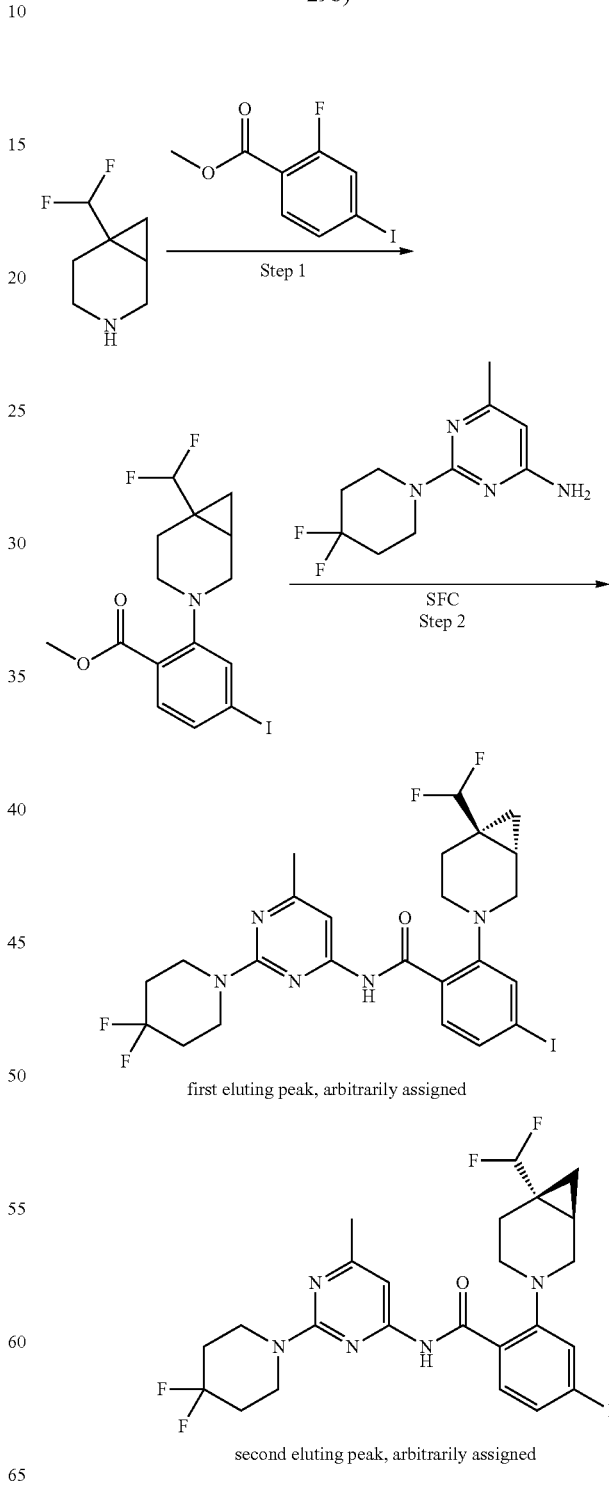

first eluting peak, arbitrarily assigned second eluting peak, arbitrarily assigned To a solution of 2-(7,7-difluoro-6-methyl-3-azabicyclo[4.1.0]heptan-3-yl)-N-(2-(4,4-difluoropiperidin-1-yl)-6-methylpyrimidin-4-yl)-4-iodobenzamide (41.2 mg, 330 μmol), copper(I) iodide (15.6 mg, 82.5 μmol), and 2-(methylamino)acetic acid (7.35 mg, 82.5 μmol) in DMF (2 mL) was added $K_3PO_4$ (175 mg, 825 μmol), and the mixture was stirred at 60° C. for 10 min under $N_2$ atmosphere. Then, 2-hydroxyethane-1-sulfonamide (100 mg, 165 μmol) was added, and the mixture was stirred at 100° C. overnight. The mixture was then filtered, and the filtrate was purified by prep-HPLC (neutral condition) to afford 2-(7,7-difluoro-6-methyl-3-azabicyclo[4.1.0]heptan-3-yl)-N-(2-(4,4-difluoropiperidin-1-yl)-6-methylpyrimidin-4-yl)-4-((2-hydroxyethyl)sulfonamido)benzamide (33.1 mg, 55.2 μmol) as a yellow solid. LCMS: MS ESI (M+1)$^+$ 601.3. $^1$H NMR (400 MHz, DMSO-$d_6$) δ=11.16 (s, 1H), 7.82 (d, J=8.4 Hz, 1H), 7.40 (s, 1H), 7.20-6.92 (m, 2H), 3.87 (br t, J=5.2 Hz, 4H), 3.75 (t, J=6.4 Hz, 2H), 3.49-3.37 (m, 1H), 3.34 (m, 2H), 3.05-2.85 (m, 2H), 2.72-2.62 (m, 1H), 2.31 (m, 4H), 2.10 (br d, J=13.4 Hz, 1H), 2.03-1.89 (m, 4H), 1.88-1.69 (m, 2H), 1.23 (s, 3H).

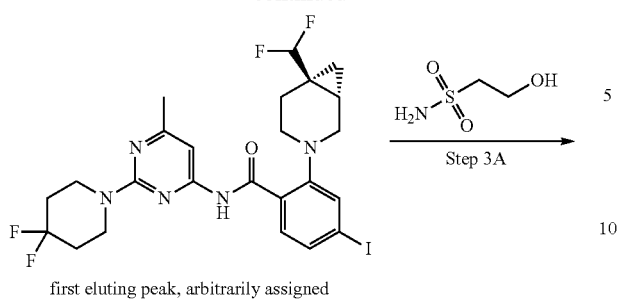

first eluting peak, arbitrarily assigned

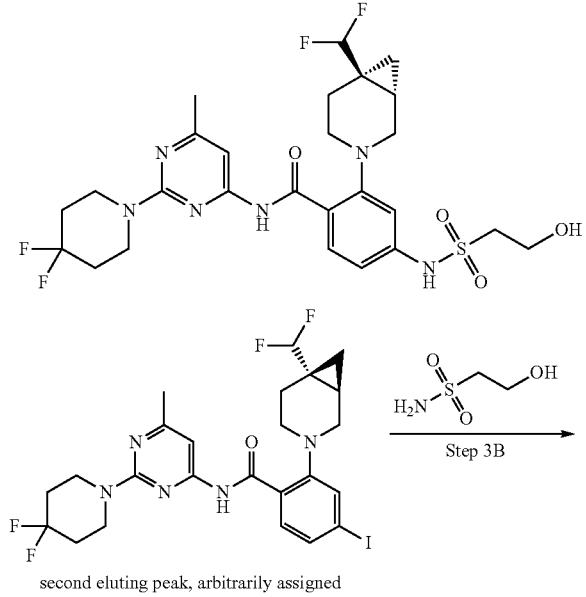

second eluting peak, arbitrarily assigned

Step 1: Preparation of methyl 2-(6-(difluoromethyl)-3-azabicyclo[4.1.0]heptan-3-yl)-4-iodobenzoate

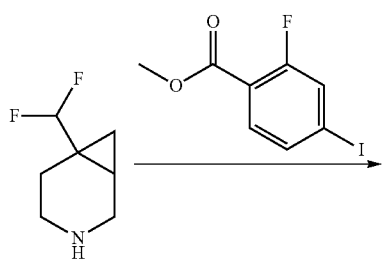

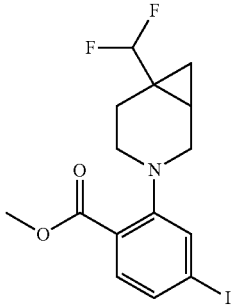

To a solution of 6-(difluoromethyl)-3-azabicyclo[4.1.0]heptane (100 mg, 679 μmol) in DMSO (2 mL) was added methyl 2-fluoro-4-iodobenzoate (190 mg, 679 μmol) and DIEA (87.7 mg, 679 μmol). The mixture was stirred at 100° C. overnight. The mixture was then poured into water (3 mL) and extracted with EtOAc (3×5 mL). The combined organic extracts were washed with brine (2×2 mL), dried over $Na_2SO_4$, filtered, and concentrated in vacuo. The residue was purified by silica gel column chromatography (PE:EA 3:1) to afford methyl 2-(6-(difluoromethyl)-3-azabicyclo[4.1.0]heptan-3-yl)-4-iodobenzoate (90.0 mg, 221 μmol) as a yellow gum. LCMS: MS ESI (M−100)$^+$ 408.0.

Step 2: Preparation of 2-((1S,6R)-6-(difluoromethyl)-3-azabicyclo[4.1.0]heptan-3-yl)-N-(2-(4,4-difluoropiperidin-1-yl)-6-methylpyrimidin-4-yl)-4-iodobenzamide and 2-((1R,6S)-6-(difluoromethyl)-3-azabicyclo[4.1.0]heptan-3-yl)-N-(2-(4,4-difluoropiperidin-1-yl)-6-methylpyrimidin-4-yl)-4-iodobenzamide

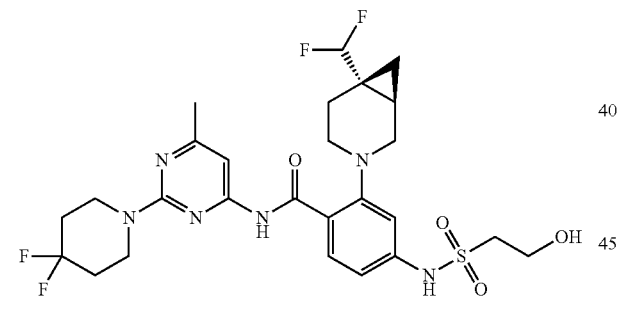

first eluting peak, arbitrarily assigned

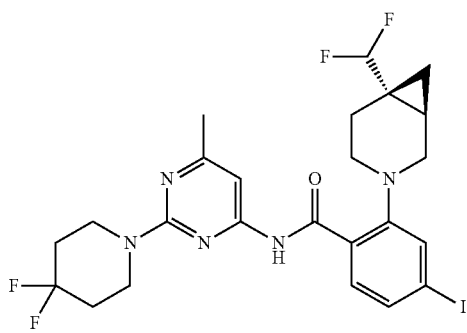

second eluting peak, arbitrarily assigned

To a solution of methyl 2-(6-(difluoromethyl)-3-azabicyclo[4.1.0]heptan-3-yl)-4-iodobenzoate (80 mg, 196 mol) and 2-(4,4-difluoropiperidin-1-yl)-6-methylpyrimidin-4-amine (89.4 mg, 392 μmol) in THF (10 mL) was added LiHMDS (0.59 mL, 0.59 mmol, 1 M in THF) at 0° C. The mixture was stirred at room temperature for 1 h. The reaction mixture was poured into saturated aqueous NH₄Cl (20 mL) and extracted with EtOAc (3×20 mL). The combined organic extracts were washed with brine (2×20 mL), dried over Na₂SO₄, filtered, and concentrated in vacuo. The residue was purified by silica gel column chromatography (PE:EA 1:1) to afford racemic 2-(6-(difluoromethyl)-3-azabicyclo[4.1.0]heptan-3-yl)-N-(2-(4,4-difluoropiperidin-1-yl)-6-methylpyrimidin-4-yl)-4-iodobenzamide. The racemate was separated by chiral SFC (DAICEL CHIRALPAK AD (250 mm×30 mm, 10 μm) CO₂-EtOH (0.1% NH₃H₂O) to afford first eluting peak, arbitrarily assigned 2-((1S,6R)-6-(difluoromethyl)-3-azabicyclo[4.1.0]heptan-3-yl)-N-(2-(4,4-difluoropiperidin-1-yl)-6-methylpyrimidin-4-yl)-4-iodobenzamide (50 mg, 82.8 μmol) and second eluting peak, arbitrarily assigned 2-((1R,6S)-6-(difluoromethyl)-3-azabicyclo[4.1.0]heptan-3-yl)-N-(2-(4,4-difluoropiperidin-1-yl)-6-methylpyrimidin-4-yl)-4-iodobenzamide (50 mg, 82.8 mol). First eluting peak LCMS: MS ESI (M−100)⁺ 604.0. Second eluting peak LCMS: MS ESI (M−100)⁺ 604.0.

Step 3A: Preparation of 2-((1S,6R)-6-(difluoromethyl)-3-azabicyclo[4.1.0]heptan-3-yl)-N-(2-(4,4-difluoropiperidin-1-yl)-6-methylpyrimidin-4-yl)-4-((2-hydroxyethyl)sulfonamido)benzamide

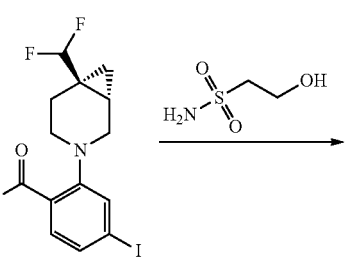

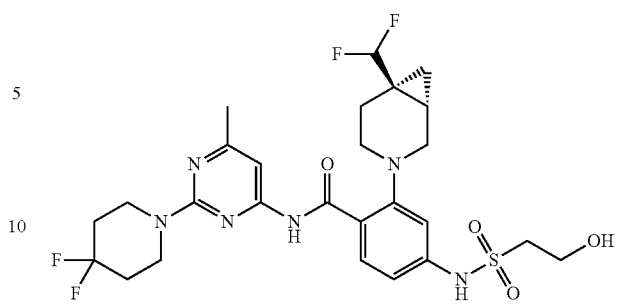

To a solution of 2-hydroxyethane-1-sulfonamide (25.9 mg, 207 μmol) in DMF (2 mL) was added 2-(methylamino)acetic acid (3.68 mg, 41.4 μmol), copper(I) iodide (15.6 mg, 82.8 μmol) and K₃PO₄ (87.8 mg, 414 μmol). The mixture was stirred at 70° C. for 20 min. 2-((1S,6R)-6-(Difluoromethyl)-3-azabicyclo[4.1.0]heptan-3-yl)-N-(2-(4,4-difluoropiperidin-1-yl)-6-methylpyrimidin-4-yl)-4-iodobenzamide (50 mg, 82.8 μmol) was added to the mixture, and the mixture was stirred at 100° C. overnight. The mixture was then poured into water (5 mL) and extracted with EtOAc (3×3 mL). The combined organic extracts were washed with brine (2×2 mL), dried over Na₂SO₄, filtered, and concentrated in vacuo. The residue was purified via prep-HPLC (TFA condition) to afford 2-((1S,6R)-6-(difluoromethyl)-3-azabicyclo[4.1.0]heptan-3-yl)-N-(2-(4,4-difluoropiperidin-1-yl)-6-methylpyrimidin-4-yl)-4-((2-hydroxyethyl)sulfonamido)benzamide (13.6 mg, 22.7 μmol) as a white solid. LCMS: MS ESI (M+1)⁺ 601.4. ¹H NMR (400 MHz, DMSO-d₆) δ=11.59 (s, 1H), 10.22 (s, 1H), 7.91 (d, J=8.6 Hz, 1H), 7.44 (s, 1H), 7.19 (s, 1H), 7.09 (dd, J=1.4, 8.4 Hz, 1H), 5.66 (br t, J=56.6 Hz, 1H), 3.88 (br d, J=5.0 Hz, 4H), 3.76 (t, J=6.4 Hz, 2H), 3.35 (t, J=6.4 Hz, 2H), 3.28 (br d, J=11.0 Hz, 1H), 3.12 (br dd, J=3.4, 11.4 Hz, 1H), 2.99-2.88 (m, 1H), 2.60-2.51 (m, 1H), 2.32 (s, 3H), 2.21-2.06 (m, 2H), 2.02-1.91 (m, 4H), 1.49 (br dd, J=4.2, 8.6 Hz, 1H), 1.37 (br d, J=4.8 Hz, 1H), 0.99 (br dd, J=4.6, 9.2 Hz, 1H).

Step 3B: Preparation of 2-((1R,6S)-6-(difluoromethyl)-3-azabicyclo[4.1.0]heptan-3-yl)-N-(2-(4,4-difluoropiperidin-1-yl)-6-methylpyrimidin-4-yl)-4-((2-hydroxyethyl)sulfonamido)benzamide

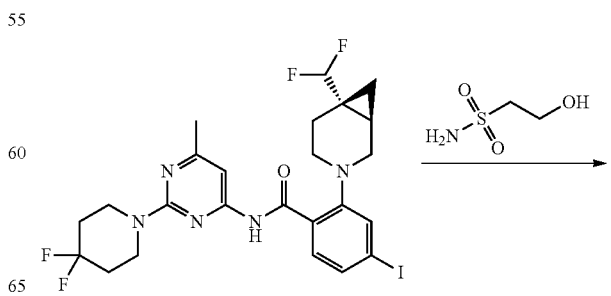

121

-continued

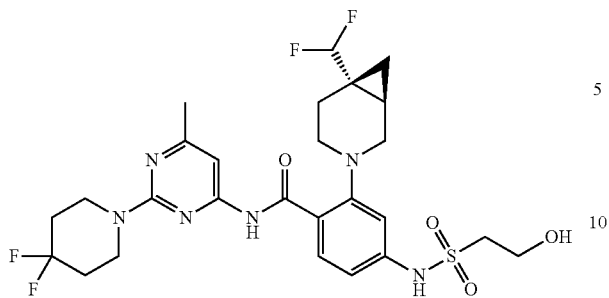

To a solution of 2-hydroxyethane-1-sulfonamide (25.9 mg, 207 μmol) in DMF (2 mL) was added 2-(methylamino)acetic acid (3.68 mg, 41.4 μmol), copper(I) iodide (15.6 mg, 82.8 μmol) and K₃PO₄ (87.8 mg, 414 μmol). The mixture was stirred at 70° C. for 20 min. 2-((1R,6S)-6-(Difluoromethyl)-3-azabicyclo[4.1.0]heptan-3-yl)-N-(2-(4,4-difluoropiperidin-1-yl)-6-methylpyrimidin-4-yl)-4-iodobenzamide (50 mg, 82.8 μmol) was added to the mixture, and the mixture was stirred at 100° C. overnight. The mixture was then poured into water (5 mL) and extracted with EtOAc (3×3 mL). The combined organic extracts were washed with brine (2×2 mL), dried over Na₂SO₄, filtered, and concentrated in vacuo. The residue was purified by prep-HPLC (TFA condition) to afford 2-((1R,6S)-6-(difluoromethyl)-3-azabicyclo[4.1.0]heptan-3-yl)-N-(2-(4,4-difluoropiperidin-1-yl)-6-methylpyrimidin-4-yl)-4-((2-hydroxyethyl)sulfonamido)benzamide (14.8 mg, 24.6 μmol) as a white solid. LCMS: MS ESI (M+1)⁺ 601.2. ¹H NMR (400 MHz, DMSO-d₆) δ=11.60 (s, 1H), 10.22 (s, 1H), 7.91 (br d, J=8.6 Hz, 1H), 7.44 (s, 1H), 7.19 (br s, 1H), 7.09 (br d, J=8.6 Hz, 1H), 5.65 (br s, 1H), 3.89 (br s, 4H), 3.76 (br t, J=6.2 Hz, 2H), 3.35 (br t, J=6.2 Hz, 2H), 3.28 (br d, J=11.2 Hz, 1H), 3.12 (br dd, J=3.2, 10.8 Hz, 1H), 2.94 (br dd, J=1.6, 7.0 Hz, 1H), 2.54 (br d, J=5.4 Hz, 1H), 2.32 (s, 3H), 2.20-2.08 (m, 2H), 1.98 (br s, 4H), 1.49 (br s, 1H), 1.37 (br d, J=4.4 Hz, 1H), 1.04-0.94 (m, 1H).

Example 30: Synthesis of N-(2-(4,4-difluoropiperidin-1-yl)-6-methylpyrimidin-4-yl)-4-((2-hydroxyethyl)sulfonamido)-2-(6-(hydroxymethyl)-3-azabicyclo[4.1.0]heptan-3-yl)benzamide

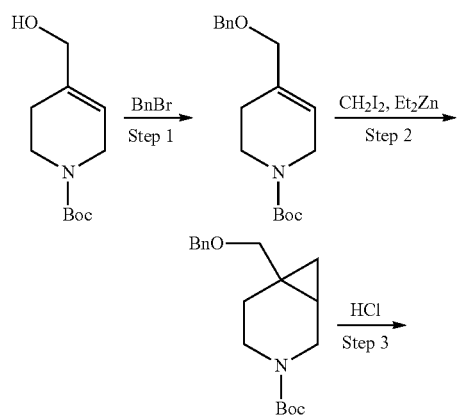

122

-continued

Step 1: Preparation of tert-butyl 4-((benzyloxy)methyl)-3,6-dihydropyridine-1(2H)-carboxylate To a solution of tert-butyl 4-(hydroxymethyl)-3,6-dihydropyridine-1(2H)-carboxylate (1.7 g, 7.97 mmol) in THF (10 mL) was added sodium hydride (349 mg, 8.76 mmol, 60% in mineral oil) at 0° C. The mixture was allowed to warm to room temperature and stirred at room temperature for 0.5 h. Benzyl bromide (1.58 g, 9.24 mmol) and TBAI (294 mg, 797 μmol) were then added, and the mixture was stirred at room temperature overnight. The reaction mixture was poured into saturated aqueous NH₄Cl (50 mL) and extracted with EtOAc (3×35 mL). The combined organic extracts were washed with brine (100 mL), dried over Na₂SO₄, filtered, and concentrated. The residue was purified by silica gel column chromatography (PE:EA gradient) to afford tert-butyl 4-((benzyloxy)methyl)-3,6-dihydropyridine-1(2H)-carboxylate (1.90 g, 6.26 mmol) as a yellow oil. ¹H NMR (400 MHz, CHLOROFORM-d) δ=7.40-7.28 (m, 5H), 5.68 (br s, 1H), 4.49 (s, 2H), 3.94 (s, 4H), 3.52 (t, J=5.6 Hz, 2H), 2.15 (br s, 2H), 1.48 (s, 9H).

Step 2: Preparation of tert-butyl 6-((benzyloxy)methyl)-3-azabicyclo[4.1.0]heptane-3-carboxylate

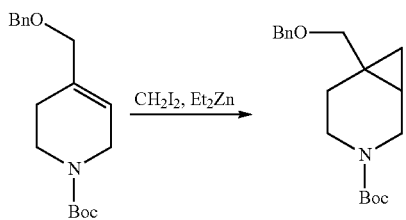

Under N₂ atmosphere, after Et₂Zn (8.3 mL, 8.3 mmol, 1.0 M in hexane) was added to DCM (12 mL) with ice cooling, a solution of TFA (0.6 mL) in DCM (3 mL) was added dropwise, and the mixture was stirred at 0° C. for 40 min. A solution of diiodomethane (2.2 g, 8.2 mmol) in DCM (3 mL) was then added dropwise. The mixture was then stirred at 0° C. for 40 min. A solution of tert-butyl 4-((benzyloxy)methyl)-3,6-dihydropyridine-1(2H)-carboxylate (1.0 g, 3.20 mmol) in DCM (9 mL) was added dropwise. The reaction was allowed to warm to room temperature and stirred overnight. After cooling to 0° C., the mixture was treated with Et₃N to adjust to pH 8. Boc₂O (0.90 g, 4.1 mmol) was then added, and the mixture was stirred at room temperature for 5 h. The mixture was then treated with saturated aqueous NH₄Cl (20 mL) and extracted with chloroform (3×30 mL). The combined organic extracts were washed with brine, dried over Na₂SO₄, and concentrated. The yellow residue was purified by silica gel column chromatography (PE:EA gradient) to afford tert-butyl 6-((benzyloxy)methyl)-3-azabicyclo[4.1.0]heptane-3-carboxylate (800 mg, 2.52 mmol) as a yellow oil.

Step 3: Preparation of 6-((benzyloxy)methyl)-3-azabicyclo[4.1.0]heptane

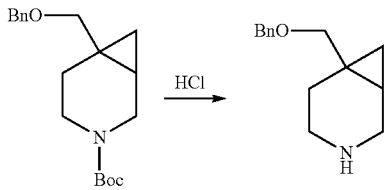

To HCl (10 mL, 40 mmol, 4 M in dioxane) was added tert-butyl 6-((benzyloxy)methyl)-3-azabicyclo[4.1.0]heptane-3-carboxylate (800 mg, 2.52 mmol). The mixture was stirred at room temperature for 1 h. The mixture was then concentrated under vacuum to afford 6-((benzyloxy)methyl)-3-azabicyclo[4.1.0]heptane (520 mg, 2.39 mmol) as a yellow solid. LCMS: MS ESI (M+1)⁺ 218.0.

Step 4: Preparation of methyl 2-(6-((benzyloxy)methyl)-3-azabicyclo[4.1.0]heptan-3-yl)-4-bromobenzoate

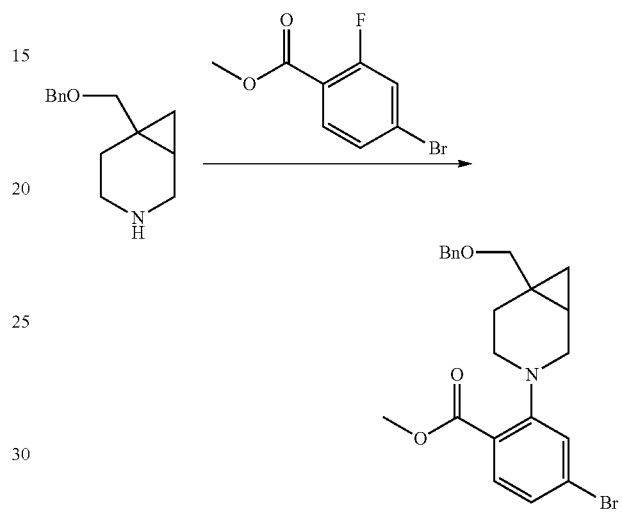

To a solution of 6-((benzyloxy)methyl)-3-azabicyclo[4.1.0]heptane (520 mg, 2.39 mmol) and methyl 4-bromo-2-fluorobenzoate (556 mg, 2.39 mmol) in DMSO (5 mL) was added DIEA (926 mg, 7.17 mmol). The mixture was stirred at 100° C. overnight. The mixture was then poured into saturated aqueous NH₄Cl (30 mL) and extracted with EtOAc (3×35 mL). The combined organic extracts were washed with brine (80 mL), dried over Na₂SO₄, filtered, and concentrated. The residue was purified by silica gel column chromatography (PE:EA gradient) to afford methyl 2-(6-((benzyloxy)methyl)-3-azabicyclo[4.1.0]heptan-3-yl)-4-bromobenzoate (350 mg, 813 mol) as a yellow oil. LCMS: MS ESI (M+1)⁺ 430.1.

Step 5: Preparation of 2-(6-((benzyloxy)methyl)-3-azabicyclo[4.1.0]heptan-3-yl)-4-bromo-N-(2-(4,4-difluoropiperidin-1-yl)-6-methylpyrimidin-4-yl)benzamide

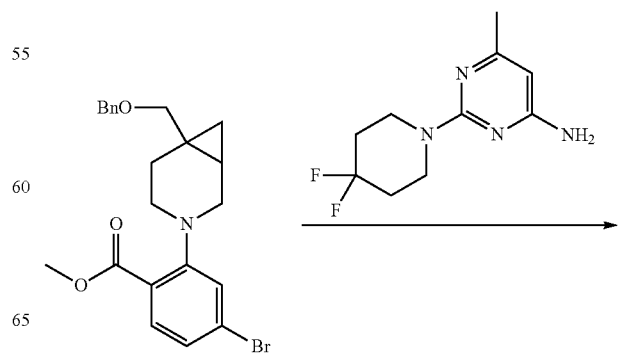

-continued

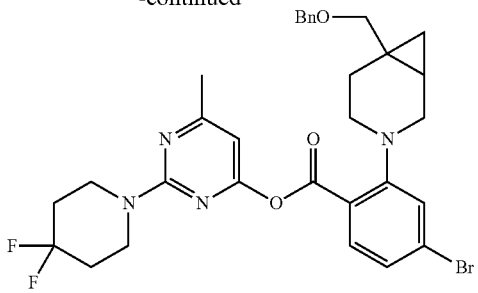

To a solution of methyl 2-(6-((benzyloxy)methyl)-3-azabicyclo[4.1.0]heptan-3-yl)-4-bromobenzoate (200 mg, 464 μmol) and 2-(4,4-difluoropiperidin-1-yl)-6-methylpyrimidin-4-amine (105 mg, 464 μmol) in THF (3 mL) was added LiHMDS (1.4 mL, 1.4 mmol, 1 M in THF) at room temperature. The mixture was stirred at room temperature for 1 h. The mixture was then poured into saturated aqueous NH₄Cl (10 mL) and extracted with EtOAc (3×15 mL). The combined organic extracts were washed with brine (30 mL), dried over Na₂SO₄, filtered, and concentrated. The residue was purified by silica gel column chromatography (PE:EA gradient) to afford 2-(6-((benzyloxy)methyl)-3-azabicyclo[4.1.0]heptan-3-yl)-4-bromo-N-(2-(4,4-difluoropiperidin-1-yl)-6-methylpyrimidin-4-yl)benzamide (130 mg, 207 μmol) as a yellow oil. LCMS: MS ESI (M+1)⁺ 626.2.

Step 6: Preparation of 2-(6-((benzyloxy)methyl)-3-azabicyclo[4.1.0]heptan-3-yl)-N-(2-(4,4-difluoropiperidin-1-yl)-6-methylpyrimidin-4-yl)-4-((2-hydroxyethyl)sulfonamido)benzamide

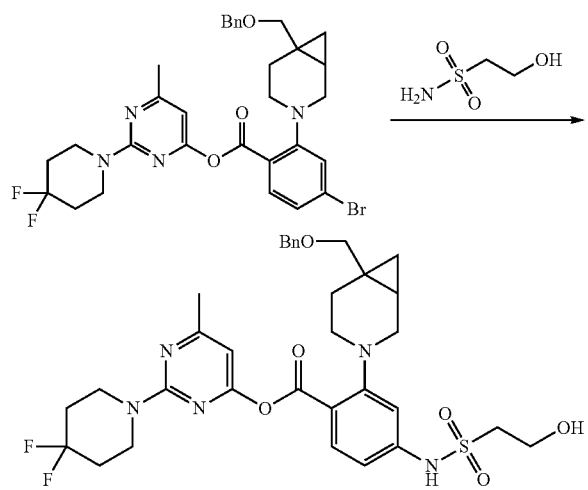

To a solution of 2-hydroxyethane-1-sulfonamide (51.8 mg, 414 μmol), 2-(methylamino)acetic acid (12.8 mg, 144 μmol) and copper(I) iodide (19.6 mg, 103 μmol) in DMF (1 mL) was added K₃PO₄ (218 mg, 1.03 mmol). The mixture was stirred at 60° C. for 10 min. Then, 2-(6-((benzyloxy)methyl)-3-azabicyclo[4.1.0]heptan-3-yl)-4-bromo-N-(2-(4,4-difluoropiperidin-1-yl)-6-methylpyrimidin-4-yl)benzamide (130 mg, 207 μmol) was added, and the mixture was stirred at 100° C. overnight. The mixture was then poured into saturated aqueous NH₄Cl (10 mL) and extracted with EtOAc (3×15 mL). The combined organic extracts were washed with brine (30 mL), dried over Na₂SO₄, filtered, and concentrated. The residue was purified by Prep-HPLC (TFA condition) to afford 2-(6-((benzyloxy)methyl)-3-azabicyclo[4.1.0]heptan-3-yl)-N-(2-(4,4-difluoropiperidin-1-yl)-6-methylpyrimidin-4-yl)-4-((2-hydroxyethyl)sulfonamido)benzamide (100 mg, 149 μmol) as a yellow oil. LCMS: MS ESI (M+1)⁺ 671.3.

Step 7: Preparation of N-(2-(4,4-difluoropiperidin-1-yl)-6-methylpyrimidin-4-yl)-4-((2-hydroxyethyl)sulfonamido)-2-(6-(hydroxymethyl)-3-azabicyclo[4.1.0]heptan-3-yl)benzamide

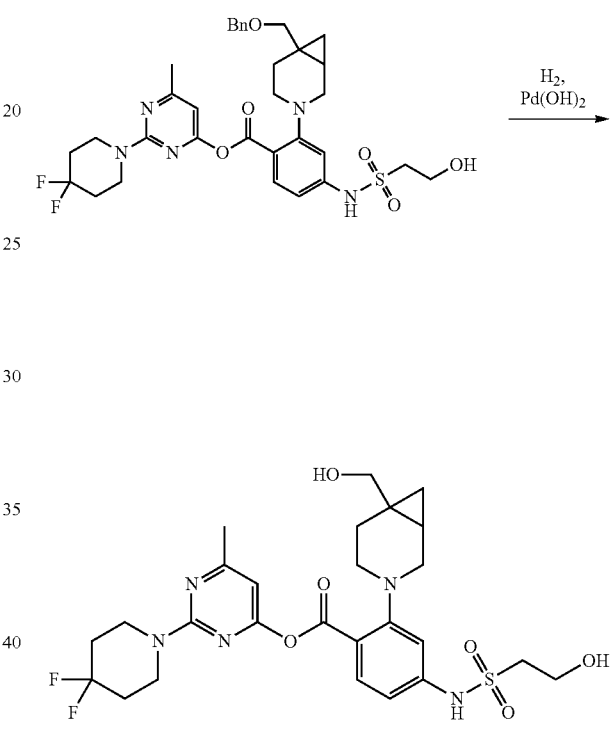

To a solution of 2-(6-((benzyloxy)methyl)-3-azabicyclo[4.1.0]heptan-3-yl)-N-(2-(4,4-difluoropiperidin-1-yl)-6-methylpyrimidin-4-yl)-4-((2-hydroxyethyl)sulfonamido)benzamide (40 mg, 59.6 μmol) in MeOH (5 mL) was added Pearlman's catalyst (10 mg, 20% Pd w/w), and the resulting suspension was stirred at 45° C. overnight under H₂ atmosphere (15 psi). The mixture was then filtered, and the filtrate was concentrated under vacuum. The residue was purified by prep-HPLC (FA condition) to afford N-(2-(4,4-difluoropiperidin-1-yl)-6-methylpyrimidin-4-yl)-4-((2-hydroxyethyl)sulfonamido)-2-(6-(hydroxymethyl)-3-azabicyclo[4.1.0]heptan-3-yl)benzamide (8.39 mg, 14.4 μmol) as a white solid. LCMS: MS ESI (M+1)⁺ 581.2. ¹H NMR (400 MHz, DMSO-d₆) δ=11.77 (br s, 1H), 7.91 (br d, J=8.4 Hz, 1H), 7.43 (s, 1H), 7.25-7.14 (m, 1H), 7.05 (br d, J=8.8 Hz, 1H), 4.59 (br s, 1H), 3.89 (br s, 4H), 3.75 (br t, J=6.4 Hz, 2H), 3.27 (br d, J=4.6 Hz, 2H), 3.23-3.09 (m, 3H), 2.89-2.77 (m, 1H), 2.56 (br dd, J=4.6, 11.6 Hz, 2H), 2.30 (s, 3H), 2.18-2.07 (m, 1H), 1.98 (br s, 5H), 1.21-0.96 (m, 2H), 0.68-0.50 (m, 1H).

Examples 31a and 31b: Synthesis of N-(2-(4,4-difluoropiperidin-1-yl)-6-methylpyrimidin-4-yl)-2-fluoro-4-((2-hydroxyethyl)sulfonamido)-6-((1S,6S)-6-methyl-3-azabicyclo[4.1.0]heptan-3-yl)benzamide (Example 31a) and N-(2-(4,4-difluoropiperidin-1-yl)-6-methylpyrimidin-4-yl)-2-fluoro-4-((2-hydroxyethyl)sulfonamido)-6-((1R,6R)-6-methyl-3-azabicyclo[4.1.0]heptan-3-yl)benzamide (Example 31b)
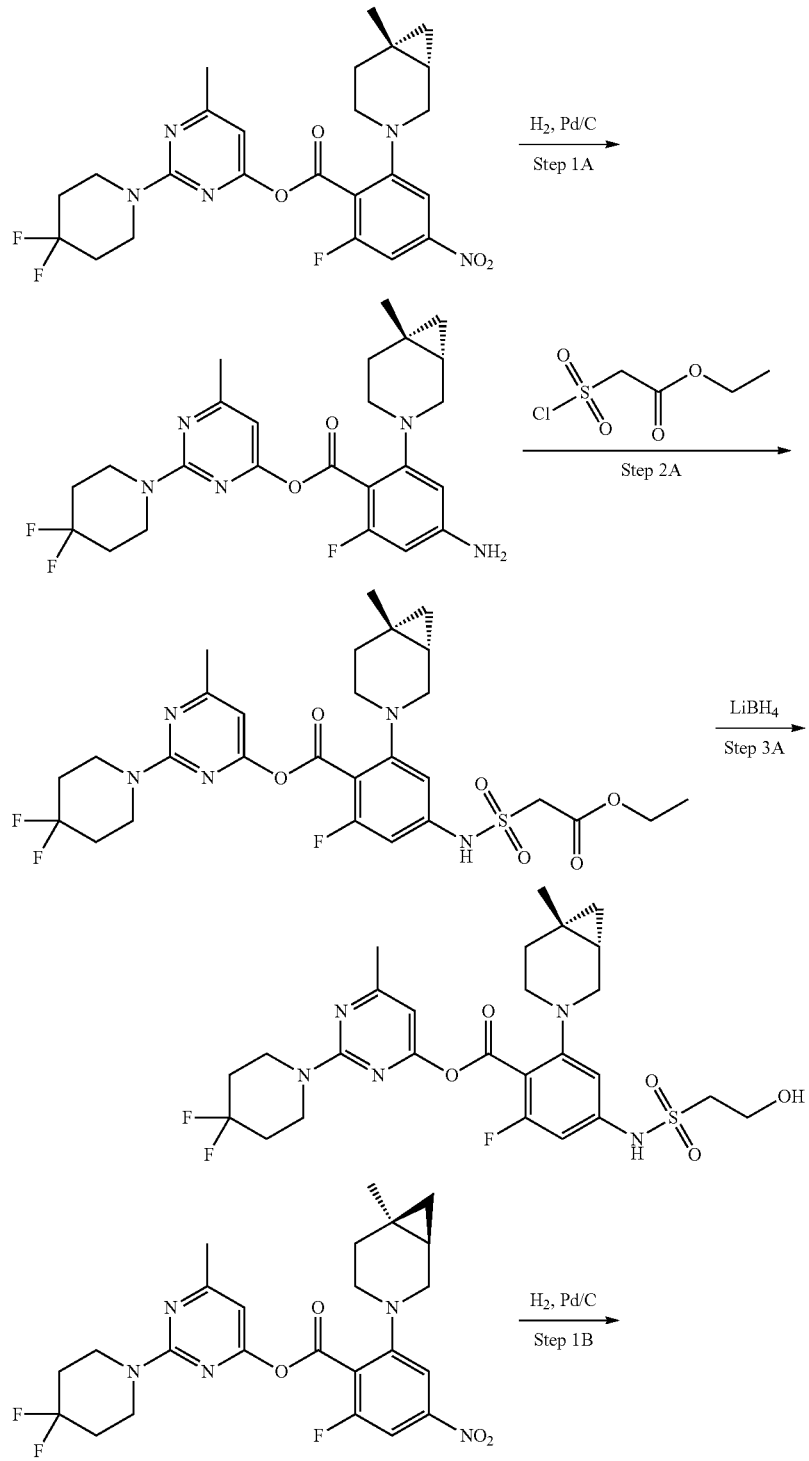

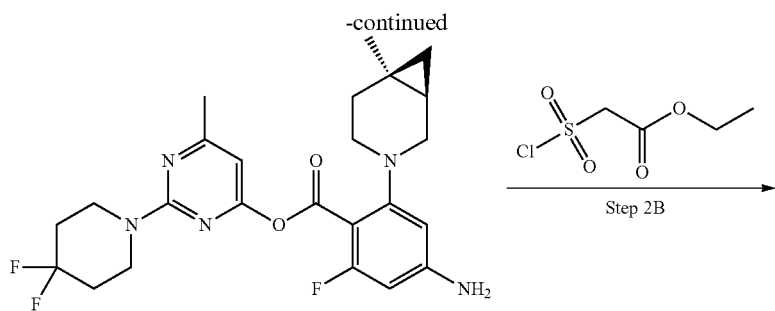

Step 2B

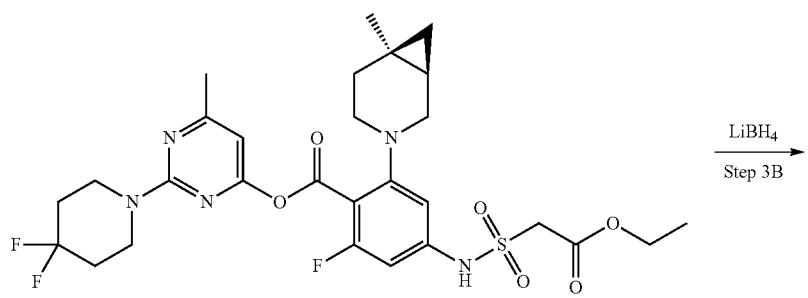

LiBH₄
Step 3B

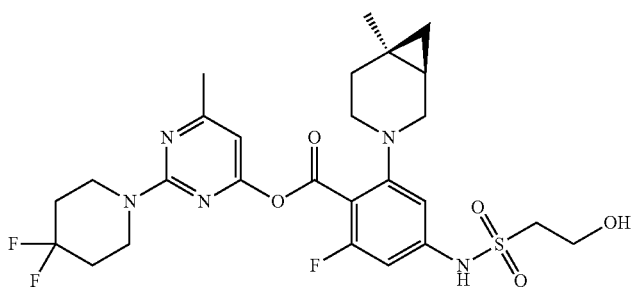

Step 1A: Preparation of 4-amino-N-(2-(4,4-difluoropiperidin-1-yl)-6-methylpyrimidin-4-yl)-2-fluoro-6-((1S,6S)-6-methyl-3-azabicyclo[4.1.0]heptan-3-yl)benzamide

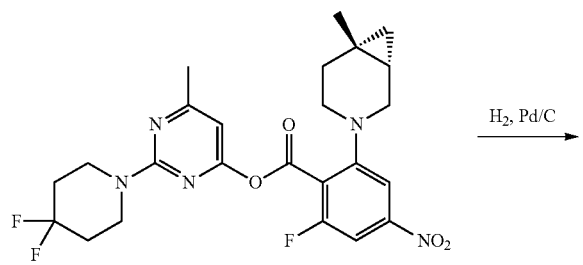

H₂, Pd/C

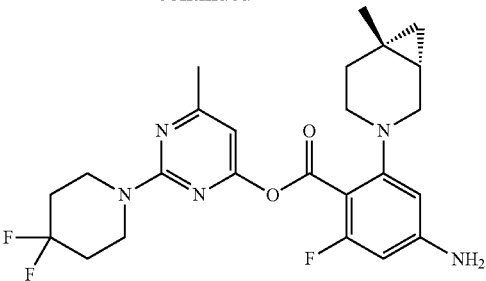

To a solution of N-(2-(4,4-difluoropiperidin-1-yl)-6-methylpyrimidin-4-yl)-2-fluoro-6-((1S,6S)-6-methyl-3-azabicyclo[4.1.0]heptan-3-yl)-4-nitrobenzamide (120 mg, 0.24 mmol) in MeOH (4 mL) was added Pd/C (50 mg, 10% w/w). The mixture was stirred at room temperature for 1 h under an atmosphere of H₂ (15 psi). The mixture was then filtered, and the filtrate was concentrated in vacuo to afford 4-amino-N-(2-(4,4-difluoropiperidin-1-yl)-6-methylpyrimidin-4-yl)-2-fluoro-6-((1S,6S)-6-methyl-3-azabicyclo[4.1.0]heptan-3-yl)benzamide (100 mg, 0.211 mmol) as a colorless solid. LCMS: MS ESI (M+1)⁺ 475.3.

Step 2A: Preparation of ethyl 2-(N-(4-((2-(4,4-difluoropiperidin-1-yl)-6-methylpyrimidin-4-yl)carbamoyl)-3-fluoro-5-((1S,6S)-6-methyl-3-azabicyclo[4.1.0]heptan-3-yl)phenyl)sulfamoyl)acetate

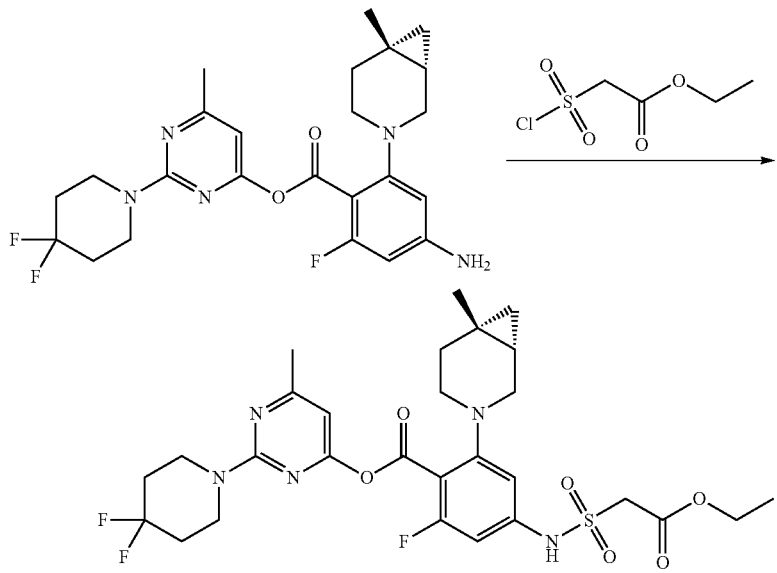

To a solution of 4-amino-N-(2-(4,4-difluoropiperidin-1-yl)-6-methylpyrimidin-4-yl)-2-fluoro-6-((1S,6S)-6-methyl-3-azabicyclo[4.1.0]heptan-3-yl)benzamide (100 mg, 0.21 mmol) in DCM (2 mL) was added ethyl 2-(chlorosulfonyl)acetate (43.2 mg, 0.23 mmol) and pyridine (50.0 mg, 0.63 mmol). The mixture was stirred at room temperature overnight. The mixture was then concentrated in vacuo and purified by silica gel column chromatography (PE:EA gradient) to afford ethyl 2-(N-(4-((2-(4,4-difluoropiperidin-1-yl)-6-methylpyrimidin-4-yl)carbamoyl)-3-fluoro-5-((1S,6S)-6-methyl-3-azabicyclo[4.1.0]heptan-3-yl)phenyl)sulfamoyl)acetate (90.0 mg, 0.14 mmol) as a white solid. LCMS: MS ESI (M+1)$^+$ 625.3.

Step 3A: Preparation of N-(2-(4,4-difluoropiperidin-1-yl)-6-methylpyrimidin-4-yl)-2-fluoro-4-((2-hydroxyethyl)sulfonamido)-6-((1S,6S)-6-methyl-3-azabicyclo[4.1.0]heptan-3-yl)benzamide

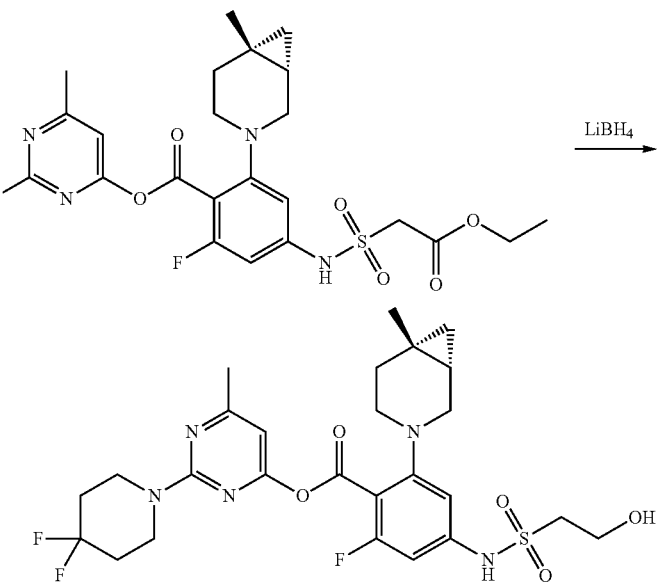

To a solution of ethyl 2-(N-(4-((2-(4,4-difluoropiperidin-1-yl)-6-methylpyrimidin-4-yl)carbamoyl)-3-fluoro-5-((1S,6S)-6-methyl-3-azabicyclo[4.1.0]heptan-3-yl)phenyl)sulfamoyl)acetate (70 mg, 0.11 mmol) in THF (1 mL) was added LiBH$_4$ (0.17 mL, 0.34 mmol, 2 M in THF). The mixture was stirred at room temperature for 0.5 h. The mixture was then treated with H$_2$O (0.1 mL) and concentrated in vacuo. The residue was purified by prep-HPLC (FA condition) to afford N-(2-(4,4-difluoropiperidin-1-yl)-6-methylpyrimidin-4-yl)-2-fluoro-4-((2-hydroxyethyl)sulfonamido)-6-((1S,6S)-6-methyl-3-azabicyclo[4.1.0]heptan-3-yl)benzamide (32.5 mg, 0.060 mmol) as a white solid. LCMS: MS ESI (M+1)$^+$ 583.4. $^1$H NMR (400 MHz, DMSO-d$_6$) δ=10.59 (br s, 1H), 8.25 (s, 1H), 7.33 (br s, 1H), 6.60 (s, 1H), 6.56 (br d, J=11.8 Hz, 1H), 3.87 (br s, 4H), 3.74 (t, J=6.6 Hz, 2H), 3.27 (br t, J=6.6 Hz, 2H), 3.22-3.12 (m, 2H), 2.87-2.69 (m, 2H), 2.30 (br s, 3H), 1.96 (br s, 4H), 1.75-1.59 (m, 2H), 1.01 (s, 3H), 0.90 (br d, J=2.6 Hz, 1H), 0.57 (br s, 1H), 0.31 (br dd, J=3.8, 8.4 Hz, 1H).

Step 1B: Preparation of 4-amino-N-(2-(4,4-difluoropiperidin-1-yl)-6-methylpyrimidin-4-yl)-2-fluoro-6-((1R,6R)-6-methyl-3-azabicyclo[4.1.0]heptan-3-yl)benzamide

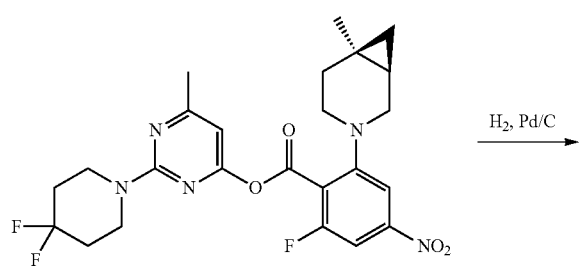

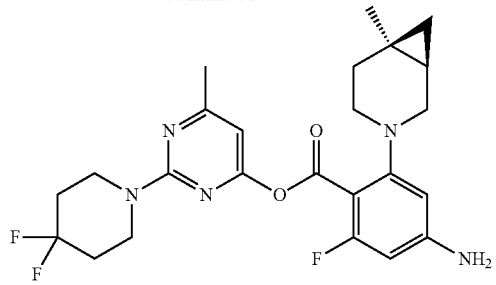

To a solution of N-(2-(4,4-difluoropiperidin-1-yl)-6-methylpyrimidin-4-yl)-2-fluoro-6-((1R,6R)-6-methyl-3-azabicyclo[4.1.0]heptan-3-yl)-4-nitrobenzamide (110 mg, 0.22 mmol) in MeOH (3 mL) was added Pd/C (46.3 mg, 10% w/w). The mixture was stirred at room temperature for 1 h under an atmosphere of H$_2$ (15 psi). The mixture was then filtered, and the filtrate was concentrated in vacuo to give 4-amino-N-(2-(4,4-difluoropiperidin-1-yl)-6-methylpyrimidin-4-yl)-2-fluoro-6-((1R,6R)-6-methyl-3-azabicyclo[4.1.0]heptan-3-yl)benzamide (100 mg, 0.22 mmol) as a colorless solid. LCMS: MS ESI (M+1)$^+$ 475.2.

Step 2B: Preparation of ethyl 2-(N-(4-((2-(4,4-difluoropiperidin-1-yl)-6-methylpyrimidin-4-yl)carbamoyl)-3-fluoro-5-((1R,6R)-6-methyl-3-azabicyclo[4.1.0]heptan-3-yl)phenyl)sulfamoyl)acetate

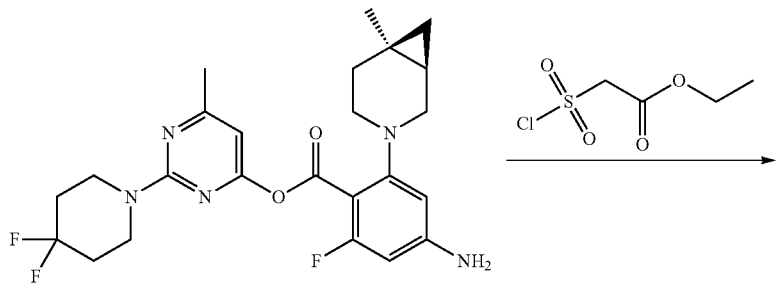

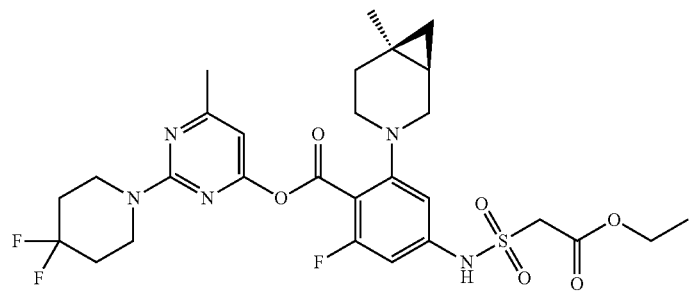

To a solution of 4-amino-N-(2-(4,4-difluoropiperidin-1-yl)-6-methylpyrimidin-4-yl)-2-fluoro-6-((1R,6R)-6-methyl-3-azabicyclo[4.1.0]heptan-3-yl)benzamide (100 mg, 0.22 mmol) in DCM (2 mL) was added ethyl 2-(chlorosulfonyl)acetate (43.2 mg, 0.23 mmol) and pyridine (50.0 mg, 0.63 mmol). The mixture was stirred at room temperature overnight. The mixture was then concentrated in vacuo and purified by silica gel column chromatography (PE:EA gradient) to afford ethyl 2-(N-(4-((2-(4,4-difluoropiperidin-1-yl)-6-methylpyrimidin-4-yl)carbamoyl)-3-fluoro-5-((1R,6R)-6-methyl-3-azabicyclo[4.1.0]heptan-3-yl)phenyl)sulfamoyl)acetate (80.0 mg, 0.13 mmol) as a white solid. LCMS: MS ESI (M+1)$^+$ 625.4.

Step 3B: Preparation of N-(2-(4,4-difluoropiperidin-1-yl)-6-methylpyrimidin-4-yl)-2-fluoro-4-((2-hydroxyethyl)sulfonamido)-6-((1R,6R)-6-methyl-3-azabicyclo[4.1.0]heptan-3-yl)benzamide

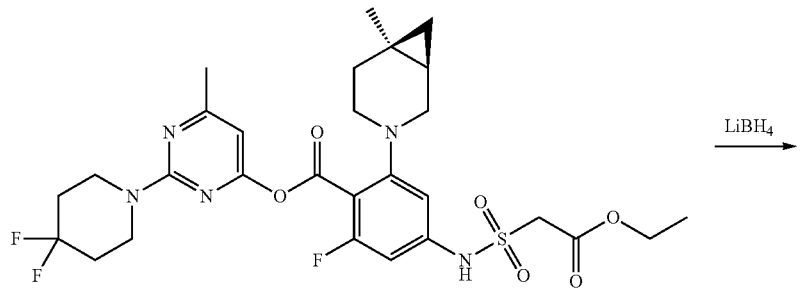

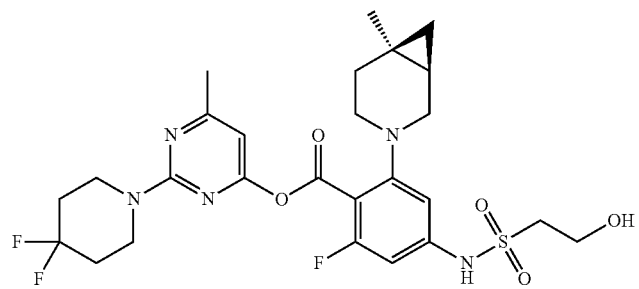

To a solution of ethyl 2-(N-(4-((2-(4,4-difluoropiperidin-1-yl)-6-methylpyrimidin-4-yl)carbamoyl)-3-fluoro-5-((1R,6R)-6-methyl-3-azabicyclo[4.1.0]heptan-3-yl)phenyl)sulfamoyl)acetate (80 mg, 0.13 mmol) in THF (1 mL) was added LiBH$_4$ (0.19 mL, 0.38 mmol, 2 M in THF). The mixture was stirred at room temperature for 0.5 h. The mixture was then treated with H$_2$O (0.1 mL) and concentrated in vacuo. The residue was purified by prep-HPLC (FA condition) to give N-(2-(4,4-difluoropiperidin-1-yl)-6-methylpyrimidin-4-yl)-2-fluoro-4-((2-hydroxyethyl)sulfonamido)-6-((1R,6R)-6-methyl-3-azabicyclo[4.1.0]heptan-3-yl)benzamide (14.5 mg, 0.030 mmol) as a white solid. LCMS: MS ESI (M+1)$^+$ 583.4. $^1$H NMR (400 MHz, DMSO-d$_6$) δ=10.59 (br s, 1H), 7.32 (br s, 1H), 6.61 (s, 11H), 6.56 (br d, J=11.4 Hz, 11H), 3.87 (br s, 41H), 3.75 (t, J=6.6 Hz, 21H), 3.30-3.27 (m, 21H), 3.23-3.11 (m, 21H), 2.88-2.70 (m, 21H), 2.30 (br s, 31H), 1.96 (br s, 41H), 1.74-1.57 (m, 21H), 1.01 (s, 31H), 0.89 (br s, 11H), 0.57 (br s, 11H), 0.31 (br dd, J=3.8, 8.2 Hz, 11H).

Examples 32-47

The following compounds were made using similar procedures to examples 28 to 31 above:

| Example Number | Structure | NMR |
|---|---|---|
| 32 | 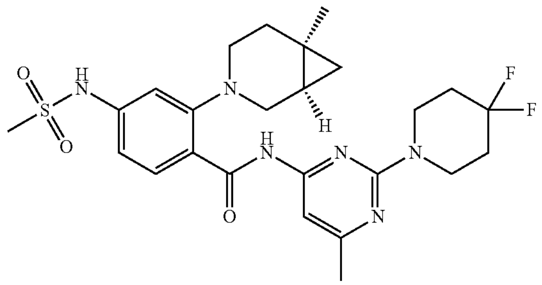 [SMILES: Cc1cc(NC(=O)c2ccc(NS(C)(=O)=O)cc2N2CC[C@@]3(C)C[C@H]3C2)nc(N2CCC(F)(F)CC2)n1] | $^1$H NMR (400 MHz, DMSO-d$_6$) δ = 11.66 (s, 1H), 10.24 (s, 1H), 7.91 (d, J = 8.6 Hz, 1H), 7.43 (s, 1H), 7.16 (d, J = 1.8 Hz, 1H), 7.06 (dd, J = 1.8, 8.6 Hz, 1H), 3.90 (br d, J = 4.3 Hz, 4H), 3.30-3.20 (m, 1H), 3.11 (s, 3H), 3.07 (br s, 1H), 2.78-2.64 (m, 2H), 2.31 (s, 3H), 2.18-2.08 (m, 1H), 2.05-1.93 (m, 4H), 1.92-1.73 (m, 1H), 1.12 (s, 3H), 1.05-0.98 (m, 1H), 0.96 (br t, J = 4.3 Hz, 1H), 0.47 (dd, J = 4.1, 8.6 Hz, 1H) |
| 33 | 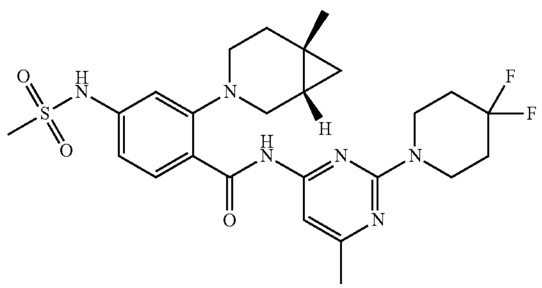 [SMILES: Cc1cc(NC(=O)c2ccc(NS(C)(=O)=O)cc2N2CC[C@]3(C)C[C@@H]3C2)nc(N2CCC(F)(F)CC2)n1] | $^1$H NMR (400 MHz, DMSO-d$_6$) δ = 11.69 (s, 1H), 10.24 (s, 1H), 7.90 (d, J = 8.6 Hz, 1H), 7.44 (s, 1H), 7.15 (d, J = 1.8 Hz, 1H), 7.06 (dd, J = 2.0, 8.6 Hz, 1H), 3.91 (br t, J = 5.2 Hz, 4H), 3.24 (dd, J = 5.1, 11.4 Hz, 1H), 3.10 (s, 3H), 3.07 (s, 1H), 2.80-2.64 (m, 2H), 2.32 (s, 3H), 2.18-2.08 (m, 1H), 2.05-1.93 (m, 4H), 1.83-1.75 (m, 1H), 1.11 (s, 3H), 1.05-0.99 (m, 1H), 0.95 (br t, J = 4.5 Hz, 1H), 0.47 (dd, J = 4.3, 8.3 Hz, 1H) |
| 34 | 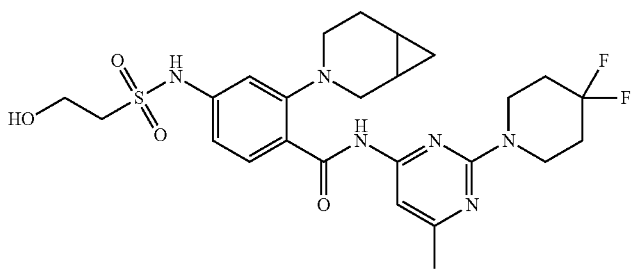 [SMILES: Cc1cc(NC(=O)c2ccc(NS(=O)(=O)CCO)cc2N2CCC3CC3C2)nc(N2CCC(F)(F)CC2)n1] | $^1$H NMR (400 MHz, DMSO-d$_6$) δ = 11.98 (s, 1H), 7.92 (d, J = 8.6 Hz, 1H), 7.43 (s, 1H), 7.16 (d, J = 1.6 Hz, 1H), 7.07 (dd, J = 1.8, 8.6 Hz, 1H), 3.90 (br t, J = 5.2 Hz, 4H), 3.75 (t, J = 6.4 Hz, 2H), 3.29-3.19 (m, 2H), 3.10 (br d, J = 11.4 Hz, 1H), 2.76-2.63 (m, 2H), 2.31 (s, 3H), 2.20-1.95 (m, 6H), 1.27-1.01 (m, 3H), 0.83-0.63 (m, 2H) |
| 35 | 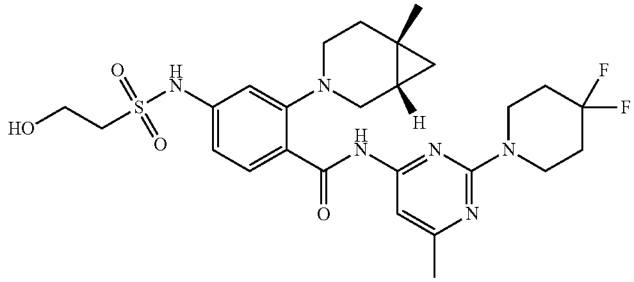 [SMILES: Cc1cc(NC(=O)c2ccc(NS(=O)(=O)CCO)cc2N2CC[C@]3(C)C[C@@H]3C2)nc(N2CCC(F)(F)CC2)n1] | $^1$H NMR (400 MHz, DMSO-d$_6$) δ = 7.85 (d, J = 8.6 Hz, 1H), 7.41 (s, 1H), 7.09 (d, J = 1.9 Hz, 1H), 6.99 (dd, J = 2.0, 8.6 Hz, 1H), 3.89 (br t, J = 5.3 Hz, 4H), 3.73 (t, J = 6.5 Hz, 2H), 3.25 (t, J = 6.5 Hz, 2H), 3.23-3.19 (m, 1H), 3.05 (br d, J = 11.1 Hz, 1H), 2.76-2.59 (m, 2H), 2.29 (s, 3H), 2.19-2.09 (m, 1H), 1.97-1.96 (m, 1H), 1.96-1.96 (m, 1H), 2.03-1.90 (m, 2H), 1.83-1.75 (m, 1H), 1.24-1.19 (m, 1H), 1.10 (s, 3H), 1.03-0.93 (m, 2H), 0.45 (dd, J = 3.9, 8.4 Hz, 1H) |
| 36 | 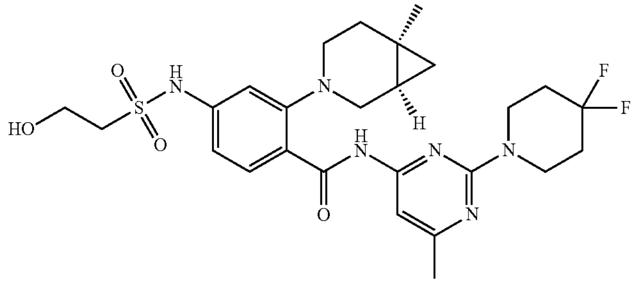 [SMILES: Cc1cc(NC(=O)c2ccc(NS(=O)(=O)CCO)cc2N2CC[C@@]3(C)C[C@H]3C2)nc(N2CCC(F)(F)CC2)n1] | $^1$H NMR (400 MHz, DMSO-d$_6$) δ = 11.75 (s, 1H), 7.81 (d, J = 8.6 Hz, 1H), 7.39 (s, 1H), 7.08 (d, J = 1.8 Hz, 1H), 6.96 (dd, J = 1.8, 8.6 Hz, 1H), 3.86 (br t, J = 5.1 Hz, 4H), 3.70 (t, J = 6.5 Hz, 2H), 3.21 (br t, J = 6.4 Hz, 2H), 3.18-3.13 (m, 1H), 3.04-2.95 (m, 1H), 2.70-2.61 (m, 2H), 2.26 (s, 3H), 2.11 (ddd, J = 5.4, 9.0, 14.2 Hz, 1H), 2.00-1.87 (m, 4H), 1.75 (td, J = 4.3, 13.6 Hz, |

| Example Number | Structure | NMR |
|---|---|---|
| | | 1H), 1.19 (s, 1H), 1.08 (s, 3H), 1.02-0.91 (m, 2H), 0.42 (br dd, J = 3.6, 8.1 Hz, 1H) |
| 37 | 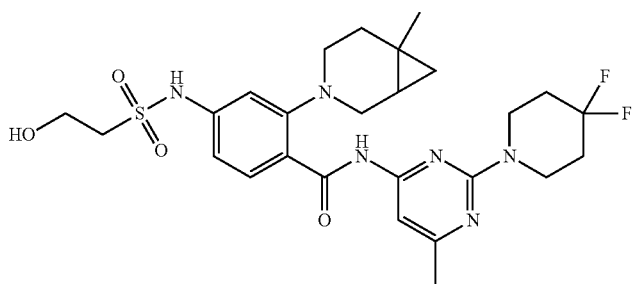 [SMILES: Cc1cc(NC(=O)c2ccc(NS(=O)(=O)CCO)cc2N2CCC3(C)CC3C2)nc(N2CCC(F)(F)CC2)n1] | $^1$H NMR (400 MHz, DMSO-$d_6$) δ = 11.65 (br s, 1H), 10.19 (br s, 1H), 8.13 (br s, 1H), 7.89 (br d, J = 7.8 Hz, 1H), 7.42 (br s, 1H), 7.17 (br s, 1H), 7.05 (br d, J = 8.2 Hz, 1H), 5.33-4.55 (m, 1H), 3.90 (br s, 4H), 3.75 (br s, 2H), 3.26-3.04 (m, 4H), 2.80-2.67 (m, 2H), 2.31 (br s, 3H), 2.20-1.93 (m, 5H), 1.86-1.73 (m, 1H), 1.12 (br s, 3H), 1.06-0.91 (m, 2H), 0.47 (br s, 1H) |
| 38* | 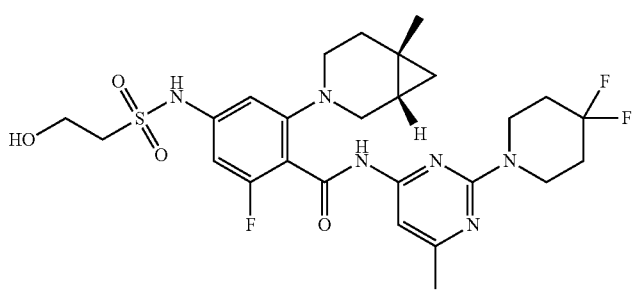 [SMILES: Cc1cc(NC(=O)c2c(F)cc(NS(=O)(=O)CCO)cc2N2CC[C@]3(C)C[C@@H]3C2)nc(N2CCC(F)(F)CC2)n1] | $^1$H NMR (400 MHz, DMSO-$d_6$) δ = 10.59 (br s, 1H), 8.25 (s, 1H), 7.33 (br s, 1H), 6.60 (s, 1H), 6.56 (br d, J = 11.8 Hz, 1H), 3.87 (br s, 4H), 3.74 (t, J = 6.6 Hz, 2H), 3.27 (br t, J = 6.6 Hz, 2H), 3.22-3.12 (m, 2H), 2.87-2.69 (m, 2H), 2.30 (br s, 3H), 1.96 (br s, 4H), 1.75-1.59 (m, 2H), 1.01 (s, 3H), 0.90 (br d, J = 2.6 Hz, 1H), 0.57 (br s, 1H), 0.31 (br dd, J = 3.8, 8.4 Hz, 1H) |
| 39 | 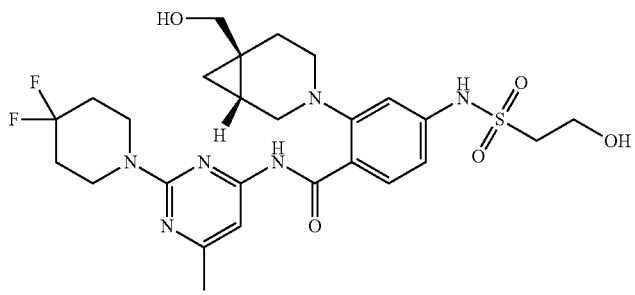 [SMILES: Cc1cc(NC(=O)c2ccc(NS(=O)(=O)CCO)cc2N2CC[C@@]3(CO)C[C@H]3C2)nc(N2CCC(F)(F)CC2)n1] | $^1$H NMR (400 MHz, DMSO-$d_6$) δ = 11.76 (s, 1H), 7.92 (d, J = 8.6 Hz, 1H), 7.43 (s, 1H), 7.20 (d, J = 1.1 Hz, 1H), 7.07 (dd, J = 1.6, 8.6 Hz, 1H), 4.60 (br t, J = 5.3 Hz, 1H), 3.90 (br t, J = 5.1 Hz, 4H), 3.75 (t, J = 6.4 Hz, 2H), 3.35 (br s, 1H), 3.27 (br s, 4H), 2.84 (br d, J = 8.9 Hz, 1H), 2.58 (br d, J = 4.5 Hz, 2H), 2.31 (s, 3H), 2.16-2.08 (m, 1H), 2.05-1.91 (m, 5H), 1.14-1.02 (m, 2H), 0.60 (dd, J = 3.9, 8.8 Hz, 1H) |
| 40 | 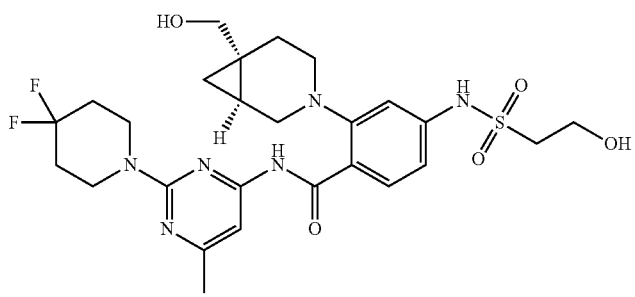 [SMILES: Cc1cc(NC(=O)c2ccc(NS(=O)(=O)CCO)cc2N2CC[C@]3(CO)C[C@@H]3C2)nc(N2CCC(F)(F)CC2)n1] | $^1$H NMR (400 MHz, DMSO-$d_6$) δ = 11.76 (s, 1H), 7.92 (d, J = 8.6 Hz, 1H), 7.43 (s, 1H), 7.19 (s, 1H), 7.10-7.00 (m, 1H), 4.60 (br t, J = 5.2 Hz, 1H), 3.89 (br s, 4H), 3.75 (t, J = 6.5 Hz, 2H), 3.28 (br s, 1H), 3.26-3.06 (m, 4H), 2.89-2.77 (m, 1H), 2.64-2.52 (m, 2H), 2.30 (s, 3H), 2.17-2.07 (m, 1H), 2.04-1.90 (m, 5H), 1.18-0.99 (m, 2H), 0.59 (br dd, J = 3.9, 8.8 Hz, 1H) |

| Example Number | Structure | NMR |
|---|---|---|
| 41* | 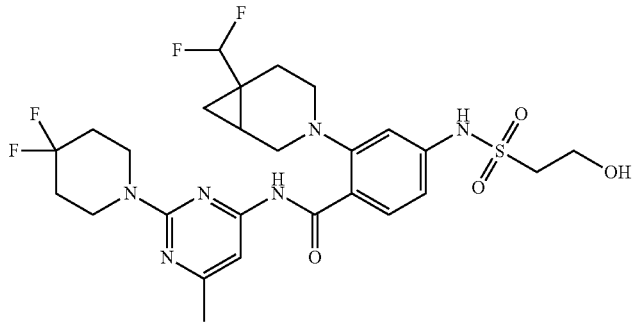 [SMILES: Cc1cc(NC(=O)c2ccc(NS(=O)(=O)CCO)cc2N2CCC3(C(F)F)CC3C2)nc(N2CCC(F)(F)CC2)n1] | ¹H NMR (400 MHz, DMSO-d₆) δ = 11.59 (s, 1H), 10.22 (s, 1H), 7.91 (d, J = 8.6 Hz, 1H), 7.44 (s, 1H), 7.19 (s, 1H), 7.09 (dd, J = 1.4, 8.4 Hz, 1H), 5.66 (br t, J = 56.6 Hz, 1H), 3.88 (br d, J = 5.0 Hz, 4H), 3.76 (t, J = 6.4 Hz, 2H), 3.35 (t, J = 6.4 Hz, 2H), 3.28 (br d, J = 11.0 Hz, 1H), 3.12 (br dd, J = 3.4, 11.4 Hz, 1H), 2.99-2.88 (m, 1H), 2.60-2.51 (m, 1H), 2.32 (s, 3H), 2.21-2.06 (m, 2H), 2.02-1.91 (m, 4H), 1.49 (br dd, J = 4.2, 8.6 Hz, 1H), 1.37 (br d, J = 4.8 Hz, 1H), 0.99 (br dd, J = 4.6, 9.2 Hz, 1H) |
| 42 | 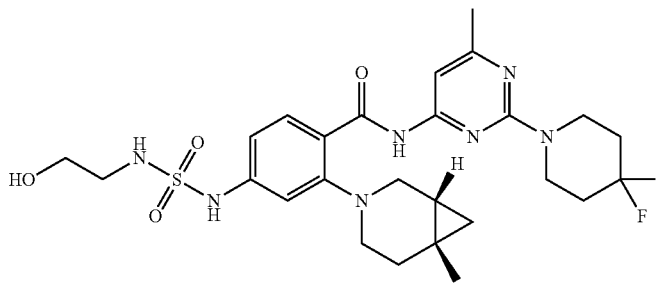 | ¹H NMR (400 MHz, DMSO-d₆) δ = 11.98-11.83 (m, 1H), 10.19 (s, 1H), 7.89 (d, J = 8.6 Hz, 1H), 7.80 (br t, J = 5.7 Hz, 1H), 7.45 (br s, 1H), 7.13 (s, 1H), 7.00 (br d, J = 8.4 Hz, 1H), 3.91 (br s, 4H), 3.36 (t, J = 6.5 Hz, 2H), 3.30-3.19 (m, 1H), 3.06 (br d, J = 11.7 Hz, 1H), 2.87 (q, J = 5.8 Hz, 2H), 2.75-2.66 (m, 2H), 2.32 (s, 3H), 2.21-2.11 (m, 1H), 2.07-1.94 (m, 4H), 1.86-1.75 (m, 1H), 1.13 (s, 3H), 1.09-0.94 (m, 2H), 0.51-0.44 (m, 1H) |
| 43 | 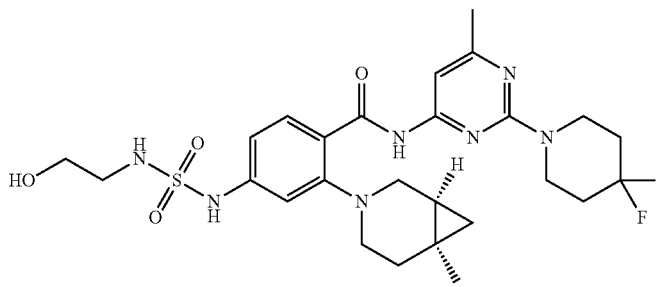 | ¹H NMR (400 MHz, DMSO-d₆) δ = 12.00-11.84 (m, 1H), 10.28-10.12 (m, 1H), 7.92-7.86 (m, 1H), 7.85-7.75 (m, 1H), 7.50-7.43 (m, 1H), 7.13 (d, J = 1.6 Hz, 1H), 7.00 (br d, J = 8.8 Hz, 1H), 3.91 (br s, 4H), 3.36 (t, J = 6.5 Hz, 2H), 3.30-3.20 (m, 1H), 3.06 (br d, J = 11.1 Hz, 1H), 2.87 (q, J = 6.3 Hz, 2H), 2.74-2.66 (m, 2H), 2.31 (s, 3H), 2.21-2.12 (m, 1H), 2.04-1.94 (m, 4H), 1.84-1.75 (m, 1H), 1.12 (s, 3H), 1.04-0.95 (m, 2H), 0.54-0.41 (m, 1H) |
| 44 | 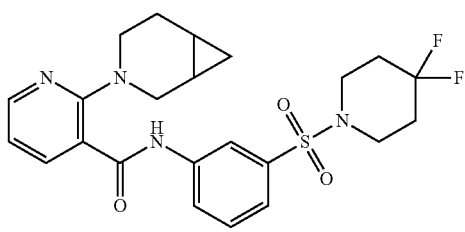 [SMILES: O=C(Nc1cccc(S(=O)(=O)N2CCC(F)(F)CC2)c1)c1cccnc1N1CCC2CC2C1] | ¹H NMR (400 MHz, DMSO-d₆) δ 10.69 (s, 1H), 8.29-8.21 (m, 2H), 8.02 (d, J = 8.1 Hz, 1H), 7.75 (dd, J = 7.3, 2.0 Hz, 1H), 7.65 (t, J = 7.9 Hz, 1H), 7.49 (d, J = 7.8 Hz, 1H), 6.87 (dd, J = 7.5, 4.8 Hz, 1H), 3.67 (d, J = 13.2 Hz, 1H), 3.46 (dd, J = 12.8, 4.8 Hz, 1H), 3.28-3.20 (m, 1H), 3.11 (t, J = 5.5 Hz, 4H), 3.01-2.89 (m, 1H), 2.15-2.00 (m, 4H), 1.94-1.82 (m, 1H), 1.68-1.57 (m, 1H), 1.12-0.90 (m, 2H), 0.51 (td, J = 8.6, 4.2 Hz, 1H), 0.33 (q, J = 4.9 Hz, 1H) |

| Example Number | Structure | NMR |
|---|---|---|
| 45 | 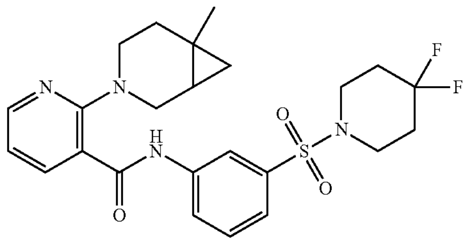 [SMILES: CC12CCN(c3ncccc3C(=O)Nc3cccc(S(=O)(=O)N4CCC(F)(F)CC4)c3)CC1C2] | $^1$H NMR (400 MHz, DMSO-$d_6$) δ 10.69 (s, 1H), 8.28-8.19 (m, 2H), 8.01 (d, J = 8.3 Hz, 1H), 7.75 (dd, J = 7.3, 1.7 Hz, 1H), 7.65 (t, J = 8.1 Hz, 1H), 7.49 (d, J = 7.6 Hz, 1H), 6.85 (dd, J = 7.3, 4.9 Hz, 1H), 3.61-3.46 (m, 2H), 3.20-3.05 (m, 6H), 2.16-1.98 (m, 4H), 1.79-1.60 (m, 2H), 1.01 (s, 3H), 0.93-0.82 (m, 1H), 0.48 (t, J = 4.5 Hz, 1H), 0.32 (dd, J = 8.4, 4.0 Hz, 1H) |
| 46 | 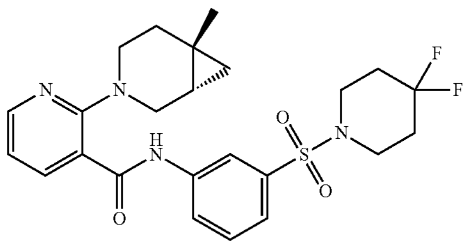 [SMILES: C[C@]12CCN(c3ncccc3C(=O)Nc3cccc(S(=O)(=O)N4CCC(F)(F)CC4)c3)C[C@H]1C2] | $^1$H NMR (400 MHz, DMSO-$d_6$) δ 10.68 (s, 1H), 8.28-8.19 (m, 2H), 8.06-7.95 (m, 1H), 7.75 (dd, J = 7.3, 2.0 Hz, 1H), 7.65 (t, J = 7.9 Hz, 1H), 7.53-7.44 (m, 1H), 6.85 (dd, J = 7.3, 4.9 Hz, 1H), 3.63-3.45 (m, 2H), 3.12 (q, J = 5.6 Hz, 6H), 2.15-2.01 (m, 4H), 1.79-1.61 (m, 2H), 1.01 (s, 3H), 0.92-0.84 (m, 1H), 0.48 (t, J = 4.5 Hz, 1H), 0.32 (dd, J = 8.6, 4.2 Hz, 1H) |
| 47 | 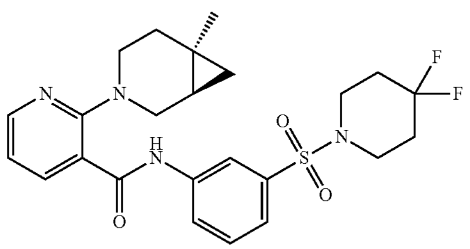 [SMILES: C[C@@]12CCN(c3ncccc3C(=O)Nc3cccc(S(=O)(=O)N4CCC(F)(F)CC4)c3)C[C@@H]1C2] | $^1$H NMR (400 MHz, DMSO-$d_6$) δ 10.68 (s, 1H), 8.29-8.20 (m, 2H), 8.05-7.97 (m, 1H), 7.75 (dd, J = 7.5, 1.8 Hz, 1H), 7.65 (t, J = 7.9 Hz, 1H), 7.49 (d, J = 8.6 Hz, 1H), 6.85 (dd, J = 7.5, 4.8 Hz, 1H), 3.62-3.45 (m, 2H), 3.11 (q, J = 5.6 Hz, 6H), 2.16-1.97 (m, 4H), 1.78-1.60 (m, 2H), 1.01 (s, 3H), 0.93-0.84 (m, 1H), 0.48 (t, J = 4.6 Hz, 1H), 0.32 (dd, J = 8.7, 4.0 Hz, 1H) |

*compound of example 38 is the same as compound of example 31a; compound 41 is the same as compound of example 29a except the stereochemistry is not depicted in the compound structure of example 41.

Example 48: 2-((1R,6S)-6-(difluoromethyl)-3-azabicyclo[4.1.0]heptan-3-yl)-N-(6-(4,4-difluoropiperidin-1-yl)-4-methylpyridin-2-yl)-4-((2-hydroxyethyl)sulfonamido)benzamide

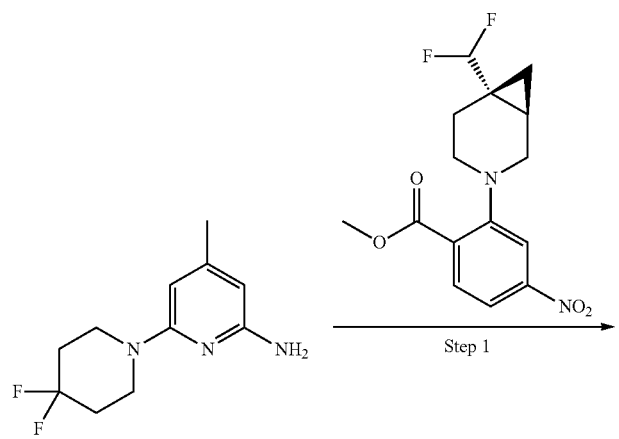

-continued
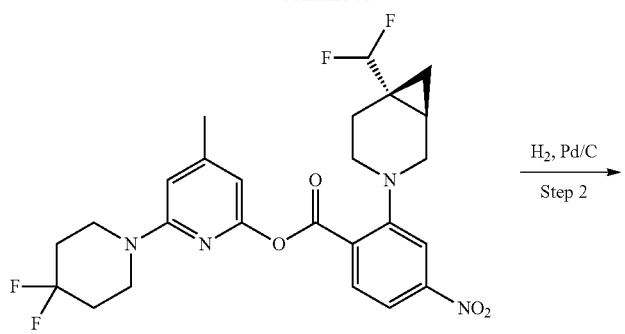
H₂, Pd/C
Step 2
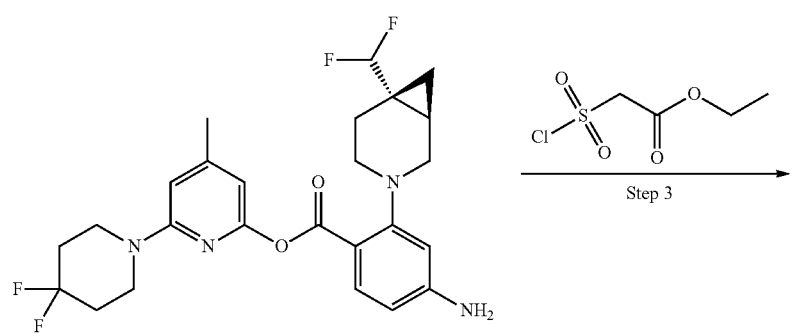
Step 3
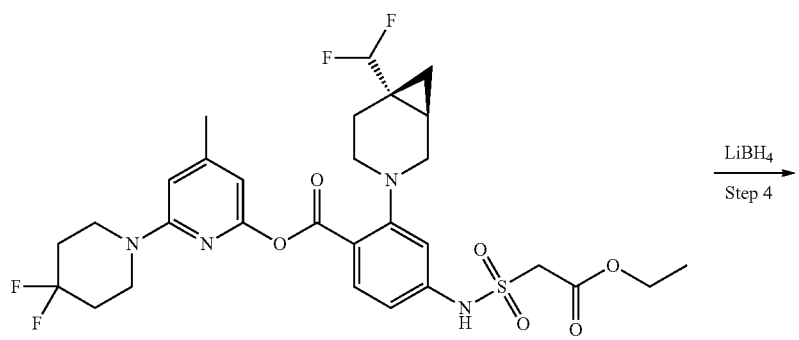
LiBH₄
Step 4
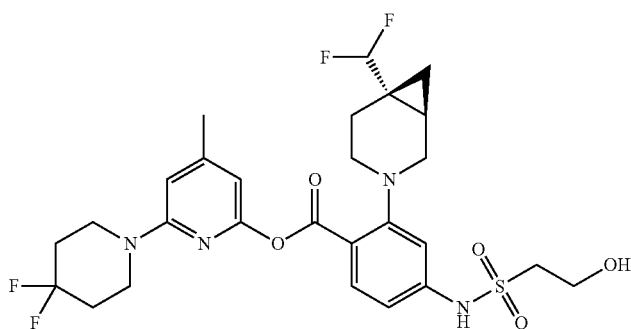

Step 1: Preparation of 2-((1R,6S)-6-(difluoromethyl)-3-azabicyclo[4.1.0]heptan-3-yl)-N-(6-(4,4-difluoropiperidin-1-yl)-4-methylpyridin-2-yl)-4-nitrobenzamide

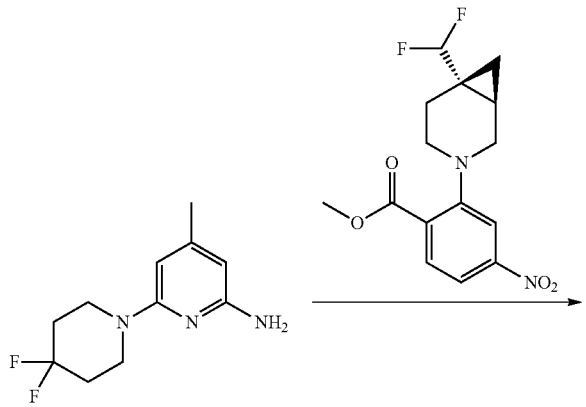

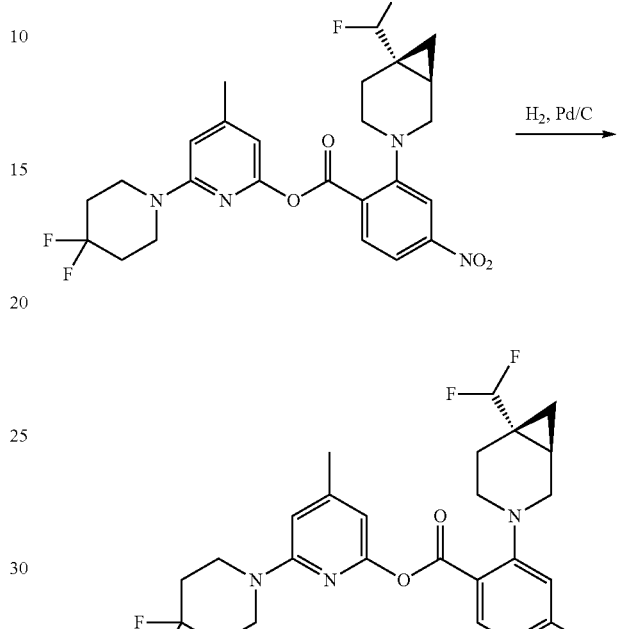

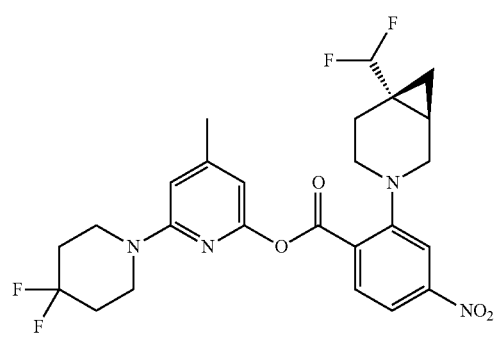

To a solution of methyl 2-((1R,6S)-6-(difluoromethyl)-3-azabicyclo[4.1.0]heptan-3-yl)-4-nitrobenzoate (342 mg, 1.05 mmol) and 6-(4,4-difluoropiperidin-1-yl)-4-methylpyridin-2-amine (200 mg, 0.880 mmol) in THF (10 mL) was added LiHMDS (2.64 mL, 2.64 mmol, 1 M in THF) at 0° C. The mixture was stirred at 25° C. for 1 h under $N_2$ atmosphere. The mixture was poured into water (10 mL) and was extracted with EtOAc (3×10 mL). The combined organic extracts were washed with brine (2×20 mL), dried over $Na_2SO_4$, filtered, and concentrated. The residue was purified by silica gel column chromatography (PE:EA=3:1) to afford 2-((1R,6S)-6-(difluoromethyl)-3-azabicyclo[4.1.0]heptan-3-yl)-N-(6-(4,4-difluoropiperidin-1-yl)-4-methylpyridin-2-yl)-4-nitrobenzamide (200 mg, 383 μmol) as a yellow solid.

Step 2: Preparation of 4-amino-2-((1R,6S)-6-(difluoromethyl)-3-azabicyclo[4.1.0]heptan-3-yl)-N-(6-(4,4-difluoropiperidin-1-yl)-4-methylpyridin-2-yl-benzamide To a solution of 2-((1R,6S)-6-(difluoromethyl)-3-azabicyclo[4.1.0]heptan-3-yl)-N-(6-(4,4-difluoropiperidin-1-yl)-4-methylpyridin-2-yl)-4-nitrobenzamide (200 mg, 383 μmol) in MeOH (10 mL) was added Pd/C (60 mg, 10% w/w). The resulting mixture was stirred at 25° C. for 1 h under $H_2$ atmosphere (15 psi). The mixture was filtered, and the filtrate was concentrated to afford 4-amino-2-((1R,6S)-6-(difluoromethyl)-3-azabicyclo[4.1.0]heptan-3-yl)-N-(6-(4,4-difluoropiperidin-1-yl)-4-methylpyridin-2-yl)benzamide (110 mg, 223 μmol) as a yellow solid. LCMS: MS ESI $(M+1)^+$ 492.3.

Step 3: Preparation of ethyl 2-(N-(3-((1R,6S)-6-(difluoromethyl)-3-azabicyclo[4.1.0]heptan-3-yl)-4-((6-(4,4-difluoropiperidin-1-yl)-4-methylpyridin-2-yl)carbamoyl)phenyl)sulfamoyl)acetate

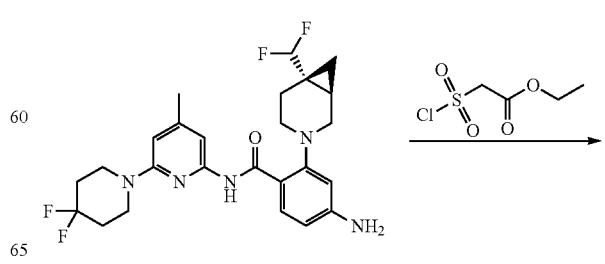

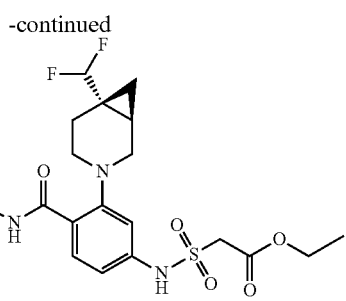

To a solution of 4-amino-2-((1R,6S)-6-(difluoromethyl)-3-azabicyclo[4.1.0]heptan-3-yl)-N-(6-(4,4-difluoropiperidin-1-yl)-4-methylpyridin-2-yl)benzamide (110 mg, 223 µmol) in DCM (10 mL) was added pyridine (35.2 mg, 446 µmol) and ethyl 2-(chlorosulfonyl)acetate (41.6 mg, 223 µmol) at 0° C. The resulting mixture was stirred at 25° C. for 1 h and then poured into water (30 mL). The mixture was extracted with EtOAc (3×30 mL), and the combined organic extracts were washed with brine (2×20 mL), dried over Na$_2$SO$_4$, filtered, and concentrated to give ethyl 2-(N-(3-((1R,6S)-6-(difluoromethyl)-3-azabicyclo[4.1.0]heptan-3-yl)-4-((6-(4,4-difluoropiperidin-1-yl)-4-methylpyridin-2-yl)carbamoyl)phenyl)sulfamoyl)acetate (130 mg, 202 µmol) as a yellow gum. LCMS: MS ESI (M+1)$^+$ 642.2.

Step 4: Preparation of 2-((1R,6S)-6-(difluoromethyl)-3-azabicyclo[4.1.0]heptan-3-yl)-N-(6-(4,4-difluoropiperidin-1-yl)-4-methylpyridin-2-yl)-4-((2-hydroxyethyl)sulfonamido)benzamide

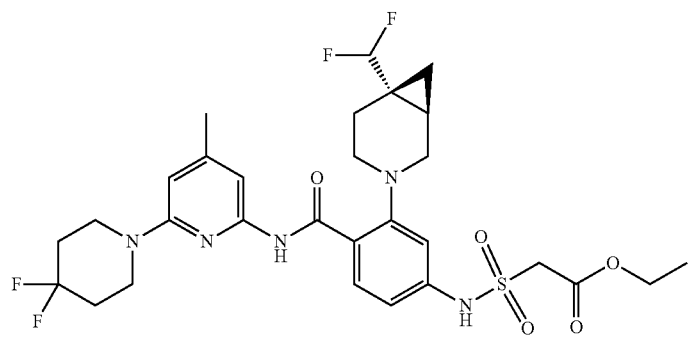

To a solution of ethyl 2-(N-(3-((1R,6S)-6-(difluoromethyl)-3-azabicyclo[4.1.0]heptan-3-yl)-4-((6-(4,4-difluoropiperidin-1-yl)-4-methylpyridin-2-yl)carbamoyl)phenyl)sulfamoyl)acetate (130 mg, 202 µmol) in THF (5 mL) was added LiBH$_4$ (0.606 mL, 0.606 mmol, 1 M in THF), and the mixture was stirred at 25° C. for 1 h. The mixture was poured into H$_2$O (10 mL) and extracted with EtOAc (3×10 mL). The combined organic extracts were washed with brine (2×10 mL), dried over Na$_2$SO$_4$, filtered, and concentrated. The residue was purified by reverse phase HPLC (TFA condition) to afford 2-((1R,6S)-6-(difluoromethyl)-3-azabicyclo[4.1.0]heptan-3-yl)-N-(6-(4,4-difluoropiperidin-1-yl)-4-methylpyridin-2-yl)-4-((2-hydroxyethyl)sulfonamido)benzamide (17.1 mg, 28.5 µmol) as a white solid. LCMS: MS ESI (M+1)$^+$ 600.3. $^1$H NMR (400 MHz, DMSO-d$_6$) δ=11.13 (s, 1H), 10.17 (s, 1H), 7.91 (d, J=8.4 Hz, 1H), 7.51 (s, 1H), 7.18 (s, 1H), 7.08 (dd, J=1.8, 8.6 Hz, 1H), 6.55 (s, 1H), 5.65 (br t, J=56.6 Hz, 1H), 3.76 (t, J=6.4 Hz, 2H), 3.68 (br d, J=5.0 Hz, 4H), 3.35 (t, J=6.4 Hz, 2H), 3.30 (br d, J=11.6 Hz, 1H), 3.10 (br dd, J=3.8, 11.2 Hz, 1H), 2.97 (br d, J=11.2 Hz, 1H), 2.54 (br s, 1H), 2.26 (s, 3H), 2.18-2.12 (m, 2H), 2.02-1.92 (m, 4H), 1.48 (br d, J=4.6 Hz, 1H), 1.37 (br d, J=4.8 Hz, 1H), 0.98 (br dd, J=4.6, 9.0 Hz, 1H).

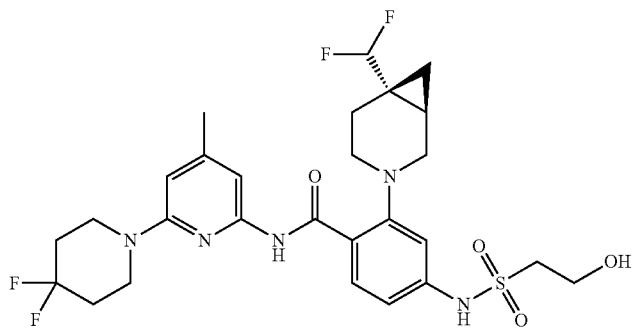

Examples 49a and 49b: N-(2-(4,4-difluoropiperidin-1-yl)-6-methylpyrimidin-4-yl)-4-((2-hydroxyethyl)sulfonamido)-2-((1S,6R)-6-(methoxymethyl)-3-azabicyclo[4.1.0]heptan-3-yl)benzamide (Example 49a) and N-(2-(4,4-difluoropiperidin-1-yl)-6-methylpyrimidin-4-yl)-4-((2-hydroxyethyl)sulfonamido)-2-((1R,6S)-6-(methoxymethyl)-3-azabicyclo[4.1.0]heptan-3-yl)benzamide (Example 49b)
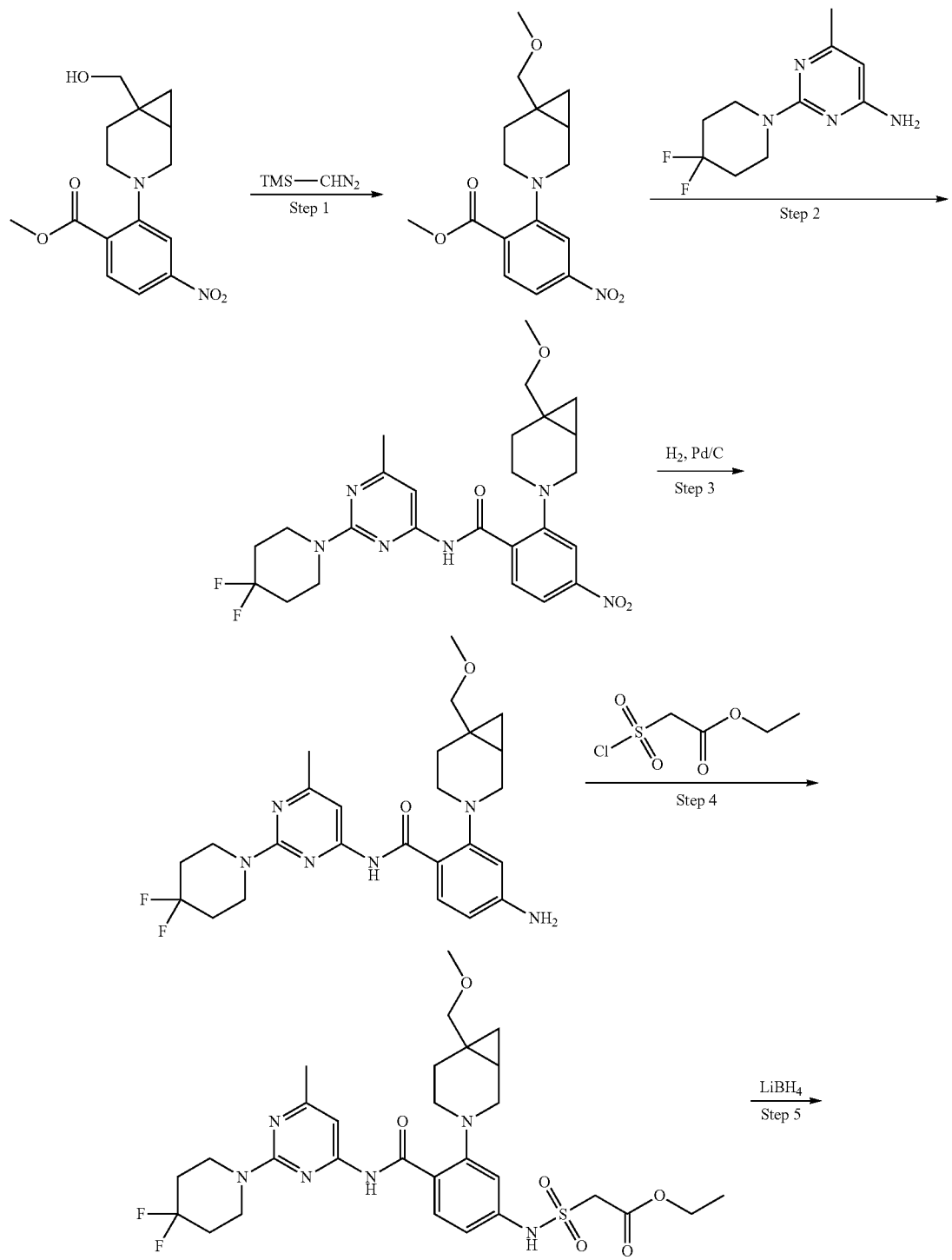

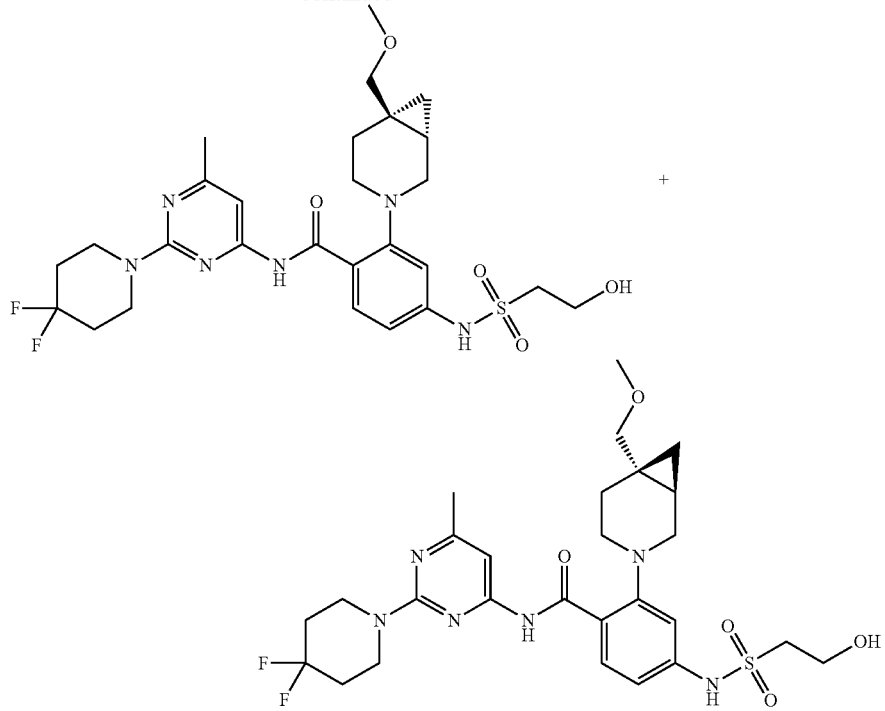

Step 1: Preparation of methyl 2-(6-(methoxymethyl)-3-azabicyclo[4.1.0]heptan-3-yl)-4-nitrobenzoate

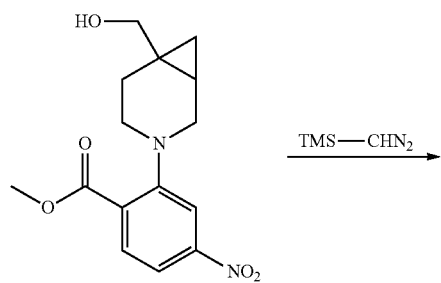

To a solution of methyl 2-(6-(hydroxymethyl)-3-azabicyclo[4.1.0]heptan-3-yl)-4-nitrobenzoate (1.00 g, 3.26 mmol) in DCM (30 mL) was added boron trifluoride diethyl etherate (46.2 mg, 326 μmol) followed by trimethylsilyldiazomethane (929 mg, 8.14 mmol) at 0° C. The mixture was stirred at 20° C. for 16 h. The mixture was concentrated, and the residue was purified by silica gel column chromatography (PE:EA gradient) to afford methyl 2-(6-(methoxymethyl)-3-azabicyclo[4.1.0]heptan-3-yl)-4-nitrobenzoate (500 mg, 1.56 mmol) as a yellow gum. LCMS: MS ESI (M+1)$^+$ 321.1.

Step 2: Preparation of N-(2-(4,4-difluoropiperidin-1-yl)-6-methylpyrimidin-4-yl)-2-(6-(methoxymethyl)-3-azabicyclo[4.1.0]heptan-3-yl)-4-nitrobenzamide

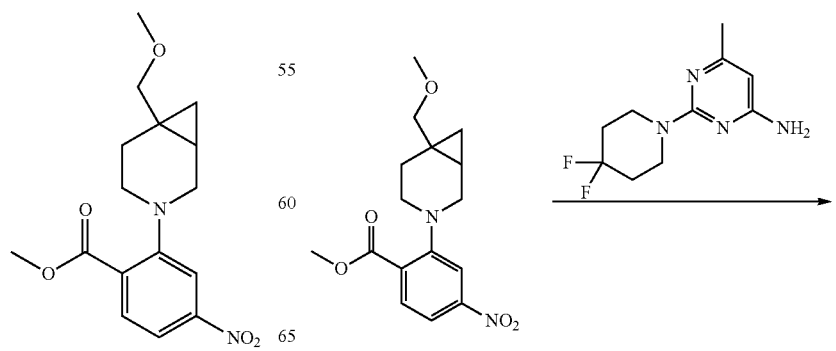

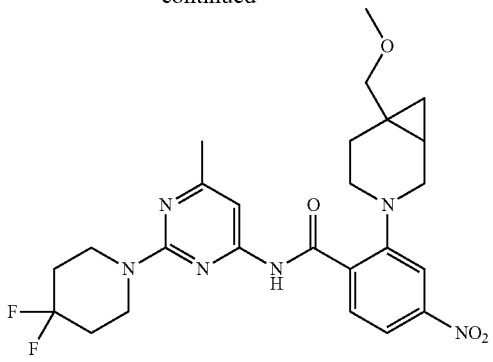
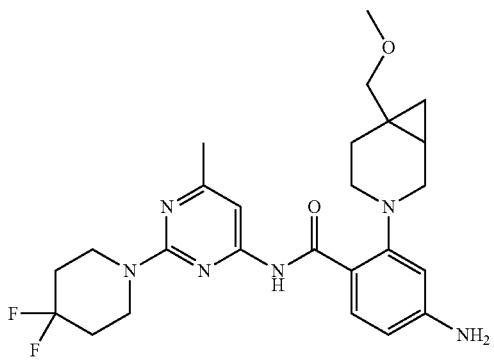

To a solution of methyl 2-(6-(methoxymethyl)-3-azabicyclo[4.1.0]heptan-3-yl)-4-nitrobenzoate (250 mg, 780 μmol) and 2-(4,4-difluoropiperidin-1-yl)-6-methylpyrimidin-4-amine (248 mg, 1.09 mmol) in THF (5 mL) was added LiHMDS (2.34 mL, 2.34 mmol, 1 M in THF) dropwise at 0° C. The mixture was stirred at 20° C. for 2 h. The reaction mixture was quenched with water (10 mL) and extracted with EtOAc (10 mL). The organic extract was concentrated and purified by silica gel column chromatography (PE:EA gradient) to afford N-(2-(4,4-difluoropiperidin-1-yl)-6-methylpyrimidin-4-yl)-2-(6-(methoxymethyl)-3-azabicyclo[4.1.0]heptan-3-yl)-4-nitrobenzamide (200 mg, 387 μmol) as a yellow gum. LCMS: MS ESI (M+1)$^+$ 517.3.

Step 3: Preparation of 4-amino-N-(2-(4,4-difluoropiperidin-1-yl)-6-methylpyrimidin-4-yl)-2-(6-(methoxymethyl)-3-azabicyclo[4.1.0]heptan-3-yl)benzamide To a solution of N-(2-(4,4-difluoropiperidin-1-yl)-6-methylpyrimidin-4-yl)-2-(6-(methoxymethyl)-3-azabicyclo[4.1.0]heptan-3-yl)-4-nitrobenzamide (250 mg, 483 μmol) in THF (2 mL) was added Pd/C (50 mg, 10% w/w), and the mixture was stirred at 20° C. for 1 h under H$_2$ atmosphere (15 psi). The mixture was filtered, and the filtrate was concentrated to give 4-amino-N-(2-(4,4-difluoropiperidin-1-yl)-6-methylpyrimidin-4-yl)-2-(6-(methoxymethyl)-3-azabicyclo[4.1.0]heptan-3-yl)benzamide (200 mg, 411 μmol) as a yellow gum. LCMS: MS ESI (M+1)$^+$ 487.3.

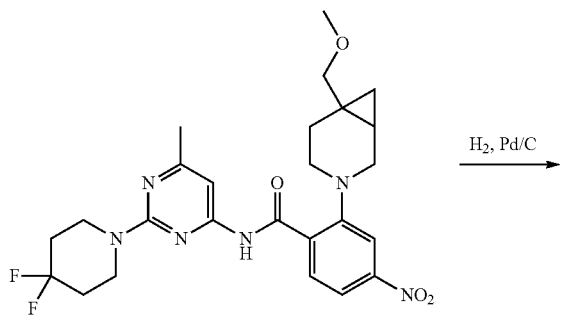

Step 4: Preparation of ethyl 2-(N-(4-((2-(4,4-difluoropiperidin-1-yl)-6-methylpyrimidin-4-yl)carbamoyl)-3-(6-(methoxymethyl)-3-azabicyclo[4.1.0]heptan-3-yl)phenyl)sulfamoyl)acetate

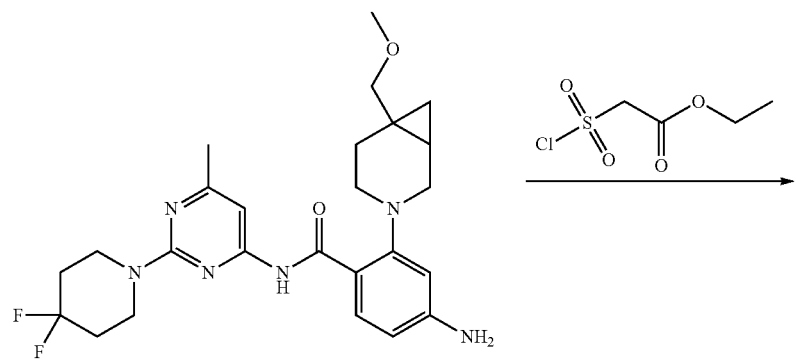

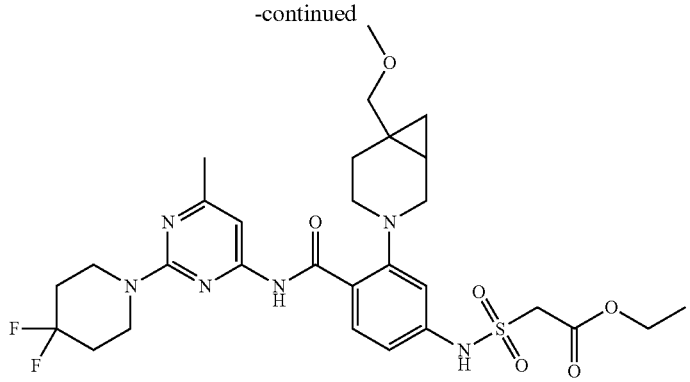

To a solution of 4-amino-N-(2-(4,4-difluoropiperidin-1-yl)-6-methylpyrimidin-4-yl)-2-(6-(methoxymethyl)-3-azabicyclo[4.1.0]heptan-3-yl)benzamide (200 mg, 411 μmol) in DCM (4 mL) was added pyridine (97.2 mg, 1.23 mmol) and ethyl 2-(chlorosulfonyl)acetate (114 mg, 616 μmol) at 0° C. The mixture was stirred at 20° C. for 2 h. The reaction mixture was purified by silica gel column chromatography (PE:EA gradient) to afford ethyl 2-(N-(4-((2-(4,4-difluoropiperidin-1-yl)-6-methylpyrimidin-4-yl)carbamoyl)-3-(6-(methoxymethyl)-3-azabicyclo[4.1.0]heptan-3-yl)phenyl)sulfamoyl)acetate (200 mg, 314 μmol) as a yellow gum. LCMS: MS ESI (M+1)+ 637.3.

Step 5: Preparation of N-(2-(4,4-difluoropiperidin-1-yl)-6-methylpyrimidin-4-yl)-4-((2-hydroxyethyl)sulfonamido)-2-((1S,6R)-6-(methoxymethyl)-3-azabicyclo[4.1.0]heptan-3-yl)benzamide and N-(2-(4,4-difluoropiperidin-1-yl)-6-methylpyrimidin-4-yl)-4-((2-hydroxyethyl)sulfonamido)-2-((1R,6S)-6-(methoxymethyl)-3-azabicyclo[4.1.0]heptan-3-yl)benzamide

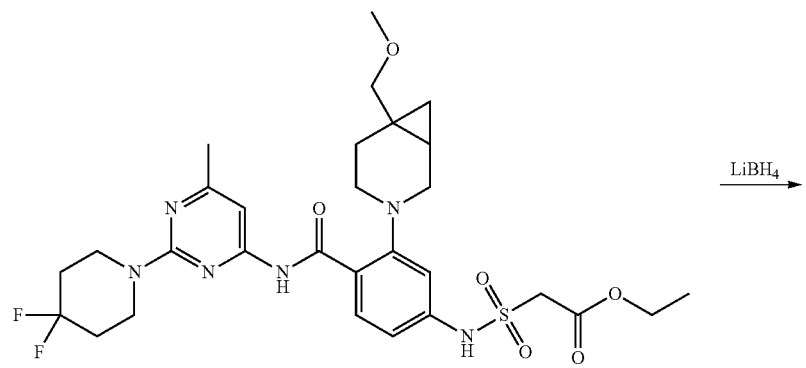

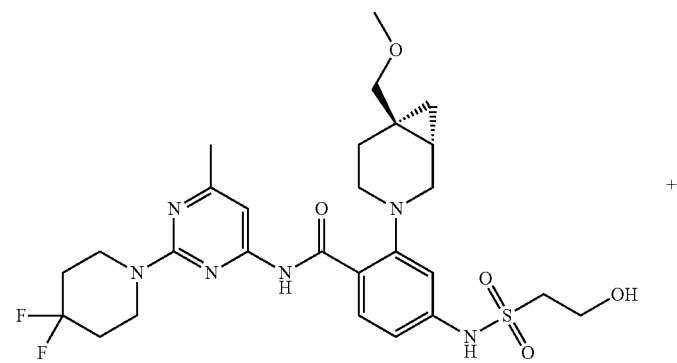

-continued

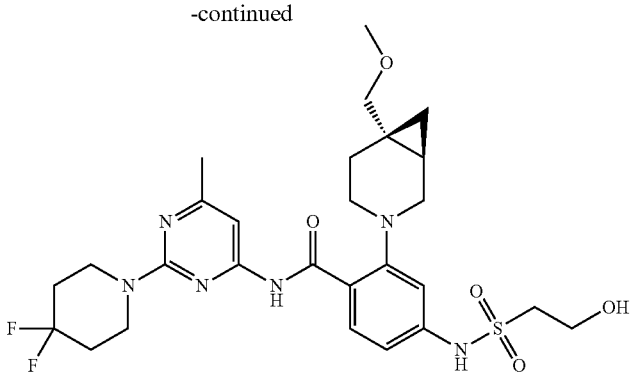

To a solution of ethyl 2-(N-(4-((2-(4,4-difluoropiperidin-1-yl)-6-methylpyrimidin-4-yl)carbamoyl)-3-(6-(methoxymethyl)-3-azabicyclo[4.1.0]heptan-3-yl)phenyl)sulfamoyl)acetate (150 mg, 235 μmol) in THF (3 mL) was added LiBH$_4$ (0.705 mL, 0.705 mmol, 1 M in THF) at 0° C. The reaction mixture was stirred at 20° C. for 2 h and then quenched with water (2 drops). The mixture was first purified by prep-HPLC (FA condition) to afford the racemic N-(2-(4,4-difluoropiperidin-1-yl)-6-methylpyrimidin-4-yl)-4-((2-hydroxyethyl)sulfonamido)-2-(6-(methoxymethyl)-3-azabicyclo[4.1.0]heptan-3-yl)benzamide. The racemic compound was separated by chiral SFC (Chiralcel OX-3 (50 mm×4.6 mm, 3 μm) CO$_2$-EtOH (0.05% diethylamine)) to afford first eluting peak, arbitrarily assigned as N-(2-(4,4-difluoropiperidin-1-yl)-6-methylpyrimidin-4-yl)-4-((2-hydroxyethyl)sulfonamido)-2-((1S,6R)-6-(methoxymethyl)-3-azabicyclo[4.1.0]heptan-3-yl)benzamide (72.7 mg, 122 μmol), as a white solid and second eluting peak, arbitrarily assigned as N-(2-(4,4-difluoropiperidin-1-yl)-6-methylpyrimidin-4-yl)-4-((2-hydroxyethyl)sulfonamido)-2-((1R,6S)-6-(methoxymethyl)-3-azabicyclo[4.1.0]heptan-3-yl)benzamide (65.6 mg, 110 μmol), as a white solid. First eluting peak LCMS: MS ESI (M+1)$^+$ 595.3. Second eluting peak LCMS: MS ESI (M+1)$^+$ 595.3. First eluting peak $^1$H NMR (400 MHz, DMSO-d$_6$) δ=11.81 (s, 1H), 7.85 (d, J=8.8 Hz, 1H), 7.43 (s, 1H), 7.07 (d, J=1.4 Hz, 1H), 6.95 (dd, J=1.8, 8.8 Hz, 1H), 3.89 (br t, J=5.4 Hz, 4H), 3.73 (t, J=6.5 Hz, 2H), 3.25 (s, 3H), 3.23-3.15 (m, 5H), 2.87-2.78 (m, 1H), 2.61-2.52 (m, 2H), 2.30 (s, 3H), 2.18-2.09 (m, 1H), 2.03-1.91 (m, 5H), 1.19-1.09 (m, 2H), 0.61 (br d, J=4.9 Hz, 1H). Second eluting peak $^1$H NMR (400 MHz, DMSO-d$_6$) δ=11.82 (s, 1H), 7.84 (d, J=8.6 Hz, 1H), 7.44 (s, 1H), 7.06 (s, 1H), 6.94 (dd, J=1.5, 8.6 Hz, 1H), 3.89 (br t, J=5.4 Hz, 4H), 3.73 (t, J=6.6 Hz, 2H), 3.25 (s, 3H), 3.23-3.15 (m, 5H), 2.90-2.76 (m, 1H), 2.61-2.51 (m, 2H), 2.30 (s, 3H), 2.21-2.10 (m, 1H), 2.03-1.90 (m, 5H), 1.20-1.07 (m, 2H), 0.61 (dd, J=2.6, 7.4 Hz, 1H).

Examples 50a, 50b, 51a, and 51b: N-(2-(4,4-difluoropiperidin-1-yl)-6-methylpyrimidin-4-yl)-2-((1R,6R)-6-fluoro-3-azabicyclo[4.2.0]octan-3-yl)-4-((2-hydroxyethyl)sulfonamido)benzamide (Example 50a), N-(2-(4,4-difluoropiperidin-1-yl)-6-methylpyrimidin-4-yl)-2-((1S,6S)-6-fluoro-3-azabicyclo[4.2.0]octan-3-yl)-4-((2-hydroxyethyl)sulfonamido)benzamide (Example 50b), N-(2-(4,4-difluoropiperidin-1-yl)-6-methylpyrimidin-4-yl)-2-((1S,6R)-6-(fluoromethyl)-3-azabicyclo[4.1.0]heptan-3-yl)-4-((2-hydroxyethyl)sulfonamido)benzamide (Example 51a), and N-(2-(4,4-difluoropiperidin-1-yl)-6-methylpyrimidin-4-yl)-2-((1R,6S)-6-(fluoromethyl)-3-azabicyclo[4.1.0]heptan-3-yl)-4-((2-hydroxyethyl)sulfonamido)benzamide (Example 51b)

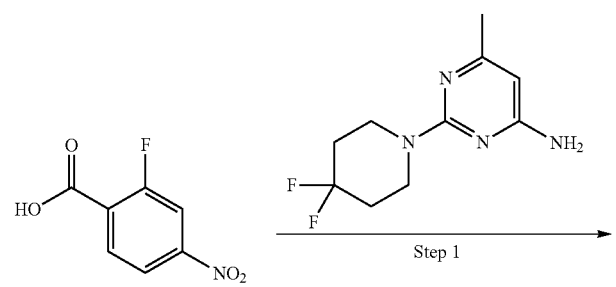

Step 1

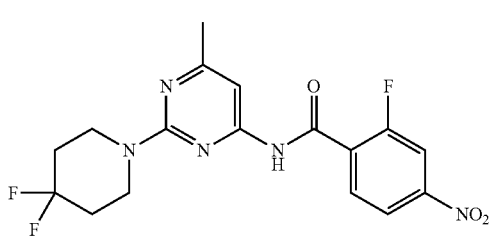 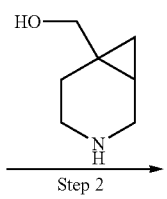

Step 2

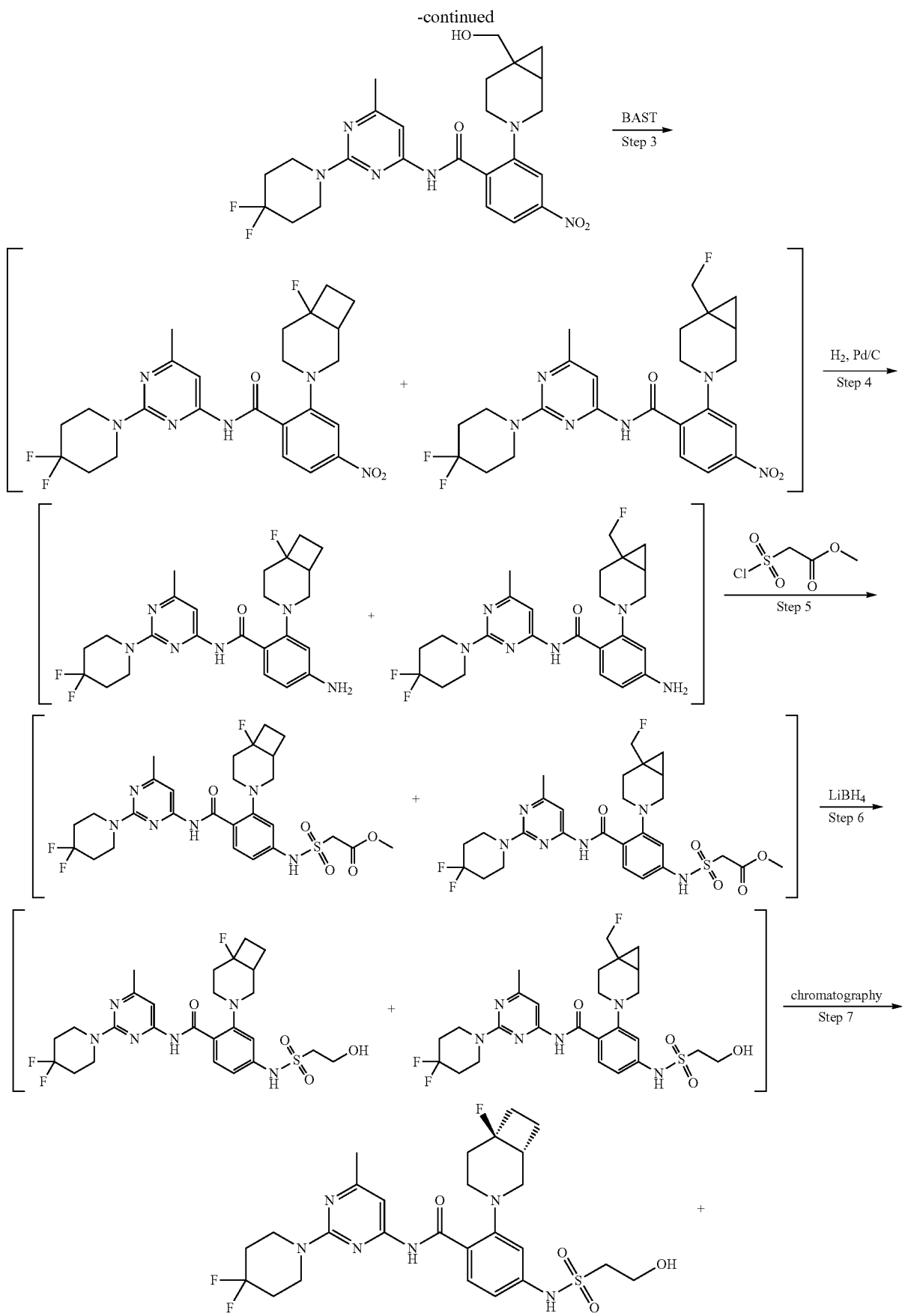

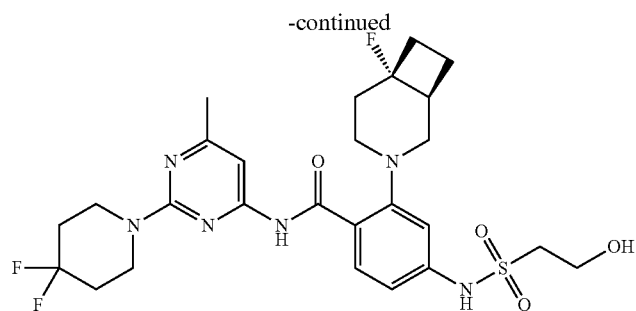
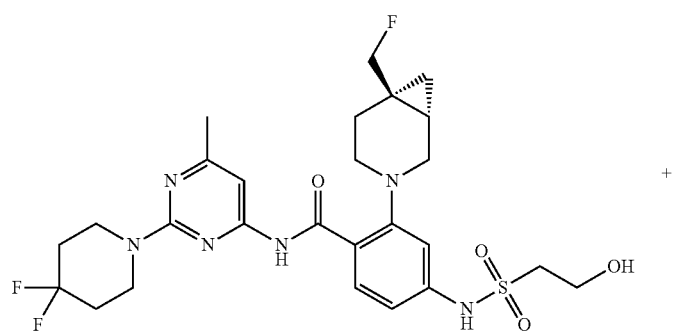
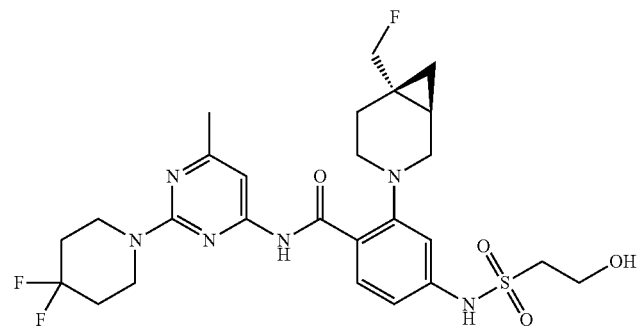
Step 1: Synthesis of N-(2-(4,4-difluoropiperidin-1-yl)-6-methylpyrimidin-4-yl)-2-fluoro-4-nitrobenzamide
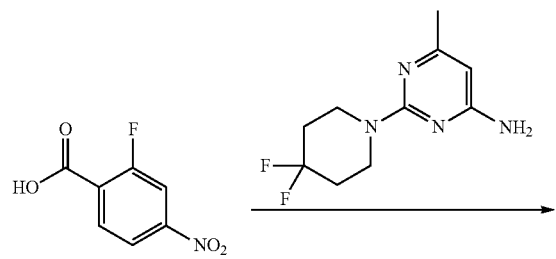
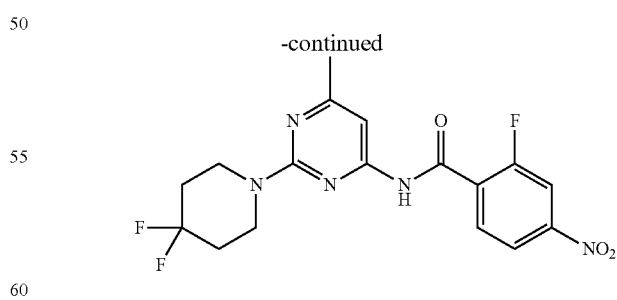
To a solution of 2-fluoro-4-nitrobenzoic acid (25.0 g, 135 mmol) and 2-(4,4-difluoropiperidin-1-yl)-6-methylpyrimidin-4-amine (27.6 g, 121 mmol) in DCE (500 mL) was added 2-chloro-1-methylpyridin-1-ium iodide (103 g, 405 mmol) and triethylamine (40.9 g, 405 mmol), and the mixture was stirred at 80° C. for 12 h. The mixture was poured into saturated aqueous NH₄Cl (100 mL) and extracted with EtOAc (3×500 mL). The combined organic extracts were washed with brine (300 mL), dried over Na₂SO₄, filtered, and concentrated. The residue was purified by silica gel column chromatography (PE:EA gradient) to afford N-(2-(4,4-difluoropiperidin-1-yl)-6-methylpyrimidin-4-yl)-2-fluoro-4-nitrobenzamide (27.0 g, 68.2 mmol) as a yellow solid. LCMS: MS ESI (M+1)⁺ 396.2. ¹H NMR (400 MHz, DMSO-d₆) δ=11.09 (s, 1H), 8.27-8.20 (m, 1H), 8.18-8.12 (m, 1H), 7.97-7.86 (m, 1H), 7.23 (br s, 1H), 3.83 (br s, 4H), 2.31 (s, 3H), 1.95 (br t, J=13.2 Hz, 4H).

Step 2: Preparation of N-(2-(4,4-difluoropiperidin-1-yl)-6-methylpyrimidin-4-yl)-2-(6-(hydroxymethyl)-3-azabicyclo[4.1.0]heptan-3-yl)-4-nitrobenzamide

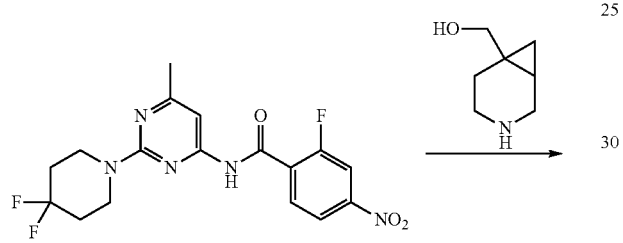

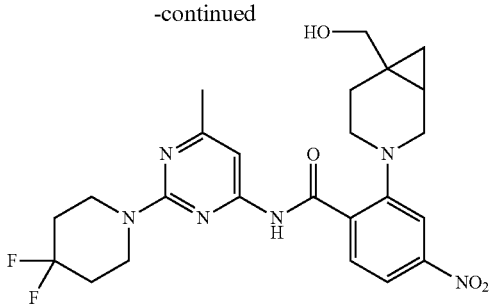

To a solution of N-(2-(4,4-difluoropiperidin-1-yl)-6-methylpyrimidin-4-yl)-2-fluoro-4-nitrobenzamide (26.0 g, 65.7 mmol) and (3-azabicyclo[4.1.0]heptan-6-yl)methanol (10.7 g, 65.7 mmol) in DMSO (250 mL) was added DIPEA (25.4 g, 197 mmol), and the mixture was stirred at 100° C. for 12 h. The mixture was poured into saturated aqueous NH₄Cl (400 mL) and extracted with EtOAc (3×450 mL). The combined organic extracts were washed with brine (100 mL), dried over Na₂SO₄, filtered, and concentrated. The residue was purified by silica gel column chromatography (PE:EA gradient) to afford N-(2-(4,4-difluoropiperidin-1-yl)-6-methylpyrimidin-4-yl)-2-(6-(hydroxymethyl)-3-azabicyclo[4.1.0]heptan-3-yl)-4-nitrobenzamide (24.0 g, 47.7 mmol) as a yellow solid. LCMS: MS ESI (M+1)⁺ 503.1.

Step 3: Preparation of mixture containing N-(2-(4,4-difluoropiperidin-1-yl)-6-methylpyrimidin-4-yl)-2-(6-fluoro-3-azabicyclo[4.2.0]octan-3-yl)-4-nitrobenzamide and N-(2-(4,4-difluoropiperidin-1-yl)-6-methylpyrimidin-4-yl)-2-(6-(fluoromethyl)-3-azabicyclo[4.1.0]heptan-3-yl)-4-nitrobenzamide

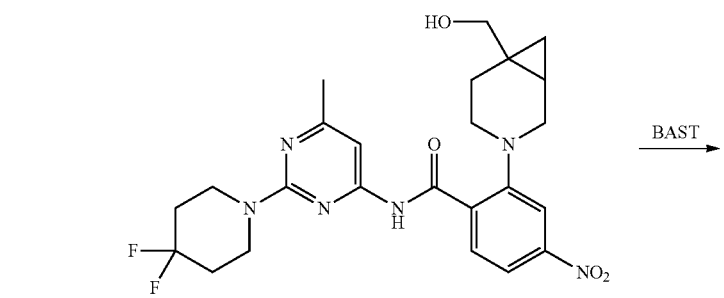

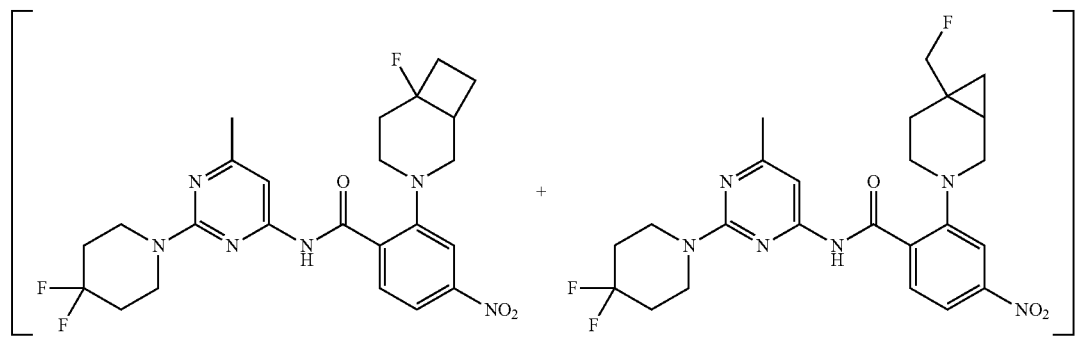

To a solution of N-(2-(4,4-difluoropiperidin-1-yl)-6-methylpyrimidin-4-yl)-2-(6-(hydroxymethyl)-3-azabicyclo[4.1.0]heptan-3-yl)-4-nitrobenzamide (24.0 g, 47.7 mmol) in DCM (240 mL) was added bis(2-methoxyethyl)aminosulfur trifluoride (21.1 g, 95.4 mmol) dropwise at 0° C., and the mixture was stirred at 25° C. for 12 h. The reaction mixture was quenched by slow addition of silica gel (15 g) at 0° C., and the mixture was concentrated in vacuo. The residue was purified by silica gel column chromatography (PE:EA gradient) to afford a mixture containing N-(2-(4,4-difluoropiperidin-1-yl)-6-methylpyrimidin-4-yl)-2-(6-fluoro-3-azabicyclo[4.2.0]octan-3-yl)-4-nitrobenzamide and N-(2-(4,4-difluoropiperidin-1-yl)-6-methylpyrimidin-4-yl)-2-(6-(fluoromethyl)-3-azabicyclo[4.1.0]heptan-3-yl)-4-nitrobenzamide (18.0 g, 35.6 mmol) as a yellow solid.

Step 4: Preparation of a mixture containing 4-amino-N-(2-(4,4-difluoropiperidin-1-yl)-6-methylpyrimidin-4-yl)-2-(6-fluoro-3-azabicyclo[4.2.0]octan-3-yl)benzamide and 4-amino-N-(2-(4,4-difluoropiperidin-1-yl)-6-methylpyrimidin-4-yl)-2-(6-(fluoromethyl)-3-azabicyclo[4.1.0]heptan-3-yl)benzamide

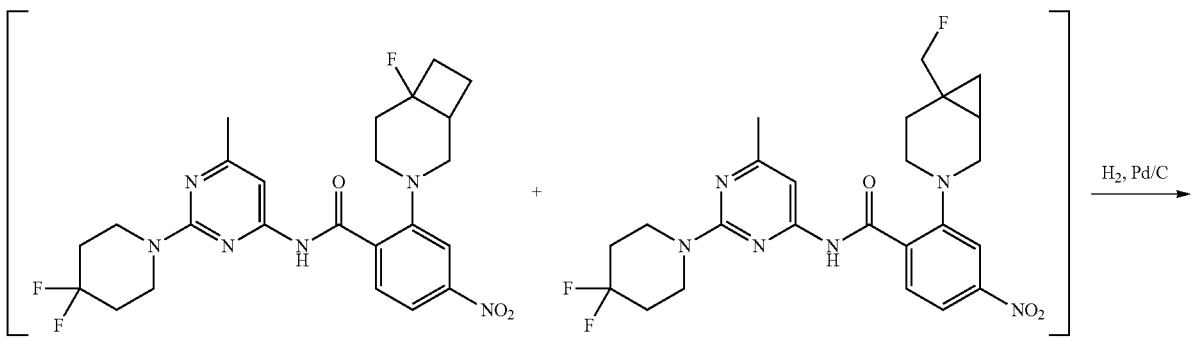

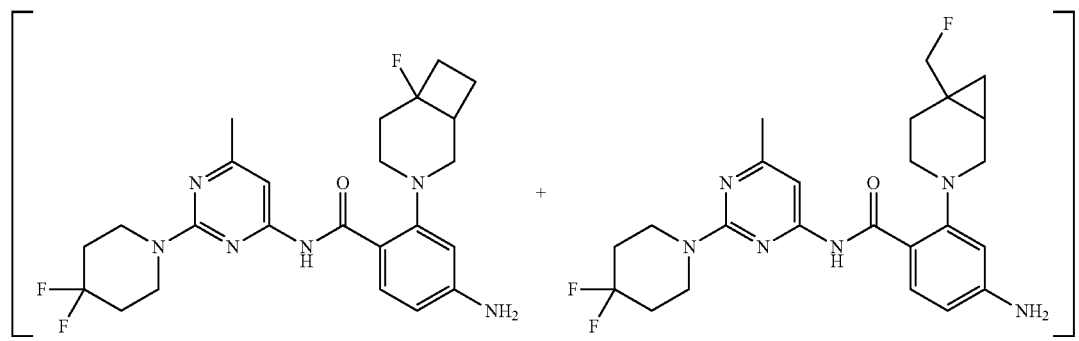

To a solution of a mixture containing N-(2-(4,4-difluoropiperidin-1-yl)-6-methylpyrimidin-4-yl)-2-(6-fluoro-3-azabicyclo[4.2.0]octan-3-yl)-4-nitrobenzamide and N-(2-(4,4-difluoropiperidin-1-yl)-6-methylpyrimidin-4-yl)-2-(6-(fluoromethyl)-3-azabicyclo[4.1.0]heptan-3-yl)-4-nitrobenzamide (18.0 g, 35.6 mmol) in THF (180 mL) was added Pd/C (3.78 g, 10% w/w), and the mixture was stirred at 25° C. for 2 h under $H_2$ atmosphere (15 psi). The reaction mixture was filtered, and the filtrate was concentrated in vacuo to afford a mixture containing 4-amino-N-(2-(4,4-difluoropiperidin-1-yl)-6-methylpyrimidin-4-yl)-2-(6-fluoro-3-azabicyclo[4.2.0]octan-3-yl)benzamide and 4-amino-N-(2-(4,4-difluoropiperidin-1-yl)-6-methylpyrimidin-4-yl)-2-(6-(fluoromethyl)-3-azabicyclo[4.1.0]heptan-3-yl)benzamide (16.8 g, 35.4 mmol) as a yellow oil. LCMS: MS ESI $(M+1)^+$ 475.3.

Step 5: Preparation of a mixture containing methyl 2-(N-(4-((2-(4,4-difluoropiperidin-1-yl)-6-methylpyrimidin-4-yl)carbamoyl)-3-(6-fluoro-3-azabicyclo[4.2.0]octan-3-yl)phenyl)sulfamoyl)acetate and methyl 2-(N-(4-((2-(4,4-difluoropiperidin-1-yl)-6-methylpyrimidin-4-yl)carbamoyl)-3-(6-(fluoromethyl)-3-azabicyclo[4.1.0]heptan-3-yl)phenyl)sulfamoyl)acetate

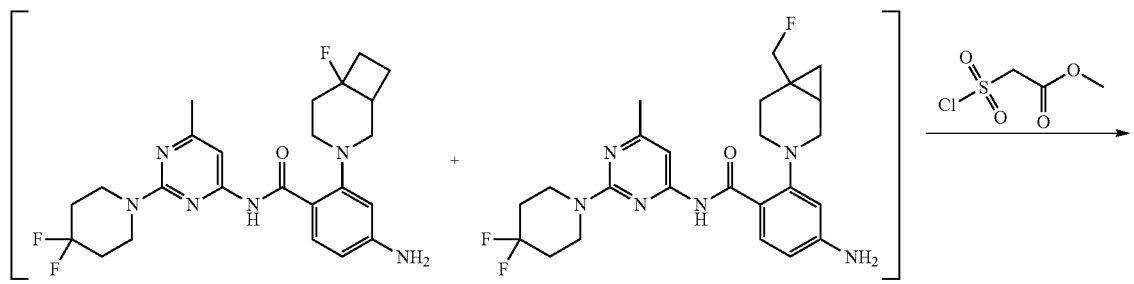

To a solution of a mixture containing 4-amino-N-(2-(4,4-difluoropiperidin-1-yl)-6-methylpyrimidin-4-yl)-2-(6-fluoro-3-azabicyclo[4.2.0]octan-3-yl)benzamide and 4-amino-N-(2-(4,4-difluoropiperidin-1-yl)-6-methylpyrimidin-4-yl)-2-(6-(fluoromethyl)-3-azabicyclo[4.1.0]heptan-3-yl)benzamide (16.8 g, 35.4 mmol) in DCM (15 mL) was added methyl 2-(chlorosulfonyl)acetate (9.16 g, 53.1 mmol) and pyridine (8.38 g, 106 mmol) at 0° C., and the mixture was stirred at 25° C. for 0.5 h. The mixture was poured into saturated aqueous NH$_4$Cl (200 mL) and extracted with EtOAc (3×150 mL). The combined organic extracts were washed with brine (150 mL), dried over Na$_2$SO$_4$, filtered, and concentrated to afford a mixture containing methyl 2-(N-(4-((2-(4,4-difluoropiperidin-1-yl)-6-methylpyrimidin-4-yl)carbamoyl)-3-(6-fluoro-3-azabicyclo[4.2.0]octan-3-yl)phenyl)sulfamoyl)acetate and methyl 2-(N-(4-((2-(4,4-difluoropiperidin-1-yl)-6-methylpyrimidin-4-yl)carbamoyl)-3-(6-(fluoromethyl)-3-azabicyclo[4.1.0]heptan-3-yl)phenyl)sulfamoyl)acetate (21.0 g, 34.3 mmol) as a yellow oil. LCMS: MS ESI (M+1)$^+$ 611.2.

Step 6: Preparation of a mixture containing N-(2-(4,4-difluoropiperidin-1-yl)-6-methylpyrimidin-4-yl)-2-(6-fluoro-3-azabicyclo[4.2.0]octan-3-yl)-4-((2-hydroxyethyl)sulfonamido)benzamide and N-(2-(4,4-difluoropiperidin-1-yl)-6-methylpyrimidin-4-yl)-2-(6-(fluoromethyl)-3-azabicyclo[4.1.0]heptan-3-yl)-4-((2-hydroxyethyl)sulfonamido)benzamide

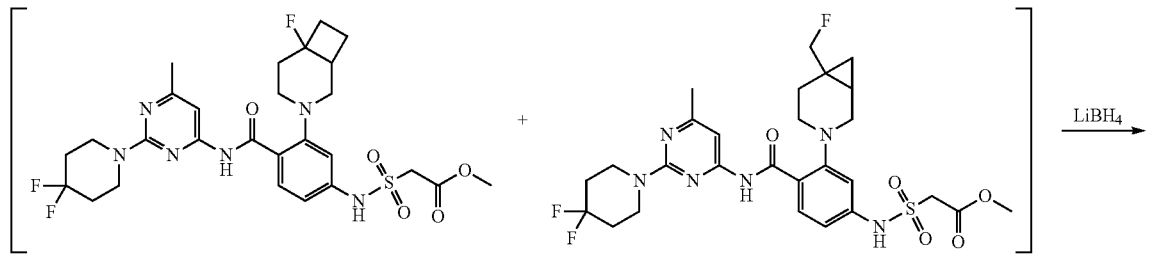

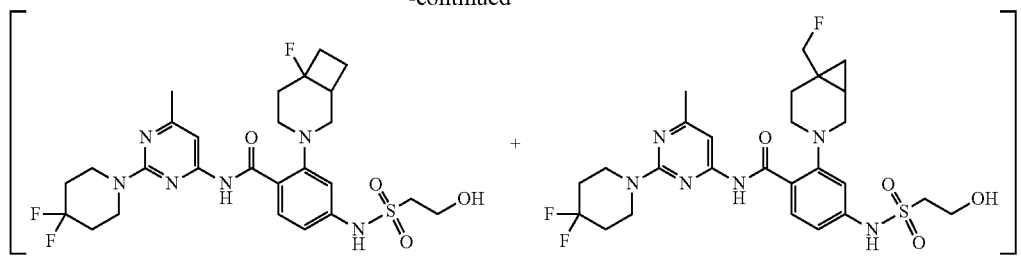

To a solution of a mixture containing methyl 2-(N-(4-((2-(4,4-difluoropiperidin-1-yl)-6-methylpyrimidin-4-yl)carbamoyl)-3-(6-fluoro-3-azabicyclo[4.2.0]octan-3-yl)phenyl)sulfamoyl)acetate and methyl 2-(N-(4-((2-(4,4-difluoropiperidin-1-yl)-6-methylpyrimidin-4-yl)carbamoyl)-3-(6-(fluoromethyl)-3-azabicyclo[4.1.0]heptan-3-yl)phenyl)sulfamoyl)acetate (21.0 g, 34.3 mmol) in THF (200 mL) was added LiBH$_4$ (68.6 mL, 68.6 mmol, 1 M in THF) at 0° C., and the mixture was stirred at 25° C. for 0.5 h. The mixture was poured into saturated aqueous NH$_4$Cl (200 mL) and extracted with EtOAc (3×150 mL). The combined organic extracts were washed with brine (250 mL), dried over Na$_2$SO$_4$, filtered, and concentrated to afford a mixture containing N-(2-(4,4-difluoropiperidin-1-yl)-6-methylpyrimidin-4-yl)-2-(6-fluoro-3-azabicyclo[4.2.0]octan-3-yl)-4-((2-hydroxyethyl)sulfonamido)benzamide and N-(2-(4,4-difluoropiperidin-1-yl)-6-methylpyrimidin-4-yl)-2-(6-(fluoromethyl)-3-azabicyclo[4.1.0]heptan-3-yl)-4-((2-hydroxyethyl)sulfonamido)benzamide (12.0 g, 20.5 mmol) as a yellow oil.

Step 7: Preparation of N-(2-(4,4-difluoropiperidin-1-yl)-6-methylpyrimidin-4-yl)-2-((1R,6R)-6-fluoro-3-azabicyclo[4.2.0]octan-3-yl)-4-((2-hydroxyethyl)sulfonamido)benzamide, N-(2-(4,4-difluoropiperidin-1-yl)-6-methylpyrimidin-4-yl)-2-((1S,6S)-6-fluoro-3-azabicyclo[4.2.0]octan-3-yl)-4-((2-hydroxyethyl)sulfonamido)benzamide, N-(2-(4,4-difluoropiperidin-1-yl)-6-methylpyrimidin-4-yl)-2-((1S,6R)-6-(fluoromethyl)-3-azabicyclo[4.1.0]heptan-3-yl)-4-((2-hydroxyethyl)sulfonamido)benzamide, and N-(2-(4,4-difluoropiperidin-1-yl)-6-methylpyrimidin-4-yl)-2-((1R,6S)-6-(fluoromethyl)-3-azabicyclo[4.1.0]heptan-3-yl)-4-((2-hydroxyethyl)sulfonamido)benzamide A mixture containing N-(2-(4,4-difluoropiperidin-1-yl)-6-methylpyrimidin-4-yl)-2-(6-fluoro-3-azabicyclo[4.2.0]octan-3-yl)-4-((2-hydroxyethyl)sulfonamido)benzamide and N-(2-(4,4-difluoropiperidin-1-yl)-6-methylpyrimidin-4-yl)-2-(6-(fluoromethyl)-3-azabicyclo[4.1.0]heptan-3-yl)-4-((2-hydroxyethyl)sulfonamido)benzamide (10 g, 17.1 mmol) was purified by silica gel column chromatography (PE:EA gradient) to afford racemic N-(2-(4,4-difluoropiperidin-1-yl)-6-methylpyrimidin-4-yl)-2-(6-fluoro-3-azabicyclo[4.2.0]octan-3-yl)-4-((2-hydroxyethyl)sulfonamido)benzamide as a colorless oil and racemic N-(2-(4,4-difluoropiperidin-1-yl)-6-methylpyrimidin-4-yl)-2-(6-(fluoromethyl)-3-azabicyclo[4.1.0]heptan-3-yl)-4-((2-hydroxyethyl)sulfonamido)benzamide as a yellow oil. Racemic N-(2-(4,4-difluoropiperidin-1-yl)-6-methylpyrimidin-4-yl)-2-(6-fluoro-3-azabicyclo[4.2.0]octan-3-yl)-4-((2-hydroxyethyl)sulfonamido)benzamide was further purified by chiral SFC (Daicel Chiralcel OJ-H (250 mm×30 mm, 5 µm); mobile phase: CO$_2$:MeOH 1:3 (0.1% NH$_3$H$_2$O)) to afford first eluting peak, arbitrarily assigned N-(2-(4,4-difluoropiperidin-1-yl)-6-methylpyrimidin-4-yl)-2-((1R,6R)-6-fluoro-3-azabicyclo[4.2.0]octan-3-yl)-4-((2-hydroxyethyl)sulfonamido)benzamide (1100 mg, 1.37 mmol) as an off-white solid and second eluting peak, arbitrarily assigned as N-(2-(4,4-difluoropiperidin-1-yl)-6-methylpyrimidin-4-yl)-2-((1S,6S)-6-fluoro-3-azabicyclo[4.2.0]octan-3-yl)-4-((2-hydroxyethyl)sulfonamido)benzamide (1.15 g, 1.97 mmol) as an off-white solid. First eluting peak LCMS: MS ESI (M+1)$^+$ 583.4. Second eluting peak LCMS: MS ESI (M+1)$^+$ 583.2. First eluting peak $^1$H NMR (400 MHz, DMSO-d$_6$) δ=11.79 (s, 1H), 7.91 (d, J=8.6 Hz, 1H), 7.47 (s, 1H), 7.20 (d, J=1.8 Hz, 1H), 7.08 (dd, J=2.0, 8.6 Hz, 1H), 3.85 (br t, J=5.4 Hz, 4H), 3.75 (t, J=6.4 Hz, 2H), 3.35-3.33 (m, 2H), 3.04-2.97 (m, 1H), 2.93 (d, J=3.0 Hz, 2H), 2.83-2.69 (m, 2H), 2.31 (s, 3H), 2.29-2.05 (m, 3H), 2.01-1.89 (m, 6H), 1.77 (quin, J=8.9 Hz, 1H). Second eluting peak $^1$H NMR (400 MHz, DMSO-d$_6$) δ=11.76 (s, 1H), 10.60-9.87 (m, 1H), 7.92 (d, J=8.6 Hz, 1H), 7.47 (s, 1H), 7.21 (d, J=1.7 Hz, 1H), 7.09 (dd, J=1.8, 8.6 Hz, 1H), 5.29-4.66 (m, 1H), 3.85 (br t, J=5.1 Hz, 4H), 3.75 (t, J=6.4 Hz, 2H), 3.35 (t, J=6.4 Hz, 2H), 3.05-2.98 (m, 1H), 2.93 (br d, J=2.8 Hz, 2H), 2.82-2.66 (m, 2H), 2.31 (s, 3H), 2.29-2.08 (m, 3H), 2.02-1.89 (m, 6H), 1.77 (br t, J=9.0 Hz, 1H). Racemic N-(2-(4,4-difluoropiperidin-1-yl)-6-methylpyrimidin-4-yl)-2-(6-(fluoromethyl)-3-azabicyclo[4.1.0]heptan-3-yl)-4-((2-hydroxyethyl)sulfonamido)benzamide was further purified by 3 successive rounds of chiral SFC (Daicel Chiralcel OJ-H (250 mm×30 mm, 5 µm); mobile phase: CO$_2$:MeOH 3:7 (0.1% NH$_3$H$_2$O)) followed by (Daicel Chiralcel OX (250 mm×30 mm, 10 µm); mobile phase: CO$_2$:MeOH 2:3 (0.1% NH$_3$H$_2$O)) followed by (Daicel Chiralpak AD (250 mm×30 mm, 10 µm); mobile phase: CO$_2$:ACN/EtOH 1:3 (0.1% NH$_3$H$_2$O)) to afford first eluting peak, arbitrarily assigned as N-(2-(4,4-difluoropiperidin-1-yl)-6-methylpyrimidin-4-yl)-2-((1S,6R)-6-(fluoromethyl)-3-azabicyclo[4.1.0]heptan-3-yl)-4-((2-hydroxyethyl)sulfonamido)benzamide (803.2 mg, 1.37 mmol) as an off-white solid and second eluting peak, arbitrarily assigned as N-(2-(4,4-difluoropiperidin-1-yl)-6-methylpyrimidin-4-yl)-2-((1R,6S)-6-(fluoromethyl)-3-azabicyclo[4.1.0]heptan-3-yl)-4-((2-hydroxyethyl)sulfonamido)benzamide (755.53 mg, 1.29 mmol) as an off-white solid. First eluting peak LCMS: MS ESI (M+1)$^+$ 583.3. Second eluting peak LCMS: MS ESI (M+1)$^+$ 583.3. First eluting peak $^1$H NMR (400 MHz, DMSO-d$_6$) δ=11.70 (s, 1H), 7.89 (d, J=8.6 Hz, 1H), 7.43 (s, 1H), 7.18 (d, J=1.2 Hz, 1H), 7.05 (dd, J=1.6, 8.6 Hz, 1H), 4.42-4.07 (m, 2H), 3.89 (br s, 4H), 3.75 (t, J=6.4 Hz, 2H), 3.32 (br s, 2H), 3.26-3.11 (m, 2H), 2.91-2.82 (m, 1H), 2.59 (dt, J=4.5, 11.6 Hz, 1H), 2.30 (s, 3H), 2.25-2.16 (m, 1H), 2.07-1.91 (m, 5H), 1.26 (br s, 2H), 0.76 (br d, J=4.8 Hz, 1H). Second eluting peak $^1$H NMR (400 MHz, DMSO-d$_6$) δ=11.98 (br s, 1H), 7.82 (br d, J=8.6 Hz, 1H), 7.45 (s, 1H), 6.98 (s, 1H), 6.88 (br d, J=8.6

Hz, 1H), 4.45-4.07 (m, 2H), 3.89 (br s, 4H), 3.72 (br t, J=6.4 Hz, 2H), 3.23-3.04 (m, 4H), 2.83 (br d, J=6.4 Hz, 1H), 2.65-2.53 (m, 1H), 2.35-2.18 (m, 4H), 2.08-1.89 (m, 5H), 1.37-1.21 (m, 2H), 0.75 (br d, J=4.8 Hz, 1H).

Examples 52-134

The following compounds were made using similar procedures to examples 1 to 9, 28 to 31, or 48 to 51 above:

| Example Number | Structure | NMR |
|---|---|---|
| 52 | 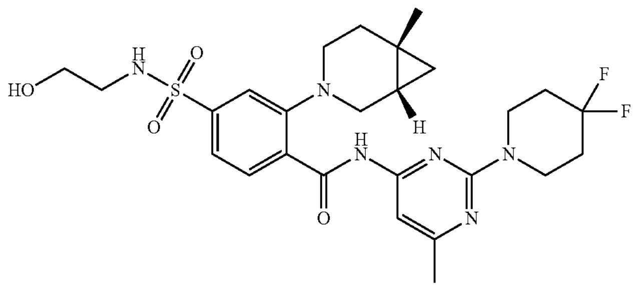 [SMILES: Cc1cc(NC(=O)c2ccc(S(=O)(=O)NCCO)cc2N2CC[C@]3(C)C[C@@H]3C2)nc(N2CCC(F)(F)CC2)n1] | $^1$H NMR (400 MHz, DMSO-$d_6$) δ = 11.21 (br s, 1H), 7.87 (br d, J = 7.3 Hz, 1H), 7.77 (br t, J = 5.9 Hz, 1H), 7.59 (s, 1H), 7.52 (br d, J = 8.0 Hz, 1H), 7.39 (br s, 1H), 3.89 (br s, 4H), 3.39-3.36 (m, 2H), 3.32 (br dd, J = 4.9, 11.3 Hz, 1H), 3.18 (br d, J = 11.1 Hz, 1H), 2.81 (q, J = 6.2 Hz, 4H), 2.32 (s, 3H), 1.97 (br d, J = 4.4 Hz, 5H), 1.78-1.69 (m, 1H), 1.08 (s, 3H), 0.99 (br d, J = 7.3 Hz, 1H), 0.83 (br s, 1H), 0.43 (br dd, J = 4.0, 8.6 Hz, 1H) |
| 53 | 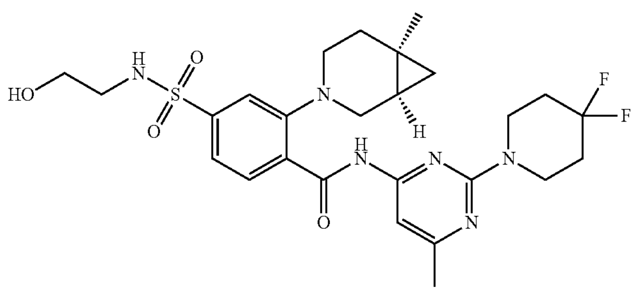 [SMILES: Cc1cc(NC(=O)c2ccc(S(=O)(=O)NCCO)cc2N2CC[C@@]3(C)C[C@H]3C2)nc(N2CCC(F)(F)CC2)n1] | $^1$H NMR (400 MHz, DMSO-$d_6$) δ = 11.25 (s, 1H), 7.86 (br d, J = 7.9 Hz, 1H), 7.77 (br t, J = 5.8 Hz, 1H), 7.60 (s, 1H), 7.52 (d, J = 7.9 Hz, 1H), 7.39 (br s, 1H), 3.89 (br s, 4H), 3.38 (t, J = 6.3 Hz, 2H), 3.32 (br dd, J = 5.2, 11.3 Hz, 1H), 3.18 (br d, J = 11.1 Hz, 1H), 2.86-2.72 (m, 4H), 2.33 (s, 3H), 2.04-1.92 (m, 5H), 1.79-1.66 (m, 1H), 1.08 (s, 3H), 1.04-0.95 (m, 1H), 0.82 (br s, 1H), 0.43 (dd, J = 3.9, 8.6 Hz, 1H) |
| 54 | 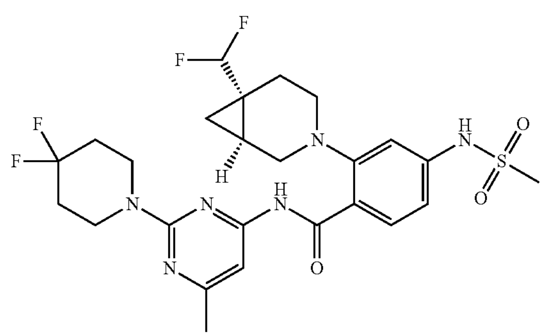 [SMILES: Cc1cc(NC(=O)c2ccc(NS(C)(=O)=O)cc2N2CC[C@]3(C(F)F)C[C@@H]3C2)nc(N2CCC(F)(F)CC2)n1] | $^1$H NMR (400 MHz, DMSO-$d_6$) δ = 11.58 (s, 1H), 10.87-10.07 (m, 1H), 8.15 (s, 1H), 7.92 (d, J = 8.5 Hz, 1H), 7.43 (s, 1H), 7.17 (d, J = 1.8 Hz, 1H), 7.08 (dd, J = 1.9, 8.6 Hz, 1H), 5.91-5.42 (m, 1H), 3.88 (br t, J = 5.1 Hz, 4H), 3.27 (br s, 1H), 3.17-3.08 (m, 4H), 2.99-2.92 (m, 1H), 2.56 (br s, 1H), 2.31 (s, 3H), 2.19-2.09 (m, 2H), 2.05-1.90 (m, 4H), 1.55-1.45 (m, 1H), 1.38 (br d, J = 4.4 Hz, 1H), 0.99 (br dd, J = 4.9, 9.2 Hz, 1H) |
| 55 | 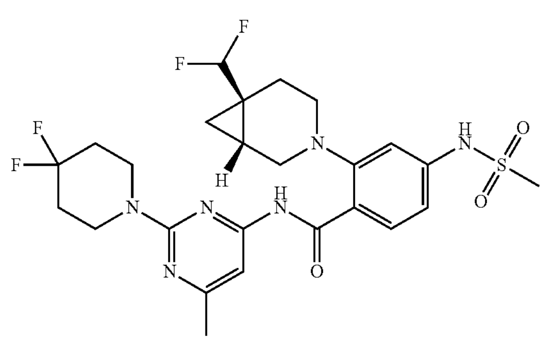 [SMILES: Cc1cc(NC(=O)c2ccc(NS(C)(=O)=O)cc2N2CC[C@@]3(C(F)F)C[C@H]3C2)nc(N2CCC(F)(F)CC2)n1] | $^1$H NMR (400 MHz, DMSO-$d_6$) δ = 11.58 (s, 1H), 10.87-10.07 (m, 1H), 8.15 (s, 1H), 7.92 (d, J = 8.5 Hz, 1H), 7.43 (s, 1H), 7.17 (d, J = 1.8 Hz, 1H), 7.08 (dd, J = 1.9, 8.6 Hz, 1H), 5.91-5.42 (m, 1H), 3.88 (br t, J = 5.1 Hz, 4H), 3.27 (br s, 1H), 3.17-3.08 (m, 4H), 2.99-2.92 (m, 1H), 2.56 (br s, 1H), 2.31 (s, 3H), 2.19-2.09 (m, 2H), 2.05-1.90 (m, 4H), 1.55-1.45 (m, 1H), 1.38 (br d, J = 4.4 Hz, 1H), 0.99 (br dd, J = 4.9, 9.2 Hz, 1H) |

| Example Number | Structure | NMR |
|---|---|---|
| 56 | 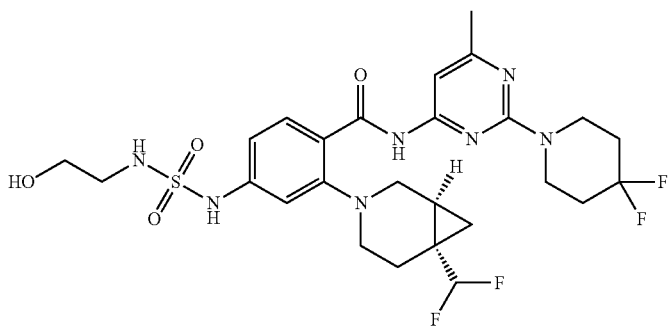 [SMILES: Cc1cc(NC(=O)c2ccc(NS(=O)(=O)NCCO)cc2N2CC[C@]3(C(F)F)C[C@@H]3C2)nc(N2CCC(F)(F)CC2)n1] | ¹H NMR (400 MHz, DMSO-d₆) δ = 11.85 (s, 1H), 10.20 (s, 1H), 7.91 (d, J = 8.7 Hz, 1H), 7.84 (t, J = 5.9 Hz, 1H), 7.45 (s, 1H), 7.16 (d, J = 1.8 Hz, 1H), 7.02 (dd, J = 1.9, 8.7 Hz, 1H), 5.80-5.51 (m, 1H), 3.89 (br t, J = 5.3 Hz, 4H), 3.36 (t, J = 6.5 Hz, 2H), 3.28-3.15 (m, 2H), 2.95-2.85 (m, 3H), 2.68-2.55 (m, 1H), 2.31 (s, 3H), 2.21-2.12 (m, 2H), 2.03-1.92 (m, 4H), 1.53-1.39 (m, 2H), 1.00 (br dd, J = 4.6, 9.2 Hz, 1H) |
| 57 | 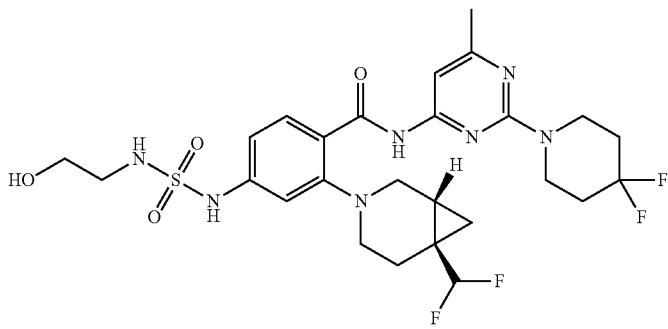 [SMILES: Cc1cc(NC(=O)c2ccc(NS(=O)(=O)NCCO)cc2N2CC[C@@]3(C(F)F)C[C@H]3C2)nc(N2CCC(F)(F)CC2)n1] | ¹H NMR (400 MHz, DMSO-d₆) δ = 11.85 (s, 1H), 10.19 (s, 1H), 7.98-7.77 (m, 2H), 7.45 (s, 1H), 7.16 (d, J = 1.8 Hz, 1H), 7.02 (dd, J = 2.1, 8.7 Hz, 1H), 5.80-5.51 (m, 1H), 3.89 (br t, J = 5.3 Hz, 4H), 3.36 (t, J = 6.5 Hz, 2H), 3.30-3.11 (m, 2H), 3.02-2.79 (m, 3H), 2.59 (dt, J = 6.1, 11.2 Hz, 1H), 2.31 (s, 3H), 2.20-2.12 (m, 2H), 2.03-1.92 (m, 4H), 1.54-1.38 (m, 2H), 0.99 (br dd, J = 4.3, 9.4 Hz, 1H) |
| 58 | 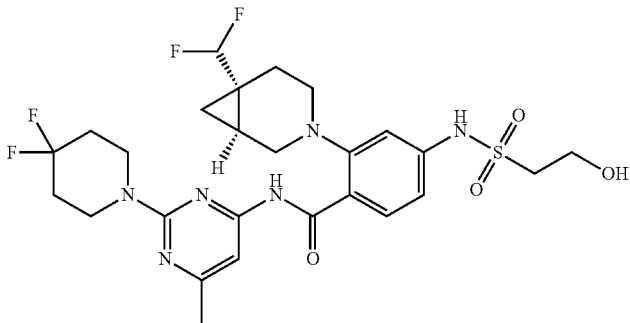 | ¹H NMR (400 MHz, DMSO-d₆) δ = 11.97 (s, 1H), 10.25 (s, 1H), 7.99 (s, 1H), 7.93 (d, J = 8.6 Hz, 1H), 7.21 (s, 1H), 7.12-7.08 (m, 1H), 5.84-5.50 (m, 1H), 3.76 (br t, J = 6.4 Hz, 2H), 3.36 (t, J = 6.4 Hz, 2H), 3.33-3.27 (m, 1H), 3.15 (br dd, J = 2.7, 11.3 Hz, 1H), 2.97-2.84 (m, 2H), 2.56 (br s, 1H), 2.45 (s, 3H), 2.15-1.87 (m, 10H), 1.56-1.44 (m, 2H), 1.05-0.92 (m, 1H) |
| 59 | 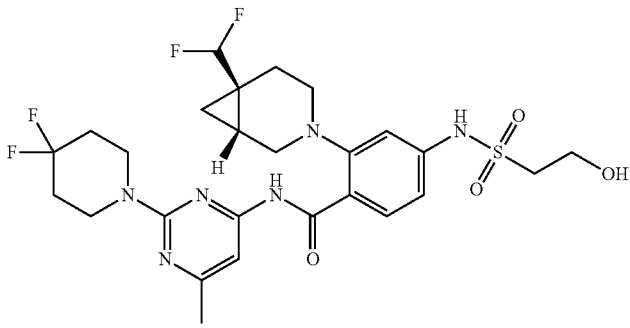 [SMILES: Cc1cc(NC(=O)c2ccc(NS(=O)(=O)CCO)cc2N2CC[C@@]3(C(F)F)C[C@H]3C2)nc(N2CCC(F)(F)CC2)n1] | ¹H NMR (400 MHz, DMSO-d₆) δ = 12.02-11.93 (m, 1H), 10.25 (s, 1H), 7.99 (s, 1H), 7.93 (d, J = 8.6 Hz, 1H), 7.21 (s, 1H), 7.11-7.08 (m, 1H), 5.85-5.48 (m, 1H), 3.76-3.74 (m, 2H), 3.36 (t, J = 6.4 Hz, 2H), 3.33-3.27 (m, 1H), 3.15 (br dd, J = 3.1, 11.4 Hz, 1H), 2.96-2.86 (m, 2H), 2.58 (br d, J = 4.1 Hz, 1H), 2.45 (s, 3H), 2.12-1.89 (m, 10H), 1.50 (br s, 2H), 1.04-0.91 (m, 1H) |

| Example Number | Structure | NMR |
|---|---|---|
| 60 | 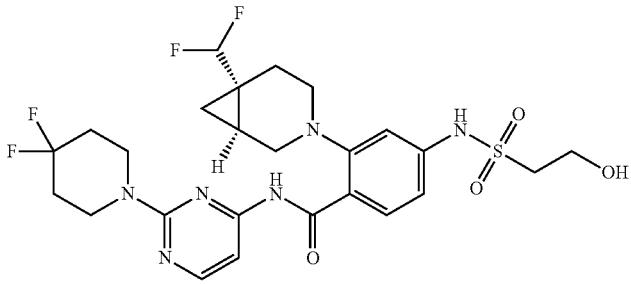 [SMILES: O=C(Nc1ccnc(N2CCC(F)(F)CC2)n1)c1ccc(NS(=O)(=O)CCO)cc1N1CC[C@]2(C(F)F)C[C@@H]2C1] | ¹H NMR (400 MHz, DMSO-d₆) δ = 11.67 (s, 1H), 10.61-9.83 (m, 1H), 8.34 (d, J = 5.5 Hz, 1H), 7.92 (d, J = 8.5 Hz, 1H), 7.51 (d, J = 5.5 Hz, 1H), 7.20 (d, J = 1.8 Hz, 1H), 7.09 (dd, J = 1.8, 8.7 Hz, 1H), 5.86-5.46 (m, 1H), 4.97 (br s, 1H), 3.89 (br t, J = 5.3 Hz, 4H), 3.76 (br t, J = 6.3 Hz, 2H), 3.37 (s, 2H), 3.29 (br d, J = 11.3 Hz, 1H), 3.12 (dd, J = 3.9, 11.4 Hz, 1H), 2.99-2.89 (m, 1H), 2.59-2.52 (m, 1H), 2.20-2.09 (m, 2H), 2.03-1.92 (m, 4H), 1.50 (br s, 1H), 1.37 (br d, J = 5.3 Hz, 1H), 1.04-0.97 (m, 1H) |
| 61 | 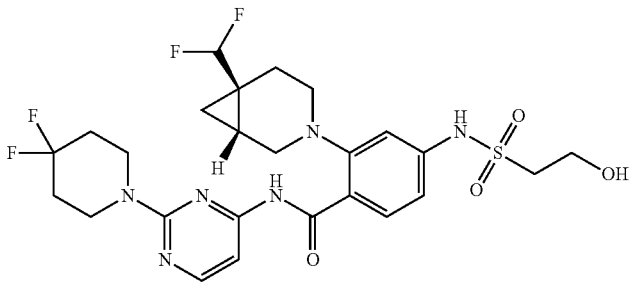 [SMILES: O=C(Nc1ccnc(N2CCC(F)(F)CC2)n1)c1ccc(NS(=O)(=O)CCO)cc1N1CC[C@@]2(C(F)F)C[C@H]2C1] | ¹H NMR (400 MHz, DMSO-d₆) δ = 11.71 (s, 1H), 8.33 (d, J = 5.5 Hz, 1H), 7.91 (d, J = 8.5 Hz, 1H), 7.51 (d, J = 5.4 Hz, 1H), 7.19 (s, 1H), 7.07 (br d, J = 8.5 Hz, 1H), 5.87-5.45 (m, 1H), 3.88 (br t, J = 4.9 Hz, 4H), 3.75 (t, J = 6.4 Hz, 2H), 3.35 (br s, 2H), 3.27 (br s, 1H), 3.17-3.07 (m, 1H), 3.01-2.90 (m, 1H), 2.62-2.53 (m, 1H), 2.21-2.09 (m, 2H), 2.03-1.90 (m, 4H), 1.49 (br d, J = 5.1 Hz, 1H), 1.41-1.33 (m, 1H), 1.00 (br dd, J = 4.4, 9.3 Hz, 1H) |
| 62 | 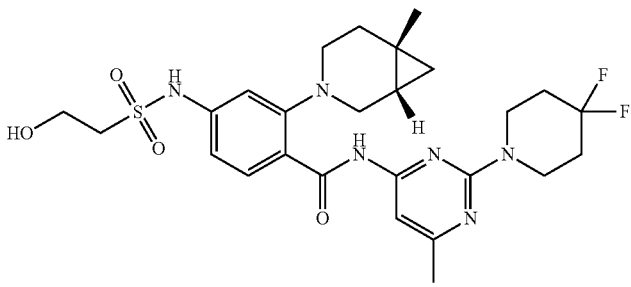 | ¹H NMR (400 MHz, DMSO-d₆) δ = 12.37 (s, 1H), 10.25 (s, 1H), 8.03 (s, 1H), 7.95 (d, J = 8.6 Hz, 1H), 7.20 (d, J = 1.5 Hz, 1H), 7.09 (dd, J = 1.6, 8.8 Hz, 1H), 3.75 (t, J = 6.4 Hz, 2H), 3.35 (t, J = 6.4 Hz, 2H), 3.28 (dd, J = 5.4, 11.4 Hz, 1H), 3.04 (br d, J = 11.4 Hz, 1H), 2.96-2.86 (m, 1H), 2.72 (br t, J = 5.9 Hz, 2H), 2.47 (s, 3H), 2.14-1.86 (m, 10H), 1.16 (s, 3H), 1.06-0.97 (m, 2H), 0.49 (dd, J = 3.8, 8.1 Hz, 1H) |
| 63 | 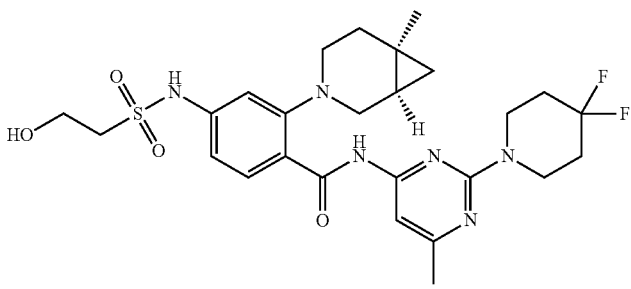 [SMILES: Cc1cc(NC(=O)c2ccc(NS(=O)(=O)CCO)cc2N2CC[C@@]3(C)C[C@H]3C2)nc(N2CCC(F)(F)CC2)n1] | ¹H NMR (400 MHz, DMSO-d₆) δ = 12.38 (s, 1H), 10.25 (s, 1H), 8.03 (s, 1H), 7.95 (d, J = 8.6 Hz, 1H), 7.20 (s, 1H), 7.13-7.02 (m, 1H), 3.75 (t, J = 6.4 Hz, 2H), 3.35 (t, J = 6.4 Hz, 2H), 3.28 (dd, J = 5.5, 11.4 Hz, 1H), 3.04 (br d, J = 11.4 Hz, 1H), 2.97-2.86 (m, 1H), 2.72 (br t, J = 5.9 Hz, 2H), 2.47 (s, 3H), 2.15-1.82 (m, 10H), 1.16 (s, 3H), 1.07-0.94 (m, 2H), 0.49 (dd, J = 3.9, 8.1 Hz, 1H) |

| Example Number | Structure | NMR |
|---|---|---|
| 64 | 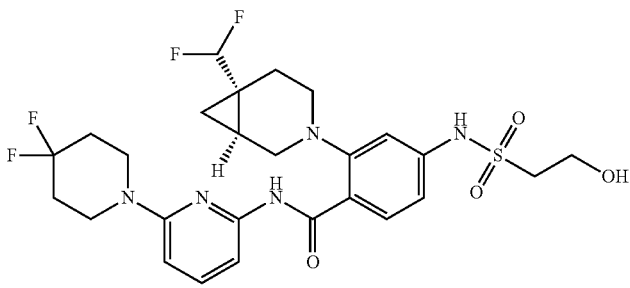 [SMILES: O=C(Nc1cccc(N2CCC(F)(F)CC2)n1)c1ccc(NS(=O)(=O)CCO)cc1N1CC[C@]2(C(F)F)C[C@@H]2C1] | ¹H NMR (400 MHz, CHLOROFORM-d) δ = 8.99-8.46 (m, 1H), 7.95 (d, J = 8.6 Hz, 1H), 7.78 (br s, 1H), 7.30 (br s, 1H), 7.22 (s, 1H), 7.10 (br d, J = 8.6 Hz, 1H), 6.61 (br d, J = 8.7 Hz, 1H), 5.42 (s, 1H), 4.14-3.91 (m, 2H), 3.77 (br t, J = 5.1 Hz, 4H), 3.42-3.13 (m, 4H), 3.04-2.78 (m, 2H), 2.35-2.09 (m, 6H), 1.47 (br d, J = 2.3 Hz, 1H), 1.16 (br s, 1H), 1.03 (br dd, J = 5.3, 9.4 Hz, 1H) |
| 65 | 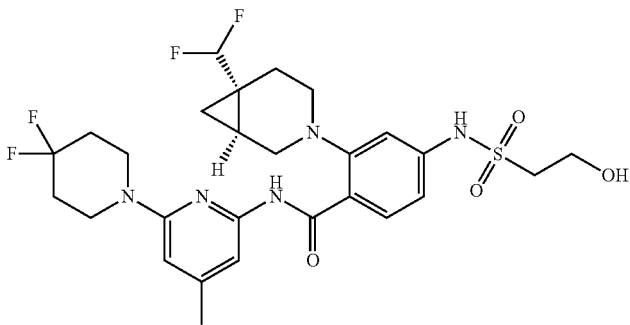 [SMILES: Cc1cc(NC(=O)c2ccc(NS(=O)(=O)CCO)cc2N2CC[C@]3(C(F)F)C[C@@H]3C2)nc(N2CCC(F)(F)CC2)c1] | ¹H NMR (400 MHz, DMSO-d₆) δ = 11.13 (s, 1H), 10.17 (s, 1H), 7.91 (d, J = 8.5 Hz, 1H), 7.51 (s, 1H), 7.18 (s, 1H), 7.08 (dd, J = 1.8, 8.6 Hz, 1H), 6.55 (s, 1H), 5.65 (br t, J = 56.6 Hz, 1H), 3.76 (t, J = 6.5 Hz, 2H), 3.68 (br d, J = 5.0 Hz, 4H), 3.35 (t, J = 6.5 Hz, 2H), 3.30 (br d, J = 11.6 Hz, 1H), 3.10 (br dd, J = 3.9, 11.3 Hz, 1H), 2.97 (br d, J = 11.3 Hz, 1H), 2.54 (br s, 1H), 2.26 (s, 3H), 2.18-2.12 (m, 2H), 2.02-1.92 (m, 4H), 1.48 (br d, J = 4.6 Hz, 1H), 1.37 (br d, J = 4.8 Hz, 1H), 0.98 (br dd, J = 4.6, 9.0 Hz, 1H) |
| 66 | 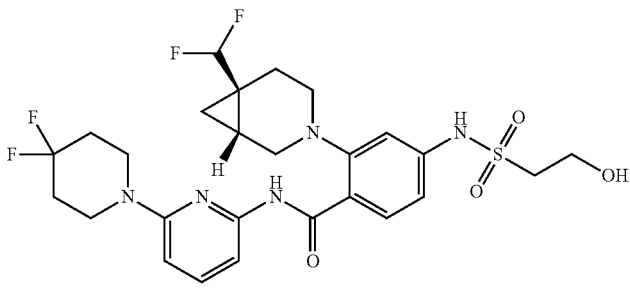 [SMILES: O=C(Nc1cccc(N2CCC(F)(F)CC2)n1)c1ccc(NS(=O)(=O)CCO)cc1N1CC[C@@]2(C(F)F)C[C@H]2C1] | ¹H NMR (400 MHz, CHLOROFORM-d) δ = 8.32-8.13 (m, 1H), 7.99 (d, J = 8.6 Hz, 1H), 7.70 (t, J = 8.2 Hz, 1H), 7.42 (br d, J = 7.8 Hz, 1H), 7.22 (s, 1H), 7.09 (dd, J = 1.5, 8.6 Hz, 1H), 6.57 (d, J = 8.7 Hz, 1H), 5.65-5.15 (m, 1H), 4.13-4.06 (m, 2H), 3.79-3.74 (m, 4H), 3.38-3.17 (m, 4H), 3.03-2.77 (m, 2H), 2.34-2.07 (m, 6H), 1.55-1.43 (m, 1H), 1.33-1.00 (m, 2H) |
| 67 | 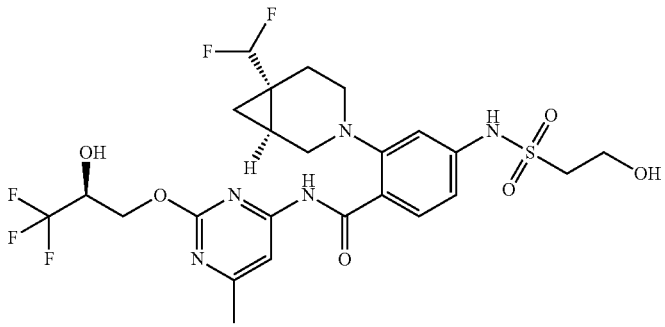 [SMILES: Cc1cc(NC(=O)c2ccc(NS(=O)(=O)CCO)cc2N2CC[C@]3(C(F)F)C[C@@H]3C2)nc(OC[C@H](O)C(F)(F)F)n1] | ¹H NMR (400 MHz, DMSO-d₆) δ = 7.60 (d, J = 8.7 Hz, 1H), 7.03-6.61 (m, 4H), 6.09-5.88 (m, 2H), 5.79-5.43 (m, 1H), 4.72 (dd, J = 3.4, 12.1 Hz, 1H), 4.49 (dd, J = 6.9, 12.0 Hz, 1H), 3.72 (t, J = 6.5 Hz, 2H), 3.30-3.22 (m, 4H), 3.18-3.12 (m, 1H), 2.98-2.85 (m, 1H), 2.65-2.57 (m, 1H), 2.11 (s, 3H), 2.04-1.78 (m, 2H), 1.44-1.33 (m, 1H), 0.94-0.69 (m, 2H) |

| Example Number | Structure | NMR |
|---|---|---|
| 68 | 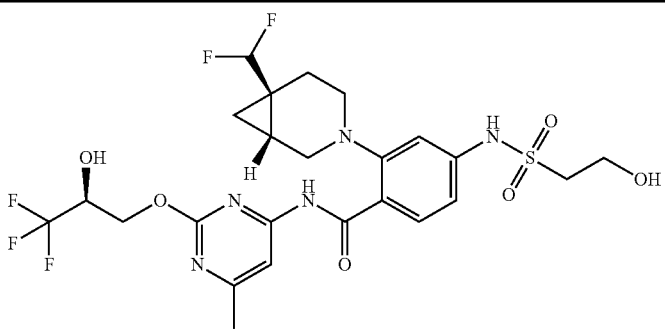 | $^1$H NMR (400 MHz, DMSO-$d_6$) δ = 7.61 (d, J = 8.6 Hz, 1H), 6.98-6.70 (m, 4H), 6.06-5.94 (m, 2H), 5.83-5.40 (m, 1H), 4.80-4.47 (m, 2H), 3.74 (br t, J = 6.4 Hz, 2H), 3.26 (br s, 4H), 3.21-3.16 (m, 1H), 2.94-2.88 (m, 1H), 2.74-2.68 (m, 1H), 2.11 (s, 3H), 2.07-1.91 (m, 2H), 1.44-1.35 (m, 1H), 0.90-0.74 (m, 2H) |
| 69 | 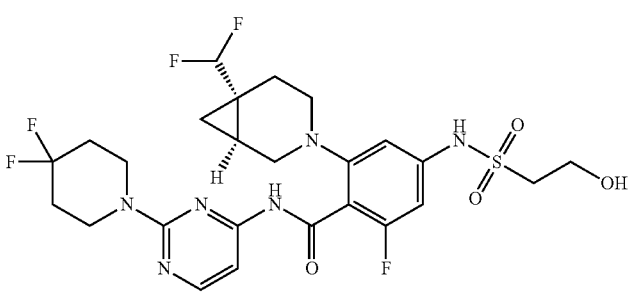 [SMILES: O=C(Nc1ccnc(N2CCC(F)(F)CC2)n1)c1c(F)cc(NS(=O)(=O)CCO)cc1N1CC[C@]2(C(F)F)C[C@@H]2C1] | $^1$H NMR (400 MHz, DMSO-$d_6$) δ = 10.75 (br s, 1H), 8.33 (br s, 1H), 7.40 (br s, 1H), 6.74-6.53 (m, 2H), 5.78-5.36 (m, 1H), 3.87 (br s, 3H), 3.76 (br t, J = 6.4 Hz, 2H), 3.28 (br d, J = 6.5 Hz, 5H), 3.14-3.01 (m, 2H), 2.64-2.52 (m, 2H), 1.96 (br d, J = 8.1 Hz, 4H), 1.71-1.57 (m, 1H), 1.35 (br s, 1H), 0.85-0.74 (m, 2H) |
| 70 | 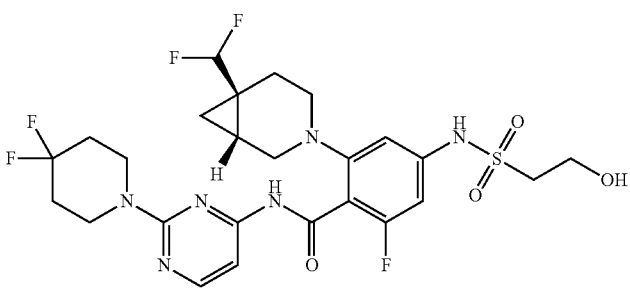 [SMILES: O=C(Nc1ccnc(N2CCC(F)(F)CC2)n1)c1c(F)cc(NS(=O)(=O)CCO)cc1N1CC[C@@]2(C(F)F)C[C@H]2C1] | $^1$H NMR (400 MHz, DMSO-$d_6$) δ = 10.76 (br s, 1H), 8.34 (br d, J = 4.3 Hz, 1H), 7.40 (br d, J = 3.6 Hz, 1H), 6.76-6.58 (m, 2H), 5.79-5.35 (m, 1H), 3.87 (br s, 3H), 3.76 (br t, J = 6.4 Hz, 2H), 3.34-3.25 (m, 5H), 3.15-2.99 (m, 2H), 2.74-2.52 (m, 2H), 1.96 (br d, J = 8.1 Hz, 4H), 1.73-1.55 (m, 1H), 1.35 (br s, 1H), 0.95-0.67 (m, 2H) |
| 71 | 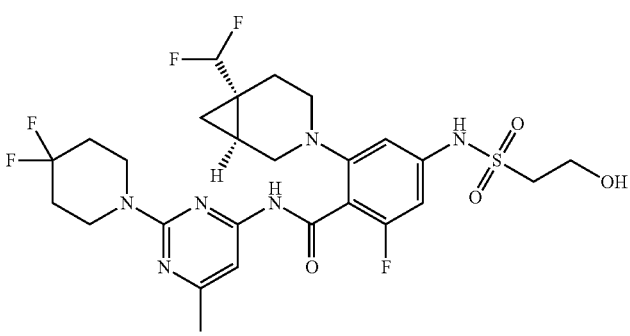 [SMILES: Cc1cc(NC(=O)c2c(F)cc(NS(=O)(=O)CCO)cc2N2CC[C@]3(C(F)F)C[C@@H]3C2)nc(N2CCC(F)(F)CC2)n1] | $^1$H NMR (400 MHz, DMSO-$d_6$) δ = 10.66 (br s, 1H), 10.20 (br s, 1H), 7.32 (br s, 1H), 6.78-6.57 (m, 2H), 5.73-5.35 (m, 1H), 3.78-3.73 (m, 6H), 3.32 (br t, J = 6.4 Hz, 2H), 3.11-3.00 (m, 2H), 2.60-2.51 (m, 2H), 2.31 (br s, 3H), 1.95 (br dd, J = 1.6, 9.4 Hz, 5H), 1.67-1.55 (m, 1H), 1.37-1.32 (m, 1H), 0.86-0.74 (m, 2H) |
| 72 | 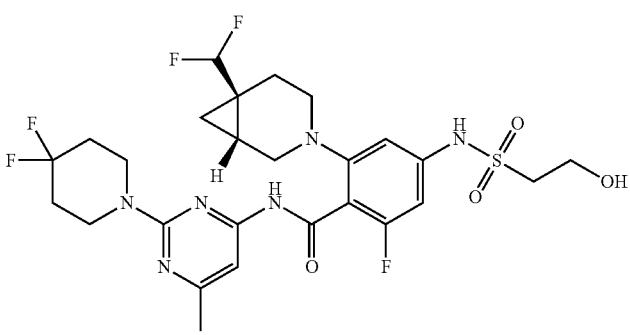 [SMILES: Cc1cc(NC(=O)c2c(F)cc(NS(=O)(=O)CCO)cc2N2CC[C@@]3(C(F)F)C[C@H]3C2)nc(N2CCC(F)(F)CC2)n1] | $^1$H NMR (400 MHz, DMSO-$d_6$) δ = 10.72 (br s, 1H), 10.28 (br s, 1H), 7.38 (br s, 1H), 6.85-6.64 (m, 2H), 5.81-5.40 (m, 1H), 4.00-3.93 (m, 4H), 3.39 (br t, J = 6.4 Hz, 4H), 3.20-3.06 (m, 2H), 2.67-2.58 (m, 2H), 2.37 (br s, 3H), 2.10-1.89 (m, 5H), 1.73-1.61 (m, 1H), 1.41 (br s, 1H), 0.92-0.81 (m, 2H) |

| Example Number | Structure | NMR |
|---|---|---|
| 73 | 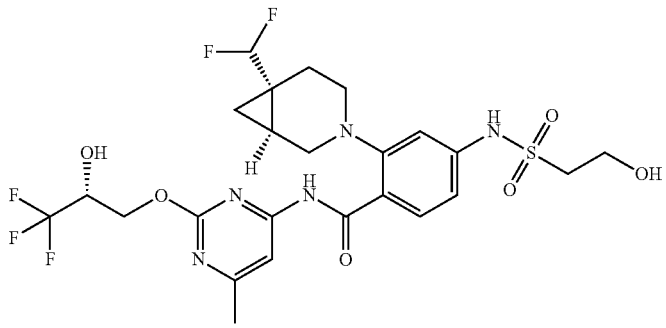 [SMILES: Cc1cc(NC(=O)c2ccc(NS(=O)(=O)CCO)cc2N2CC[C@]3(C(F)F)C[C@@H]3C2)nc(OC[C@@H](O)C(F)(F)F)n1] | $^1$H NMR (400 MHz, DMSO-$d_6$) δ = 7.60 (d, J = 8.6 Hz, 1H), 6.93-6.71 (m, 4H), 6.08-5.93 (m, 2H), 5.78-5.45 (m, 1H), 4.72 (dd, J = 3.6, 12.3 Hz, 1H), 4.49 (dd, J = 7.0, 12.0 Hz, 1H), 3.72 (t, J = 6.5 Hz, 2H), 3.29-3.21 (m, 4H), 3.18-3.09 (m, 1H), 2.99-2.88 (m, 1H), 2.67-2.55 (m, 1H), 2.11 (s, 3H), 2.06-1.97 (m, 1H), 1.93-1.80 (m, 1H), 1.43-1.33 (m, 1H), 0.92-0.74 (m, 2H) |
| 74 | 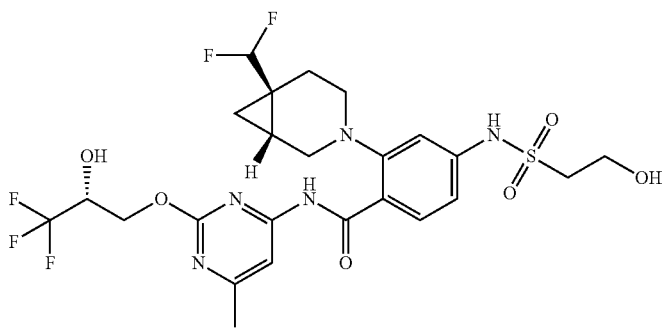 [SMILES: Cc1cc(NC(=O)c2ccc(NS(=O)(=O)CCO)cc2N2CC[C@@]3(C(F)F)C[C@H]3C2)nc(OC[C@@H](O)C(F)(F)F)n1] | $^1$H NMR (400 MHz, DMSO-$d_6$) δ = 7.59 (d, J = 8.7 Hz, 1H), 6.90-6.70 (m, 4H), 6.02-5.92 (m, 2H), 5.79-5.42 (m, 1H), 4.72 (br dd, J = 3.0, 11.8 Hz, 1H), 4.52 (dd, J = 6.8, 12.3 Hz, 1H), 3.72 (t, J = 6.4 Hz, 2H), 3.28 (br s, 4H), 3.19-3.13 (m, 1H), 2.93-2.86 (m, 1H), 2.71-2.61 (m, 1H), 2.11 (s, 3H), 2.04-1.92 (m, 2H), 1.41-1.34 (m, 1H), 0.90-0.78 (m, 2H) |
| 75 | 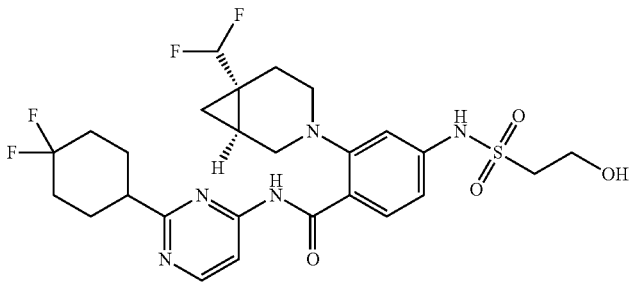 [SMILES: O=C(Nc1ccnc(C2CCC(F)(F)CC2)n1)c1ccc(NS(=O)(=O)CCO)cc1N1CC[C@]2(C(F)F)C[C@@H]2C1] | $^1$H NMR (400 MHz, DMSO-$d_6$) δ = 12.10 (br s, 1H), 8.65 (br d, J = 5.5 Hz, 1H), 8.08 (br d, J = 5.8 Hz, 1H), 7.94 (br d, J = 8.3 Hz, 1H), 7.20 (s, 1H), 7.09 (br d, J = 8.9 Hz, 1H), 5.94-5.45 (m, 1H), 3.76 (br t, J = 6.4 Hz, 2H), 3.28-3.12 (m, 2H), 3.02-2.86 (m, 2H), 2.42-2.33 (m, 2H), 2.16-1.86 (m, 11H), 1.54-1.43 (m, 2H), 1.06-0.95 (m, 1H) |
| 76 | 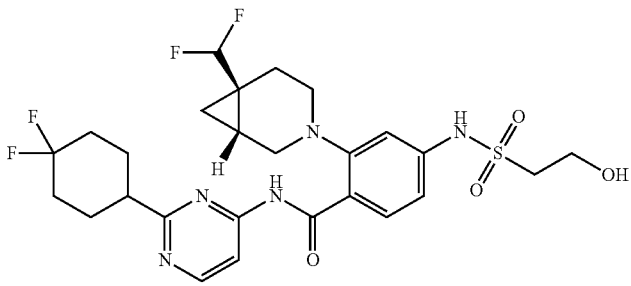 [SMILES: O=C(Nc1ccnc(C2CCC(F)(F)CC2)n1)c1ccc(NS(=O)(=O)CCO)cc1N1CC[C@@]2(C(F)F)C[C@H]2C1] | $^1$H NMR (400 MHz, DMSO-$d_6$) δ = 12.10 (s, 1H), 8.66 (d, J = 5.6 Hz, 1H), 8.09 (d, J = 5.6 Hz, 1H), 7.94 (d, J = 8.6 Hz, 1H), 7.21 (d, J = 1.9 Hz, 1H), 7.09 (dd, J = 1.9, 8.6 Hz, 1H), 5.68 (s, 1H), 3.83-3.66 (m, 2H), 3.17 (br dd, J = 3.1, 11.1 Hz, 2H), 2.99-2.85 (m, 2H), 2.75-2.53 (m, 2H), 2.10-1.82 (m, 11H), 1.51 (br s, 2H), 1.05-0.92 (m, 1H) |

| Example Number | Structure | NMR |
|---|---|---|
| 77 | 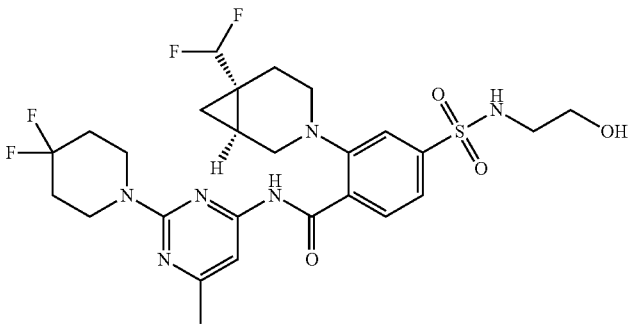 [SMILES: Cc1cc(NC(=O)c2ccc(S(=O)(=O)NCCO)cc2N2CC[C@]3(C(F)F)C[C@@H]3C2)nc(N2CCC(F)(F)CC2)n1] | ¹H NMR (400 MHz, DMSO-d₆) δ = 11.13 (s, 1H), 7.87 (br d, J = 7.1 Hz, 1H), 7.77 (t, J = 5.8 Hz, 1H), 7.62 (s, 1H), 7.56 (br d, J = 7.8 Hz, 1H), 7.39 (br s, 1H), 5.85-5.39 (m, 1H), 3.88 (br s, 4H), 3.40 (br s, 1H), 3.21 (br dd, J = 3.6, 11.2 Hz, 2H), 3.00 (br dd, J = 4.8, 11.5 Hz, 1H), 2.82 (q, J = 6.1 Hz, 2H), 2.69-2.56 (m, 2H), 2.32 (s, 3H), 2.11-2.04 (m, 1H), 1.94 (br d, J = 12.2 Hz, 5H), 1.46 (br s, 1H), 1.27-1.15 (m, 1H), 0.92 (br dd, J = 4.3, 8.9 Hz, 1H) |
| 78 | 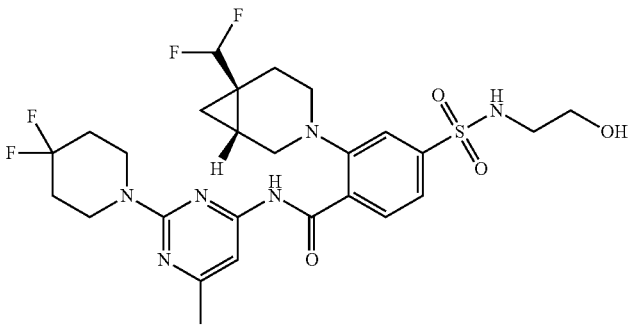 [SMILES: Cc1cc(NC(=O)c2ccc(S(=O)(=O)NCCO)cc2N2CC[C@@]3(C(F)F)C[C@H]3C2)nc(N2CCC(F)(F)CC2)n1] | ¹H NMR (400 MHz, DMSO-d₆) δ = 11.13 (br s, 1H), 7.87 (br d, J = 6.7 Hz, 1H), 7.77 (br t, J = 5.6 Hz, 1H), 7.63 (br s, 1H), 7.56 (br d, J = 7.9 Hz, 1H), 7.40 (br s, 1H), 5.79-5.44 (m, 1H), 4.73 (br t, J = 5.4 Hz, 1H), 3.88 (br s, 4H), 3.39 (br s, 1H), 3.28-3.14 (m, 2H), 3.00 (br d, J = 6.7 Hz, 1H), 2.82 (q, J = 6.0 Hz, 2H), 2.62 (dt, J = 4.3, 12.0 Hz, 2H), 2.32 (s, 3H), 2.11-2.05 (m, 1H), 1.96 (br s, 5H), 1.46 (br s, 1H), 1.21 (br d, J = 11.6 Hz, 1H), 0.97-0.87 (m, 1H) |
| 79 | 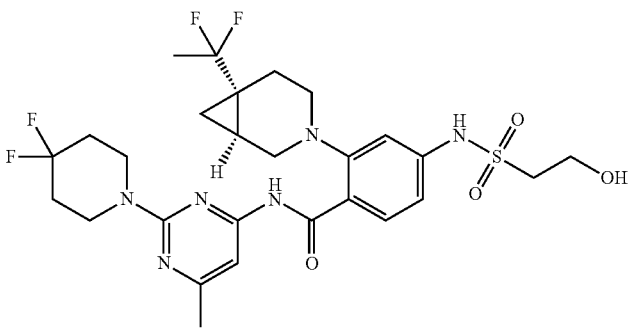 [SMILES: Cc1cc(NC(=O)c2ccc(NS(=O)(=O)CCO)cc2N2CC[C@]3(C(C)(F)F)C[C@@H]3C2)nc(N2CCC(F)(F)CC2)n1] | ¹H NMR (400 MHz, DMSO-d₆) δ = 11.67 (s, 1H), 7.87 (d, J = 8.6 Hz, 1H), 7.43 (s, 1H), 7.13 (d, J = 1.6 Hz, 1H), 7.02 (dd, J = 1.8, 8.6 Hz, 1H), 3.88 (br t, J = 5.3 Hz, 4H), 3.74 (t, J = 6.5 Hz, 2H), 3.27 (br d, J = 6.5 Hz, 4H), 3.10 (br dd, J = 3.7, 11.4 Hz, 1H), 2.92 (br d, J = 11.1 Hz, 1H), 2.30 (s, 3H), 2.14 (br d, J = 4.9 Hz, 1H), 2.01-1.93 (m, 4H), 1.62 (br t, J = 18.6 Hz, 3H), 1.55-1.49 (m, 1H), 1.31 (br s, 1H), 1.23 (br s, 2H) |
| 80 | 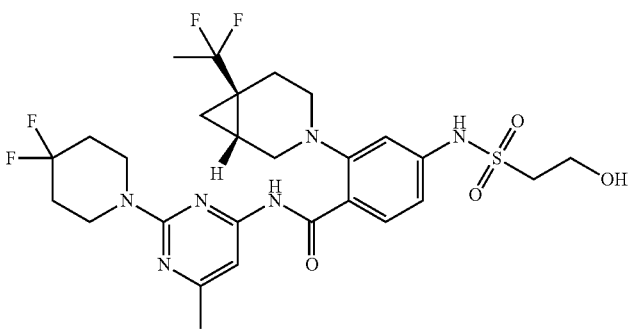 [SMILES: Cc1cc(NC(=O)c2ccc(NS(=O)(=O)CCO)cc2N2CC[C@@]3(C(C)(F)F)C[C@H]3C2)nc(N2CCC(F)(F)CC2)n1] | ¹H NMR (400 MHz, DMSO-d₆) δ = 11.68 (s, 1H), 7.87 (d, J = 8.6 Hz, 1H), 7.43 (s, 1H), 7.13 (d, J = 1.5 Hz, 1H), 7.02 (dd, J = 1.8, 8.6 Hz, 1H), 3.88 (br t, J = 5.3 Hz, 4H), 3.74 (t, J = 6.5 Hz, 2H), 3.26 (br t, J = 6.4 Hz, 4H), 3.12-3.08 (m, 1H), 2.92 (br d, J = 11.8 Hz, 1H), 2.30 (s, 3H), 2.14 (br d, J = 4.4 Hz, 1H), 2.02-1.92 (m, 4H), 1.62 (br t, J = 18.6 Hz, 3H), 1.52 (br d, J = 3.3 Hz, 1H), 1.31 (br t, J = 4.9 Hz, 1H), 1.22 (br s, 2H) |

| Example Number | Structure | NMR |
|---|---|---|
| 81 | 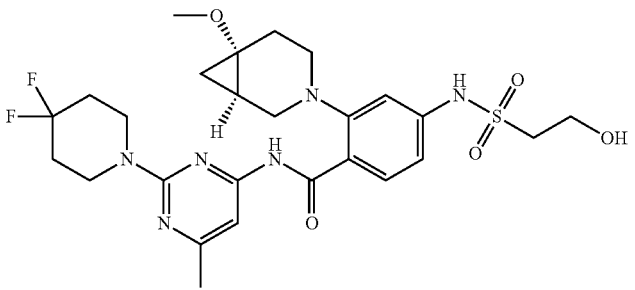 [SMILES: CO[C@]12CCN(c3cc(NS(=O)(=O)CCO)ccc3C(=O)Nc3cc(C)nc(N4CCC(F)(F)CC4)n3)C[C@H]1C2] | ¹H NMR (400 MHz, DMSO-d$_6$) δ = 11.75 (s, 1H), 7.86 (d, J = 8.7 Hz, 1H), 7.44 (s, 1H), 7.10 (s, 1H), 7.02 (br d, J = 8.3 Hz, 1H), 3.90 (br t, J = 5.3 Hz, 4H), 3.74 (t, J = 6.5 Hz, 2H), 3.28-3.22 (m, 3H), 3.19 (s, 3H), 2.96 (d, J = 11.4 Hz, 1H), 2.79 (br dd, J = 5.3, 6.7 Hz, 2H), 2.42-2.35 (m, 1H), 2.30 (s, 3H), 2.27-2.19 (m, 1H), 2.04-1.92 (m, 4H), 1.45 (td, J = 5.4, 10.6 Hz, 1H), 1.04-0.90 (m, 2H) |
| 82 | 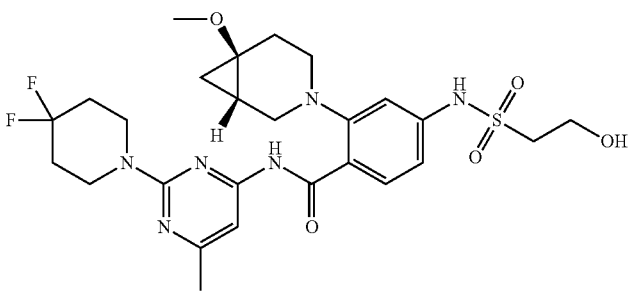 [SMILES: CO[C@@]12CCN(c3cc(NS(=O)(=O)CCO)ccc3C(=O)Nc3cc(C)nc(N4CCC(F)(F)CC4)n3)C[C@@H]1C2] | ¹H NMR (400 MHz, DMSO-d$_6$) δ = 11.77 (br s, 1H), 7.86 (d, J = 8.7 Hz, 1H), 7.44 (s, 1H), 7.09 (s, 1H), 7.05-6.96 (m, 1H), 3.90 (br t, J = 5.4 Hz, 4H), 3.73 (t, J = 6.5 Hz, 2H), 3.28-3.23 (m, 3H), 3.19 (s, 3H), 2.96 (br d, J = 11.0 Hz, 1H), 2.79 (br t, J = 6.2 Hz, 2H), 2.42-2.35 (m, 1H), 2.30 (s, 3H), 2.26-2.18 (m, 1H), 2.03-1.91 (m, 4H), 1.51-1.40 (m, 1H), 1.01 (t, J = 5.7 Hz, 1H), 0.97-0.90 (m, 1H) |
| 83 | 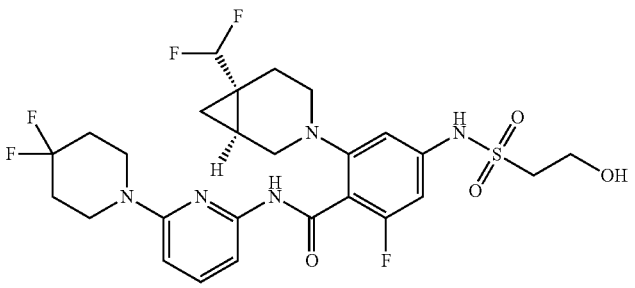 [SMILES: O=C(Nc1cccc(N2CCC(F)(F)CC2)n1)c1c(F)cc(NS(=O)(=O)CCO)cc1N1CC[C@]2(C(F)F)C[C@@H]2C1] | ¹H NMR (400 MHz, DMSO-d$_6$) δ = 10.25-9.91 (m, 1H), 7.61-7.40 (m, 2H), 6.64 (br d, J = 7.8 Hz, 1H), 6.54-6.36 (m, 2H), 5.74-5.30 (m, 1H), 3.75-3.61 (m, 6H), 3.08-2.97 (m, 4H), 1.94 (br d, J = 7.9 Hz, 5H), 1.75-1.67 (m, 1H), 1.32 (br s, 1H), 1.23 (s, 2H), 0.95 (br d, J = 3.1 Hz, 1H), 0.79-0.69 (m, 1H) |
| 84 | 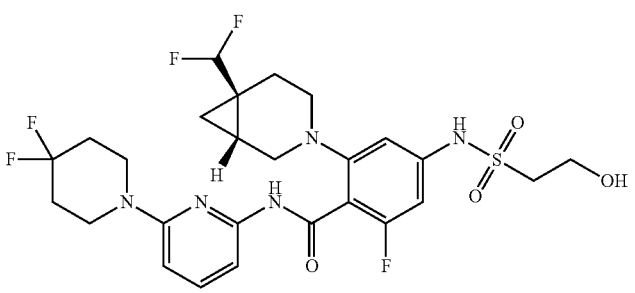 [SMILES: O=C(Nc1cccc(N2CCC(F)(F)CC2)n1)c1c(F)cc(NS(=O)(=O)CCO)cc1N1CC[C@@]2(C(F)F)C[C@H]2C1] | ¹H NMR (400 MHz, DMSO-d$_6$) δ = 10.16-10.05 (m, 1H), 7.61-7.46 (m, 2H), 6.64 (br d, J = 8.6 Hz, 1H), 6.55-6.38 (m, 2H), 5.98-5.03 (m, 1H), 3.69 (br d, J = 6.5 Hz, 6H), 3.07-2.98 (m, 4H), 2.00-1.90 (m, 5H), 1.76-1.67 (m, 1H), 1.33 (td, J = 2.0, 3.7 Hz, 1H), 1.23 (br s, 2H), 0.98-0.93 (m, 1H), 0.78-0.72 (m, 1H) |
| 85 | 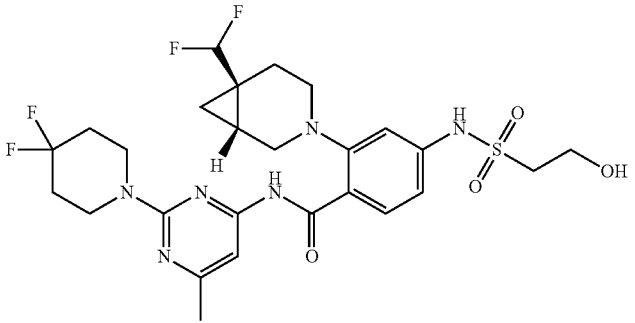 [SMILES: Cc1cc(NC(=O)c2ccc(NS(=O)(=O)CCO)cc2N2CC[C@@]3(C(F)F)C[C@H]3C2)nc(N2CCC(F)(F)CC2)n1] | ¹H NMR (400 MHz, DMSO-d$_6$) δ = 11.64 (s, 1H), 7.80 (d, J = 8.6 Hz, 1H), 7.44 (s, 1H), 7.00 (d, J = 1.8 Hz, 1H), 6.92 (dd, J = 1.9, 8.6 Hz, 1H), 3.88 (br t, J = 5.4 Hz, 4H), 3.72 (t, J = 6.6 Hz, 2H), 3.24 (br d, J = 11.6 Hz, 1H), 3.20-3.10 (m, 3H), 2.94 (br dd, J = 4.8, 11.8 Hz, 1H), 2.57 (dt, J = 4.5, 12.1 Hz, 1H), 2.29 (s, 3H), 2.28-2.22 (m, 1H), 2.21-2.13 (m, 1H), 2.07-1.88 (m, 4H), 1.80-1.66 (m, 1H), 1.55 (br t, J = 5.4 Hz, 1H), 1.32-1.13 (m, 2H) |

| Example Number | Structure | NMR |
|---|---|---|
| 86 | 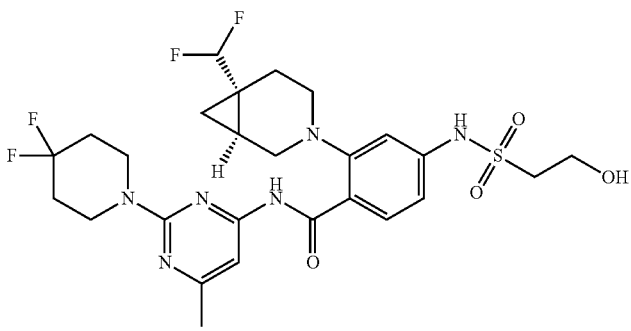 [SMILES: Cc1cc(NC(=O)c2ccc(NS(=O)(=O)CCO)cc2N2CC[C@]3(C(F)F)C[C@@H]3C2)nc(N2CCC(F)(F)CC2)n1] | ¹H NMR (400 MHz, DMSO-d₆) δ = 11.49 (s, 1H), 11.40-11.39 (m, 1H), 10.30 (s, 1H), 7.84 (d, J = 8.6 Hz, 1H), 7.50 (s, 1H), 7.20 (d, J = 1.8 Hz, 1H), 7.09 (dd, J = 1.8, 8.6 Hz, 1H), 3.92 (br t, J = 5.3 Hz, 4H), 3.76 (t, J = 6.5 Hz, 2H), 3.35 (t, J = 6.4 Hz, 2H), 3.30 (br d, J = 11.5 Hz, 1H), 3.23-3.09 (m, 1H), 3.04-2.92 (m, 1H), 2.67-2.55 (m, 1H), 2.39 (s, 3H), 2.28-2.12 (m, 2H), 2.08-1.88 (m, 4H), 1.77-1.67 (m, 1H), 1.43 (br t, J = 5.4 Hz, 1H), 1.26-1.15 (m, 1H) |
| 87 | 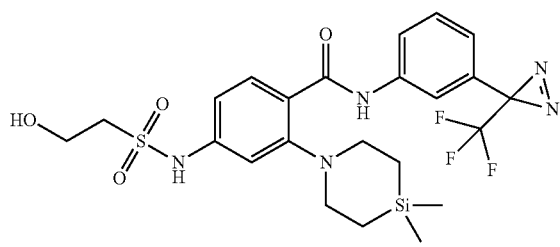 [SMILES: C[Si]1(C)CCN(c2cc(NS(=O)(=O)CCO)ccc2C(=O)Nc2cccc(C3(C(F)(F)F)N=N3)c2)CC1] | ¹H NMR (400 MHz, DMSO-d₆) δ = 11.77 (s, 1H), 10.23-9.91 (m, 1H), 7.83 (s, 1H), 7.79 (br s, 1H), 7.76 (d, J = 8.4 Hz, 1H), 7.51 (t, J = 8.0 Hz, 1H), 7.12 (d, J = 1.6 Hz, 1H), 7.02-6.94 (m, 2H), 5.10-4.79 (m, 1H), 3.75 (br t, J = 6.4 Hz, 2H), 3.30 (d, J = 2.4 Hz, 2H), 3.18 (br t, J = 6.1 Hz, 4H), 0.87 (br t, J = 6.0 Hz, 4H), 0.09 (s, 6H) |
| 88 | 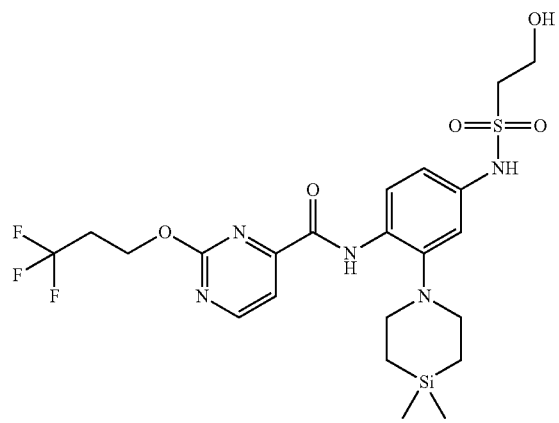 [SMILES: C[Si]1(C)CCN(c2cc(NS(=O)(=O)CCO)ccc2NC(=O)c2ccnc(OCCC(F)(F)F)n2)CC1] | ¹H NMR (400 MHz, DMSO-d₆) δ = 10.62 (s, 1H), 8.96 (d, J = 4.8 Hz, 1H), 8.33 (d, J = 8.8 Hz, 1H), 7.82 (d, J = 4.8 Hz, 1H), 7.12 (d, J = 2.4 Hz, 1H), 6.99 (dd, J = 2.4, 8.8 Hz, 1H), 4.66 (t, J = 6.0 Hz, 2H), 3.73 (t, J = 6.8 Hz, 2H), 3.21 (t, J = 6.8 Hz, 2H), 3.10-2.95 (m, 4H), 2.84 (tq, J = 5.6, 11.2 Hz, 2H), 1.04-0.94 (m, 4H), 0.16 (s, 6H) |
| 89 | 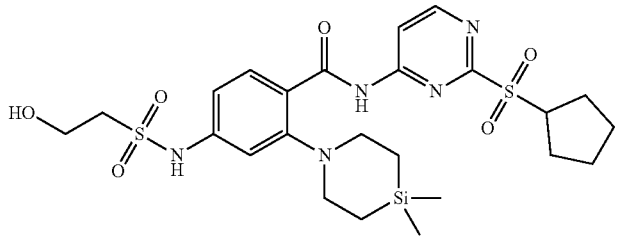 [SMILES: C[Si]1(C)CCN(c2cc(NS(=O)(=O)CCO)ccc2C(=O)Nc2ccnc(S(=O)(=O)C3CCCC3)n2)CC1] | ¹H NMR (400 MHz, DMSO-d₆) δ = 14.05 (s, 1H), 10.28 (s, 1H), 8.92 (d, J = 5.8 Hz, 1H), 8.45 (d, J = 5.6 Hz, 1H), 8.06 (d, J = 8.6 Hz, 1H), 7.29 (d, J = 2.0 Hz, 1H), 7.15 (dd, J = 2.0, 8.6 Hz, 1H), 4.21-4.09 (m, 1H), 3.76 (t, J = 6.4 Hz, 2H), 3.37 (t, J = 6.4 Hz, 2H), 3.24-3.09 (m, 4H), 2.01-1.86 (m, 4H), 1.77-1.52 (m, 4H), 1.10-0.95 (m, 4H), 0.19 (s, 6H) |

| Example Number | Structure | NMR |
|---|---|---|
| 90 | 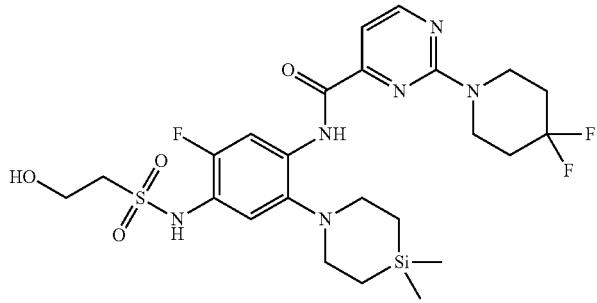 [SMILES: C[Si]1(C)CCN(c2cc(NS(=O)(=O)CCO)c(F)cc2NC(=O)c2ccnc(N3CCC(F)(F)CC3)n2)CC1] | ¹H NMR (400 MHz, CHLOROFORM-d) δ = 10.69 (br s, 1H), 8.63 (d, J = 4.8 Hz, 1H), 8.31 (br d, J = 12.4 Hz, 1H), 7.47-7.45 (m, 1H), 6.62 (s, 1H), 4.15-4.10 (m, 6H), 3.32 (t, J = 5.2 Hz, 2H), 3.11-3.08 (m, 4H), 2.48 (br s, 1H), 2.12-2.02 (m, 4H), 0.95-0.91 (m, 4H), 0.19 (s, 6H) |
| 91 | 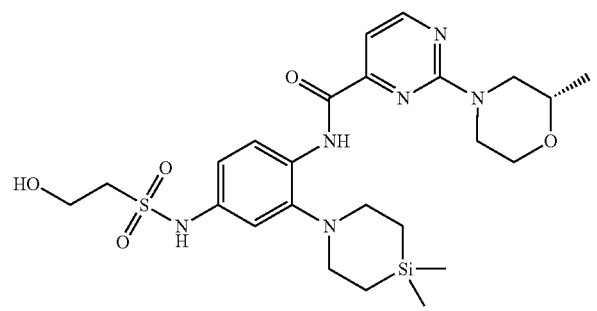 [SMILES: C[C@H]1CN(c2nccc(C(=O)Nc3ccc(NS(=O)(=O)CCO)cc3N3CC[Si](C)(C)CC3)n2)CCO1] | ¹H NMR (400 MHz, DMSO-d₆) δ = 10.28 (s, 1H), 8.69 (d, J = 4.8 Hz, 1H), 8.17 (d, J = 8.8 Hz, 1H), 7.31 (d, J = 4.8 Hz, 1H), 7.14 (d, J = 2.2 Hz, 1H), 6.98 (dd, J = 2.4, 8.6 Hz, 1H), 4.56 (br t, J = 14.4 Hz, 2H), 3.92 (dd, J = 2.4, 11.4 Hz, 1H), 3.72 (t, J = 6.8 Hz, 2H), 3.63-3.52 (m, 2H), 3.20 (t, J = 6.8 Hz, 2H), 3.11-2.69 (m, 6H), 1.17 (d, J = 6.2 Hz, 3H), 0.92-0.77 (m, 4H), 0.14 (s, 6H) |
| 92 | 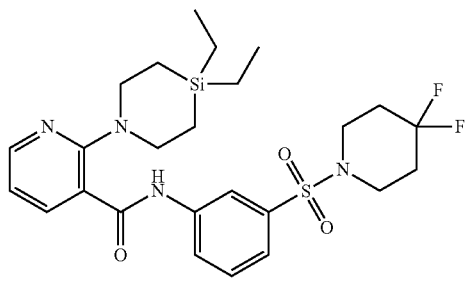 [SMILES: CC[Si]1(CC)CCN(c2ncccc2C(=O)Nc2cccc(S(=O)(=O)N3CCC(F)(F)CC3)c2)CC1] | ¹H NMR (400 MHz, DMSO-d₆) δ = 10.79 (s, 1H), 8.32 (t, J = 1.8 Hz, 1H), 8.25 (dd, J = 4.6, 2.0 Hz, 1H), 7.92 (dd, J = 8.2, 1.1 Hz, 1H), 7.73 (dd, J = 7.6, 2.0 Hz, 1H), 7.63 (t, J = 8.1 Hz, 1H), 7.48 (d, J = 8.6 Hz, 1H), 6.84 (dd, J = 7.5, 4.8 Hz, 1H), 3.67-3.54 (m, 4H), 3.10 (t, J = 5.5 Hz, 4H), 2.15-1.96 (m, 4H), 0.89-0.71 (m, 10H), 0.50 (q, J = 7.8 Hz, 4H) |
| 93 | 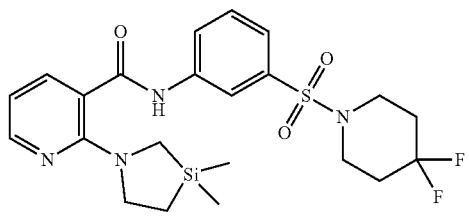 [SMILES: C[Si]1(C)CCN(c2ncccc2C(=O)Nc2cccc(S(=O)(=O)N3CCC(F)(F)CC3)c2)C1] | ¹H NMR (400 MHz, DMSO-d₆) δ = 10.73 (br. s., 1H), 8.31-8.14 (m, 2H), 7.97 (d, J = 7.8 Hz, 1H), 7.76-7.56 (m, 2H), 7.47 (d, J = 7.6 Hz, 1H), 6.74 (dd, J = 7.2, 4.8 Hz, 1H), 3.62 (t, J = 7.3 Hz, 2H), 3.11 (br. s., 4H), 2.63 (s, 2H), 2.14-2.00 (m, 4H), 0.86 (t, J = 7.2 Hz, 2H), 0.14 (s, 6H) |
| 94 | 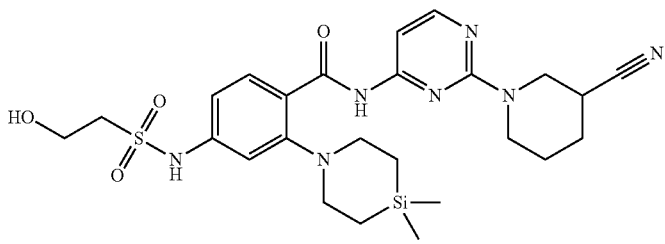 [SMILES: C[Si]1(C)CCN(c2cc(NS(=O)(=O)CCO)ccc2C(=O)Nc2ccnc(N3CCCC(C#N)C3)n2)CC1] | ¹H NMR (400 MHz, DMSO-d₆) δ = 12.80 (s, 1H), 10.21 (s, 1H), 8.33 (d, J = 5.6 Hz, 1H), 8.00 (d, J = 8.8 Hz, 1H), 7.53 (d, J = 5.6 Hz, 1H), 7.26 (d, J = 2.0 Hz, 1H), 7.10 (dd, J = 1.6, 8.8 Hz, 1H), 4.09-4.01 (m, 1H), 3.91 (br dd, J = 3.2, 13.2 Hz, 1H), 3.87-3.79 (m, 1H), 3.74 (t, J = 6.4 Hz, 2H), 3.70-3.62 (m, 1H), 3.35 (t, J = 6.4 Hz, 2H), 3.22-3.13 (m, 4H), 3.09-3.01 (m, 1H), 2.00-1.85 (m, 2H), 1.69-1.50 (m, 2H), 1.05-0.96 (m, 4H), 0.15 (s, 6H) |

| Example Number | Structure | NMR |
|---|---|---|
| 95 | 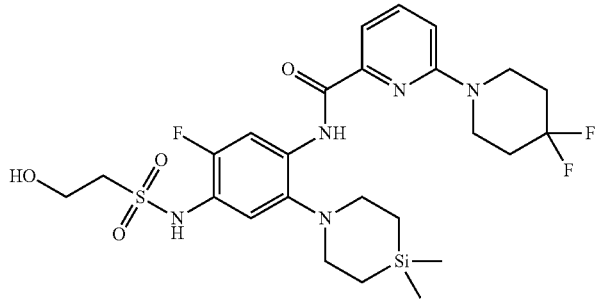 [SMILES: C[Si]1(C)CCN(c2cc(NS(=O)(=O)CCO)c(F)cc2NC(=O)c2cccc(N3CCC(F)(F)CC3)n2)CC1] | ¹H NMR (400 MHz, DMSO-d₆) δ =10.55 (s, 1H), 8.25 (d, J =12.6 Hz, 1H), 7.92-7.74 (m, 1H), 7.51 (d, J = 7.2 Hz, 1H),7.40-7.23 (m, 2H), 3.86 (br t, J = 5.4 Hz, 4H), 3.78 (t, J = 6.7 Hz, 2H), 3.22 (t, J = 6.7 Hz, 2H), 3.07-2.95 (m, 4H), 2.12-2.00 (m, 4H), 0.96-0.77 (m, 1H), 0.15 (s, 1H) |
| 96 | 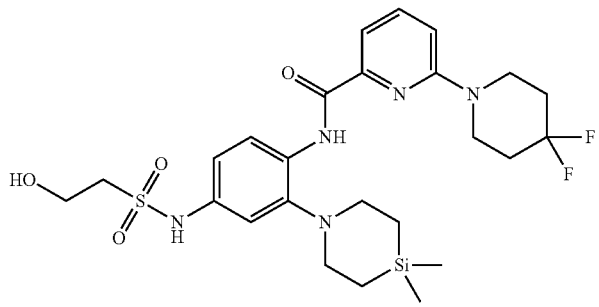 [SMILES: C[Si]1(C)CCN(c2cc(NS(=O)(=O)CCO)ccc2NC(=O)c2cccc(N3CCC(F)(F)CC3)n2)CC1] | ¹H NMR (400 MHz, DMSO-d₆) δ = 10.35 (s, 1H), 9.88-9.13 (m, 1H), 8.23 (d, J = 8.6 Hz, 1H), 7.82 (dd, J = 7.4, 8.4 Hz, 1H), 7.49 (d, J = 7.2 Hz, 1H), 7.27 (d, J = 8.6 Hz, 1H), 7.14 (d, J = 2.2 Hz, 1H), 6.97 (dd, J = 2.2, 8.6 Hz, 1H), 5.27-4.67 (m, 1H), 3.85 (br t, J = 5.4 Hz, 4H), 3.73 (t, J = 6.6 Hz, 2H), 3.20 (t, J = 6.6 Hz, 2H), 3.06-2.95 (m, 4H), 2.09-2.01 (m, 4H), 0.97-0.74 (m, 4H), 0.13 (s, 6H) |
| 97 | 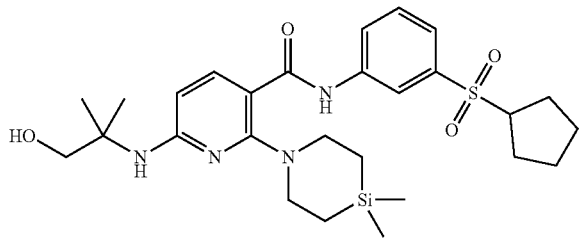 [SMILES: CC(C)(CO)Nc1ccc(C(=O)Nc2cccc(S(=O)(=O)C3CCCC3)c2)c(N2CC[Si](C)(C)CC2)n1] | ¹H NMR (400 MHz, DMSO-d₆) δ = 10.55 (s, 1H), 8.56 (t, J = 1.6 Hz, 1H), 8.41 (s, 1H), 8.13-8.01 (m, 2H), 7.65-7.51 (m, 2H), 6.50 (d, J = 8.6 Hz, 1H), 4.19 (s, 2H), 3.96-3.81 (m, 4H), 3.78-3.68 (m, 1H), 1.94-1.77 (m, 4H), 1.69-1.51 (m, 4H), 1.18 (s, 6H), 0.88-0.71 (m, 4H), 0.10 (s, 6H) |
| 98 | 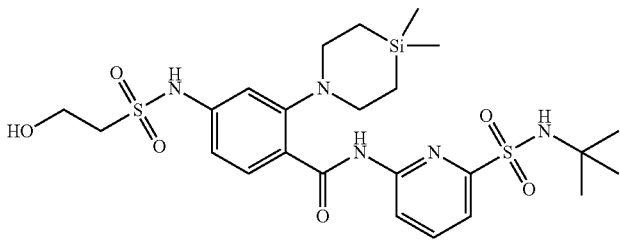 [SMILES: CC(C)(C)NS(=O)(=O)c1cccc(NC(=O)c2ccc(NS(=O)(=O)CCO)cc2N2CC[Si](C)(C)CC2)n1] | ¹H NMR (400 MHz, DMSO-d₆) δ = 12.89 (s, 1H), 8.28 (d, J = 8.4 Hz, 1H), 7.91 (t, J = 8.0 Hz, 1H), 7.83 (d, J = 8.8 Hz, 1H), 7.52 (d, J = 7.6 Hz, 1H), 7.22 (s, 1H), 7.07 (d, J = 1.6 Hz, 1H), 6.91 (dd, J = 2.0, 8.7 Hz, 1H), 3.57 (t, J = 6.4 Hz, 2H), 3.13 (br s, 2H), 3.02-2.92 (m, 4H), 0.97 (s, 9H), 0.88-0.74 (m, 4H), 0.00 (s, 6H) |
| 99 | 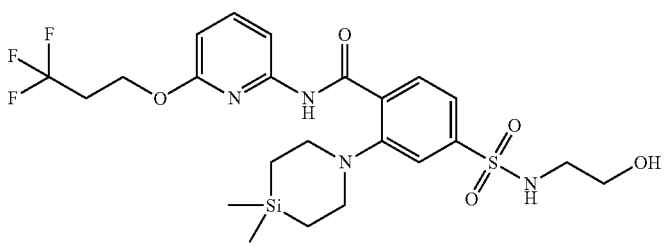 [SMILES: C[Si]1(C)CCN(c2cc(S(=O)(=O)NCCO)ccc2C(=O)Nc2cccc(OCCC(F)(F)F)n2)CC1] | ¹H NMR: (400 MHz, DMSO-d₆) δ = 12.16 (s, 1H), 8.07 (d, J = 8.2 Hz, 1H), 7.91 (d, J = 7.8 Hz, 1H), 7.82-7.75 (m, 2H), 7.61 (dd, J = 1.2, 8.2 Hz, 1H), 6.61 (d, J = 7.8 Hz, 1H), 4.72 (br d, J = 5.0 Hz, 1H), 4.45 (t, J = 6.2 Hz, 2H), 3.38 (br d, J = 5.0 Hz, 2H), 3.28 (br dd, J = 6.4, 12.2 Hz, 4H), 2.91-2.67 (m, 4H), 1.11-0.82 (m, 4H), 0.11 (s, 6H) |

| Example Number | Structure | NMR |
|---|---|---|
| 100 | 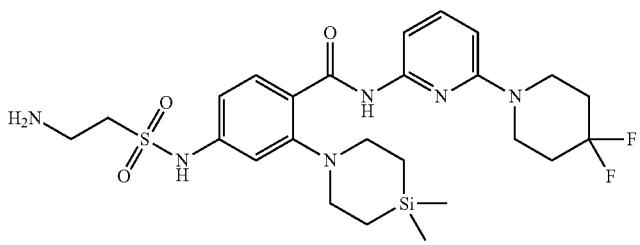 [SMILES: C[Si]1(C)CCN(c2cc(NS(=O)(=O)CCN)ccc2C(=O)Nc2cccc(N3CCC(F)(F)CC3)n2)CC1] | ¹H NMR (400 MHz, DMSO-d₆) δ = 12.41 (s, 1H), 7.94-7.92 (d, 8.80 Hz, 1H), 7.66-7.57 (m, 2H), 7.08 (d, J = 1.60 Hz, 1H), 7.00-6.97 (d, 8.80 Hz, 1H), 6.69-6.67 (d, J = 8.00 Hz, 1H), 3.68-3.66 (m, 4H), 3.27-3.23 (m, 2H), 3.18-3.15 (m, 4H), 3.04 (m, 2H), 2.02-1.95 (m, 4H), 1.01-0.99 (m, 4H), 0.14 (s, 6H). |
| 101 | 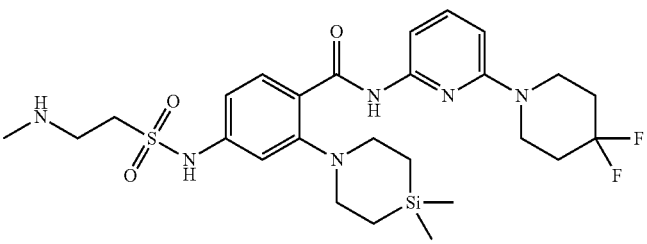 [SMILES: CNCCS(=O)(=O)Nc1ccc(C(=O)Nc2cccc(N3CCC(F)(F)CC3)n2)c(N2CC[Si](C)(C)CC2)c1] | ¹H NMR (400 MHz, DMSO-d₆) δ = 12.37 (s, 1H), 7.96-7.94 (d, 8.40 Hz, 1H), 7.66-7.58 (m, 2H), 7.13 (d, J = 1.60 Hz, 1H), 7.02-7.00 (d, J = 8.80 Hz, 1H), 6.70-6.68 (d, J = 8.00 Hz, 1H), 3.69-3.66 (m, 4H), 3.29-3.25 (m, 2H), 3.18-3.15 (m, 4H), 2.95-2.94 (m, 2H), 2.32 (s, 3H), 2.00-1.95 (m, 4H), 1.02-0.99 (m, 4H), 0.14 (s, 6H). |
| 102 | 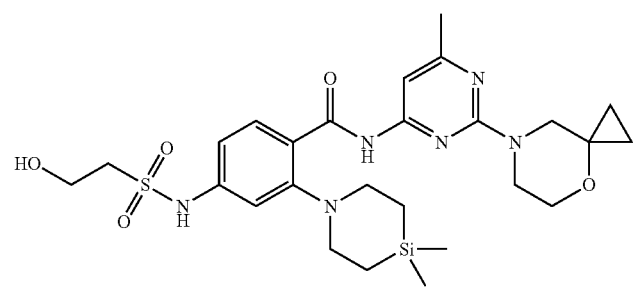 [SMILES: Cc1cc(NC(=O)c2ccc(NS(=O)(=O)CCO)cc2N2CC[Si](C)(C)CC2)nc(N2CCOC3(CC3)C2)n1] | ¹H NMR (400 MHz, DMSO-d₆) δ = 12.60 (s, 1H), 10.20 (s, 1H), 7.99-7.97 (d, J = 8.40 Hz, 1H), 7.45 (s, 1H), 7.23 (s, 1H), 7.11-7.09 (m, 1H), 3.77-3.68 (m, 8H), 3.37-3.34 (m, 2H), 3.17-3.14 (m, 4H), 2.31 (s, 3H), 0.99-0.96 (m, 4H), 0.74-0.71 (t, J = 6.4 Hz, 11.60 Hz, 2H), 0.59-0.56 (t, J = 6.40 Hz, 11.60 Hz, 2H), 0.14 (s, 6H) |
| 103 | 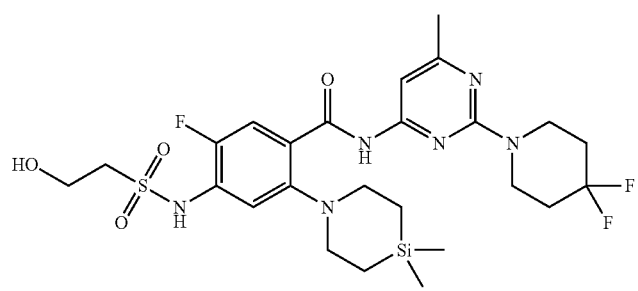 [SMILES: Cc1cc(NC(=O)c2cc(F)c(NS(=O)(=O)CCO)cc2N2CC[Si](C)(C)CC2)nc(N2CCC(F)(F)CC2)n1] | ¹H NMR (400 MHz, DMSO-d₆) δ = 13.03-12.85 (m, 1H), 7.80 (d, J = 11.5 Hz, 1H), 7.55 (br d, J = 7.2 Hz, 1H), 7.45 (s, 1H), 3.79 (t, J = 6.4 Hz, 2H), 3.40-3.31 (m, 6H), 3.19-3.13 (m, 4H), 2.32 (s, 3H), 2.04-1.92 (m, 4H), 1.00 (br d, J = 5.4 Hz, 4H), 0.15 (s, 6H) |
| 104 | 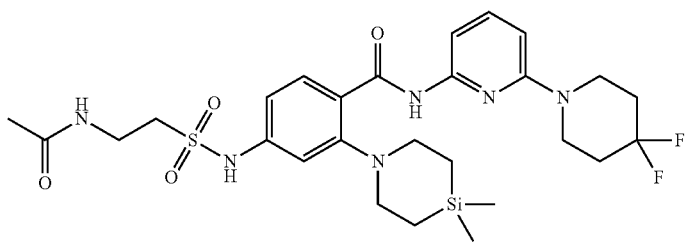 [SMILES: CC(=O)NCCS(=O)(=O)Nc1ccc(C(=O)Nc2cccc(N3CCC(F)(F)CC3)n2)c(N2CC[Si](C)(C)CC2)c1] | ¹H NMR (400 MHz, DMSO-d₆) δ = 12.26 (s, 1H), 10.23 (s, 1H), 8.02-7.96 (m, 2H), 7.66-7.61 (m, 2H), 7.24 (s, 1H), 7.09-7.07 (m, 1H), 6.72-6.70 (d, J = 7.60 Hz, 1H), 3.69-3.68 (m, 4H), 3.41-3.31 (m, 4H), 3.20-3.17 (m, 4H), 2.02-1.95 (m, 4H), 1.47 (s, 3H), 1.01-0.99 (m, 4H), 0.14 (s, 6H) |

| Example Number | Structure | NMR |
|---|---|---|
| 105 | 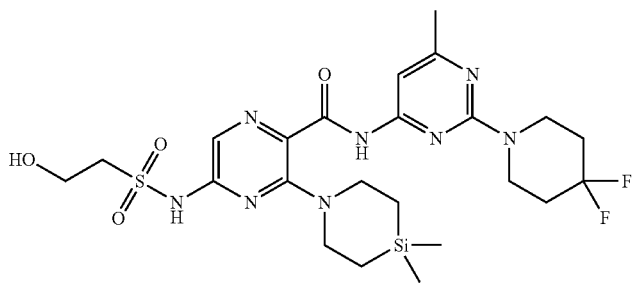 [SMILES: Cc1cc(NC(=O)c2ncc(NS(=O)(=O)CCO)nc2N2CC[Si](C)(C)CC2)nc(N2CCC(F)(F)CC2)n1] | ¹H NMR (400 MHz, DMSO-d₆) δ = 10.19 (br s, 1H), 7.39 (s, 1H), 7.27 (br s, 1H), 3.84 (br s, 4H), 3.79-3.73 (m, 2H), 3.69-3.62 (m, 4H), 3.61-3.54 (m, 2H), 2.29 (s, 3H), 2.01-1.90 (m, 4H), 0.89-0.82 (m, 4H), 0.06 (s, 6H) |
| 106 | 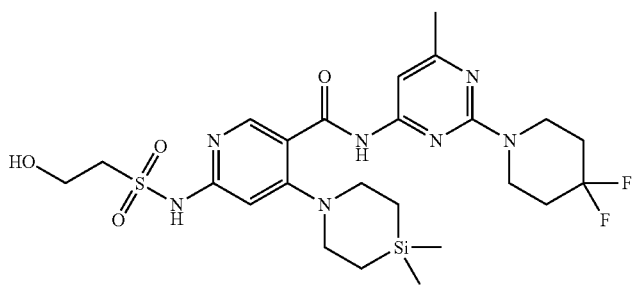 [SMILES: Cc1cc(NC(=O)c2cnc(NS(=O)(=O)CCO)cc2N2CC[Si](C)(C)CC2)nc(N2CCC(F)(F)CC2)n1] | ¹H NMR (400 MHz, DMSO-d₆) δ = 11.04 (br s, 1H), 8.08 (br s, 1H), 7.32 (br s, 1H), 6.52 (s, 1H), 3.85 (br s, 4H), 3.73 (t, J = 7.2 Hz, 2H), 2.29 (s, 3H), 2.05-1.88 (m, 4H), 0.87 (br t, J = 5.6 Hz, 4H), 0.09 (s, 6H) |
| 107 | 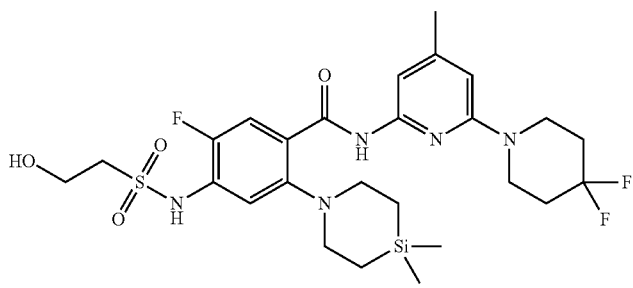 [SMILES: Cc1cc(NC(=O)c2cc(F)c(NS(=O)(=O)CCO)cc2N2CC[Si](C)(C)CC2)nc(N2CCC(F)(F)CC2)c1] | ¹H NMR (400 MHz, DMSO-d₆) δ = 12.52 (s, 1H), 10.0 (s, 1H), 7.82-7.79 (d, J = 11.60 Hz, 1H), 7.52-7.51 (d, J = 4.00 Hz, 2H), 6.59 (s, 1H), 3.79-3.78 (m, 2H), 3.66-3.65 (m, 4H), 3.47 (m, 2H), 3.40-3.38 (m, 4H), 2.27 (s, 3H), 1.99-1.96 (m, 4H), 1.01-0.98 (m, 4H), 0.14 (s, 6H). |
| 108 | 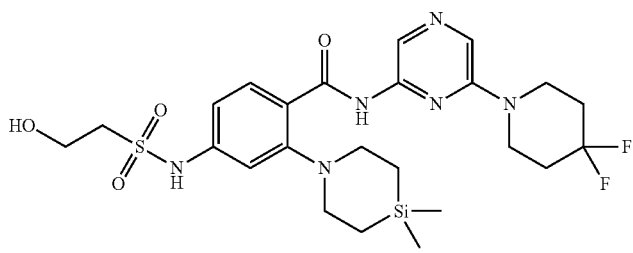 [SMILES: C[Si]1(C)CCN(c2cc(NS(=O)(=O)CCO)ccc2C(=O)Nc2cncc(N3CCC(F)(F)CC3)n2)CC1] | ¹H NMR (400 MHz, DMSO-d₆) δ = 12.69 (s, 1H), 1.0.18 (s, 1H), 8.84 (s, 1H), 8.20-8.19 (br s, 1H), 8.04-8.02 (d, J = 8.40 Hz, 1H), 7.26 (s, 1H), 7.12-7.09 (dd, J = 2.00 Hz, 8.80 Hz, 1H), 3.77-3.72 (m, 6H), 3.36-3.33 (m, 2H), 3.18-3.15 (m, 4H), 2.07-2.00 (m, 4H), 1.01-0.98 (m, 4H), 0.14 (s, 6H) |
| 109 | 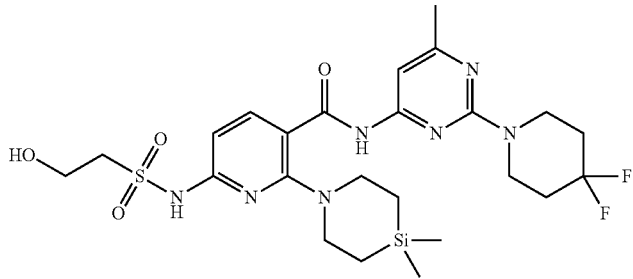 [SMILES: Cc1cc(NC(=O)c2ccc(NS(=O)(=O)CCO)nc2N2CC[Si](C)(C)CC2)nc(N2CCC(F)(F)CC2)n1] | ¹H NMR (400 MHz, DMSO-d₆) δ = 11.25 (br s, 1H), 7.89-7.87 (d, J = 8.00 Hz, 1H), 7.34 (s, 1H), 6.46-6.44 (d, J = 8.40 Hz, 1H), 3.86 (m, 4H), 3.78-377 (m, 2H), 3.69-3.67 (m, 2H), 3.45-342 (m, 5H), 2.30 (s, 3H), 2.00-1.93 (m, 4H), 0.91-0.88 (m, 4H), 0.08 (s, 6H) |

| Example Number | Structure | NMR |
|---|---|---|
| 110 | 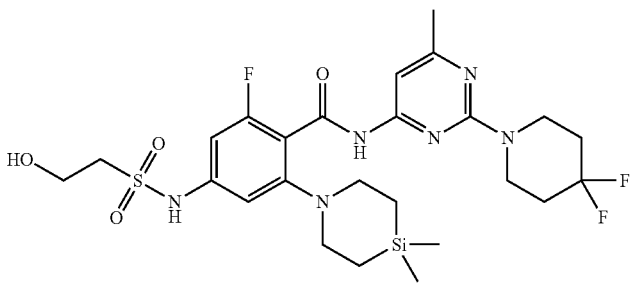 [SMILES: Cc1cc(NC(=O)c2c(F)cc(NS(=O)(=O)CCO)cc2N2CC[Si](C)(C)CC2)nc(N2CCC(F)(F)CC2)n1] | ¹H NMR (400 MHz, DMSO-d₆) δ = 10.67 (br s, 1H), 7.34 (br s, 1H), 6.71 (br s, 1H), 6.59 (br d, J = 11.4 Hz, 1H), 3.86 (br s, 2H), 3.76 (t, J = 6.6 Hz, 2H), 3.32 (br t, J = 6.4 Hz, 4H), 3.25 (br s, 4H), 2.30 (br s, 3H), 1.95 (br s, 4H), 0.73 (br s, 4H), 0.00 (s, 6H) |
| 111 | 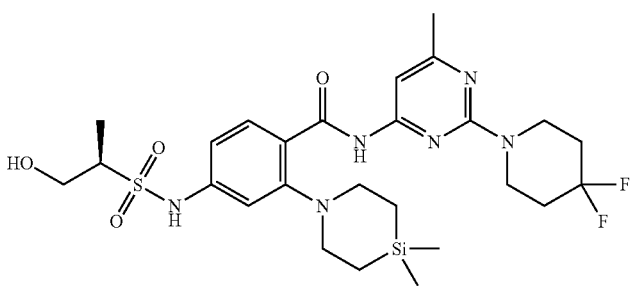 [SMILES: Cc1cc(NC(=O)c2ccc(NS(=O)(=O)[C@H](C)CO)cc2N2CC[Si](C)(C)CC2)nc(N2CCC(F)(F)CC2)n1] | ¹H NMR (400 MHz, DMSO-d₆ + D₂O) δ = 8.24 (s, 1H), 7.83 (br d, J = 8.7 Hz, 1H), 7.31 (s, 1H), 7.10 (s, 1H), 6.97 (br d, J = 8.8 Hz, 1H), 3.72 (br d, J = 5.1 Hz, 4H), 3.67 (br d, J = 4.6 Hz, 1H), 3.41-3.34 (m, 1H), 3.19-3.08 (m, 1H), 3.01 (br s, 4H), 2.18 (s, 3H), 1.84 (br t, J = 13.0 Hz, 4H), 1.15 (br d, J = 6.7 Hz, 3H), 0.86 (br s, 4H), 0.00 (s, 6H) |
| 112 | 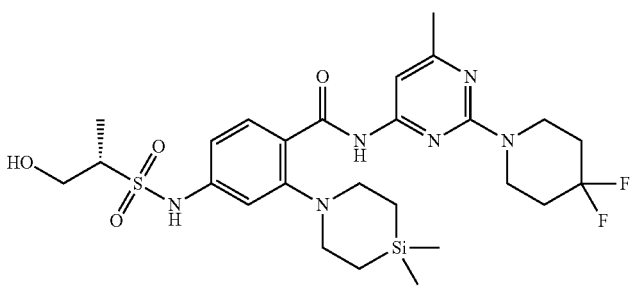 [SMILES: Cc1cc(NC(=O)c2ccc(NS(=O)(=O)[C@@H](C)CO)cc2N2CC[Si](C)(C)CC2)nc(N2CCC(F)(F)CC2)n1] | ¹H NMR (400 MHz, DMSO-d₆ + D₂O) δ = 8.23 (s, 1H), 7.83 (br d, J = 8.7 Hz, 1H), 7.31 (s, 1H), 7.11 (br s, 1H), 6.98 (br d, J = 8.4 Hz, 1H), 3.72 (br s, 4H), 3.68 (br d, J = 4.4 Hz, 1H), 3.38 (br s, 1H), 3.14 (br d, J = 6.6 Hz, 1H), 3.01 (br s, 4H), 2.18 (s, 3H), 1.89-1.77 (m, 4H), 1.15 (br d, J = 6.6 Hz, 3H), 0.86 (br s, 4H), 0.00 (s, 6H) |
| 113 | 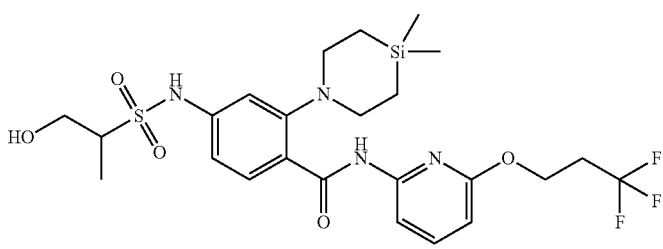 | ¹H NMR (400 MHz, DMSO-d₆) δ = 12.52 (s, 1H), 10.15 (s, 1H), 8.03-7.86 (m, 2H), 7.76 (t, J = 7.8 Hz, 1H), 7.26 (d, J = 2.0 Hz, 1H), 7.11 (dd, J = 2.0, 8.6 Hz, 1H), 6.57 (d, J = 8.2 Hz, 1H), 4.44 (t, J = 6.2 Hz, 2H), 3.83 (br dd, J = 4.4, 11.2 Hz, 1H), 3.48 (br d, J = 3.6 Hz, 1H), 3.31-3.24 (m, 1H), 3.21-3.11 (m, 4H), 2.85-2.71 (m, 2H), 1.28 (d, J = 6.8 Hz, 3H), 1.08-0.91 (m, 4H), 0.13 (s, 6H) |
| 114 | 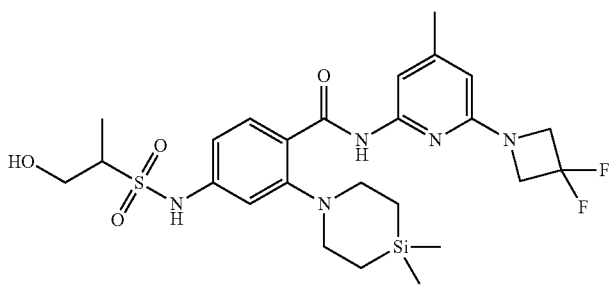 [SMILES: Cc1cc(NC(=O)c2ccc(NS(=O)(=O)C(C)CO)cc2N2CC[Si](C)(C)CC2)nc(N2CC(F)(F)C2)c1] | ¹H NMR (400 MHz, DMSO-d₆) δ = 12.45 (s, 1H), 10.14 (s, 1H), 7.97 (d, J = 8.6 Hz, 1H), 7.59 (s, 1H), 7.24 (s, 1H), 7.15-7.07 (m, 1H), 6.18 (s, 1H), 4.32 (br t, J = 12.4 Hz, 4H), 3.82 (br dd, J = 4.5, 11.1 Hz, 2H), 3.27 (br dd, J = 4.6, 7.0 Hz, 1H), 3.19-3.11 (m, 4H), 2.27 (s, 3H), 1.27 (d, J = 6.8 Hz, 3H), 1.05-0.95 (m, 4H), 0.14 (s, 6H) |

| Example Number | Structure | NMR |
|---|---|---|
| 115 | 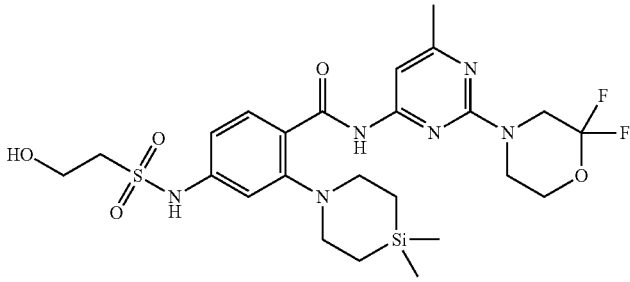 [SMILES: Cc1cc(NC(=O)c2ccc(NS(=O)(=O)CCO)cc2N2CC[Si](C)(C)CC2)nc(N2CCOC(F)(F)C2)n1] | ¹H NMR (400 MHz, DMSO-d₆) δ = 12.69 (s, 1H), 10.22 (s, 1H), 8.00-7.98 (d, J = 8.80 Hz, 1H), 7.55 (s, 1H), 7.26-7.25 (d, J = 1.60 Hz, 1H), 7.12 (d, J = 6.80 Hz, 1H), 7.10 (d, 2.00 Hz, 1H), 4.16-4.12 (m, 4H), 3.85 (m, 2H), 3.77-3.74 (t, J = 6.40 Hz, 16.80 Hz, 2H), 3.36 (t, 2H), 3.18-3.16 (m, 4H), 2.35 (s, 3H), 1.01-0.98 (m, 4H), 0.15 (s, 6H) |
| 116 | 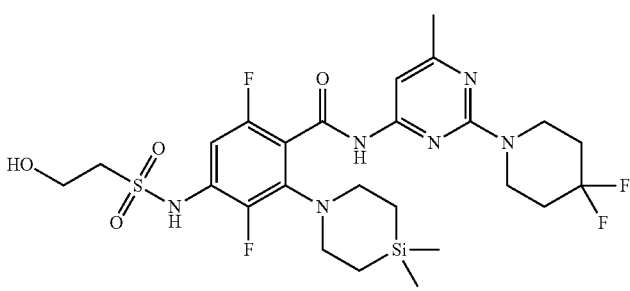 [SMILES: Cc1cc(NC(=O)c2c(F)cc(NS(=O)(=O)CCO)c(F)c2N2CC[Si](C)(C)CC2)nc(N2CCC(F)(F)CC2)n1] | ¹H NMR (400 MHz, DMSO-d₆) δ = 10.85 (br s, 1H), 7.33 (br s, 1H), 7.08-6.85 (m, 1H), 4.02-3.70 (m, 6H), 3.23 (br s, 6H), 2.36-2.23 (m, 3H), 2.12-1.70 (m, 4H), 0.70 (br s, 4H),-0.06 (br s, 6H) |
| 117 | 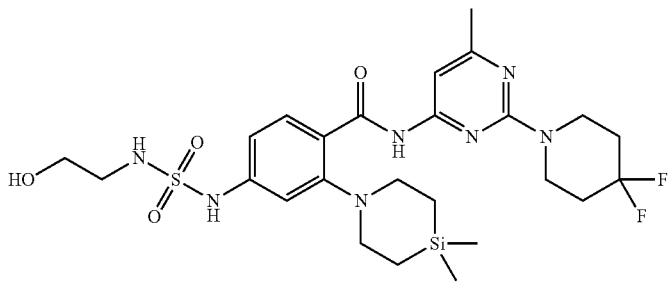 [SMILES: Cc1cc(NC(=O)c2ccc(NS(=O)(=O)NCCO)cc2N2CC[Si](C)(C)CC2)nc(N2CCC(F)(F)CC2)n1] | ¹H NMR (400 MHz, DMSO-d₆) δ = 13.53 (s, 1H), 10.18 (s, 1H), 8.07 (s, 1H), 8.01 (d, J = 8.8 Hz, 1H), 7.81 (br t, J = 5.7 Hz, 1H), 7.21 (d, J = 1.9 Hz, 1H), 7.07 (dd, J = 2.0, 8.8 Hz, 1H), 3.36 (t, J = 6.6 Hz, 2H), 3.26-3.10 (m, 4H), 2.89 (q, J = 6.3 Hz, 3H), 2.48 (s, 3H), 2.21-1.74 (m, 8H), 1.10-0.96 (m, 4H), 0.19 (s, 6H) |
| 118 | 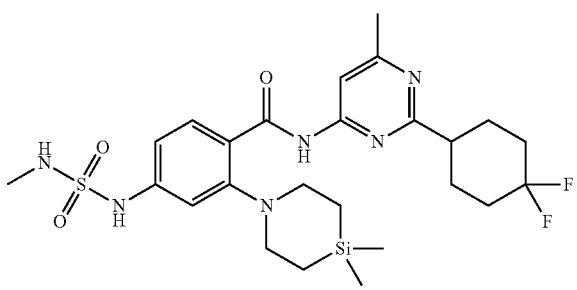 [SMILES: CNS(=O)(=O)Nc1ccc(C(=O)Nc2cc(C)nc(C3CCC(F)(F)CC3)n2)c(N2CC[Si](C)(C)CC2)c1] | ¹H NMR (400 MHz, DMSO-d₆) δ = 13.42 (s, 1H), 10.17 (s, 1H), 8.14-7.83 (m, 2H), 7.62 (br d, J = 4.8 Hz, 1H), 7.21 (d, J = 2.0 Hz, 1H), 7.08 (dd, J = 2.0, 8.8 Hz, 1H), 3.26-3.08 (m, 4H), 2.95-2.80 (m, 1H), 2.49-2.43 (m, 6H), 2.12-1.79 (m, 8H), 1.09-1.00 (m, 4H), 0.19 (s, 6H |
| 119 | 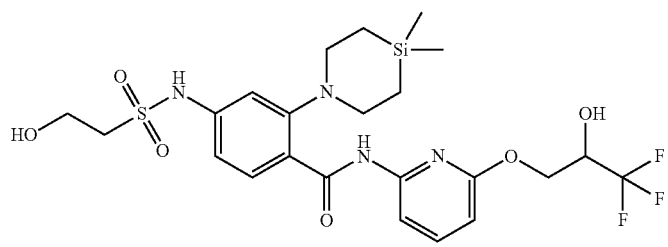 | ¹H NMR (400 MHz, DMSO-d₆) δ = 12.44 (s, 1H), 10.14 (s, 1H), 7.97 (d, 1H), 7.91 (d, 1H), 7.78 (m, 1H), 7.23 (s, 1H), 7.08 (d, 1H), 6.59 (d, 1H), 4.41 (m, 4H), 3.75 (m, 2H), 3.34 (m, 2H), 3.20 (m, 4H), 0.98 (m, 4H), 0.13 (s, 6H) |

| Example Number | Structure | NMR |
|---|---|---|
| 120 | 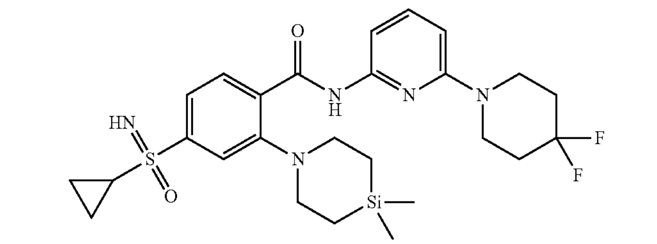 [SMILES: C[Si]1(C)CCN(c2cc(S(=N)(=O)C3CC3)ccc2C(=O)Nc2cccc(N3CCC(F)(F)CC3)n2)CC1] | ¹H NMR (400 MHz, DMSO-d₆) δ = 8.09 (br d, J = 7.5 Hz, 1H), 7.81 (br s, 1H), 7.76-7.57 (m, 3H), 6.71 (br d, J = 5.1 Hz, 1H), 3.64 (br s, 4H), 3.25 (br s, 4H), 2.73 (br s, 1H), 1.96 (br s, 4H), 1.17-1.08 (m, 1H), 0.95 (br s, 7H), 0.10 (br s, 6H) |
| 121 | 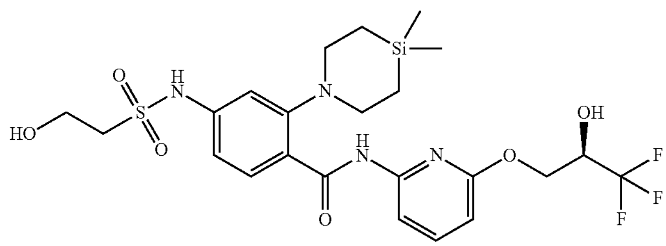 [SMILES: C[Si]1(C)CCN(c2cc(NS(=O)(=O)CCO)ccc2C(=O)Nc2cccc(OC[C@@H](O)C(F)(F)F)n2)CC1] | ¹H NMR (400 MHz, METHANOL-d₄) δ = 7.88 (d, J = 8.8 Hz, 1H), 7.75 (d, J = 7.8 Hz, 1H), 7.55 (t, J = 7.9 Hz, 1H), 7.09 (d, J = 2.0 Hz, 1H), 6.95 (dd, J = 2.0, 8.6 Hz, 1H), 6.43 (d, J = 8.1 Hz, 1H), 4.41-4.14 (m, 3H), 3.77 (t, J = 6.2 Hz, 2H), 3.18 (s, 2H), 3.13-3.08 (m, 4H), 0.99-0.86 (m, 4H), 0.00 (s, 6H) |
| 122 | 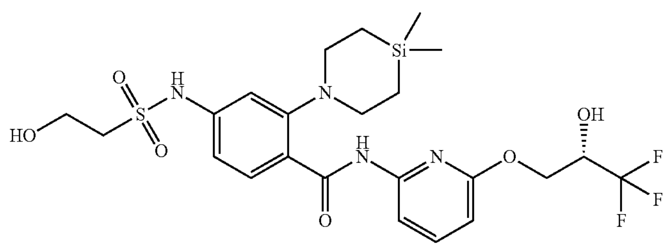 | ¹H NMR (400 MHz, METHANOL-d₄) δ = 8.06 (d, J = 8.6 Hz, 1H), 7.92 (d, J = 7.9 Hz, 1H), 7.72 (t, J = 7.9 Hz, 1H), 7.27 (d, J = 2.0 Hz, 1H), 7.12 (dd, J = 2.0, 8.6 Hz, 1H), 6.60 (d, J = 8.0 Hz, 1H), 4.51 (dd, J = 3.9, 11.0 Hz, 1H), 4.44-4.29 (m, 2H), 3.94 (t, J = 6.2 Hz, 2H), 3.35 (t, J = 6.2 Hz, 2H), 3.30-3.24 (m, 4H), 1.13-1.04 (m, 4H), 0.17 (s, 6H) |
| 123 | 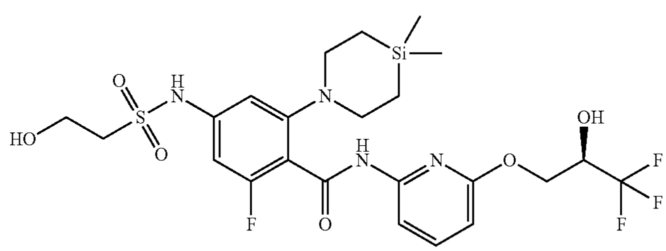 [SMILES: C[Si]1(C)CCN(c2cc(NS(=O)(=O)CCO)cc(F)c2C(=O)Nc2cccc(OC[C@@H](O)C(F)(F)F)n2)CC1] | ¹H NMR (400 MHz, DMSO-d₆) δ = 7.82-7.71 (m, 2H), 6.72 (s, 1H), 6.63-6.56 (m, 2H), 4.49-4.35 (m, 2H), 4.33-4.22 (m, 1H), 3.75 (t, J = 6.5 Hz, 2H), 3.32 (br t, J = 6.5 Hz, 2H), 3.27 (br t, J = 5.8 Hz, 4H), 0.71 (br t, J = 5.9 Hz, 4H), −0.02 (s, 6H) |
| 124 | 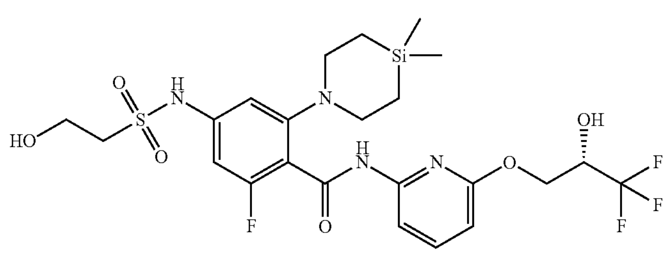 [SMILES: C[Si]1(C)CCN(c2cc(NS(=O)(=O)CCO)cc(F)c2C(=O)Nc2cccc(OC[C@H](O)C(F)(F)F)n2)CC1] | ¹H NMR (400 MHz, DMSO-d₆) δ = 10.60 (s, 1H), 7.85-7.68 (m, 2H), 6.72 (s, 1H), 6.63-6.55 (m, 2H), 4.49-4.37 (m, 2H), 4.32-4.23 (m, 1H), 3.75 (t, J = 6.5 Hz, 2H), 3.32 (br t, J = 6.5 Hz, 2H), 3.27 (br t, J = 5.6 Hz, 4H), 0.72 (br t, J = 5.9 Hz, 4H), −0.02 (s, 6H) |
| 125 | 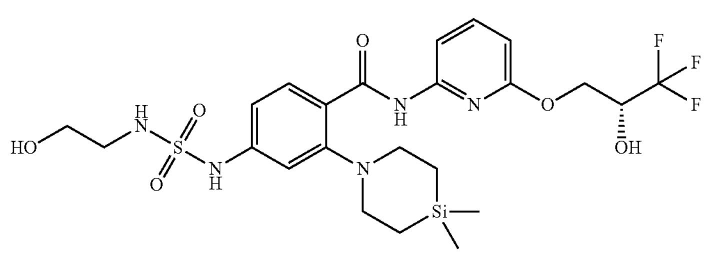 [SMILES: C[Si]1(C)CCN(c2cc(NS(=O)(=O)NCCO)ccc2C(=O)Nc2cccc(OC[C@@H](O)C(F)(F)F)n2)CC1] | ¹H NMR (400 MHz, DMSO-d₆) δ = 12.60 (br s, 1H), 10.11 (s, 1H), 7.93 (dd, J = 8.4, 16.1 Hz, 2H), 7.83-7.72 (m, 2H), 7.16 (s, 1H), 7.07-6.99 (m, 1H), 6.59 (d, J = 7.8 Hz, 2H), 4.48-4.28 (m, 3H), 3.36 (t, J = 6.5 Hz, 2H), 3.18 (br s, 4H), 2.88 (q, J = 6.2 Hz, 2H), 1.05-0.92 (m, 4H), 0.14 (s, 6H) |

| Example Number | Structure | NMR |
|---|---|---|
| 126 | 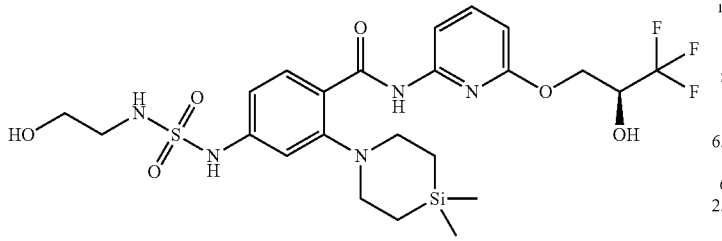 | ¹H NMR (400 MHz, DMSO-$d_6$) δ = 12.59 (br s, 1H), 10.12 (s, 1H), 7.93 (dd, J = 8.3, 17.5 Hz, 2H), 7.82-7.72 (m, 2H), 7.16 (s, 1H), 7.03 (dd, J = 1.7, 8.6 Hz, 1H), 6.59 (d, J = 7.9 Hz, 2H), 4.47-4.27 (m, 3H), 3.36 (t, J = 6.6 Hz, 2H), 3.19 (br s, 4H), 2.88 (q, J = 6.4 Hz, 2H), 1.06-0.91 (m, 4H), 0.14 (s, 6H) |
| 127 | 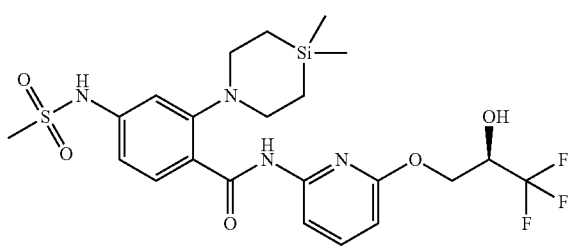 [SMILES: C[Si]1(C)CCN(c2cc(NS(C)(=O)=O)ccc2C(=O)Nc2cccc(OC[C@@H](O)C(F)(F)F)n2)CC1] | ¹H NMR (400 MHz, DMSO-$d_6$) δ = 12.45 (s, 1H), 10.19 (s, 1H), 7.99 (d, J = 8.6 Hz, 1H), 7.91 (d, J = 7.9 Hz, 1H), 7.77 (t, J = 8.0 Hz, 1H), 7.22 (d, J = 1.8 Hz, 1H), 7.09 (dd, J = 1.9, 8.6 Hz, 1H), 6.60 (d, J = 8.0 Hz, 1H), 4.33 (br dd, J = 4.3, 9.3 Hz, 3H), 3.19 (br s, 4H), 3.10 (s, 3H), 1.11-0.90 (m, 4H), 0.13 (s, 6H) |
| 128 | 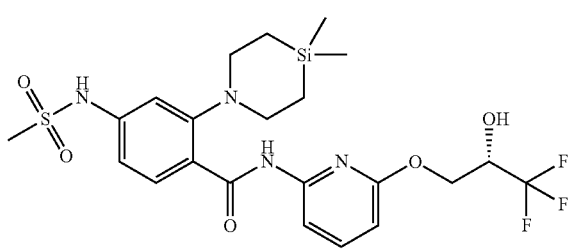 [SMILES: C[Si]1(C)CCN(c2cc(NS(C)(=O)=O)ccc2C(=O)Nc2cccc(OC[C@H](O)C(F)(F)F)n2)CC1] | ¹H NMR (400 MHz, DMSO-$d_6$) δ = 12.51-12.40 (m, 1H), 10.19 (s, 1H), 7.99 (d, J = 8.6 Hz, 1H), 7.91 (d, J = 7.9 Hz, 1H), 7.77 (t, J = 8.0 Hz, 1H), 7.21 (d, J = 1.9 Hz, 1H), 7.09 (dd, J = 2.1, 8.6 Hz, 1H), 6.60 (d, J = 7.9 Hz, 1H), 4.44-4.37 (m, 3H), 3.25-3.14 (m, 4H), 3.11 (s, 3H), 0.99 (br d, J = 6.0 Hz, 4H), 0.13 (s, 6H) |
| 129 | 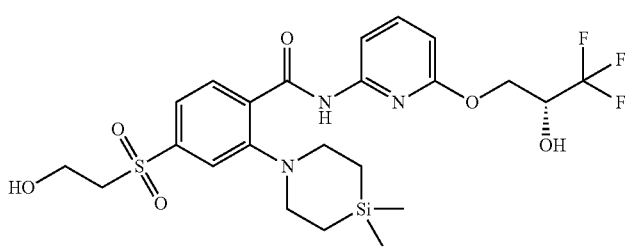 [SMILES: C[Si]1(C)CCN(c2cc(S(=O)(=O)CCO)ccc2C(=O)Nc2cccc(OC[C@@H](O)C(F)(F)F)n2)CC1] | ¹H NMR (400 MHz, DMSO-$d_6$) δ = 12.08-11.91 (m, 1H), 8.10-8.01 (m, 1H), 7.90 (s, 1H), 7.81 (s, 2H), 7.73-7.66 (m, 1H), 6.64 (d, J = 8.0 Hz, 1H), 4.48-4.32 (m, 3H), 3.71 (t, J = 6.2 Hz, 2H), 3.56-3.49 (m, 2H), 3.35-3.26 (m, 4H), 0.98-0.89 (m, 4H), 0.11 (s, 6H) |
| 130 | 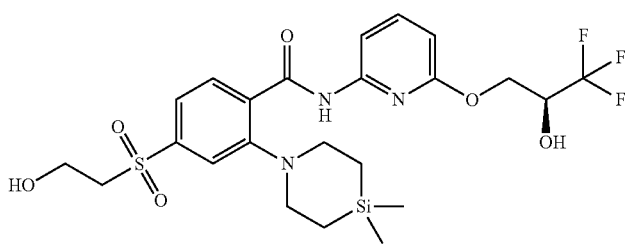 [SMILES: C[Si]1(C)CCN(c2cc(S(=O)(=O)CCO)ccc2C(=O)Nc2cccc(OC[C@H](O)C(F)(F)F)n2)CC1] | ¹H NMR (400 MHz, DMSO-$d_6$) δ = 12.03 (s, 1H), 8.07 (d, J = 8.1 Hz, 1H), 7.91 (d, J = 7.9 Hz, 1H), 7.87-7.76 (m, 2H), 7.73-7.55 (m, 1H), 6.64 (d, J = 8.0 Hz, 1H), 4.46-4.34 (m, 3H), 3.71 (s, 2H), 3.53 (s, 2H), 3.39-3.24 (m, 4H), 0.93 (br d, J = 6.0 Hz, 4H), 0.11 (s, 6H) |
| 131 | 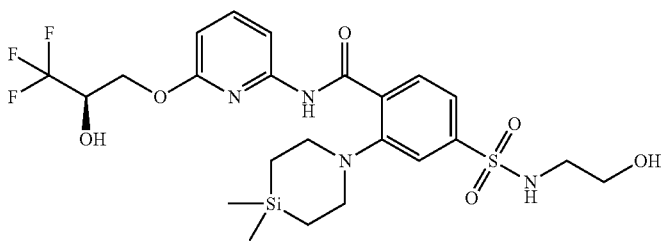 [SMILES: C[Si]1(C)CCN(c2cc(S(=O)(=O)NCCO)ccc2C(=O)Nc2cccc(OC[C@@H](O)C(F)(F)F)n2)CC1] | ¹H NMR (400 MHz, DMSO-$d_6$) δ = 8.05 (d, J = 8.1 Hz, 1H), 7.88 (d, J = 7.8 Hz, 1H), 7.79 (t, J = 7.9 Hz, 1H), 7.71 (s, 1H), 7.60 (br d, J = 8.0 Hz, 1H), 6.63 (d, J = 8.0 Hz, 1H), 4.45-4.36 (m, 2H), 4.32 (br dd, J = 3.9, 8.9 Hz, 1H), 3.35 (t, J = 6.2 Hz, 2H), 3.24 (br s, 4H), 2.80 (t, J = 6.1 Hz, 2H), 0.92 (br s, 4H), 0.08 (s, 6H) |

| Example Number | Structure | NMR |
|---|---|---|
| 132 | 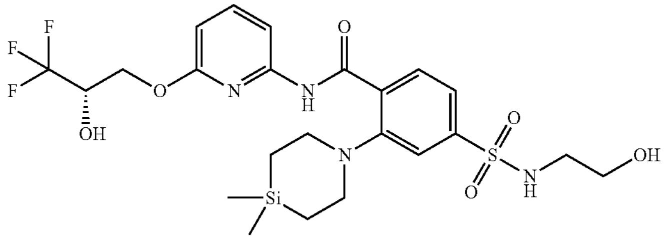 [SMILES: C[Si]1(C)CCN(c2cc(S(=O)(=O)NCCO)ccc2C(=O)Nc2cccc(OC[C@H](O)C(F)(F)F)n2)CC1] | $^1$H NMR (400 MHz, DMSO-$d_6$) δ = 8.05 (br d, J = 8.1 Hz, 1H), 7.93-7.85 (m, 1H), 7.79 (br t, J = 7.9 Hz, 1H), 7.71 (s, 1H), 7.59 (br d, J = 8.1 Hz, 1H), 6.63 (br d, J = 8.0 Hz, 1H), 4.39 (br s, 2H), 4.32 (br dd, J = 3.9, 8.9 Hz, 1H), 3.36 (br t, J = 6.1 Hz, 2H), 3.24 (br s, 4H), 2.80 (br t, J = 6.1 Hz, 2H), 0.91 (br s, 4H), 0.08 (s, 6H) |
| 133 | 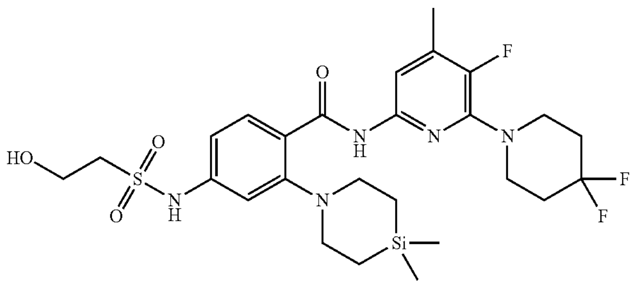 [SMILES: Cc1cc(NC(=O)c2ccc(NS(=O)(=O)CCO)cc2N2CC[Si](C)(C)CC2)nc(N2CCC(F)(F)CC2)c1F] | $^1$H NMR (400 MHz, DMSO-$d_6$) δ = 12.45-12.23 (m, 1H), 10.24-10.01 (m, 1H), 8.07-7.91 (m, 1H), 7.83-7.66 (m, 1H), 7.23 (s, 1H), 7.15-7.01 (m, 1H), 3.76-3.73 (m, 2H), 3.51-3.45 (m, 4H), 3.34 (t, J = 6.4 Hz, 2H), 3.21-3.09 (m, 4H), 2.25 (s, 3H), 2.13-2.02 (m, 4H), 1.05-0.93 (m, 4H), 0.13 (s, 6H) |
| 134 | 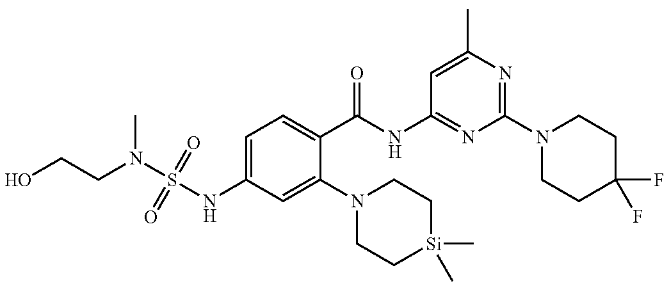 [SMILES: Cc1cc(NC(=O)c2ccc(NS(=O)(=O)N(C)CCO)cc2N2CC[Si](C)(C)CC2)nc(N2CCC(F)(F)CC2)n1] | $^1$H NMR (400 MHz, DMSO-$d_6$) δ = 13.45 (s, 1H), 10.34 (s, 1H), 8.05-8.01 (m, 2H), 7.24-7.20 (m, 1H), 7.07 (dd, J = 1.9, 8.6 Hz, 1H), 3.47 (br s, 2H), 3.17 (br dd, J = 6.4, 12.5 Hz, 6H), 2.92-2.86 (m, 1H), 2.82-2.78 (m, 3H), 2.47 (s, 3H), 2.08-1.98 (m, 4H), 1.94-1.75 (m, 4H), 1.05-1.01 (m, 4H), 0.17 (s, 6H) |

Comparator "Compound A", whose structure is shown below, was also synthesized according to known methods and tested in the biological assays disclosed below.

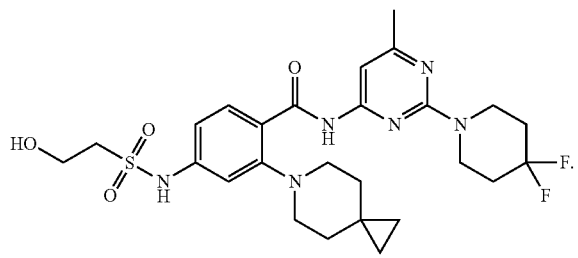

(Compound A)

As can be seen in the data table below, many of the compounds of the present invention have a better efflux ratio than Compound A.

Assays

1. Caco-2 Permeation Assay: Evaluation of the Bidirectional Permeabilities of Compounds.

Samples were analyzed through LC/MS/MS for estimating the apparent permeability coefficients ($P_{app}$) of compounds across Caco-2 cell monolayers. Caco-2 cells (American Type Culture Collection) were incubated and seeded onto HTS Transwell-96 Well Permeable Supports (Corning Corporation) for 14 days using a cell medium consisting of Dulbecco's Modified Eagle's Medium (DMEM) with high glucose and L-glutamine supplemented with 10% FBS, 1× penicillin-streptomycin mixture and 1×non-essential amino acids (NEAA). Cell monolayer integrity was measured using an automated tissue resistance measuring system (World Precision Instruments). Stock solutions of compounds and control compounds in DMSO were diluted with HBSS (10 mM HEPES, pH 7.4) to reach a final concentration of 5 μM with a final concentration of DMSO<0.1%. HBSS was then removed after 30 minutes of preincubation, and 75 μL of test compound was added to the apical compartment of the Transwell insert. The basolateral compartment was filled with 235 μL of HBSS (10 mM HEPES, pH 7.4) containing 2% BSA. Rate of drug transport in the basolateral to apical direction was obtained by adding 235 μL of test compound to the receiver plate wells (basolateral compartment) and filling with 75 μL of HBSS (10 mM HEPES, pH 7.4) containing 2% BSA. Time 0 samples were prepared by transferring 25 μL of 5 μM working solution to wells of the 96-deepwell plate containing 25 μL HBSS (10 mM HEPES and 2% BSA, pH 7.4), followed by the addition 200 μL of cold methanol containing appropriate internal standards (100 nM alprazolam, 200 nM labetalol, 200 nM caffeine and 200 nM diclofenac). After incubating at 37° C. for 2 h, 25 μL samples from donor sides (apical compartment) were transferred to a 96-well plate containing 25 µL HBSS (10 mM HEPES and 2% BSA, pH 7.4). 25 µL samples from receiver sides (basolateral compartment) were removed and transferred to a new plate containing 25 µL HBSS (10 mM HEPES, pH 7.4). 200 µL of cold methanol containing internal standards (100 nM alprazolam, 200 nM labetalol, 200 nM caffeine and 200 nM diclofenac) was added to terminate the reaction. Samples were vortexed for 5 minutes and then centrifuged at 3,220 g for 40 minutes. An aliquot of 100 µL of the supernatant is mixed with 100 µL of ultra-pure water for LC-MS/MS analysis. All incubations are performed in duplicate. Solutions were discarded from the transwell plate. 100 µL Lucifer Yellow solution (100 µM in HBSS) was added to each well of transwell insert and 300 µL of HBSS to each well of receiver. After incubating at 37° C. for 30 minutes, 80 µL was aliquotted from each well of apical and basolateral sides to a solid black plate. The plate was then read with Tecan Infinite™ M 200 (Excitation/Emission wavelength 485 nM/530 nM).

All calculations were carried out using Microsoft Excel. Peak areas were determined from extracted ion chromatograms. The leakage of Lucifer Yellow, in unit of percentage (%), can be calculated using the following equation:

$$\% LY \text{ leakage} = 100 \times \frac{[LY]_{acceptor}}{[LY]_{donor} + [LY]_{acceptor}}$$

LY leakage of <1% is acceptable to indicate the well-qualified Caco-2 monolayers. The apparent permeability coefficient ($P_{app}$), in units of centimeter per second, can be calculated for Caco-2 drug transport assays using the following equation:

$$P_{app} = \frac{V_A}{area \times time} \times \frac{[drug]_{acceptor}}{[drug]_{initial,donor}}$$

Where $V_A$ is the volume (in mL) in the receiver well (0.235 mL for Ap→Bl flux and 0.075 mL for Bl→Ap flux), Area is the surface area of the membrane (0.143 cm² for HTS Transwell-96 Well Permeable Supports), and time is the total transport time in seconds. The efflux ratio can be determined using the following equation:

$$\text{Efflux Ratio} = \frac{P_{app(B-A)}}{P_{app(A-B)}}$$

Where $P_{app\,(B-A)}$ indicates the apparent permeability coefficient in basolateral to apical direction, and $P_{app\,(A-B)}$ indicates the apparent permeability coefficient in apical to basolateral direction.

The recovery can be determined using the following equation:

$$\text{Recovery \%} = \frac{[drug]_{acceptor} \times V_A + [drug]_{donor} \times V_D}{[drug]_{initial,donor} \times V_D} \times 100$$

Where $V_A$ is the volume (in mL) in the acceptor well (0.235 mL for Ap→Bl flux, and 0.075 mL for Bl→Ap), $V_D$ is the volume (in mL) in the donor well (0.075 mL for Ap→Bl flux, and 0.235 mL for Bl→Ap).

2. KIF18A Biochemical Assay

A KIF18A ATPase assay was performed in small-volume, nonbinding, 384-well white plates at a final volume of 10 µL/well. Test compounds (10 mM solution in DMSO; 100 nL/well) were serially diluted 3-fold over 10-point concentration range. A solution of KIF18A (0.4 nM, 5 µL/well; 1-367) in assay buffer (15 mM Tris-HCl [pH 7.5](Boston Bioproducts Inc), 10 mM MgCl$_2$ (Boston Bioproducts Inc), 0.01% Pluronic F-68 (Gibco Inc), 1 uM Taxol (Cytoskeleton Inc), 30 mg/ml pre-formed porcine Microtubules (Cytoskeleton Inc)). The reaction was initiated by the addition of 5 µL of substrate solution (10 µM Ultra-Pure ATP in assay buffer) into the wells. The plates were incubated at room temperature for 45 minutes. After the indicated incubation times, 10 µL ADP-Glo reagent was added to the reactions and the plate was incubated at room temperature for 40 min. Then, 20 µL of kinase detection reagent was added and after an incubation time of 40 min, luminescence was recorded on Envision plate reader (Perkin Elmer, Billerica, MA).

3. In Vitro Anti-Proliferative Activity Assay of KIF18A Inhibitors in Cancer Cell Line OVCAR-3

To assess the anti-proliferative activity of KIF18A inhibitors in cancer cells in vitro, a 4- or 7-day growth assay was performed in ovarian cancer cell line OVCAR-3 using CellTiter-GLO 2.0 Luminescent Cell Viability Assay (CTG assay, Promega), which uses ATP as an indicator of cell viability. Briefly, OVCAR-3 cells were seeded at a 1,000 cells/mL density in black 384-well tissue culture plates in 40 µL of RPMI growth media containing 10% FBS. After 24 hours, cells were treated with KIF18A inhibitor (10-point concentration range 10.0 µM to 0.00051 µM, 3-fold dilution). The assay was performed in duplicate. After 4 or 7 days of treatment, 30 µL of CTG reagent was added to each well and luminescence was detected using Envision plate reader (Perkin Elmer). % Inhibition was calculated based on the following formula:

$$\% \text{Inhibition} = 100 \times \left\{ \frac{LumHC - LumSample}{LumHC - LumLC} \right\}$$

where HC=high control and LC=low control. High control was obtained from DMSO treated cells and low control was obtained from cells treated with 10 uM staurosporin.

Data for Assays 1-3

| Example Number | KIF18A Biochemical Assay IC$_{50}$ (uM) | OVCAR-3 cellular antiproliferation assay IC$_{50}$ (uM) | Caco-2 assay efflux ratio |
|---|---|---|---|
| 1 | ++++ | ++++[a] | ** |
| 2 | ++++ | ++++[a] | ** |
| 3 | ++++ | ++++[a] | NT |
| 4 | ++ | +++[a] | ** |
| 5 | ++++ | ++++[a] | ** |
| 6 | ++++ | ++++[a] | ** |
| 7 | ++++ | ++++[a] | * |
| 8 | +++ | ++++[a] | ** |
| 9 | +++ | ++++[a] | ** |
| 10 | ++++ | ++[a] | * |
| 11 | ++++ | ++++[a] | ** |
| 12 | ++ | +[a] | ** |
| 13 | ++++ | ++[a] | NT |
| 14 | ++++ | ++++[a] | NT |
| 15 | ++++ | +[a] | NT |
| 16 | ++++ | ++++[a] | ** |
| 17 | ++++ | ++++[a] | * |
| 18 | ++++ | ++++[a] | NT |
| 19 | ++++ | ++++[a] | NT |

| Example Number | KIF18A Biochemical Assay IC$_{50}$ (uM) | OVCAR-3 cellular antiproliferation assay IC$_{50}$ (uM) | Caco-2 assay efflux ratio |
|---|---|---|---|
| 20 | +++ | +++$^a$ | ** |
| 21 | +++ | +++$^a$ | ** |
| 22 | +++ | ++++$^a$ | NT |
| 23 | +++ | +++$^a$ | NT |
| 24 | NT | +++$^a$ | NT |
| 25 | + | NT | NT |
| 26 | ++++ | +++$^a$ | NT |
| 27 | + | +$^a$ | NT |
| 28 | ++++ | +++$^a$ | ** |
| 29a | ++++ | ++++$^a$ | NT |
| 29b | ++++ | ++++$^a$ | * |
| 30 | +++ | +$^a$ | NT |
| 31a | ++++ | +++$^b$ | NT |
| 31b | ++++ | +++$^b$ | NT |
| 32 | ++++ | +$^a$ | NT |
| 33 | ++++ | +++$^a$ | NT |
| 34 | ++++ | +++$^a$ | * |
| 35 | ++++ | +++$^a$ | ** |
| 36 | ++++ | +++$^a$ | NT |
| 37 | ++++ | ++++$^a$ | ** |
| 38 | ++++ | +++ | NT |
| 39 | +++ | +$^a$ | NT |
| 40 | + | +$^a$ | NT |
| 41 | ++++ | ++++ | NT |
| 42 | ++++ | +$^a$ | NT |
| 43 | ++++ | +$^a$ | NT |
| 44 | + | NT | NT |
| 45 | NT | +$^a$ | NT |
| 46 | NT | +$^a$ | NT |
| 47 | + | NT | NT |
| 48 | ++++ | ++++$^a$ | * |
| 49a | ++++ | +++$^b$ | NT |
| 49b | ++++ | ++++$^b$ | ** |
| 50a | ++++ | +++$^b$ | NT |
| 50b | ++++ | +++$^b$ | ** |
| 51a | NT | NT | NT |
| 51b | NT | NT | NT |
| 52 | ++++ | +++$^b$ | NT |
| 53 | ++++ | +++$^b$ | NT |
| 54 | ++++ | +++$^b$ | ** |
| 55 | ++++ | ++b | NT |
| 56 | ++++ | +++$^b$ | * |
| 57 | +++ | +$^b$ | NT |
| 58 | ++++ | ++++$^b$ | * |
| 59 | ++++ | +++$^b$ | NT |
| 60 | ++++ | ++++$^b$ | * |
| 61 | ++++ | +++$^b$ | NT |
| 62 | ++++ | ++++$^b$ | ** |
| 63 | ++++ | ++++$^b$ | NT |
| 64 | ++++ | ++++$^b$ | NT |
| 65 | ++++ | ++++$^b$ | NT |
| 66 | ++++ | ++++$^b$ | ** |
| 67 | + | +$^b$ | NT |
| 68 | + | +$^b$ | NT |
| 69 | ++++ | +$^b$ | NT |
| 70 | ++++ | ++++$^b$ | * |
| 71 | +++ | +$^b$ | NT |
| 72 | ++++ | +++$^b$ | * |
| 73 | + | +$^b$ | NT |
| 74 | + | +$^b$ | NT |
| 75 | ++++ | ++++$^b$ | ** |
| 76 | ++++ | +++$^b$ | NT |
| 77 | +++ | +++$^b$ | NT |
| 78 | ++++ | +++$^b$ | ** |
| 79 | +++ | +$^b$ | NT |
| 80 | +++ | +++$^b$ | NT |
| 81 | ++++ | ++$^b$ | NT |
| 82 | ++++ | ++$^b$ | NT |
| 83 | ++++ | ++$^b$ | NT |
| 84 | ++++ | +++$^b$ | ** |
| 85 | ++++ | +++$^b$ | NT |
| 86 | ++++ | +++$^b$ | ** |
| 87 | ++++ | +++$^b$ | NT |
| 88 | +++ | ++$^b$ | ** |
| 89 | NT | +++$^b$ | NT |
| 90 | NT | +++$^b$ | ** |
| 91 | NT | +++$^b$ | NT |
| 92 | NT | +$^b$ | NT |
| 93 | NT | +$^b$ | NT |
| 94 | NT | +++$^a$ | ** |
| 95 | NT | ++++$^a$ | NT |
| 96 | NT | ++++$^a$ | ** |
| 97 | + | +$^b$ | NT |
| 98 | ++++ | ++++$^a$ | ** |
| 99 | ++++ | ++++$^b$ | NT |
| 100 | ++++ | +++$^b$ | ** |
| 101 | ++++ | +++$^b$ | NT |
| 102 | ++++ | ++++$^b$ | * |
| 103 | ++++ | +++$^b$ | NT |
| 104 | ++++ | +++$^b$ | ** |
| 105 | + | +$^b$ | NT |
| 106 | ++++ | ++++$^b$ | ** |
| 107 | ++++ | ++++$^b$ | ** |
| 108 | ++++ | ++++$^b$ | ** |
| 109 | ++++ | ++$^b$ | ** |
| 110 | ++++ | ++++$^b$ | ** |
| 111 | ++++ | ++++$^b$ | * |
| 112 | ++++ | +++$^b$ | * |
| 113 | ++++ | +++$^b$ | ** |
| 114 | ++++ | ++++$^b$ | NT |
| 115 | ++++ | +++$^b$ | * |
| 116 | ++ | +$^b$ | NT |
| 117 | +++ | +++$^b$ | ** |
| 118 | ++++ | +++$^b$ | ** |
| 119 | ++++ | ++++$^b$ | ** |
| 120 | ++++ | ++++$^b$ | ** |
| 121 | ++++ | ++++$^b$ | ** |
| 122 | ++++ | ++++$^b$ | NT |
| 123 | ++++ | ++$^b$ | NT |
| 124 | ++++ | +++$^b$ | NT |
| 125 | ++++ | +++$^b$ | NT |
| 126 | ++++ | +++$^b$ | NT |
| 127 | ++++ | ++++$^b$ | ** |
| 128 | ++++ | +++$^b$ | NT |
| 129 | ++++ | +++$^b$ | NT |
| 130 | ++++ | +++$^b$ | NT |
| 131 | ++++ | ++++$^b$ | NT |
| 132 | ++++ | ++++$^b$ | NT |
| 133 | ++++ | +++$^b$ | NT |
| 134 | ++++ | +++$^b$ | ** |
| Compound A | +++ | ++++$^a$ | * |

"++++" means <0.1 µM; "+++" means 0.1-0.5 µM; "++" means >0.5-1 µM; "+" means >1 µM;
"**" means efflux ratio of <10; "*" means efflux ratio of >=10;
NT means not tested;
$^a$indicates the 4-day assay;
$^b$indicates the 7-day assay.

4. Evaluation of KIF18A Compounds in a Human Megakaryocyte Progenitor Colony Formation Assay Clonogenic progenitors of human megakaryocyte (CFU-MK) progenitors were assessed in a collagen-based media formulation containing 3% BSA, rhIL-3 (10 ng/mL), rhIL-6 (10 ng/mL) and rhTpo (50 ng/mL).

Human bone marrow mononuclear cells (lot #0221006, ReachBio Research Labs, Seattle, WA) were stored at −152° C. until required for the assay. On the day of the experiment, the cells were thawed rapidly, the contents were diluted in 10 mL of Iscove's modified Dulbecco's medium containing 10% fetal bovine serum (IMDM+10% FBS) and washed by centrifugation (approximately 1500 r.p.m. for 10 minutes, room temperature). The supernatant was discarded, and the cell pellets resuspended in a known volume of IMDM+10% FBS. A cell count (3% glacial acetic acid) and viability assessment (trypan blue exclusion test) were performed for the bone marrow sample.

Compounds were tested at final concentrations of 10, 3, 1, 0.3, 0.1 and 0.01 μM. DMSO was added as the solvent control of CFU-MK assay. 5-Fluorouracil (5-FU) was evaluated at 1.0, 0.1 and 0.01 μg/mL as a positive control for toxicity for all lineages. Solvent control cultures (containing no compound but 0.1% DMSO) as well as standard controls (containing no compound or DMSO) were also initiated.

The cultures were incubated for 14 days. The human megakaryocyte cultures were then transferred from the 35 mm dishes to labeled glass slides, fixed with methanol/acetone fixative and then stained with anti-human CD41 antibody and an alkaline phosphate detection system according to manufacturers' instructions. The colonies were assessed microscopically and scored by trained personnel and divided into the following categories based on size: CFU-MK (3-20), CFU-MK (21-49), and CFU-MK (≥50).

The mean±1 standard deviation of three replicate cultures was calculated for the megakaryocyte progenitors. Two-tailed student's t-tests were performed to assess if there was a difference in the number of colonies generated between solvent control and treated cultures. Due to the potential subjectivity of colony enumeration, a p-value of less than 0.01 was deemed significant. To calculate the concentration of 50% inhibition of colony growth ($IC_{50}$), a dose response curve was generated plotting the log of the compound concentration versus the percentage of control colony growth using GraphPad Prism 9. The concentration of 50% inhibition of colony growth ($IC_{50}$) was calculated based on the sigmoid curve fit using Dose-Response, One-Site Model formula:

$$y = A + [(B - A)/(1 + ((C/x)^\wedge D))],$$

where A=the initial value (baseline response), B=maximum response, C=center (drug concentration that provokes a response halfway between A and B) and D=slope of the curve at midpoint.

Binding of compounds to components of the assay buffer system was also evaluated. BSA and collagen were added to DMEM to obtain a final concentration similar to the buffer described above. Working solutions of test compounds and control compound were prepared in DMSO at the concentration of 5 mM, and then the working solutions were spiked into DMEM with BSA and collagen. The final concentration of compound was 25 μM. The final concentration of DMSO was 0.5%. Ketoconazole was used as positive control in the assay.

The dialysis membranes were soaked in ultrapure water for 60 minutes to separate strips, then in 20% ethanol for 20 minutes, finally in dialysis buffer for 20 minutes. The dialysis set up assembled according to the manufacturer's instruction. Each cell was treated with 150 μL of sample and dialyzed against equal volume of dialysis buffer (blank DMEM). The assay was performed in duplicate. The dialysis plate was sealed and incubated in an incubator at 37° C. with 5% $CO_2$ at 100 rpm for 6 h. At the end of incubation, 50 μL of samples from both buffer and samples were transferred to wells of a 96-well plate.

50 μL of blank DMEM with BSA and collagen was added to each buffer sample and an equal volume of blank DMEM was supplemented to the collected DMEM with BSA and collagen sample. 400 μL of precipitation buffer acetonitrile containing internal standards (IS, 100 nM alprazolam, 200 nM labetalol, 200 nM imipramine and 2 μM ketoprofen) was added to precipitate protein and release compounds. Samples were vortexed for 2 minutes and centrifuged for 30 minutes at 3,220 g. An aliquot of 100 μL of the supernatant was diluted by 100 μL ultra-pure $H_2O$, and the mixture was used for LC-MS/MS analysis.

All calculations were carried out using Microsoft Excel. The concentrations of test compounds in the buffer and DMEM with BSA and collagen chambers were determined from peak area ratios. The percentages of bound compound were calculated as follows:

% Free = (Peak Area Ratio buffer chamber/

Peak Area Ratio2% BSA and collagen chamber) * 100%

% Bound = 100% − % Free

Free-fraction adjusted $IC_{50}$s for compounds tested are found in Table 1 and were calculated using the following formula:

Free−fraction adjusted $CFU-MK\ IC_{50}$ (μM) =

$CFU-MK\ IC_{50}$ (μM) * % Free

As can be seen, most of the compounds tested have significantly less potency against the bone marrow mononuclear cells, in comparison to comparator Compound A, which indicates a significantly decreased risk of cytopenia or thrombocytopenia for these compounds.

TABLE 1

Free-fraction adjusted CFU-MK $IC_{50}$ values for several examples

| Example Number | Free-fraction adjusted CFU-MK $IC_{50}$ (μM) |
|---|---|
| 1 | 0.017 |
| 14 | 0.061 |
| 29b | 0.11 |
| 36 | 0.082 |
| 107 | 0.047 |
| Compound A | 0.048 |

5. In Vivo Pharmacokinetic (PK) Evaluation of KIF18A Compounds in Mouse

The pharmacokinetics of test compounds were evaluated following a single intravenous bolus (IV) of solution at a dose of 3 mg/kg and oral administration (PO) of solution/suspension at doses of 10 mg/kg in female balb/c nude mice using a parallel study design. Blood samples for the IV dose groups were collected at 0.083, 0.25, 0.5, 1, 2, 4, 7, 12, and 24 hours post dose. Blood samples for PO dose groups were collected at 0.25, 0.5, 1, 2, 4, 7, 12, and 24 hours post dose.

The desired serial concentrations of working solutions were achieved by diluting stock solution of analyte with 50% acetonitrile in water solution. 5 μL of working solutions (1, 2, 4, 10, 20, 100, 200, 1000, 2000, 4000 ng/mL) were added to 10 μL of the blank female balb/c nude mouse plasma to achieve calibration standards of 0.5-2000 ng/mL (0.5, 1, 2, 5, 10, 50, 100, 500, 1000, 2000 ng/mL) in a total volume of 15 μL. Five quality control samples at 1 ng/mL, 2 ng/mL, 5 ng/mL, 50 ng/mL and 1600 ng/mL for plasma were prepared independently of those used for the calibration curves. These QC samples were prepared on the day of analysis in the same way as calibration standards.

15 µL standards, 15 µL QC samples and 15 µL unknown sample (10 µL plasma with 5 µL blank solution) were added to 200 µL of acetonitrile containing IS mixture for precipitating protein respectively. Then the samples were vortexed for 30 s. After centrifugation at 4° C., 4000 rpm for 15 min, the supernatant was diluted 3 times with water. 10 µL of diluted supernatant was injected into the LC/MS/MS system for quantitative analysis. PK parameters were estimated using Phoenix (WinNonlin) pharmacokinetic software version 8.3 using a non-compartmental model.

Treatment with Example 1, Example 9, and Example 29b, and Example 50b at 3 mg/kg IV and 10 mg/kg PO was compared with Compound A at 10 mg/kg PO (Table 2).

TABLE 2

PK Parameters for Example 1, Example 9, Example 29b, Example 50b and Compound A at 3 mg/kg IV and 10 mg/kg PO dosing in mouse

| Example Number | IV Clearance (mL/ming/kg) | IV $V_{ss}$ (L/kg) | PO $T_{1/2}$ (h) | PO $C_{max}$ (ng/mL) |
|---|---|---|---|---|
| 1 | 3.6 | 2.7 | 8.9 | 2,900 |
| 9 | 1.7 | 2.5 | 14.5 | 3,100 |
| 29b | 3.3 | 0.97 | 3.7 | 4,700 |
| 50b | 0.74 | 0.51 | 10.6 | 10,100 |
| Compound A | 4.1 | 2.0 | 6.0 | 2,130 |

6. In Vivo Efficacy Demonstration for KIF18A Compounds

Experiments were performed in female NOD SCID mice (GenPharmatech Co.). Animals were allowed to acclimate for 7 days before the study. The general health of the animals were evaluated by a veterinarian, and complete health checks were performed prior to the study. General procedures for animal care and housing were in accordance with the standard, Commission on Life Sciences, National Research Council, Standard Operating Procedures (SOPs) of Pharmaron, Inc. The mice were kept in laminar flow rooms at constant temperature and humidity with 3-5 mice in each cage. Animals were housed in polycarbonate cages which had dimensions of 300×180×150 mm³ and in an environmentally monitored, well-ventilated room maintained at a temperature of 23±3° C. and a relative humidity of 40%-70%. Fluorescent lighting provided illumination approximately 12 hours per day. Animals had free access to irradiation sterilized dry granule food during the entire study period except for time periods specified by the protocol, as well as sterile drinking water in a bottle that was available ad libitum during the quarantine and study periods.

The OVCAR-3 (ATCC) tumor cell lines were maintained in vitro as a monolayer in RPMI 1640 medium supplemented with 20% heat inactivated FBS, at 37° C. in an atmosphere of 5% $CO_2$ in air. The tumor cells were subcultured, not exceeding 4-5 passages, and cells growing in an exponential growth phase were harvested and counted for tumor inoculation. Each mouse was inoculated subcutaneously on the right flank with OVCAR-3 tumor cells ($2×10^7$) in 0.2 mL of RPMI-1640 with Matrigel (1:1) for model development.

Treatment was started when the mean tumor size reached approximately 150-200 mm³, at which time the mice were randomized into treatment groups such that the average starting tumor size is similar for each treatment group. Animals were then treated with vehicle or indicated mg/kg (10-100) of compound at a given frequency (e.g., BID, QD, 4 days on treatment followed by 3 days off treatment) by oral gavage at a final dosing volume of 10 mL/kg.

All study animals were monitored for not only tumor growth but also behavior such as mobility, food and water consumption (by cage side checking only), body weight (BW), eye/hair matting and any other abnormal effects. Body weights of all animals was measured and recorded twice per week throughout the study. Body weight change, expressed in %, was calculated using the following formula:

$$BW \text{ change (\%)} = (BW\text{Day}_{PG-DX}/BW\text{Day}_{PG-D1}) \times 100;$$

$PG-D1$ is the first day of dosing.

The measurement of tumor size was conducted with a caliper and recorded twice per E week. The tumor volume (TV) (mm³) was estimated using the formula: $TV = a \times b^2/2$, where "a" and "b" are long and short diameters of a tumor, respectively.

The TVs were used for calculation of the tumor growth inhibition and tumor growth delay. For the tumor growth inhibition (TGI), the value using the formula:

$$\% T/C = (TreatedTV_{final} - TreatedTV_{initial})/$$
$$(VehicleTV_{final} - VehicleTV_{initial}) \times 100$$

$$\% TGI = [1 - (TreatedTV_{final} - TreatedVT_{initial})/$$
$$(VehicleTV_{final} - VehicleTV_{initial})] \times 100$$

The "$TV_{final}$" and "$TV_{initial}$" are the mean tumor volumes on the final day and initial day, respectively.

All statistical tests was conducted on GraphPad, and the level of significance was set at 5% or $P<0.05$. The group means and standard deviations were calculated for all measurement parameters. Two-way RM ANOVA followed by Tukeys post hoc comparisons of the means was applied among groups.

On Day 1, about 30-60 µL of whole blood was collected into tubes containing EDTA anticoagulant. These collections took place 6 hours and 24 hours after the first dose for all treatment groups. Plasma was harvested by centrifugation at 4,000 g×5 min and stored at −80° C. until analysis.

The desired serial concentrations of working solutions were achieved by diluting stock solution of analyte with 50% acetonitrile in water solution. 5 µL of working solutions (1, 2, 4, 10, 20, 100, 200, 1000, 2000 ng/mL) were added to 10 µL of the blank NOD SCID mice plasma to achieve calibration standards of 0.5-1000 ng/mL (0.5, 1, 2, 5, 10, 50, 100, 500, 1000 ng/mL) in a total volume of 15 µL. Five quality control samples at 1 ng/mL, 2 ng/mL, 5 ng/mL, 50 ng/mL and 800 ng/mL were prepared independently of those used for the calibration curves. These QC samples were prepared on the day of analysis in the same way as calibration standards.

15 µL standards, 15 µL QC samples and 15 µL unknown samples (10 µL plasma with 5 µL blank solution) were added to 200 µL of acetonitrile containing IS mixture for precipitating protein respectively. Then the samples were vortexed for 30 s, centrifugated at 4° C., 4000 rpm for 15 min. The supernatant was diluted 3 times with water. 10 µL of diluted supernatant was injected into the LC/MS/MS system for quantitative analysis. PK parameters were estimated using Phoenix (WinNonlin) pharmacokinetic software version 8.3 using a non-compartmental model.

On Day 28, tissues were collected from animals. About 30-60 µL of whole blood was collected into tubes containing EDTA anticoagulant, and plasma was harvested by centrifugation at 4,000 g×5 min and stored at −80° C. until analysis. Plasma analysis followed the same protocol as for the Day 1 plasma analysis. Additionally, the femurs of the mice were cut and put in pre-weighed tubes. The bone marrow was harvested by centrigation at 8,000 g×15 min. Then, the total weight of both the bone marrow and the tube was recorded. The bone marrow was stored at −80° C. until analysis.

Treatment was initiated with, for example, Example 9 and Compound A treated at 10 and 100 mg/kg using QD (once daily) oral application when the tumor volume was an average of approximately 150-200 mm³ (n=8/group). The initial treatment period with Example 9 and Compound A was 28 days, after which overall efficacy and tolerability were evaluated based on tumor volume and body weight changes observed during the treatment period (FIG. 1a and FIG. 1b). Additionally, after compound treatment, the animals were observed an additional 28 days without compound treatment.

On day 28, Example 9 dosed orally at 100 mg/kg once daily induced an antitumor response against OVCAR-3 xenografts in mice, where the % T/C value was −4% and the % TGI was 104%, with a p-value=<0.0001 when compared with vehicle control using a one way ordinary ANOVA test (FIG. 1a). Based on body weight, dosing of all concentrations of Example 9 was well tolerated (FIG. 1b).

Treatment was initiated with, for example, Example 1 at 100 mg/kg using QD (once daily), 100 mg/kg QOD (every other day), 100 mg/kg once daily dosing for 4 days followed by 3 days of no dosing, and Compound A 100 mg/kg using QD (once daily) oral application when the tumor volume was an average of approximately 150-200 mm³ (n=8/group). The initial treatment period with Example 1 was 28 days, after which overall efficacy and tolerability were evaluated based on tumor volume and body weight changes observed during the treatment period (FIG. 2a and FIG. 2b).

Figure 2A:
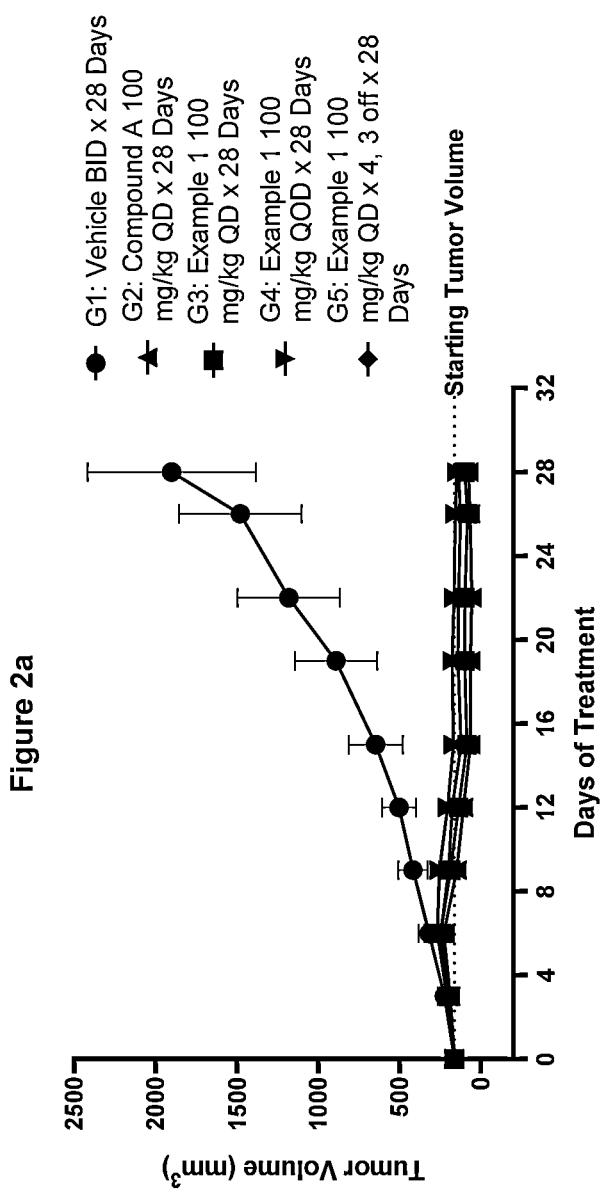
FIG. 2a shows 28 day in vivo efficacy for compound of Example 1 and Compound A in OVCAR-3 Xenografts: Tumor Volume Over Time.
Figure 2B:
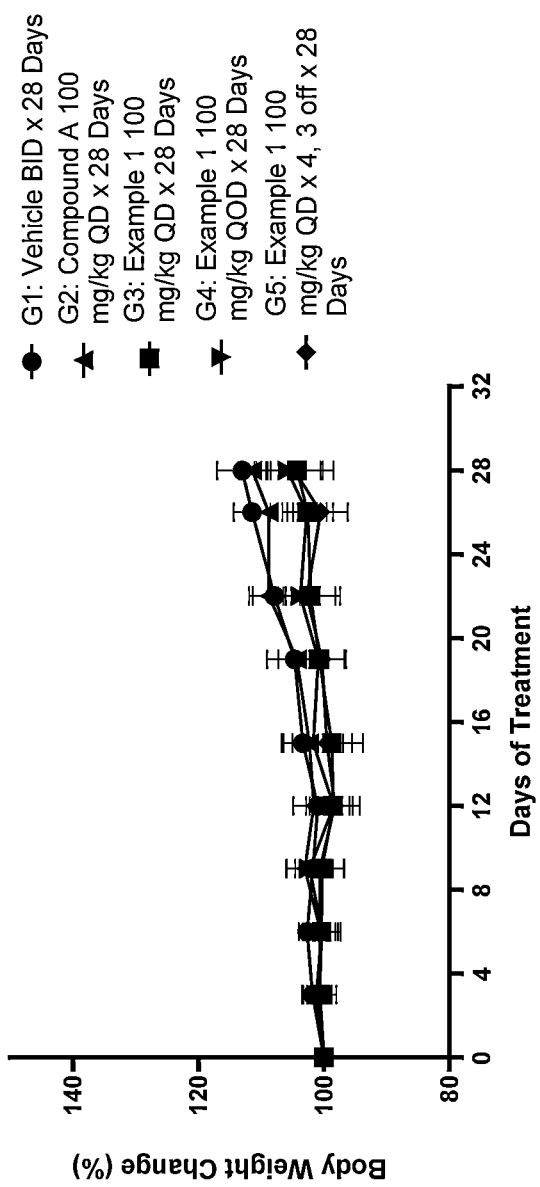
FIG. 2b shows tolerabitliy for compound of Example 1 and Compound A in a 28 day in vivo efficacy study in OVCAR-3 Xenografts.

On day 28, Example 1 dosed orally at 100 mg/kg once daily dosing for 4 days followed by 3 days of no dosing induced an antitumor response against OVCAR-3 xenografts in mice, where the % T/C value was −2% and the % TGI was 102%, with a p-value=<0.0001 when compared with vehicle control using a one way ordinary ANOVA test (FIG. 2a). Based on body weight, dosing of all concentrations of Example 1 was well tolerated (FIG. 2b).

Treatment was initiated with, for example, Example 29b at 10 mg/kg and 30 mg/kg using QD, and Compound A 100 mg/kg using QD oral application when the tumor volume was an average of approximately 150-200 mm³ (n=8/group). The initial treatment period with Example 1 was 28 days, after which overall efficacy and tolerability were evaluated based on tumor volume and body weight changes observed during the treatment period (FIG. 3a and FIG. 3b).

Figure 3A:
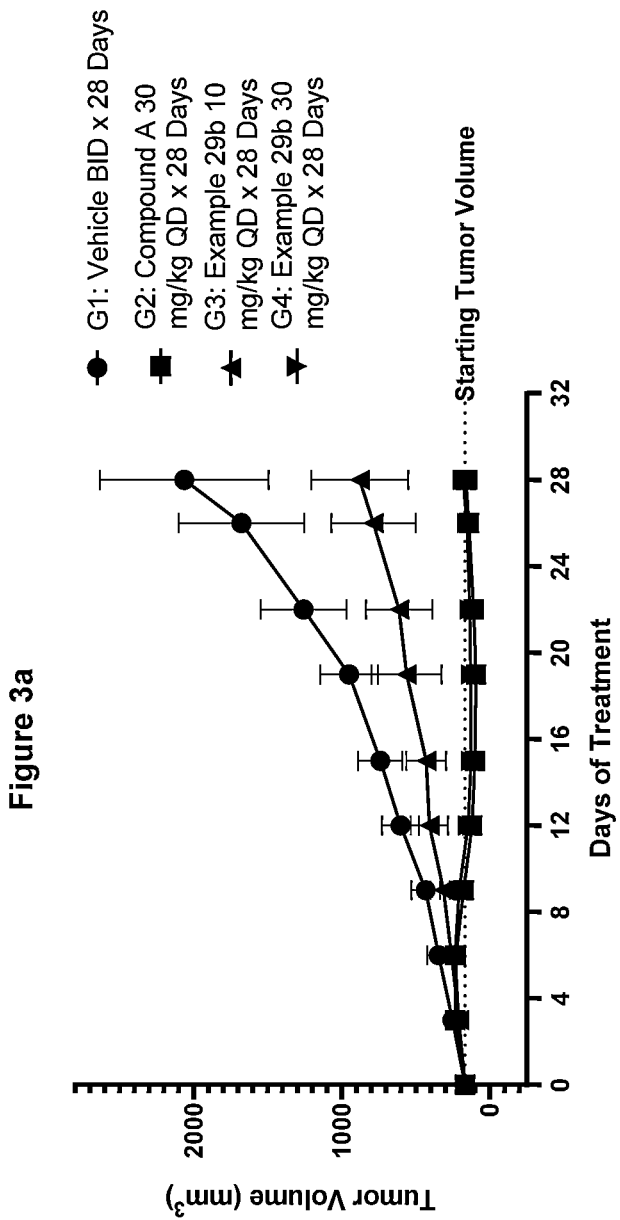
FIG. 3a shows 28 day in vivo efficacy for compound of Example 29b and Compound A in OVCAR-3 Xenografts.
Figure 3B:
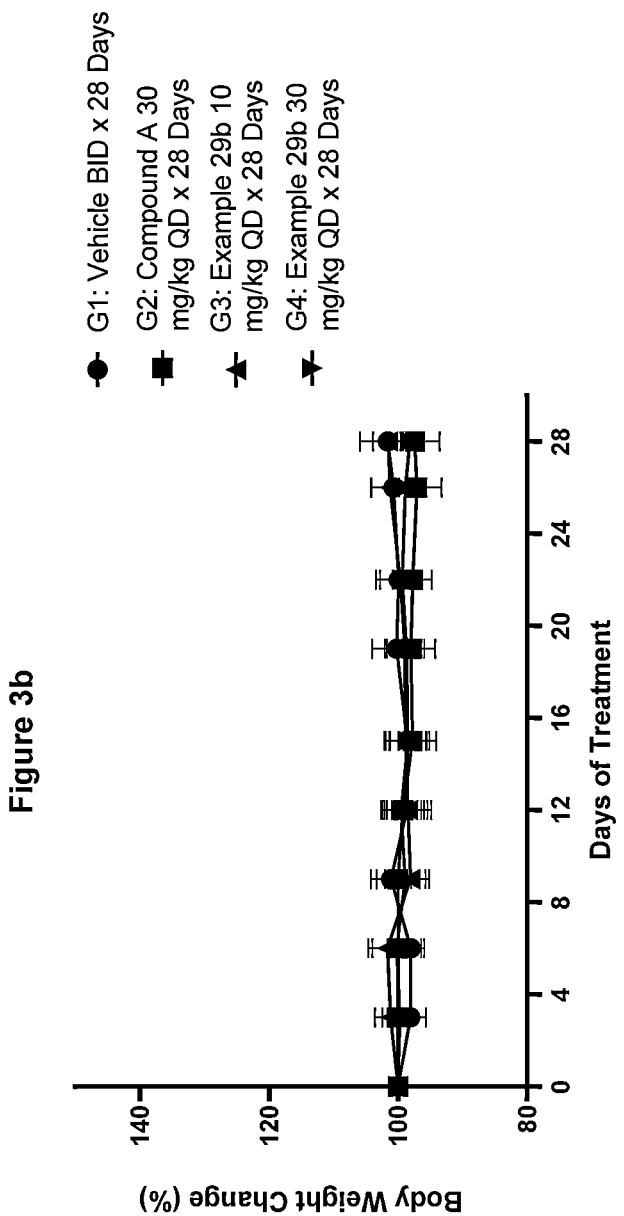
FIG. 3b shows tolerability for compound of Example 29b and Compound A in a 28 day in vivo efficacy study in OVCAR-3 Xenografts.

On day 28, Example 29b dosed orally at 30 mg/kg once daily dosing induced an antitumor response against OVCAR-3 xenografts in mice, where the % T/C value was 1% and the % TGI was 99%, with a p-value=<0.0001 when compared with vehicle control using a one way ordinary ANOVA test (FIG. 3a). Based on body weight, dosing of all concentrations of Example 29b was well tolerated (FIG. 3b). As can be seen, despite having a shorter half-life and faster clearance, Example 29b shows significant reduction in tumor growth in a dose-dependent manner.

Additionally, bone marrow was collected from mice treated orally with 10 mg/kg QD and 30 mg/kg QD dosing with Example 29b and 30 mg/kg QD Compound A, and the total concentration of compound observed in bone marrow is shown in Table 3. Samples were collected from animals 6 h after the last dose of compound and at 24 h after the last dose of compound.

TABLE 3

Concentration of Example 29b and Compound A in Bone Marrow at 6 h and 24 h Post-Last Dose in 28 day in vivo efficacy in OVCAR-3 Xenografts

| Example Number and Dose | Bone marrow concentration at 6 h post-last dose (ng/g) | Bone marrow concentration at 24 h post-last dose (ng/g) |
| --- | --- | --- |
| 29b (10 mg/kg QD) | 2,800 | 210 |
| 29b (30 mg/kg QD) | 10,500 | 900 |
| Compound A (30 mg/kg QD) | 17,000 | 4,100 |

What is claimed is:

1. A compound represented by Formula (IIIA):

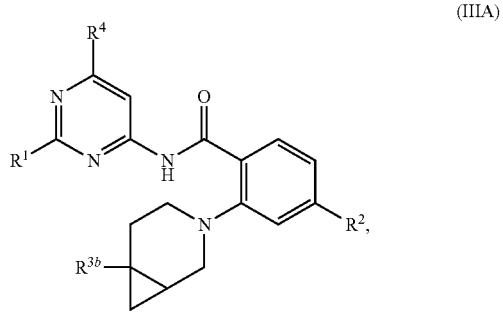

(IIIA)

or a pharmaceutically acceptable salt thereof, wherein:
R¹ is cyclohexyl, morpholinyl, or piperdinyl, wherein the cyclohexyl, morpholinyl, and piperdinyl are each optionally substituted with 1 to 2 R¹ᵇ;
each R¹ᵇ is —F;
R² is —NHS(O)₂CH₂CH₂OH or —NHS(O)₂C(CH₃)₃;
R³ᵇ is H, —F, —CH₃, —CH₂F, or —CHF₂; and
R⁴ is H or —CH₃.

2. The compound of claim 1, or a pharmaceutically acceptable salt thereof, wherein R¹ is represented by the following structural formula:

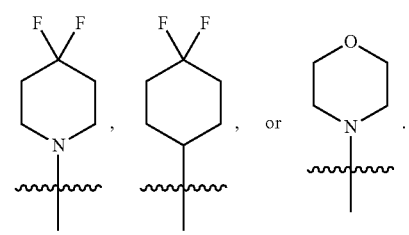

3. The compound of claim 2, or a pharmaceutically acceptable salt thereof, wherein R³ᵇ is H, —CH₃, or —CHF₂.

4. The compound of claim 1, wherein the compound is:

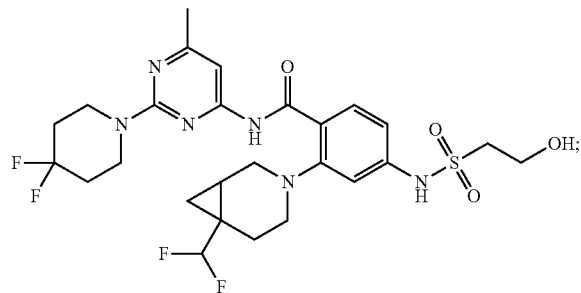 [SMILES: Cc1cc(NC(=O)c2ccc(NS(=O)(=O)CCO)cc2N2CCC3(C(F)F)CC3C2)nc(N2CCC(F)(F)CC2)n1]

or a pharmaceutically acceptable salt thereof.

5. The compound of claim 1, wherein the compound is:

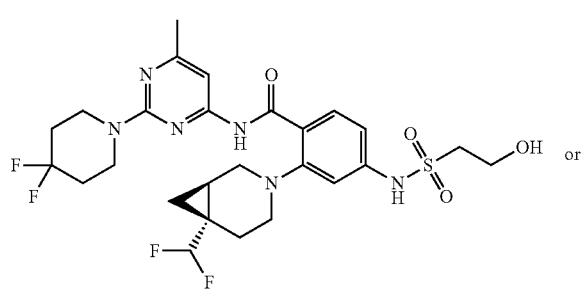

or

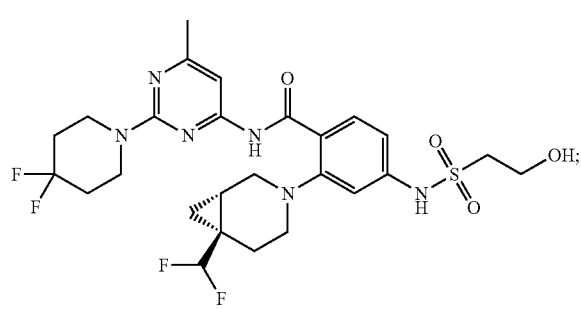

or a pharmaceutically acceptable salt thereof.

6. The compound of claim 1, wherein the compound is:

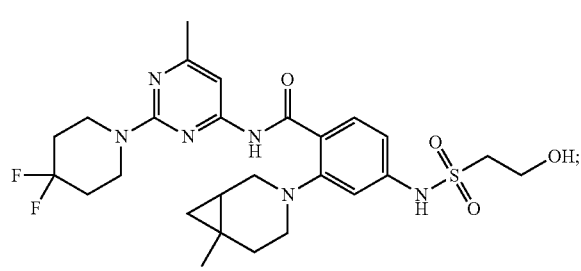 [SMILES: Cc1cc(NC(=O)c2ccc(NS(=O)(=O)CCO)cc2N2CCC3(C)CC3C2)nc(N2CCC(F)(F)CC2)n1]

or a pharmaceutically acceptable salt thereof.

7. The compound of claim 1, wherein the compound is:

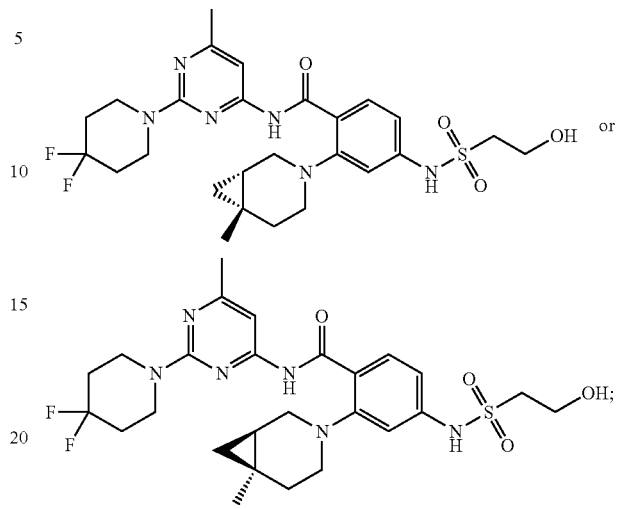

or a pharmaceutically acceptable salt thereof.

8. The compound of claim 1, wherein the compound is:

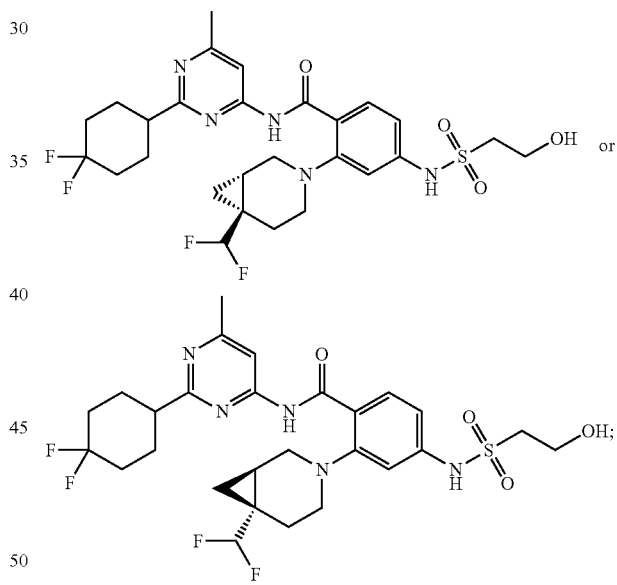

or a pharmaceutically acceptable salt thereof.

9. The compound of claim 1, wherein the compound is:

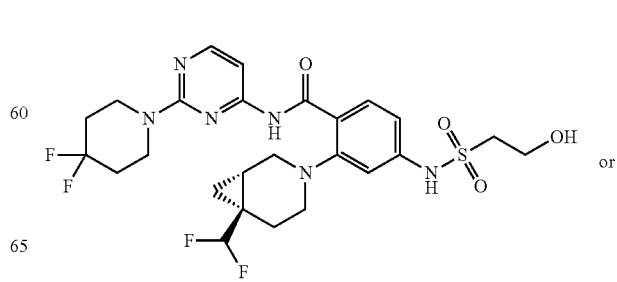

or

-continued

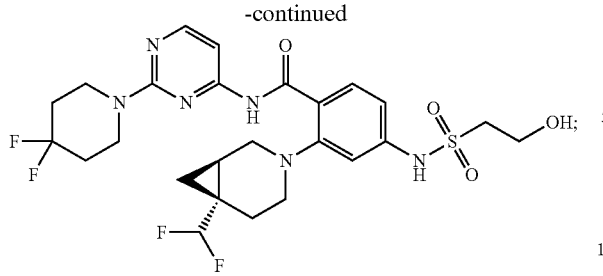

or a pharmaceutically acceptable salt thereof.

10. The compound of claim 1, wherein the compound is:

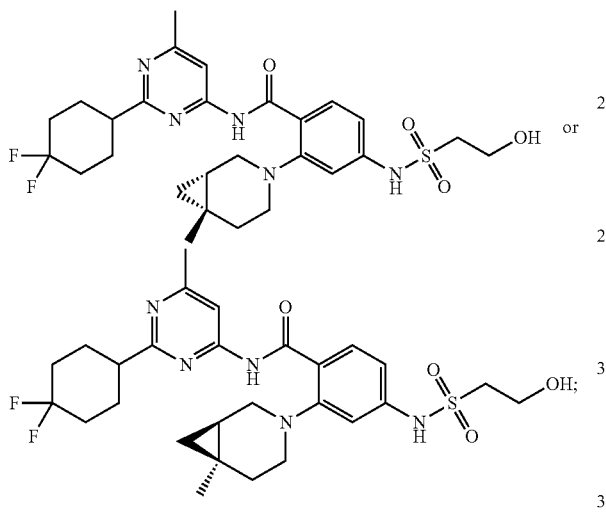

or a pharmaceutically acceptable salt thereof.

11. The compound of claim 1, wherein the compound is:

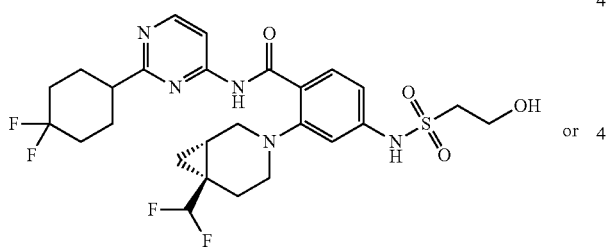

or

-continued

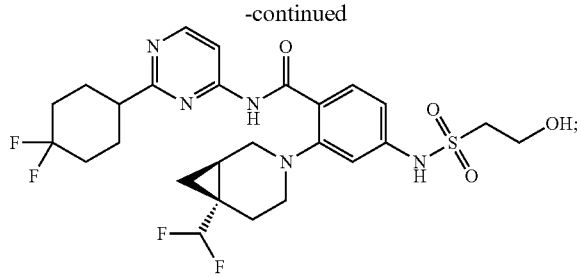

or a pharmaceutically acceptable salt thereof.

12. A pharmaceutical composition comprising a compound of claim 1, or a pharmaceutically acceptable salt thereof, and a pharmaceutically acceptable excipient.

13. A pharmaceutical composition comprising a compound of claim 4, or a pharmaceutically acceptable salt thereof, and a pharmaceutically acceptable excipient.

14. A pharmaceutical composition comprising a compound of claim 5, or a pharmaceutically acceptable salt thereof, and a pharmaceutically acceptable excipient.

15. A pharmaceutical composition comprising a compound of claim 6, or a pharmaceutically acceptable salt thereof, and a pharmaceutically acceptable excipient.

16. A pharmaceutical composition comprising a compound of claim 7, or a pharmaceutically acceptable salt thereof, and a pharmaceutically acceptable excipient.

17. A pharmaceutical composition comprising a compound of claim 8, or a pharmaceutically acceptable salt thereof, and a pharmaceutically acceptable excipient.

18. A pharmaceutical composition comprising a compound of claim 9, or a pharmaceutically acceptable salt thereof, and a pharmaceutically acceptable excipient.

19. A pharmaceutical composition comprising a compound of claim 10, or a pharmaceutically acceptable salt thereof, and a pharmaceutically acceptable excipient.

20. A pharmaceutical composition comprising a compound of claim 11, or a pharmaceutically acceptable salt thereof, and a pharmaceutically acceptable excipient.

\* \* \* \* \*